US009487587B2

(12) United States Patent
Koenig

(10) Patent No.: US 9,487,587 B2
(45) Date of Patent: Nov. 8, 2016

(54) BISPECIFIC MOLECULES THAT ARE IMMUNOREACTIVE WITH IMMUNE EFFECTOR CELLS OF A COMPANION ANIMAL THAT EXPRESS AN ACTIVATING RECEPTOR AND CELLS THAT EXPRESS B7-H3 AND USES THEREOF

(71) Applicant: MacroGenics, Inc., Rockville, MD (US)

(72) Inventor: Scott Koenig, Rockville, MD (US)

(73) Assignee: MacroGenics, Inc., Rockville, MD (US)

( * ) Notice: Subject to any disclaimer, the term of this patent is extended or adjusted under 35 U.S.C. 154(b) by 0 days.

(21) Appl. No.: 14/196,871

(22) Filed: Mar. 4, 2014

(65) Prior Publication Data

US 2014/0255407 A1 Sep. 11, 2014

Related U.S. Application Data

(60) Provisional application No. 61/772,931, filed on Mar. 5, 2013.

(51) Int. Cl.

*A61K 39/395* (2006.01)
*C07K 16/28* (2006.01)
*C07K 16/30* (2006.01)

(52) U.S. Cl.

CPC ....... *C07K 16/2827* (2013.01); *C07K 16/2809* (2013.01); *C07K 16/30* (2013.01); *C07K 2317/31* (2013.01); *C07K 2317/33* (2013.01); *C07K 2317/526* (2013.01); *C07K 2317/528* (2013.01); *C07K 2317/626* (2013.01); *C07K 2317/73* (2013.01)

(58) Field of Classification Search

None

See application file for complete search history.

(56) References Cited

U.S. PATENT DOCUMENTS

| | | | |
|---|---|---|---|
| 3,842,067 | A | 10/1974 | Sarantakis |
| 3,862,925 | A | 1/1975 | Sarantakis et al. |
| 3,972,859 | A | 8/1976 | Fujino et al. |
| 4,105,603 | A | 8/1978 | Vale, Jr. et al. |
| 4,179,337 | A | 12/1979 | Davis et al. |
| 4,752,601 | A | 6/1988 | Hahn |
| 4,816,567 | A | 3/1989 | Cabilly et al. |
| 5,024,835 | A | 6/1991 | Rao et al. |
| 5,116,964 | A | 5/1992 | Capon et al. |
| 5,169,933 | A | 12/1992 | Anderson et al. |
| 5,225,539 | A | 7/1993 | Winter |
| 5,348,876 | A | 9/1994 | Michaelson et al. |
| 5,565,332 | A | 10/1996 | Hoogenboom et al. |
| 5,576,184 | A | 11/1996 | Better et al. |
| 5,580,717 | A | 12/1996 | Dower et al. |
| 5,585,089 | A | 12/1996 | Queen et al. |
| 5,624,821 | A | 4/1997 | Winter et al. |
| 5,648,260 | A | 7/1997 | Winter et al. |
| 5,656,444 | A | 8/1997 | Webb et al. |
| 5,693,761 | A | 12/1997 | Queen et al. |
| 5,693,762 | A | 12/1997 | Queen et al. |
| 5,698,449 | A | 12/1997 | Baumann et al. |
| 5,711,944 | A | 1/1998 | Gilbert et al. |
| 5,723,584 | A | 3/1998 | Schatz |
| 5,731,168 | A | 3/1998 | Carter et al. |
| 5,733,743 | A | 3/1998 | Johnson et al. |
| 5,736,135 | A | 4/1998 | Goeddel et al. |
| 5,736,137 | A | 4/1998 | Anderson et al. |
| 5,807,706 | A | 9/1998 | Carter et al. |
| 5,807,715 | A | 9/1998 | Morrison et al. |
| 5,821,333 | A | 10/1998 | Carter et al. |
| 5,837,243 | A | 11/1998 | Deo et al. |
| 5,866,692 | A | 2/1999 | Shitara et al. |
| 5,874,239 | A | 2/1999 | Schatz |
| 5,877,396 | A | 3/1999 | Ravetch et al. |
| 5,885,573 | A | 3/1999 | Bluestone et al. |
| 5,888,533 | A | 3/1999 | Dunn |
| 5,932,433 | A | 8/1999 | Schatz |
| 5,945,115 | A | 8/1999 | Dunn et al. |
| 5,985,599 | A | 11/1999 | Mckenzie et al. |
| 5,997,867 | A | 12/1999 | Waldmann et al. |
| 6,019,968 | A | 2/2000 | Platz et al. |
| 6,025,485 | A | 2/2000 | Kamb et al. |
| 6,054,297 | A | 4/2000 | Carter et al. |
| 6,054,561 | A | 4/2000 | Ring |
| 6,114,147 | A | 9/2000 | Frenken et al. |
| 6,132,764 | A | 10/2000 | Li et al. |
| 6,132,992 | A | 10/2000 | Ledbetter et al. |
| 6,165,745 | A | 12/2000 | Ward et al. |
| 6,180,370 | B1 | 1/2001 | Queen et al. |
| 6,180,377 | B1 | 1/2001 | Morgan et al. |
| 6,194,551 | B1 | 2/2001 | Idusogie et al. |
| 6,218,149 | B1 | 4/2001 | Morrison et al. |
| 6,242,195 | B1 | 6/2001 | Idusogie et al. |

(Continued)

FOREIGN PATENT DOCUMENTS

| | | |
|---|---|---|
| EP | 0327378 | 8/1989 |
| EP | 0332865 | 9/1989 |

(Continued)

OTHER PUBLICATIONS

Cell 2014;157(1): 255-266.*

(Continued)

*Primary Examiner* — Ilia Ouspenski

(74) *Attorney, Agent, or Firm* — AuerbachSchrot LLC; William C. Schrot; Jeffrey I. Auerbach

(57) ABSTRACT

The present invention relates to bispecific molecules that are immunoreactive to an activating receptor of a companion animal immune effector cell and to B7-H3, and to the use of such bispecific molecules in the treatment of cancer in companion animals.

14 Claims, 8 Drawing Sheets

(56) References Cited

U.S. PATENT DOCUMENTS

| | | | |
|---|---|---|---|
| 6,265,150 | B1 | 7/2001 | Terstappen et al. |
| 6,277,375 | B1 | 8/2001 | Ward |
| 6,300,065 | B1 | 10/2001 | Kieke et al. |
| 6,331,415 | B1 | 12/2001 | Cabilly et al. |
| 6,339,069 | B1 | 1/2002 | Meers et al. |
| 6,420,149 | B1 | 7/2002 | Fukuda et al. |
| 6,423,538 | B1 | 7/2002 | Wittrup et al. |
| 6,455,263 | B2 | 9/2002 | Payan |
| 6,472,511 | B1 | 10/2002 | Leung et al. |
| 6,492,123 | B1 | 12/2002 | Hollinger et al. |
| 6,528,624 | B1 | 3/2003 | Idusogie et al. |
| 6,538,124 | B1 | 3/2003 | Idusogie et al. |
| 6,548,640 | B1 | 4/2003 | Winter |
| 6,623,940 | B1 | 9/2003 | Ledbetter et al. |
| 6,696,550 | B2 | 2/2004 | Larosa et al. |
| 6,737,056 | B1 | 5/2004 | Presta |
| 6,821,505 | B2 | 11/2004 | Ward |
| 6,891,030 | B2 | 5/2005 | Chen |
| 6,965,018 | B2 | 11/2005 | Mikesell et al. |
| 6,982,321 | B2 | 1/2006 | Winter |
| 7,122,637 | B2 | 10/2006 | Presta |
| 7,183,387 | B1 | 2/2007 | Presta |
| 7,261,890 | B2 | 8/2007 | Krah, III et al. |
| 7,276,586 | B2 | 10/2007 | Goddard et al. |
| 7,279,567 | B2 | 10/2007 | Mikesell et al. |
| 7,315,786 | B2 | 1/2008 | Dahiyat et al. |
| 7,317,091 | B2 | 1/2008 | Lazar et al. |
| 7,332,581 | B2 | 2/2008 | Presta |
| 7,335,742 | B2 | 2/2008 | Presta |
| 7,351,803 | B2 | 4/2008 | Johnson et al. |
| 7,355,008 | B2 | 4/2008 | Stavenhagen et al. |
| 7,358,354 | B2 | 4/2008 | Mikesell et al. |
| 7,368,554 | B2 | 5/2008 | Mikesell et al. |
| 7,371,826 | B2 | 5/2008 | Presta |
| 7,416,727 | B2 | 8/2008 | Presta |
| 7,425,619 | B2 | 9/2008 | Koenig et al. |
| 7,425,620 | B2 | 9/2008 | Koenig et al. |
| 7,429,652 | B2 | 9/2008 | Wang et al. |
| 7,521,542 | B2 | 4/2009 | Johnson et al. |
| 7,527,969 | B2 | 5/2009 | Mather et al. |
| 7,618,628 | B2 | 11/2009 | Johnson et al. |
| 7,632,497 | B2 | 12/2009 | Stavenhagen |
| 7,642,228 | B2 | 1/2010 | Carter et al. |
| 7,655,229 | B2 | 2/2010 | Chan et al. |
| 7,662,926 | B2 | 2/2010 | Chan et al. |
| 7,695,936 | B2 | 4/2010 | Carter et al. |
| 7,700,100 | B2 | 4/2010 | Johnson et al. |
| 7,718,774 | B2 | 5/2010 | Mather et al. |
| 7,786,270 | B2 | 8/2010 | Johnson et al. |
| 7,838,635 | B2 | 11/2010 | Johnson et al. |
| 7,960,512 | B2 | 6/2011 | Stavenhagen et al. |
| 8,003,774 | B2 | 8/2011 | Stavenhagen et al. |
| 8,039,592 | B2 | 10/2011 | Lazar et al. |
| 8,044,180 | B2 | 10/2011 | Koenig et al. |
| 8,124,731 | B2 | 2/2012 | Lazar et al. |
| 8,133,982 | B2 | 3/2012 | Johnson et al. |
| 8,137,668 | B2 | 3/2012 | Li |
| 8,183,357 | B2 | 5/2012 | Mather et al. |
| 8,187,593 | B2 | 5/2012 | Koenig et al. |
| 8,187,594 | B2 | 5/2012 | Mather et al. |
| 8,188,231 | B2 | 5/2012 | Lazar et al. |
| 8,192,737 | B2 | 6/2012 | Stavenhagen et al. |
| 8,193,318 | B2 | 6/2012 | Koenig et al. |
| 8,216,570 | B2 | 7/2012 | Mather et al. |
| 8,216,574 | B2 | 7/2012 | Stavenhagen et al. |
| 8,216,578 | B2 | 7/2012 | Mather et al. |
| 8,216,579 | B2 | 7/2012 | Johnson et al. |
| 8,216,800 | B2 | 7/2012 | Fabrega et al. |
| 8,217,147 | B2 | 7/2012 | Stavenhagen et al. |
| 8,586,713 | B2 | 11/2013 | Davis et al. |
| 2001/0036459 | A1 | 11/2001 | Ravetch |
| 2002/0028486 | A1 | 3/2002 | Morrison et al. |
| 2002/0127227 | A1 | 9/2002 | Holmes et al. |
| 2002/0168762 | A1 | 11/2002 | Chen |
| 2003/0077282 | A1 | 4/2003 | Bigler et al. |
| 2003/0103963 | A1 | 6/2003 | Cheung |
| 2003/0103976 | A1 | 6/2003 | Serizawa et al. |
| 2003/0115614 | A1 | 6/2003 | Kanda et al. |
| 2003/0158389 | A1 | 8/2003 | Idusogie et al. |
| 2003/0185827 | A1 | 10/2003 | Rodriguez et al. |
| 2003/0190319 | A1 | 10/2003 | Adolf et al. |
| 2003/0207346 | A1 | 11/2003 | Arathoon et al. |
| 2004/0002587 | A1 | 1/2004 | Watkins et al. |
| 2004/0038339 | A1 | 2/2004 | Kufer et al. |
| 2004/0058400 | A1 | 3/2004 | Hollinger et al. |
| 2004/0110226 | A1 | 6/2004 | Lazar et al. |
| 2004/0132101 | A1 | 7/2004 | Lazar et al. |
| 2004/0185045 | A1 | 9/2004 | Koenig et al. |
| 2004/0191244 | A1 | 9/2004 | Presta |
| 2004/0220388 | A1 | 11/2004 | Mertens et al. |
| 2004/0235065 | A1 | 11/2004 | Hansen et al. |
| 2004/0236078 | A1 | 11/2004 | Carter et al. |
| 2005/0025764 | A1 | 2/2005 | Watkins et al. |
| 2005/0037000 | A1 | 2/2005 | Stavenhagen et al. |
| 2005/0054832 | A1 | 3/2005 | Lazar et al. |
| 2005/0064514 | A1 | 3/2005 | Stavenhagen et al. |
| 2005/0090648 | A1 | 4/2005 | Tsurushita et al. |
| 2005/0202536 | A1 | 9/2005 | Chen |
| 2005/0215767 | A1 | 9/2005 | Koenig et al. |
| 2005/0260213 | A1 | 11/2005 | Koenig et al. |
| 2006/0013810 | A1 | 1/2006 | Johnson et al. |
| 2006/0018899 | A1 | 1/2006 | Kao et al. |
| 2006/0024298 | A1 | 2/2006 | Lazar et al. |
| 2006/0073142 | A1 | 4/2006 | Chan et al. |
| 2006/0134709 | A1 | 6/2006 | Stavenhagen et al. |
| 2006/0154313 | A1 | 7/2006 | Anderson et al. |
| 2006/0177439 | A1 | 8/2006 | Koenig et al. |
| 2006/0193849 | A1 | 8/2006 | Krauss et al. |
| 2007/0004909 | A1 | 1/2007 | Johnson et al. |
| 2007/0036799 | A1 | 2/2007 | Stavenhagen et al. |
| 2007/0077246 | A1 | 4/2007 | Koenig et al. |
| 2007/0135338 | A1 | 6/2007 | O'Neil et al. |
| 2007/0140966 | A1 | 6/2007 | Chang et al. |
| 2007/0244303 | A1 | 10/2007 | Johnson et al. |
| 2007/0253948 | A1 | 11/2007 | Chan et al. |
| 2008/0044417 | A1 | 2/2008 | Johnson et al. |
| 2008/0044429 | A1 | 2/2008 | Johnson et al. |
| 2008/0050371 | A1 | 2/2008 | Johnson et al. |
| 2008/0051563 | A1 | 2/2008 | Lazar et al. |
| 2008/0081346 | A1 | 4/2008 | Moretta et al. |
| 2008/0085277 | A1 | 4/2008 | Cho et al. |
| 2008/0095766 | A1 | 4/2008 | Koenig et al. |
| 2008/0112961 | A1 | 5/2008 | Stavenhagen et al. |
| 2008/0131435 | A1 | 6/2008 | Stavenhagen et al. |
| 2008/0138344 | A1 | 6/2008 | Stavenhagen et al. |
| 2008/0138349 | A1 | 6/2008 | Stavenhagen et al. |
| 2008/0177045 | A1 | 7/2008 | Lee et al. |
| 2008/0286819 | A1 | 11/2008 | Ravetch et al. |
| 2009/0017023 | A1 | 1/2009 | Koenig et al. |
| 2009/0017026 | A1 | 1/2009 | Koenig et al. |
| 2009/0017027 | A1 | 1/2009 | Koenig et al. |
| 2009/0018315 | A1 | 1/2009 | Chen |
| 2009/0022747 | A1 | 1/2009 | Chen |
| 2009/0053218 | A1 | 2/2009 | Koenig et al. |
| 2009/0060910 | A1 | 3/2009 | Johnson et al. |
| 2009/0074771 | A1 | 3/2009 | Koenig et al. |
| 2009/0076251 | A1 | 3/2009 | Koenig et al. |
| 2009/0087416 | A1 | 4/2009 | Chen |
| 2009/0092610 | A1 | 4/2009 | Koenig et al. |
| 2009/0098124 | A1 | 4/2009 | Stavenhagen et al. |
| 2009/0191195 | A1 | 7/2009 | Tuaillon et al. |
| 2009/0202537 | A1 | 8/2009 | Johnson et al. |
| 2009/0252732 | A1 | 10/2009 | Siadak et al. |
| 2010/0015142 | A1 | 1/2010 | Koenig et al. |
| 2010/0086969 | A1 | 4/2010 | Mather et al. |
| 2010/0174053 | A1 | 7/2010 | Johnson et al. |
| 2010/0183605 | A1 | 7/2010 | Mather et al. |
| 2010/0196362 | A1 | 8/2010 | Stavenhagen et al. |
| 2010/0196372 | A1 | 8/2010 | Johnson et al. |
| 2010/0322851 | A1 | 12/2010 | Liang et al. |
| 2010/0322924 | A1 | 12/2010 | Johnson et al. |
| 2011/0045006 | A1 | 2/2011 | Mather et al. |
| 2011/0081347 | A1 | 4/2011 | Gorlatov |
| 2011/0097323 | A1 | 4/2011 | Johnson et al. |

(56) References Cited

U.S. PATENT DOCUMENTS

| | | | |
|---|---|---|---|
| 2011/0117089 A1 | 5/2011 | Johnson et al. | |
| 2011/0152504 A1 | 6/2011 | Johnson et al. | |
| 2011/0243941 A1 | 10/2011 | Stavenhagen et al. | |
| 2011/0305714 A1 | 12/2011 | Stavenhagen et al. | |
| 2012/0009186 A1 | 1/2012 | Koenig et al. | |
| 2012/0034221 A1 | 2/2012 | Bonvini et al. | |
| 2012/0141476 A1 | 6/2012 | Johnson et al. | |
| 2012/0294796 A1* | 11/2012 | Johnson ................ | A61K 45/06 424/1.11 |
| 2014/0099318 A1* | 4/2014 | Huang ............... | C07K 16/2803 424/139.1 |

FOREIGN PATENT DOCUMENTS

| | | |
|---|---|---|
| EP | 0629703 | 12/1994 |
| EP | 0359096 | 11/1997 |
| EP | 0953639 | 11/1999 |
| EP | 1006183 | 6/2000 |
| EP | 0343950 | 10/2000 |
| EP | 1327638 | 7/2003 |
| EP | 1354600 | 10/2003 |
| EP | 1514933 | 3/2005 |
| EP | 1292619 | 2/2008 |
| EP | 1892251 | 2/2008 |
| FR | 2894982 | 6/2007 |
| WO | WO 88/07089 | 9/1988 |
| WO | WO 89/07142 | 8/1989 |
| WO | WO 92/16562 | 10/1992 |
| WO | WO 93/22332 | 11/1993 |
| WO | WO 94/18330 | 8/1994 |
| WO | WO 94/29351 | 12/1994 |
| WO | WO 95/05468 | 2/1995 |
| WO | WO 96/40878 | 12/1996 |
| WO | WO 97/28267 | 8/1997 |
| WO | WO 97/34631 | 9/1997 |
| WO | WO 97/44362 | 11/1997 |
| WO | WO 98/05787 | 2/1998 |
| WO | WO 98/23289 | 6/1998 |
| WO | WO 98/52975 | 11/1998 |
| WO | WO 99/19362 | 4/1999 |
| WO | WO 99/41285 | 8/1999 |
| WO | WO 99/43713 | 9/1999 |
| WO | WO 99/46281 | 9/1999 |
| WO | WO 99/51642 | 10/1999 |
| WO | WO 99/58572 | 11/1999 |
| WO | WO 00/09560 | 2/2000 |
| WO | WO 00/42072 | 7/2000 |
| WO | WO 00/47625 | 8/2000 |
| WO | WO 00/68266 | 11/2000 |
| WO | WO 01/18021 | 3/2001 |
| WO | WO 01/18204 | 3/2001 |
| WO | WO 01/43869 | 6/2001 |
| WO | WO 01/43869 A2 | 6/2001 |
| WO | WO 01/79299 | 10/2001 |
| WO | WO 01/94413 | 12/2001 |
| WO | WO 02/02781 | 1/2002 |
| WO | WO 02/10187 | 2/2002 |
| WO | WO 02/32375 | 4/2002 |
| WO | WO 02/060919 | 8/2002 |
| WO | WO 02/086070 | 10/2002 |
| WO | WO 03/035835 | 5/2003 |
| WO | WO 03/066095 | 8/2003 |
| WO | WO 03/074679 | 9/2003 |
| WO | WO 03/094859 | 11/2003 |
| WO | WO 03/101485 | 12/2003 |
| WO | WO 2004/001381 | 12/2003 |
| WO | WO 2004/016750 | 2/2004 |
| WO | WO 2004/029207 | 4/2004 |
| WO | WO 2004/093894 | 4/2004 |
| WO | WO 2004/063351 | 7/2004 |
| WO | WO 2004/065423 | 8/2004 |
| WO | WO 2004/074455 | 9/2004 |
| WO | WO 2004/099249 | 11/2004 |
| WO | WO 2005/018669 | 3/2005 |
| WO | WO 2005/061547 | 7/2005 |
| WO | WO 2005/070963 | 8/2005 |
| WO | WO 2005/110474 | 11/2005 |
| WO | WO 2005/115452 | 12/2005 |
| WO | WO 2005/121179 | 12/2005 |
| WO | WO 2006/016276 | 2/2006 |
| WO | WO 2006/020114 | 2/2006 |
| WO | WO 2006/028956 | 3/2006 |
| WO | WO 2006/053301 | 5/2006 |
| WO | WO 2006/066078 | 6/2006 |
| WO | WO 2006/076584 | 7/2006 |
| WO | WO 2006/083852 | 8/2006 |
| WO | WO 2006/084075 | 8/2006 |
| WO | WO 2006/084092 | 8/2006 |
| WO | WO 2006/084226 | 8/2006 |
| WO | WO 2006/088494 | 8/2006 |
| WO | WO 2006/110593 | 10/2006 |
| WO | WO 2006/113665 | 10/2006 |
| WO | WO 2007/009064 | 1/2007 |
| WO | WO 2007/009065 | 1/2007 |
| WO | WO 2007/021841 | 2/2007 |
| WO | WO 2007/024249 | 3/2007 |
| WO | WO 2007/080277 | 7/2007 |
| WO | WO 2007/106707 | 9/2007 |
| WO | WO 2007/117600 | 10/2007 |
| WO | WO 2007/147090 | 12/2007 |
| WO | WO 2008/002933 | 1/2008 |
| WO | WO 2008/009545 | 1/2008 |
| WO | WO 2008/019199 | 2/2008 |
| WO | WO 2008/066691 | 6/2008 |
| WO | WO 2008/091908 | 7/2008 |
| WO | WO 2008/105886 | 9/2008 |
| WO | WO 2008/116219 | 9/2008 |
| WO | WO 2008/140603 | 11/2008 |
| WO | WO 2008/157379 | 12/2008 |
| WO | WO 2009/021754 | 2/2009 |
| WO | WO 2009/073533 | 6/2009 |
| WO | WO 2009/083009 | 7/2009 |
| WO | WO 2009/151717 | 9/2009 |
| WO | WO 2009/123894 | 10/2009 |
| WO | WO 2010/027797 | 3/2010 |
| WO | WO 2010/033279 | 3/2010 |
| WO | WO 2010/080538 | 7/2010 |
| WO | WO 2011/044368 | 4/2011 |
| WO | WO 2011/109400 | 9/2011 |
| WO | WO 2012/018687 | 2/2012 |

OTHER PUBLICATIONS

Fan et al., Journal of Hematology & Oncology (2015) 8:130; 14 pages.*

US 6,331,391, 12/2001, Wittrup et al. (withdrawn).

Abra et al. (2002) "*The Next Generation of Liposome Delivery Systems: Recent Experience With Tumor-Targeted, Sterically-Stabilized Immunoliposomes and Active-Loading Gradients*," J Liposome Res. 12(1-2):1-3.

Abrams, J.R. et al. (1999) "*CTLA4Ig-Mediated Blockade of T-Cell Costimulation in Patients With Psoriasis Vulgaris*," J. Clin Invest. 103(9):1243-1252.

Agarwal, A. et al. (2008) "*The Role of Positive Costimulatory Molecules in Transplantation and Tolerance*," Curr. Opin. Organ Transplant. 13:366-372.

Alegre, M.L. et al. (1994) "*A Non-Activating "Humanized" Anti-CD3 Monoclonal Antibody Retains Immunosuppressive Properties In Vivo*," Transplantation 57:1537-1543.

Alison, M.R. et al. (2009) "Stem Cells and Lung Cancer: Future Therapeutic Targets?" Expert Opin. Biol. Ther. 9(9):1127-1141.

Alt et al. (1999) "*Novel Tetravalent and Bispecific IgG-Like Antibody Molecules Combining Single-Chain Diabodies With the Immunoglobin Gamma 1 Fc or CH3 Region*," FEBS Letters 454:90-94.

Altman et al. (1996) "*Phenotypic Analysis of Antigen-Specific T Lymphocytes*," Science 274:94-96.

Amit et al. (1986) "*Three-Dimensional Structure of an Antigen-Antibody Complex at 2.8 A Resolution*," Science 233:747-753.

Angal et al. (1993) "*A Single Amino Acid Substitution Abolishes the Heterogeneity of Chimeric Mouse/Human (Igg4) Antibody*," Mol. Immunol. 30:105-108.

(56) References Cited

OTHER PUBLICATIONS

Anonymous, (2000) "*New Products for Molecular Biotechnology*," Molec. Biol. 16:293-294.
Armour et al. (2003) "*Differential Binding to Human Fcgammariia and FcgammaRIIB Receptors by Human IgG Wildtype and Mutant Antibodies*," Mol. Immunol 40:585-593.
Armour et al. (1999) "*Recombinant Human IgG Molecules Lacking Fcgamma Receptor I Binding and Monocyte Triggering Activities*," Eur. J. Immunol 29:2613-2624.
Armour et al. (2002) "*The Contrasting IgG-Binding Interactions of Human and Herpes Simplex Virus Fc Receptors*," Biochemical Society Transactions 30:495-500.
Armstrong, K.M. et al. (2008) "*Conformational Changes and Flexibility in T-Cell Receptor Recognition of Peptide—MHC Complexes*," Biochem. J. 415(Pt 2):183-196.
Armstrong, S.S. et al. (1987) "*Heterogeneityy of IgG1 Monoclonal Anti-Rh(D): An Investigation Using ADCC and Macrophage Binding Assays* ," Br. J. Haematol. 66:257-262.
Aruffo, A. et al. (1987) "*Molecular Cloning of a CD28 cDNA by a High-Efficiency COS Cell Expression System*," Proc. Natl. Acad. Sci. (U.S.A.) 84:8573-8577.
Asano, R. et al. (2004) "*A Diabody for Cancer Immunotherapy and Its Functional Enhancement by Fusion of Human Fc Region*," Abstract 3P-683, J. Biochem. 76(8):992.
Asano, R. et al. (2012) "*Construction and Humanization of a Functional Bispecific EGFR CD16 Diabody Using a Refolding System*," FEBS Journal 279:223-233.
Atwell et al. (1997) "*Stable Heterodimers From Remodeling the Domain Interface of a Homodimer Using a Phage Display Library*," J. Mol. Biol. 270:26-35.
Bachmann et al. (2005) "*Recall Proliferation of Memory CD8+ T Cells and Antiviral Protection*," J. Immunol. 175:4677-4685.
Baeuerle, P.A. et al. (2009) "*Bispecific T-Cell Engaging Antibodies for Cancer Therapy*," Cancer Res. 69(12):4941-4944.
Baeuerle, P. et al. (2008) "*BiTE: A New Class of Antibodies That Recruit T Cells*," Drugs of the Future 33: 137-147.
Baggiolini, M. et al. (1988) "*Cellular Models for the Detection and Evaluation of Drugs That Modulate Human Phagocyte Activity*," Experientia Oct. 15;44(10):841-848.
Bargou et al. (2008) "*Tumor Regression in Cancer Patients by Very Low Doses of a T Cell-Engaging Antibody*," Science 321:974-977.
Bedzyk et al. (1989) "*Comparison of Variable Region Primary Structures Within an Anti-Fluorescein Idiotype Family*," J. Biol. Chem, 264(3):1565-1569.
Beier, K.C. et al. (2007) "*Master Switches of T-Cell Activation and Differentiation*," Eur. Respir. J. 29:804-812.
Bendas, G. (2001) "*Immunoliposomes: A Promising Approach to Targeting Cancer Therapy*," BioDrugs. 15(4):215-224.
Bendig, M.M. (1995) "*Humanization of Rodent Monoclonal Antibodies*," Methods: A Companion to Methods in Enzymology 8:83-93.
Bernard et al. (1986) "*A Unique Epitope on the CD2 Molecule Defined by the Monoclonal Antibody 9-1: Epitope-Specific Modulation of the E-Rosette Receptor and Effects on T-Cell Functions*," Hum. Immunol. 17(4):388-405.
Bernard, A. et al. (2005) "*T and B Cell Cooperation: A Dance of Life and Death*," Transplantation 79:S8-S11.
Berntzen, G. et al. (2009) "*Identification of a High Affinity FcRIIA-binding Peptide That Distinguishes FcRIIA from FcRIIB and Exploits FcgammaRIIA-mediated Phagocytosis and Degradation*," J. Biol. Chem. 284(2):1126-1135.
Bertram, E.M. et al. (2004) "*Role of T cell Costimulation in anti-viral immunity*," Semin. Immunol. 16:185-198.
Bewarder et al., 1996, "*In Vivo and In Vitro Specificity of Protein Tyrosine Kinases for Immunoglobulin G Receptor (FcgammaRII) Phosphorylation*," Mol. Cell. Biol. 16(9):4735-43.
Billadeau et al. (2002) "*ITAMs Versus ITIMs: Striking a Balance During Cell Regulation*," J. Clin. Invest. 109(2):161-168.
Bird et al. (1988) "*Single-Chain Antigen-Binding Proteins*," Science 242:423-426.
Blazar, B.R. et al. (1999) "*Opposing Roles of CD28:B7 and CTLA-4:B7 Pathways in Regulating In Vivo Alloresponses in Murine Recipients of MHC Disparate T Cells*," J. Immunol. 162(11):6368-6377.
Boder et al. (1997) "*Yeast Surface Display for Screening Combinatorial Polypeptide Libraries*", Nature Biotechnology 15:553-557.
Boder et al. (1998) "*Optimal Screening of Surface-Displayed Polypeptide Libraries*," Biotechnol. Prog. 14:55-62.
Boder et al. (2000), "*Yeast Surface Display for Directed Evolution of Protein Expression, Affinity, and Stability*," Methods in Enzymology 328:430-444.
Boder et al. (2000), "*Directed Evolution of Antibody Fragments With Monovalent Femtomolar Antigen-Binding Affinity*," Proc. Natl. Acad. Sci. U.S.A. 97:10701-10705.
Bolland et al. (1999) "*Inhibitory pathways triggered by ITIM-containing receptors*," Adv. Immunol. 72:149-177.
Bolland et al. (2002) "*Genetic Modifiers of Systemic Lupus Erythematosus in Fc.gamma.RIIB(-/-) Mice*," J. Exp. Med. 195(9):1167-1174.
Boruchov et al. (2003) "*Expression and Modulation of the Inhibitory Fcγ Receptor, FcγRIIB (CD32B), on Human Dendritic Cells (DCs)*," Blood 102(11):Abstract #1908.
Boruchov et al. (2005) "*Activating and Inhibitory IgG Fc Receptors on Human DCs Mediate Opposing Functions*," J. Clin. Invest. 115(10):2914-2923.
Boyer et al. (1999)"*Relative Cytotoxic Activity of Immunotoxins Reactive With Different Epitopes on the Extracellular Domain of the c-erbB-2 (HER-2/neu) Gene Product p. 185*," Int. J. Cancer. 82(4):525-531.
Brauweiler et al. (2001) "*Partially Distinct Molecular Mechanisms Mediate Inhibitory Fc.gamma.RIIB Signaling in Resting and Activated B Cells*," J. Immunol. 167:204-211.
Bredius et al. (1994) "*Role of Neutrophil Fc gamma RIIa (CD32) and Fc gamma RIIIb (CD16) Polymorphic Forms in Phagocytosis of Human IgG1- and IgG3-Opsonized Bacteria and Erythrocytes*," Immunology 83:624-630.
Brekke et al. (1994) "*Human IgG isotype-specific amino acid residues affecting complement-mediated cell lysis and phagocytosis*," Eur. J. Immunol. 24:2542-2547.
Brown et al. (1987) "*Tumor-Specific Genetically Engineered Murine/Human Chimeric Monoclonal Antibody*," Cancer Res. 47:3577-3583.
Brown, E.J. (1994) "*In Vitro Assays of Phagocytic Function of Human Peripheral Blood Leukocytes: Receptor Modulation and Signal Transduction*," vol. 45 (Microbes as Tools for Cell Biology) in *Methods in Cell Biololgy*, Russell ed., Academic Press Inc., NY, pp. 147-164.
Brown M. et al. (1996) "*Tolerance to single, but not multiple, amino acid replacements in antibody VH CDR 2: a means of minimizing B cell wastage from somatic hypermutation?*" The Journal of Immunology 156(9): 3285-3291.
Brown (2001) "*Factors Modifying the Migration of Lymphocytes Across the Blood-Brain Barrier*," Int. Immunopharmacol. 1(12):2043-2062.
Brunet, J.F. et al. (1987) "*A New Member of the Immunoglobulin Superfamily-CTLA-4*," Nature 328:267-270.
Budde et al. (1995) "*Specificity of CD32 mAB for Fc.gamma.RIIa, Fc.gamma.RIIb1, and Fc.gamma.RIIb2 Expressed in Transfected Mouse B cells and BHK-21 Cells*," Leukocyte Typing V: White cell differentiation antigens. pp. 828-832 (Schlossman, et al., eds.).
Burgess et al. (1990) "*Possible Dissociation of the Heparin-Binding and Mitogenic Activities of the Heparin-Binding (Acidic Fibroblast) Growth Factor-1 From Its Receptor Binding Activities by Site Directed Mutagenesis of a Single Lysine Residue*," J. Cell Biol. 111:2129-2138.
Burmeister et al. (1994) "*Crystal Structure of the Complex of Rat Neonatal Fc Receptor With Fc*," Nature 372:379-383.
Burton (1985) "*Immunoglobulin G: Functional Sites*," Mol Immunol 22:161-206.
Burton et al. (1988) "*Molecular Recognition of Antibody (IgG) by Cellular Fc Receptor (FcRI)*," Mol. Immunol. 25:1175-1181.

(56) References Cited

OTHER PUBLICATIONS

Burton et al. (1992) "*Human Antibody Effector Function*," Advances in Immunology 51:1-84.
Callanan et al. (2000) "*The IgG Fc Receptor, Fc.Gamma.RIIB is a Target for Deregulation by Chromosomal Translocation in Malignant Lymphoma*," Proc. Natl. Acad. Sci. (U.S.A.) 97(1):309-314.
Cameron et al. (2002) "*Differentiation of the Human Monocyte Cell Line, U937, With Dibutyryl Cyclicamp Induces the Expression of the Inhibitory Fc Receptor, Fc.gamma.RIIb*," Immunol. Lett. 83(3):171-179.
Camilleri-Broet et al. (2004) "*Fc.gamma.RIIB is Differentially Expressed During B Cell Maturation and in B-Cell Lymphomas*," Br. J. Haematol. 124(1):55-62.
Campbell et al. (2003) "*Monoclonal Antibody Therapy for Lymphoma*," Blood Rev. 17(3):143-152.
Canfield et al. (1991) "*The Binding Affinity of Human IgG for Its High Affinity Fc Receptor is Determined by Multiple Amino Acids in the CH2 Domain and is Modulated by the Hinge Region*," J. Exp. Med. 173:1483-1491.
Caron et al. (1992) "*Engineered Humanized Dimeric Forms of IgG Are More Effective Antibodies*," J. Exp. Med. 176:1191-1195.
Carter et al. (1992) "*Humanization of an Anti-p185HER2 Antibody for Human Cancer Therapy*," Proc. Natl. Acad. Sci. U.S.A. 89:4285-4289.
Cartron et al. (2002) "*Therapeutic Activity of Humanized Anti-CD20 Monoclonal Antibody and Polymorphism in IgG Fc Receptor FcgammaRIIIa Gene*," Blood 99:754-758.
Cassard et al. (2002) "*Modulation of Tumor Growth by Inhibitory Fc.Gamma. Receptor Expressed by Human Melanoma Cells*," J. Clin. Invest. 110(10):1549-1557.
Casset et al. (2003) "*A Peptide Mimetic of an Anti-CD4 Monoclonal Antibody by Rational Design*," Biochem. Biophs. Res. Commun. 307:198-205.
Castriconi et al. (2004) "*Identification of 4Ig-B7-H3 as a Neuroblastoma-Associated Molecule That Exerts a Protective Role From an NK Cell-Mediated Lysis*," Proc. Natl. Acad. Sci. (U.S.A.) 101(34):12640-12645.
Cavacini et al. (1995) "*Influence of Heavy Chain Constant Regions on Antigen Binding and HIV-1 Neutralization by a Human Monoclonal Antibody*," J. Immunol. 155(7):3638-3644.
Chapoval, A. et al. (2001) "*B7-H3: A Costimulatory Molecule for T Cell Activation and IFN-γ Production*," Nature Immunol. 2:269-274.
Chapoval, A. et al. (2003) "*B7-H3*," In: The B7-CD28 Family Molecules, Kluwer Academic, NY; pp. 91-99.
Chappel et al. (1991) "*Identification of the Fc Gamma Receptor Class I Binding Site in Human IgG Through the Use of Recombinant IgG1/IgG2 Hybrid and Point-Mutated Antibodies*," Proc. Natl. Acad. Sci U.S.A. 88:9036-9040, 1991.
Chappel et al. (1993) "*Identification of a Secondary Fc Gamma RI Binding Site Within a Genetically Engineered Human IgG Antibody*," J. Biol. Chem 268:25124-25131.
Charafe-Jauffret, E. et al. (2009) "*Breast Cancer Stem Cells: Tools and Models to Rely on*," BMC Cancer 9:202 (10 pages).
Chattergee et al. (1994) "*Idiotypic Antibody Immunotherapy of Cancer*," Cancer Immunol. Immunother. 38:75-82.
Chen, et al. (1999) "Selection and Analysis of an Optimized Anti-VEGF Antibody: Crystal Structure of an Affinity-Matured Fab in Complex with Antigen," J. Molec. Biol. 293:865-881.
Chen et al. (2000) "*Surface Antigen Expression and Complement Susceptibility of Differentiated Neuroblastoma Clones*," Amer. J. Pathol. 156(3):1085-1091.
Chen et al. (2008) "*The Immunoregulatory Protein Human B7H3 is a Tumor-Associated Antigen that Regulates Tumor Cell Migration and Invasion*," Curr. Cancer Drug Targets 8:404-413.
Chen et al. (2011) "*Cloning and Characterization of Porcine 4Ig-B7-H3: A Potent Inhibitor of Porcine T-Cell Activation*," PLOS ONE 6(6):E21341.
Cheung, N.K. et al. (1990) "*Immunology and Targeted Immunotherapy of Human Neuroblastoma*," In: Neuroblastoma: Tumor Biology and Therapy, CRC Press, Boca Raton; pp. 52-68.
Cheung, N.K. et al. (2000) "*Immunotherapy of Neuroblastoma*," In: Neuroblastoma, Elsevier, NY (10 pages).
Cheung, N.K. et al. (2002) "*Oral* (1→3), (1→4)-*beta-D-Glucan Synergizes with Antiganglioside GD2 Monoclonal Antibody 3F8 in the Therapy of Neuroblastoma*," Clin. Canc. Res. 8:1217-1223.
Chu, P. G. et al. (2001) "*CD79: A Review*," Appl. Immunohistochem. Molec. Morphol. 9(2):97-106.
Ciccimarra et al. (1975) "*Localization of the IgG Effector Site for Monocyte Receptors*," Proc. Natl. Acad. Sci. U.S.A. 72 :2081-2083, 1975.
Clynes et al. (1995) "*Cytotoxic Antibodies Trigger Inflammation Through Fc Receptors*," Immunity 3:21-26.
Clynes et al. (1998) "Fc receptors are required in passive and active immunity to melanoma," Proc. Natl. Acad. Sci U.S.A. 95:652-656.
Clynes et al. (1998) "*Uncoupling of Immune Complex Formation and Kidney Damage in Autoimmune Glomerulonephritis*," Science 279:1052-1054.
Clynes et al. (1999) "*Modulation of Immune Complex-Induced Inflammation In Vivo by the Coordinate Expression of Activation and Inhibitory Fc Receptors*," J. Exp. Med. 189:179-185.
Clynes et al. (2000) "*Inhibitory Fc Receptors Modulate In Vivo Cytoxicity Against Tumor Targets*," Nature Medicine 6:443-446.
Co, M. S. et al. (1991) "*Humanized Antibodies for Antiviral Therapy*," Proc. Natl. Acad. Sci. (U.S.A.) 88:2869-2873.
Co, M.S. et al. (1992) "*Chimeric and Humanized Antibodies With Specificity for the CD33 Antigen*," J. Immunol. 148:1149-1154.
Collins, M. et al. (2005) "*The B7 Family of Immune-Regulatory Ligands*," Genome Biol. 6:223.1-223.7.
Colman, P.M. (1994) "*Effects of Amino Acid Sequence Changes on Antibody-Antigen Interactions*," Res. Immunol. 145:33-36.
Coyle, A.J. et al. (2001) "*The Expanding B7 Superfamily: Increasing Complexity in Costimulatory Signals Regulating T Cell Function*," Nature Immunol. 2(3):203-209.
Crispen, P.L. et al. (2008) "*Tumor Cell and Tumor Vasculature Expression of B7-H3 Predict Survival in Clear Cell Renal Cell Carcinoma*," Clin Cancer Res. 14(16):5150-5157 Epub Aug. 11, 2008.
Daeron et al. (1995) "*The Same Tyrosine Based Inhibition Motif, in the Intracytoplasmic Domain of Fc.gamma.RIIB, Regulates Negatively BCR, TCR- and FcR Dependent Cell Activation*," Immunity 3:635-646.
Daeron, M. (1997) "*Fc Receptor Biology*," Annu. Rev. Immunol. 15:203-234.
Damle et al. (2002) "*B-Cell Chronic Lymphocytic Leukemia Cells Express a Surface Membrane Phenotype of Activated, Antigen-Experienced B Lymphocytes*," Blood 99(11):4087-4093.
Daugherty et al. (1991) "*Polymerase Chain Reaction Facilitates the Cloning, CDR-Grafting, and Rapid Expression of a Murine Monoclonal Antibody Directed Against the CD18 Component of Leukocyte Integrins*," Nucl. Acids Res. 19:2471-2476.
Davies et al. (1995) "*Antibody VH Domains as Small Recognition Units*," Bio/Technology 13:475-479.
Davies J. et al. (1996) "*Affinity Improvement of Single Antibody VH Domains: Residues in All Three Hypervariable Regions Affect Antigen Binding*," Immunotechnology 2(3):169-179.
Davies et al. (2001) "*Expression of GnTIII in a Recombinant Anti-CD20 CHO Production Cell Line: Expression of Antibodies With Altered Glycoforms Leads to an Increase in ADCC Through Higher Affinity for FCgamma. RIII*," Biotechnol. Bioeng. 74(4):288-294.
de Haas et al. (2001) "*IgG-Fc Receptors and the Clinical Relevance of Their Polymorphisms*," Wien Klin Wochenscha 113:825-831.
De Santes et al. (1992) "*Radiolabeled Antibody Targeting of the Her-2/neu Oncoprotein*," Cancer Res. 52:1916-1923.
Deisenhofer (1981) "*Crystallographic Refinement and Atomic Models of a Human Fc Fragment and Its Complex With Fragment B of Protein A from Staphylococcus aureus at 2.9- and 2.8-A Resolution*," Biochem. 20:2361-2370.

(56) References Cited

OTHER PUBLICATIONS

Deo et al. (1997) "*Clinical Significance of IgG Fc Receptors and Fc gamma R-Directed Immunotherapies*," Immunology Today 18:127-135.
DePascalis et al. (2002) "*Grafting of Abbreviated Complementarity Determining Regions Containing Specificity Determining Residues Essential for Ligand Contact to Engineer a Less Immunogenic humanized monoclonal antibody*," J. Immunol. 169:3076-3084.
Dermer (1994) "*Another Anniversary for the War on Cancer*," Biotechnology 12:320 (1 page).
Ding et al. (2001) "*Inhibition of the Function of the Fc.gamma.RIIB by a Monoclonal Antibody to Thymic Shared Antigen-1, a Ly-6 Family Antigen*," Immunology 104(1):28-36.
Dong, H. et al. (1999) "*B7-H1, a Third Member of the B7 Family, Co-Stimulates T-Cell Proliferation and Interleukin-10 Secretion*," Nature Med. 5(12):1365-1369.
Dong, C. et al. (2003) "*Immune Regulation by Novel Costimulatory Molecules*," Immunolog. Res. 28(1):39-48.
Dumoulin et al. (2002) "*Single-Domain Antibody Fragments With High Conformational Stability*," Protein Science 11:500-512.
Duncan et al. (1988) "*Localization of the Binding Site for the Human High-Affinity Fc Receptor on IgG*," Nature 332:563-564.
Duncan et al. (1988) "*The Binding Site for C1q on IgG*," Nature 332:738-740.
Edberg et al. (1994) "*Modulation of Fcgamma and Complement Receptor Function by the Glycosyl-Phosphatidylinositol-Anchored Form of FcgammaRIII*," J. Immunol. 152: 5826-5835.
Efferson et al. (2005) "*Stimulation of Human T Cells by an Influenza A Vector Expressing a CTL Epitope from the HER-2/neu Protooncogene Results in Higher Numbers of Antigen Specific TCRhi Cells than Stimulation with Peptide*," Anticancer Research 25:715-724.
Elkabetz et al. (2005) "*Cysteines in CH1 Underlie Retention of Unassembled Ig Heavy Chains*," J. Biol. Chem. 280:14402-14412.
Ellman, J. et al. (1991) "*Biosynthetic Method for Introducing Unnatural Amino Acids Site-Specifically into Proteins*," Methods Enzymol. 202:301-336.
Emamaullee, J. et al. (2009) "*Costimulatory Blockade With Belatacept in Clinical and Experimental Transplantation—A Review*," Expert Opin Biol Ther. 9(6):789-796.
Eppstein et al. (1985) "*Biological Activity of Liposome-Encapsulated Murine Interferon .Gamma. is Mediated by a Cell Membrane Receptor*," Proc. Natl. Acad. Sci. (U.S.A.) 82(11):3688-3689.
Fanger et al. (1994) "*Production and Use of Anti-FcR Bispecific Antibodies*," Immunomethods. 4(1):72-81.
Farag, et al. (2003) "*Fc.gamma.RIIIa and Fc.gamma.RIIIa Polymorphisms Do Not Predict Response to Rituximab in B-Cell Chronic Lymphocytic Leukemia*," Blood. [Published Online] (15 pp.).
Fidler, I. J. (1985) "*Macrophages and Metastasis—A Biological Approach to Cancer Therapy*," Cancer Res. 45(10):4714-4726.
Fieger, C.B. et al. (2008) "*The Anti-B7-H3-41g Antibody TES7 Recognizes Cancer Stem Cell Lines, Modulates Angiogenic Factor Secretion, and Exhibits Potent Anti-Tumor Activity in vivo*," Proc. Amer. Assoc. Cancer Res. Annual Meeting (99$^{th}$ Annual Meeting of the American Association for Cancer Research; San Diego, CA, USA (Apr. 12-16, 2008) 49:606, Abstract 2555 (1 page).
FitzGerald, et al. (1997) "*Improved Tumour Targeting by Disulphide Stabilized Diabodies Expressed in Pichia pastoris*," Protein Engineering 10(10): 1221-1225.
Fleit et al. (1995) "*Cross-Linking of mAb to FC.gamma.RII Results in Tyrosine Phosphorylation of Multiple Polypeptides Including FC.gamma.RII Itself*" Leukocyte Typing V: White cell differentiation antigens 826-827 (Schlossman, Boumsell, Gilks, Harlan, Kishomoto, eds.).
Flesch et al. (2000) "*Functions of the Fc Receptors for Immunoglobulin G*," J. Clin. Lab. Anal. 14:141-156.
Flies, D.B. et al. (2007) "*The New B7s: Playing a Pivotal Role in Tumor Immunity*," J. Immunother. 30(3):251-260.
Fukushima, A. et al. (2007) "*B7—H3 Regulates the Development of Experimental Allergic Conjunctivitis in Mice*," Immunol Lett. 113:52-57.
Gamberale et al. (2003) "*To the Editor: Expression of Fc.gamma. receptors type II (Fc.gamma.RII) in chronic lymphocytic leukemia B cells*," Blood (Correspondence) 102(7):2698-2699.
Ganesan, A. (2006) "*Solid-Phase Synthesis in the Twenty-First Century*," Mini Rev. Med. Chem. 6(1):3-10.
Gerber et al. (2001) "*Stimulatory and Inhibitory Signals Originating From the Macrophage Fc.Gamma. Receptors*," Microbes Infect. 3(2):131-139.
Gergely et al. (1984) "*Fc Receptors on Lymphocytes and K Cells*," Biochem. Soc. Trans. 12:739-743.
Gergely et al. (1990) "*The Two Binding-Site Models of Human IgG Binding Fc Gamma Receptors*," FASEB J. 4:3275-3283.
Ghotra, V.P. et al. (2009) "*The Cancer Stem Cell Microenvironment and Anti-Cancer Therapy*," Int. J. Radiat. Biol. 85(11):955-962.
Giusti, A. M. et al. (1987) "*Somatic Diversification of S107 from an Antiphosphocholine to an anti-DNA Autoantibody is Due to a Single Base Change in its Heavy Chain Variable Region*," Proc. Natl. Acad. Sci. (U.S.A.) 84:2926-2930.
Gorman, S. D. et al. (1991) "*Reshaping a Therapeutic CD4 Antibody*," Proc. Natl. Acad. Sci. (U.S.A.) 88:4181-4185.
Greenwald, R.J. et al. (2005) "*The B7 Family Revisited*," Ann. Rev. Immunol. 23:515-548.
Greenwood et al. (1993) "*Effector Functions of Matched Sets of Recombinant Human IgG Subclass Antibodies*" (final version edited Feb. 11, 1993) pp. 1-23.
Greenwood et al.(1993) "*Structural Motifs Involved in Human IgG Antibody Effector Functions*," Eur. J. Immunol. 23:1098-1104.
Greenwood et al. (1994) "*Engineering Multiple-Domain Forms of the Therapeutic Antibody CAMPATH-1H: Effects on Complement Lysis*," Therapeutic Immunology 1:247-255.
Gruber, M. et al. (1994) "*Efficient Tumor Cell Lysis Mediated by a Bispecific Single Chain Antibody Expressed in Escherichia coli*," J. Immunol. 152(11): 5368-5374.
Gupta, P.B. et al. (2009) "*Cancer Stem Cells: Mirage or Reality?*" Nat. Med. 15(9):1010-1012.
Gura (1997) "*Systems for Identifying New Drugs Are Often Faulty*," Science 278:1041-1042.
Guy, C.S. et al. (2009) "*Organization of Proximal Signal Initiation at the TCR: CD3 Complex*," Immunol Rev. 232(1):7-21.
Hadley et al. (1992) "*The Functional Activity of Fc Gamma RII and Fc Gamma RIII on Subsets of Human Lymphocytes*," Immunology 76:446-451.
Hashiguchi, M. et al. (2008) "*Triggering Receptor Expressed on Myeloid Cell-Like Transcript 2 (TLT-2) is a Counter-Receptor for B7—H3 and Enhances T Cell Responses*," Proc. Natl. Acad. Sci. (U.S.A.) 105(30):10495-10500.
Hatta et al. (1999) "*Association of Fc Gamma Receptor IIIB, but Not of Fc Gamma Receptor IIA and IIIA Polymorphisms With Systemic Lupus Erythematosus in Japanese*," Genes Immunity 1:53-60.
Hayes, Fc (2003) "*Engineering to Enhance Monoclonal Antibody Effector Functions*," (Xencor Presentation).
Henry et al. (2004) "*A Prostate-Specific Membrane Antigen-Targeted Monoclonal Antibody-Chemotherapeutic Conjugate Designed for the Treatment of Prostate Cancer*," Cancer Res. 64(21):7995-8001.
Henry, J. et al. (1999) "*Structure and Evolution of the Extended B7 Family*," Immunol Today. 20(6):285-288.
Hermann, P.C. et al. (2009) "*Pancreatic Cancer Stem Cells—Insights and Perspectives*," Expert Opin. Biol. Ther. 9(10):1271-1278.
Herzenberg et al. (2002) "*The History and Future of the Fluorescence Activated Cell Sorter and Flow Cytometry: A View From Stanford*," Clin. Chem. 48:1819-1827.
Heyman (2000) "*Regulation of Antibody Responses Via Antibodies, Complement, and Fc Receptors*," Annu. Rev. Immunol. 18:709-737.
Hofmeyer, K. et al. (2008) "*The Contrasting Role of B7—H3*," Proc. Natl. Acad. Sci. (U.S.A.) 105(30):10277-10278.
Hogarth et al. (1994) "*Characterization of Fcr Ig-Binding Sites and Epitope Mapping*," Immunomethods 4:17-24.

(56) References Cited

OTHER PUBLICATIONS

Holler et al. (2000) "*In Vitro Evolution of a T Cell Receptor With High Affinity for Peptide/MHC*," Proc. Natl. Acad. Sci. (U.S.A.) 97:5387-5392.
Holliger, P. (1993) "*Diabodies: Small Bivalent and Bispecific Antibody Fragments*," Proc. Natl. Acad. Sci. (U.S.A.) 90(14):6444-6448.
Holliger et al. (2005) "*Engineered Antibody Fragments and the Rise of Single Domains*," Nature Biotechnol. 23(9):1126-1135.
Holm et al. (2007) "*Functional Mapping and Single Chain Construction of the Anti-Cytokeratin 8 Monoclonal Antibody TS1*," Molecular Immunology 44:1075-1084.
Holmes et al. (1985) "*Alleles of the Ly-17 Alloantigen Define Polymorphisms of the Murine IgG Fc Receptor*," Proc. Natl. Acad. Sci. (U.S.A.) 82(22):7706-7710.
Holt, L.J. (2003) "*Domain Antibodies: Proteins for Therapy*," TRENDS in Biochem. 21(11):484-490.
Houghten, R.A. (1985) "*General Method for the Rapid Solid-Phase Synthesis of Large Numbers of Peptides: Specificity of Antigen-Antibody Interaction at the Level of Individual Amino Acids*," Proc. Natl. Acad. Sci. (U.S.A.) 82(15):5131-5135.
Houghton, A.N. et al. (2000) "*Monoclonal Antibody Therapies—A 'Constant' Threat to Cancer*," Nature Medicine 6(4):373-374.
Hulett et al. (1991) "*Chimeric Fc Receptors Identify Functional Domains of the Murine High Affinity Receptor for IgG*," J. Immunol. 147:1863-1868.
Hulett et al. (1994) "*Identification of the IgG Binding Site of the Human Low Affinity Receptor for IgG Fc Gamma RII. Enhancement and Ablation of Binding by Site-Directed Mutagenesis*," J. Biol. Chem. 269:15287-15293.
Hulett et al. (1995) "*Multiple Regions of Human Fc Gamma RII (CD32) Contribute to the Binding of IgG*," J. Biol. Chem. 270:21188-21194.
Hutchins et al. (1995) "*Improved Biodistribution, Tumor Targeting, and Reduced Immunogenicity in Mice With a Gamma 4 Variant of Campath-1H*," Proc. Natl. Acad. Sci. (U.S.A.) 92:11980-11984.
Hwang et al. (1980) "*Hepatic Uptake and Degradation of Unilamellar Sphingomyelin/Cholesterol Liposomes: A Kinetic Study*," Proc. Natl. Acad. Sci. (U.S.A.) 77(7):4030-4034.
Ibragimova et al. (1999) "*Stability of the Beta-Sheet of the WW Domain: A Molecular Dynamics Simulation Study*," Biophys. J. 77(4):2191-2198.
Idusogie et al. (2000) "*Mapping of the C1q Binding Site on Rituxan, a Chimeric Antibody With a Human IgG1 Fc*," J Immunol 164: 4178-4184.
Idusogie et al. (2001) "*Engineered Antibodies With Increased Activity to Recruit Complement*," J. Immunol. 166:2571-2575.
Indik, Z.K. et al. (1995) "*The Molecular Dissection of Fcgamma Receptor Mediated Phagocytosis*," Blood 86(12):4389-4399.
Isaacs et al. (1996) "*A Therapeutic Human IgG4 Monoclonal Antibody That Depletes Target Cells in Humans*," Clin. Exp. Immunol. 106:427-433.
Isaacs et al. (1992) "*Therapy With Monoclonal Antibodies. An In Vivo Model for the Assessment of Therapeutic Potential*," J. Immunol. 148:3062-3071.
Isaacs et al. (1998) "*Therapy With Monoclonal Antibodies. II. The Contribution of Fc Gamma Receptor Binding and the Influence of C(H)1 and C(H)3 Domains on In Vivo Effector Function*," J. Immunol. 161:3862-3869.
Jain et al. (1994) "Barriers to Drug Delivery in Solid Tumors," Scientific American Jul. 1994:58-65.
Jassal et al. (1998) "*Remodeling Glycans on IgG by Genetic Re-Engineering*," Biochem. Soc. Trans. 26:S113.
Jefferis et al. (1990) "*Molecular Definition of Interaction Sites on Human IgG for Fc Receptors (huFc Gamma R)*," Mol. Immunol. 27:1237-1240.
Jefferis et al. (1995) "*Recognition Sites on Human IgG for Fc Gamma Receptors: The Role of Glycosylation*," Immunol. Lett. 44:111-117.
Jefferis, R. et al. (1996) "Modulation of Fc(Gamma)R and Human Complement Activation by IgG3-Core Oligosaccharide Interactions," Immunol. Lett. 54:101-104.
Jefferis et al. (1998) "*IgG-Fc-Mediated Effector Functions: Molecular Definition of Interaction Sites for Effector Ligands and the Role of Glycosylation*," Immunol. Rev. 163:59-76.
Jefferis et al. (2002) "*Interaction Sites on Human IgG-Fc for FcgammaR: Current Models*," Immunology Letters 82 :57-65.
Jendeberg et al. (1997) "*Engineering of Fc(1) and Fc(3) From Human Immunoglobulin G to Analyse Subclass Specificity for Staphylococcal Protein A*," J. Immunol. Meth. 201:25-34.
Jiang et al. (2004) "*A Novel Peptide Isolated From a Phage Display Peptide Library With Trastuzumab Can Mimic Antigen Epitope of HER-2*," J. Biol. Chem. 280(6):4656-4662.
Johnson et al. (2010) "*Effector Cell Recruitment with Novel Fv-based Dual-affinity Re-targeting Protein Leads to Potent Tumor Cytolysis and in Vivo B-cell Depletion*," J. Mol. Biol (399):436-449.
Jones et al. (1986) "*Replacing the Complementarity-Determining Regions in a Human Antibody With Those From a Mouse*," Nature 321:522-525.
Kadar et al. (1991) "*Modulatory Effect of Synthetic Human IgG Fc Peptides on the In Vitro Immune Response of Murine Spleen Cells*," Int. J. Immunpharmacol. 13:1147-55.
Kadar et al. (1992) "*Synthetic Peptides Comprising Defined Sequences of CH-2 and CH-3 Domains of Human IgG1 Induce Prostaglandin E2 Production From Human Peripheral Blood Mononuclear Cells*," Immunol Lett 32:59-63.
Kagari et al. (2003) "*Essential Role of Fc.Gamma. Receptors in Anti-Type II Collagen Antibody Induced Arthritis*," J. Immunol. 170:4318-24.
Kalergis, A.M. et al. (2002) "*Inducing Tumor Immunity through the Selective Engagement of Activating Fcgamma Receptors on Dendritic Cells*," J. Exper. Med. 195(12):1653-1659.
Kang, C.Y. et al. (1988) "*Inhibition of Self-Binding Antibodies (Autobodies) by a VH-Derived Peptide*," Science 240(4855):1034-1036.
Kato et al. (2000) "*Structural Basis of the Interaction Between IgG and Fcγ Receptors*," J. Molec. Biol. 295:213-224.
Keler et al. (2000) "*Differential Effect of Cytokine Treatment on Fc Alpha Receptor I- and Fc Gamma Receptor I-Mediated Tumor Cytotoxicity by Monocyte-Derived Macrophages*," J. Immunol. 164:5746-5752.
Kelsey, J.L. et al. (1998) "*Epidemiologic Studies of Risk Factors for Cancer in Pet Dogs*," Epidemiologic Reviews 20(2):204-217.
Kepley et al. (2004) "*Co-aggregation of FcgammaRII with FcepsilonRI on Human Mast Cells Inhibits Antigeninduced Secretion and Involves SHIP-Grb2-Dok Complexes*" J. Biol. Chem. 279(34) 35139-35149.
Kettleborough, C. A. et al. (1991) "*Humanization of a Mouse Monoclonal Antibody by CDR-Grafting: The Importance of Framework Residues on Loop Conformation*," Protein Engineering 4:773-3783.
Khawli, L.A. et al. (2008) "*Cytokine, Chemokine, and Co-Stimulatory Fusion Proteins for the Immunotherapy of Solid Tumors*," Exper. Pharmacol. 181:291-328.
Kieke et al. (1999) "*Selection of Functional T Cell Receptor Mutants From a Yeast Surface-Display Library*," Proc. Natl. Acad. Sci. (U.S.A.) 96:5651-5656.
Kiick et al. (2001) "*Identification of an Expanded Set of Translationally Active Methionine Analogues in Escherichia*," FEBS Lett. 502(1-2):25-30.
Kim et al. (2001) "*Analysis of FcγRIII and IgG Fc Polymorphism Reveals Functional and Evolutionary Implications of Protein-Protein Interaction*," J. Molec. Evol. 53:1-9.
Kim et al. (2002) "*Both the Epitope Specificity and Isotype Are Important in the Antitumor Effect of Monoclonal Antibodies Against Her-2/Neu Antigen*," Int. J. Cancer. 102(4):428-434.
Kimura et al. (1981) "*A New Mouse Cell-Surface Antigen (Ly-M20) Controlled by a Gene Linked to Mls Locus and Defined by Monoclonal Antibodies*," Immunogenetics. 14(1-2):3-14.

(56) References Cited

OTHER PUBLICATIONS

King, R.G. et al. (2006) "*Trem-Like Transcript 2 is Expressed on Cells of the Myeloid/Granuloid and B Lymphoid Lineage and is Up-Regulated in Response to Inflammation*," J. Immunol. 176:6012-6021.
Kipps et al. (1985) "*Importance of Immunoglobin Isotype in Human Antibody-Dependent, Cell-Mediated Cytotoxicity Directed by Murine Monoclonal Antbodies*," J. Exper. Med. 161:1-17.
Kirk, A.D. et al. (1997) "*CTLA4-Ig and Anti-CD40 Ligand Prevent Renal Allograft Rejection in Primates*," Proc. Natl. Acad. Sci. (U.S.A.) 94(16):8789-8794.
Klein et al. (1981) "*Expression of Biological Effector Functions by Immunoglobulin G Molecules Lacking the Hinge Region*," Proc. Natl. Acad. Sci. (U.S.A.) 78:524-528.
Klesney-Tait, J. et al. (2006) "*The TREM Receptor Family and Signal Integration*," Nat. Immunol. 7:1266-1273.
Koene et al. (1997) "*Fc gammaRIIIa-158V/F Polymorphism Influences the Binding of IgG by Natural Killer Cell Fc gammaRIIIa, Independently of the Fc GammaRIIIa-48L/R/H Phenotype*," Blood 90:1109-1114.
Köhler G, et al. (1975) "*Continuous Cultures of Fused Cells Secreting Antibody of Predefined specificity*," Nature. 256:495-497.
Korman, A.J. et al. (2007) "*Checkpoint Blockade in Cancer Immunotherapy*," Adv. Immunol. 90:297-339.
Kranz et al. (1982) "*Mechanisms of Ligand Binding by Monoclonal Anti-Fluorescyl Antibodies*," J. Biol. Chem. 257:6987-6995.
Kristiansen, O.P. et al. (2000) "*CTLA-4 in Autoimmune Diseases—A General Susceptibility Gene to Autoimmunity?*" Genes Immun. 1(3):170-184.
Kussie P.H. et al. (1994) "*A Single Engineered Amino Acid Substitution Changes Antibody Fine Specificity*," Journal of Immunology 152:146-152.
Kudo, T. et al. (1993) "*A Novel Human Monoclonal Antibody Directed to a Tumor-associated Antigen*," Jpn. J. Cancer Res. 84:760-769.
Kumpel, B.M. (1989) "*Human Monoclonal Anti-D Antibodies*," Brit. J. Haematol. 71:415-420.
Kurlander et al. (1986) "*Comparison of Intravenous Gamma Globulin and a Monoclonal Anti-Fc Receptor Antibody as Inhibitors of Immune Clearance In Vivo in Mice*." J. Clin. Invest. 77(6):2010-2018.
Larsen, C.P. et al. (1996) "*Long-Term Acceptance of Skin and Cardiac Allografts After Blocking CD40 and CD28 Pathways*," Nature 381(6581):434-438.
Law, C.L. et al. (2002) "*Expression and Characterization of Recombinant Soluble Human CD3 Molecules Presentation of Antigenic Epitopes Defined on the Native TCR-CD3 Complex*," Intl. Immunol. 14(4):389-400.
Lawson, J.C. et al. (2009) "*Cancer Stem Cells in Breast Cancer and Metastasis*," Breast Cancer Res. Treat. 118(2):241-254.
Lazar et al. (1988) *Transforming Growth Factor A: Mutation of Aspartic Acid 47 and Leucine 48 Results in Different Biological Activities*, Molec. Cell. Biol. 8:1247-1252.
Le Gall, F. et al. (2004) "*Effect of Linker Sequences Between the Antibody Variable Domains on the Formation, Stability and Biological Activity of a Bispecific Tandem Diabody*," Protein Eng. Des. Sel. 17(4):357-366.
Leach, D.R. et al. (1996) "*Enhancement of Antitumor Immunity by CTLA-4 Blockade*," Science. 271(5256):1734-1736.
Lehmann et al. (2000) "*Phagocytosis: Measurement by Flow Cytometry*," J. Immunol. Meth. 243(1-2):229-242.
Lehrnbecher et al. (1999) "*Variant Genotypes of the Low-Affinity Fcgamma Receptors in Two Control Populations and a Review of Low-Affinity Fcgamma Receptor Polymorphisms in Control and Disease Populations*," Blood 94:4220-4232.
Lenschow, D.J. et al. (1996) "*CD28/B7 System of T Cell Costimulation*," Ann. Rev. Immunol. 14:233-258.
Lewis et al. (1993) "*Differential Responses of Human Tumor Cell Lines to Anti-p185HER2 Monoclonal Antibodies*," Cancer Immunol. Immunother. 37(4):255-263.
Li et al. (1996) "*Reconstitution of Human Fc Gamma RIII Cell Type Specificity in Transgenic Mice*," J. Exp. Med. 183:1259-1263.
Li et al. (2010) "*Monocyte Surface Expression of Fcγ Receptor RI (CD64), a Biomarker Reflecting Type-I Interferon Levels in Systemic Lupus Erythematosus*," Arthritis Res. Ther. 12:R90 (12 pages).
Liang, T.W-y. et al. (2008) "*TES7, a monoclonal Antibody Targeting B7—H3, Potently Inhibits Hs-700T Growth In Vivo*," FASEB J. 22:321.11.
Lifely et al. (1995) "*Glycosylation and Biological Activity of CAMPATH-1H Expressed in Different Cell Lines and Grown Under Different Culture Conditions*," Glycobiology 5(8):813-22.
Lim, S.H. et al. (2011) "*Fc Gamma Receptor IIb on Target B Cells Promotes Rituximab Internalization and Reduces Clinical Efficacy*," Blood 118(9):2530-2540.
Lin et al. (2001) "*Colony-Stimulating Factor 1 Promotes Progression of Mammary Tumors to Malignancy*," J. Exper. Med. 193(6):727-739.
Lin et al. (2002) "*The Macrophage Growth Factor CSF-1 in Mammary Gland Development and Tumor Progression*," J. Mammary Gland Biol. Neoplasia.7(2):147-162.
Linsley, P.S. et al. (1994) "*Extending the B7 (CD80) Gene Family*," Prot. Sci. 3:1341-1343.
Linsley, P.S. et al. (2009) "*The Clinical Utility of Inhibiting CD28-Mediated Costimulation*," Immunol. Rev. 229:307-321.
Liu et al. (1987) "*Production of a Mouse-Human Chimeric Monoclonal Antibody to CD20 With Potent Fc-Dependent Biologic Activity*," J. Immunol. 139:3521-3526.
Liu Z. et al. (1999) "*Fine mapping of the antigen-antibody interaction of scFv215, a recombinant antibody inhibiting RNA polymerase II from Drosophia melangogaster*," Journal of Molecular Recognition 12:103-111.
LoBuglio, A.F. et al. (1989) "*Mouse/Human Chimeric Monoclonal Antibody in Man: Kinetics and Immune Response*," Proc. Natl. Acad. Sci. (U.S.A.) 86:4220-4224.
Loke, P. et al. (2004) "*Emerging Mechanisms of Immune Regulation: The Extended B7 Family and Regulatory T Cells*," Arthritis Res. Ther. 6:208-214.
Lonberg, N. et al. (1995) "*Human Antibodies from Transgenic Mice*," Int. Rev. Immunol. 13:65-93.
Loo, D. et al. (2012) "*Development of an Fc-Enhanced Anti-B7—H3 Monoclonal Antibody with Potent Antitumor Activity*," J. Clin. Transl. Res.18(14):3717-3845.
Looney et al. (1986) "*Human Monocytes and U937 Cells Bear Two Distinct Fc Receptors for IgG*," J. Immunol. 136(5):1641-1647.
Lu, D. et al. (2003) "*Di-Diabody: A Novel Tetravalent Bispecific Antibody Molecule by Design*," J. Immunol. Meth. 279: 219-232.
Lu, D. et al., (2004) "*The Effect of Variable Domain Orientation and Arrangement on the Antigen-Binding Activity of a Recombinant Human Bispecific Diabody*," BBRC 318: 507-513.
Lu, et al., (2005) "*A Fully Human Recombinant IgG-like Bispecific Antibody to Both the Epidermal Growth Factor Receptor and the Insulin-like Growth Factor Receptor for Enhanced Antitumor Activity*," J. Biol. Chem. 280(20):19665-19672.
Lund, J. et al. (1991) "*Human Fc Gamma RI and Fc Gamma RII Interact With Distinct But Overlapping Sites on Human IgG*," J. Immunol. 147:2657-2662.
Lund, J. et al. (1992) "*Multiple Binding Sites on the CH2 Domain of IgG for Mouse Fc Gamma R11*," Mol. Immunol. 29:53-59.
Lund, J. et al. (1995) "*Oligosaccharide-Protein Interactions in IgG Can Modulate Recognition by Fc Gamma Receptors*," FASEB J. 9:115-119.
Lund, J. et al. (1996) "*Multiple Interactions of IgG With Its Core Oligosaccharide Can Modulate Recognition by Complement and Human Fc Gamma Receptor I and Influence the Synthesis of Its Oligosaccharide Chains*," J. Immunol. 157:4963-4969.
Lund et al. (2000) "*Expression and Characterization of Truncated Forms of Humanized L243 IgG1. Architectural Features Can Influence Synthesis of Its Oligosaccharide Chains and Affect Superoxide Production Triggered Through Human Fcgamma Receptor I*," Eur. J. Biochem. 267:7246-7257.

(56) References Cited

OTHER PUBLICATIONS

Lyden et al. (2001) "*The Fc Receptor for IgG Expressed in the Villus Endothelium of Human Placenta is Fc.Gamma.RIIB2*," J. Immunol. 166(6):3882-3889.
MacCallum et al. (1996) "*Antibody-Antigen Interactions: Contact Analysis and Binding Site Topography*," J. Molec. Biol. 262:732-745.
Maeda, H. et al. (1991) "*Construction of Reshaped Human Antibodies With HIV-Neutralizing Activity*," Human Antibodies Hybridoma 2:124-134 (Abstract Only).
Maenaka et al. (2001) "*The Human Low Affinity Fcgamma Receptors Iia, Iib, and III Bind IgG With Fast Kinetics and Distinct Thermodynamic Properties*," J. Biol. Chem. 48:44898-904.
Mahato et al. (1997) "*Cationic Lipid-Based Gene Delivery Systems: Pharmaceutical Perspectives*," Pharm. Res. 14:853-859.
Mahnke, K. et al. (2007) "*Induction of Immunosuppressive Functions of Dendritic Cells In Vivo by CD4+CD25+ Regulatory T Cells: Role of B7—H3 Expression and Antigen Presentation*." Eur J Immunol. Aug. 2007;37(8):2117-26.
Malbec et al. (1998) "*Fcs Receptor I-Associated Lyn-Dependent Phosphorylation of Fc.Gamma. Receptor IIB During Negative Regulation of Mast Cell Activation*," J. Immunol. 160(4):1647-1658.
Mallone, R. et al. (2005) "*Targeting T Lymphocytes for Immune Monitoring and Intervention in Autoimmune Diabetes*," Amer. J. Ther. 12(6):534-550.
Mangham, D.C. et al. (1999) "*A Novel Immunohistochemical Detection System Using Mirror Image Complementary Antibodies (MICA)*," Histopathology 35(2):129-33.
Maresco et al. (1999) "*The SH2-Containing 5'-Inositol Phosphatase (SHIP) is Tyrosine Phosphorylated after Fc.gamma. Receptor Clustering in Monocytes*," J. Immunol. 162:6458-6465.
Martin-Orozco, N. et al. (2007) "*Inhibitory Costimulation and Anti-Tumor Immunity*," Semin. Cancer Biol. 17(4):288-298.
Maruyama, K. (2000) "*In Vivo Targeting by Liposomes*," Biol. Pharm. Bull. 23(7):791-799.
Marvin et al. (2005) "*Recombinant Approaches to IgG-Like Bispecific Antibodies*," Acta Pharmacologica Sinica, 26(6): 649-658.
Masui et al. (1986) "*Mechanism of Antitumor Activity in Mice for Anti-Epidermal Growth Factor Receptor Monoclonal Antibodies With Different Isotypes*," Canc. Res. 46:5592-5598.
Maynard J. et al. (2000) "*Antibody Engineering*," Annu. Rev. Biomed. Eng. 2:339-76.
McDevitt et al. (2000) "*An Alpha-Particle Emitting Antibody ([213Bi]J591) for Radioimmunotherapy of Prostate Cancer*," Cancer Res. 60(21):6095-6100.
Melero et al. (1998) "*The Frequent Expansion of a Subpopulation of B Cells That Express RF-Associated Cross-Reactive Idiotypes: Evidence From Analysis of a Panel Autoreactive Monoclonal Antibodies*," Scand. J. Immunol. 48:152-158.
Merino, M.E. et al. (2001) "*Immunomagnetic Purging of Ewing's Sarcoma from Blood and Bone Marrow:Quantitation by Real-Time Polymerase Chain Reaction*," J. Clin. Oncol. 19(16):3649-3659.
Mertens, N. et al., "*New Recombinant Bi- and Trispecific Antibody Derivatives*," In: Novel Frontiers in the Production of Compounds for Biomedical Use, vol. 1; van Broekhoven, A. et al. (Eds.); Kluwer Academic Publishers, Dordrecht, The Netherlands.
Merrifield, B. (1986) "*Solid Phase Synthesis*," Science 232(4748):341-347.
Metcalfe (1997) "*Mast Cells*," Physiol Rev. 77(4):1033-1079.
Michaelsen et al. (1994) "*One Disulfide Bond in Front of the Second Heavy Chain Constant Region is Necessary and Sufficient for Effector Functions of Human IgG3 Without a Genetic Hinge*," Immunol. 91:9243-9247.
Micklem et al. (1990) "*Different isoforms of human FcRII distinguished by CDw32 antibodies*," J. Immunol. 144:2295-2303.
Mittal, S. et al. (2009) "*Cancer Stem Cells: The Other Face of Janus*," Amer. J. Med. Sci. 338(2):107-112.
Modak, S. et al. (1998) "*Novel Tumor-Associated Surface Antigen: Broad Distribution among Neuroectodermal, Mesenchymal and Epithelial Tumors, with Restricted Expression among Normal Tissues*," Pediatric Res. 43(4):136.
Modak, S. et al. (Mar. 1999) "*Disialoganglioside GD2 and Antigen 8H9: Potential Targets for Antibody-Based Immunotherapy Against Desmoplastic Small Round Cell Tumor (DSRCT) and Rhabdomyosarcoma (RMS)*," Proceedings of the American Association for Cancer Research Annual Meeting, vol. 40:474 ($90^{th}$ Annual Meeting of the American Association for Cancer Research; Philadelphia, Pennsylvania, US; Apr. 10-14, 1999 #3133.
Modak, S. et al. (2000) "*Radioimmunotargeting to Human Rhabdomyosarcoma Using Monoclonal Antibody 8H9*," Proc. Am. Assoc. Cancer Res.41:724.
Modak, S. et al. (2001) "*Monoclonal Antibody 8H9 Targets a Novel Cell Surface Antigen Expressed by a Wide Spectrum of Human Solid Tumors*," Cancer Res. 61(10):4048-4054.
Modak, S. et al. (2002) "*Disialoganglioside GD2 and a Novel Tumor Antigen: Potential Targets for Immunotherapy of Desmoplastic Small Round Cell Tumor*," Med Pediatr Oncol 39:547-551.
Modak, S. et al. (2007) "*Disialoganglioside Directed Immunotherapy of Neuroblastoma*," Cancer Investig. 25:67-77.
Modak, S. et al. (2005) "*Radioimmunotargeting of Human Rhabdomyosarcom using Monoclonal Antibody 8H9*," Cancer Biotherapy & Radiopharmaceuticals 20:534-546.
Morgan et al. (1995) "*The N-Terminal End of the CH2 Domain of Chimeric Human IgG1 Anti-HLA-DR is Necessary for C1q, Fc Gamma RI and Fc Gamma RIII Binding*," Immunol. 86:319-324.
Morrison et al. (1994) "*Structural Determinants of IgG Structure*," Immunologist 2:119-124.
Munn et al. (1990) "*Phagocytosis of Tumor Cells by Human Monocytes Cultured in Recombinant Macrophage Colony-Stimulating Factor*," J. Exper. Med. 172(1):231-237.
Nagarajan et al. (1995) "*Ligand Binding and Phagocytosis by CD16 (Fc Gamma Receptor III) Isoforms. Phagocytic Signaling by Associated Zeta and Gamma Subunits in Chinese Hamster Ovary Cells*," J. Biol. Chem. 270:25762-25770.
Nakamura, T. et al. (1992) "*Heterogeneity of Immunoglobulin-Associated Molecules on Human B Cells Identified by Monoclonal Antibodies*," Proc. Natl. Acad. Sci. (U.S.A.) 89:8522-8526).
Nakamura, A. et al. (2000) "*Fc.Gamma. Receptor IIB-Deficient Mice Develop Goodpasture's Syndrome Upon Immunization With Type IV Collagen: A Novel Murine Model for Autoimmune Glomerular Basement Membrane Disease*," J. Exper. Med. 191(5):899-905.
Nakamura, A. et al. (2005) "*Fc Receptor Targeting in the Treatment of Allergy, Autoimmune Diseases and Cancer*," Expert Opin. Ther. Targets 9(1):169-190.
Neuberger et al. (1984) "*Recombinant Antibodies Possessing Novel Effector Functions*," Nature 312:604-608.
Norderhaug et al. (1991) "*Chimeric Mouse Human IgG3 Antibodies With an Igg4-Like Hinge Region Induce Complement-Mediated Lysis More Efficiently Than IgG3 With Normal Hinge*," Eur. J. Immunol. 21:2379-2384.
Nordstrom, J.L. et al. (2011) "*Anti-Tumor Activity and Toxicokinetics Analysis of MGAH22, an Anti-HER2 Monoclonal Antibody With Enhanced FcG Receptor Binding Properties*," Breast Cancer Research 13:R123 (14 pages).
Noren, C.J. et al. (1989) "*A General Method for Site-Specific Incorporation of Unnatural Amino Acids into Proteins*," Science 244:182-188.
Norris et al. (1998) "*A Naturally Occurring Mutation in Fc.Gamma. RIIA: A Q to K.Sup.127 Change Confers Unique IgG Binding Properties to the R.Sup.131 Allelic Form of the Receptor*," Blood. 91(2):656-662.
Nose et al. (1989) "*Substitution of Asparagine324 With Aspartic Acid in the Fc Portion of Mouse Antibodies Reduces Their Capacity for C1q Binding*," Eur. J. Immunol. 19:2179-2181.
Okazaki et al. (2004) "*Fucose Depletion From Human IgG1 Oligosaccharide Enhances Binding Enthalpy and Association Rate Between IgG1 and FcgammaRIIIA*," J. Molec. Biol. 336:1239-1249.

(56) References Cited

OTHER PUBLICATIONS

Olafsen et al. (2004) "*Covalent Disulfide-Linked Anti-CEA Diabody Allows Site-Specific Conjugation and Radiolabeling for Tumor Targeting Applications*," Protein Eng. Des. Sel. 17(1):21-27.
Onda, M. et al. (2004) "*In Vitro and In Vivo Cytotoxic Activities of Recombinant Immunotoxin 8H9(Fv)-PE38 against Breast Cancer, Osteosarcoma, and Neuroblastoma*," Canc. Res. 64:1419-1424.
Orfao et al. (1996) "*General Concepts About Cell Sorting Techniques*," Clinical Biochem. 29:5-9.
Ott, V.L. et al. (2002) "*Downstream of Kinase, P62.Sup.Dok, is a Mediator of Fc.Gamma.RIIB Inhibition of Fc.Epsilon.RI Signaling*," J. Immunol. 168:4430-4439.
Ott, V.L. et al. (2001) "*FcGammaRIIB as a Potential Molecular Target for Intravenous Gamma Globulin Therapy*," J. Allergy Clin Immunol. 108(4):S95-S98.
Panchal, R.G. (1998) "*Novel Strategies to Selectively Kill Cancer Cells*," Biochem. Pharmacol. 55:247-252.
Panka et al. (1988) "*Variable Region Framework Differences Result in Decreased or Increased Affinity of Variant Anti-Digoxin Antibodies*," Proc. Natl. Acad. Sci. (U.S.A.) 85:3080-3084.
Pardridge et al. (2003) "*Blood-Brain Barrier Drug Targeting: The Future of Brain Drug Development*," Molecular Interventions 3(2):90-105 (particularly pp. 91-96).
Park et al. (1997) "*Immunoliposomes for Cancer Treatment*," Adv. Pharmacol. 40:399-435.
Park, Y.S. (2002) "*Tumor-Directed Targeting of Liposomes*," Biosci. Rep. 22(2):267-281.
Partridge et al. (1986) "*The Use of Anti-IgG Monoclonal Antibodies in Mapping the Monocyte Receptor Site on IgG*," Mol Immunol. 23(12):1365-1372.
Paul, William E, (1993) "*Fundamental Microbiology, 3 Ed*." pf. 242, 292-296.
Peeters et al. (2001) "*Production of Antibodies and Antibody Fragments in Plants*," Vaccine 19:2756-2761.
Pereira et al. (1998) "*Cardiolipin Binding a Light Chain From Lupus-Prone Mice*," Biochem. 37:1460-1437.
Perussia (2000) "*Human Natural Killer Cell Protocols*" in Methods Molecular Biology. vol. 121 (Campbell et al. eds.) Humana Press Inc., Totowa, NJ. 179-192.
Pettersen et al. (1999) "*CD47 Signals T Cell Death*," J. Immunol. 162(12):7031-7040.
Pini A. (1998) "*Design and Use of a Phage Display Library Human Antibodies With Subnanomolar Affinity Against a Marker of Angiogenesis Eluted From a Two-Dimensional Gel*," J. Biol. Chem. 272(34):21769-21779.
Pluckthun, A. et al. (1997) "*New Protein Engineering Approaches to Multivalent and Bispecific Antibody Fragments*," Immunotechnology 3(2):83-105.
Polson, A.G. et al. (2007) "*Antibody-Drug Conjugates Targeted to CD79 for the Treatment of Non-Hodgkin Lymphoma*," Blood. 110(2):616-623.
Pollock et al. (1999) "*Transgenic Milk as a Method for the Production of Recombinant Antibodies*," J. Immunol Methods 231:147-157.
Poul, M.A. et al. (2000) "*Selection of Tumor-Specific Internalizing Human Antibodies from Phage Libraries*," J. Molec. Biol. 301:1149-1161.
Prasad, D.V. et al. (2004) "*Murine B7—H3 is a Negative Regulator of T Cells*," J. Immunol. 173:2500-2506.
Presta, L.G. (2002) "*Engineering Antibodies for Therapy*," Curr. Pharm. Biotechnol. 3(3):237-256.
Presta, L.G. et al. (2002) "*Engineering Therapeutic Antibodies for Improved Function*," Biochem. Soc. Trans. 30(4):487-490.
Presta, L.G. et al. (2005) "*Selection, Design and Engineering of Therapeutic Antibodies*," J. Allergy Clin. Immunol. 116(4):731-736.
Pricop et al. (2001) "*Differential Modulation of Stimulatory and Inhibitory Fc.Gamma. Receptors on Human Monocytes by Th1 and Th2 Cytokines*," J. Immunol. 166(1):531-537.
Pulford et al. (1986) "*A New Monoclonal Antibody (KB61) Recognizing a Novel Antigen Which is Selectively Expressed on a Subpopulation of Human B Lymphocytes*," Immunol. 57(1):71-76.
Pulford et al. (1995) "*M6.5: The Immunocytochemical Distribution of CD16, CD32, and CD64 Antigens*," Leukocyte Typing V: White cell differentiation antigens 817-821 (Schlossman, Boumsell, Gilks, Harlan, Kishomoto, eds.); pp. 817-821.
Qin et al. (2000) "*Fc.Gamma. Receptor IIB on Follicular Dendritic Cells Regulates the B Cell Recall Response*," J. Immunol. 164:6268-6275.
Radaev et al. (2001) "*Recognition of Immunoglobulins by Fcgamma Receptors*," Molec. Immunol. 38:1073-1083.
Rader, C. et al. (1998) "*A Phage Display Approach for Rapid Antibody Humanization: Designed Combinatorial V Gene Libraries*," Proc. Natl. Acad. Sci. (U.S.A.) 95:8910-8915.
Rankin, et al. (2006) "*CD32B, The Human Inhibitory Fc-Y Receptor IIB, as a Target for Monoclonal Antibody Therapy of B-Cell Lymphoma*," Blood J. 108(7):2384-2391.
Ravetch et al. (1991) "*Fc Receptors*," Annu. Rev. Immunol. 9:457-492.
Ravetch et al. (1994) "*Fc Receptors: Rubor Redux*," Cell 78(4):553-560.
Ravetch et al. (1998) "*Divergent Roles for Fc Receptors and Complement In Vivo*," Annu. Rev. Immunol. 16:421-432.
Ravetech et al. (2000) "*Immune Inhibitory Receptors*," Science 290:84-89.
Ravetech et al. (2001) "*IgG Fc receptors*," Annu. Rev. Immunol. 19:275-290.
Reali et al. (2001) "*Iges Targeted on Tumor Cells: Therapeutic Activity and Potential in the Design of Tumor Vaccines*," Cancer Res. 61(14): 5517-5522.
Reddy, M.P. et al. (2000) "*Elimination of Fc Receptor-Dependent Effector Functions of a Modified IgG4 Monoclonal Antibody to Human CD4*," J. Immunol. 164:1925-1933.
Redpath et al. (1998) "*The Influence of the Hinge Region Length in Binding of Human IgG to Human Fcgamma Receptors*," Hum Immunol 59:720-727.
Reff et al. (1994) "*Depletion of B Cells In Vivo by a Chimeric Mouse Human Monoclonal Antibody to CD20*," Blood 83:435-445.
Reff et al. (2001) "*A Review of Modifications to Recombinant Antibodies: Attempt to Increase Efficacy in Oncology Applications*," Critical Reviews in Oncology/Hematology 40: 25-35.
Renders, L. et al. (2003) "*Engineered CD3 Antibodies for Immunosuppression*," Clin. Exp. Immunol. 133(3):307-309.
Ridgway et al. (1996) "'*Knobs-Into-Holes' Engineering of Antibody CH3 Domains for Heavy Chain Heterodimerization*," Protein Engr. 9:617-621.
Riechmann et al. (1988) "*Reshaping Human Antibodies for Therapy*," Nature 332(6162):323-327.
Riemer et al. (2005) "*Matching of Trastuzumab (Herceptin) Epitope Mimics Onto the Surface of Her-2/Neu—A New Method of Epitope Definition*," Molec. Immunol. 42(9):1121-1124.
Routledge et al. (1995) "*The Effect of Aglycosylation on the Immunogenicity of a Humanized Therapeutic CD3 Monoclonal Antibody*," Transplantation 60(8):847-853.
Rudikoff et al. (1982) "*Single Amino Acid Substitution Altering Antigen-Binding Specificity*" Proc. Natl. Acad. Sci. (U.S.A.) 79:1979-1983.
Saatian, B. et al. (2004) "*Expression of Genes for B7—H3 and Other T Cell Ligands by Nasal Epithelial Cells During Differentiation and Activation*," Amer. J. Physiol. Lung Cell. Mol. Physiol. 287:L217-L225.
Samsom et al. (2005) "*Fc Gamma RIIB Regulates Nasal and Oral Tolerance: A Role for Dendritic Cells*," Immunol. 174:5279-5287.
Samuelsson et al. (2001) "*Anti-Inflammatory Activity of IVIG Mediated Through the Inhibitory Fc Receptor*," Science 291:484-486.
Sarkar et al. (1996) "*Negative Signaling Via Fc.Gamma.RIIB1 in B Cells Blocks Phospholipase Cgamma2 Tyrosine Phosphorylation but Not Syk or Lyn Activation*," J. Biol. Chem. 271(33):20182-20186.
Sarmay et al. (1984) "*Ligand Inhibition Studies on the Role of Fc Receptors in Antibody-Dependent Cell-Mediated Cytotoxicity*," Molec. Immunol. 21:43-51.

(56) References Cited

OTHER PUBLICATIONS

Sarmay et al. (1988) "*The Effect of Synthetic Peptides Corresponding to Fc Sequences in Human IgG1 on Various Steps in the B Cell Activation Pathway*," Eur. J. Immunol. 18:289-294.
Sarmay et al. (1992) "*Mapping and Comparison of the Interaction Sites on the Fc Region of IgG Responsible for Triggering Antibody Dependent Cellular Cytotoxicity (ADCC) Through Different Types of Human Fc Gamma Receptor*," Mol Immunol 29:633-639.
Sato, K. et al. (1993) "*Reshaping a Human Antibody to Inhibit the Interleukin 6-Dependent Tumor Cell Growth*," Cancer Res 53:851-856.
Sautes-Fridman et al. (2003) "*Fc Gamma Receptors: A Magic Link With the Outside World*," ASHI Quarterley, 4$^{th}$ Quarter:148-151.
Schaffner et al. (1995) "*Chimeric Interleukin 2 Receptor Alpha Chain Antibody Derivatives With Fused Mu and Gamma Chains Permit Improved Recruitment of Effector Functions*," Mol Immunol 32 :9-20, 1995 (Erratum in 32 :1299).
Schatton, T. et al. (2009) "*Identification and Targeting of Cancer Stem Cells*," Bioessays 31(10):1038-1049.
Schatz et al. (2000) "*Use of Peptide Libraries to Map the Substrate Specificity of a Peptide-Modifying Enzyme: A 13 Residue Consensus Peptide Specifies Biotinylation in Escherichia Coli*," Bio/Technology 11:1138-1143.
Schildbach J.F. et al. (1993) "*Heavy Chain Position 50 is a Determinism of Affinity and Specificity for the Anti-digoxin Antibody2 6-10*," The Journal of Biological Chemistry 268(29):21739-21747.
Schildbach J.F. et al. (1994) "*Contribution of a single heavy chain residue to specificity of an anti-digozin monoclonal antibody*," Protein Science 3:737-749.
Scholl et al. (1993) "*Is Colony-Stimulating Factor-1 a Key Mediator of Breast Cancer Invasion and Metastasis*?," Molec. Carcinogen. 7(4):207-211.
Schuna et al. (2000) "*New Drugs for the Treatment of Rheumatoid Arthritis*," Amer. J. Health Syst. Pharm. 57:225-237.
Scopelliti, A. et al. (2009) "*Therapeutic Implications of Cancer Initiating Cell*," Expert Opin. Biol. Ther. 9(8):1005-1016.
Seaver (1994) "*Monoclonal Antibodies in Industry: More Difficult than Originally Thought*," Genetic Engineering News 14(14):10, 21.
Sedmak, D.D. et al. (1991) "*Expression of IgG Fc Receptor Antigens in Placenta and on Endothelial Cells in Humans*," Amer. J. Pathol. 138(1):175-181.
Sensel et al. (1997) "*Amino Acid Differences in the N-Terminus of C(H)2 Influence the Relative Abilities of IgG2 and IgG3 to Activate Complement*," Molecular Immunology 34:1019-1029.
Sharpe, A.H. et al. (2002) "*The B7-CD28 Superfamily*," Nature Rev. Immunol. 2:116-126.
Shaw et al. (1987) "*Characterization of a Mouse/Human Chimeric Monoclonal Antibody (17-1A) to a Colon Cancer Tumor-Associated Antigen*," J. Immunol. 138:4534-4538.
Shields et al. (2001) "*High resolution mapping of the binding site on human IgG1 for Fc gamma RI, Fc gamma RII, Fc gamma RIII, and FcRn and design of IgG1 variants with improved binding to the Fc gamma R*," J Biol Chem 276:6591-6604.
Shields et al. (2002) "*Lack of Fucose on Human IgG1 N-Linked Oligosaccharide Improves Binding to Human Fc.Gamma. RIII and Antibody-Dependent Cellular Toxicity*," J. Biol. Chem. 277(30):26733-26740.
Shopes et al. (1990) "*Recombinant Human IgG1-Murine Ige Chimeric Ig. Construction, Expression, and Binding to Human Fc Gamma Receptors*," J. Immunol. 145:3842-3848.
Shopes (1992) "*A genetically engineered human IgG mutant with enhanced cytolytic activity*," J. Immunol 148:2918-2922.
Shopes (1993) "*A Genetically Engineered Human IgG With Limited Flexibility Fully Initiates Cytolysis Via Complement*," Molec. Immunol. 30:603-609.
Shusta et al. (1998) "*Increasing the Secretory Capacity of Saccharomyces Cerevisiae for Production of Single-Chain Antibody Fragments*," Nature Biotechnology 16:773-777.
Shusta et al. (1999) "*Yeast Polypeptide Fusion Surface Display Levels Predict Thermal Stability and Soluble Secretion Efficiency*," J. Mol. Biol. 292:949-956.
Shusta et al. (2000) "*Directed Evolution of a Stable Scaffold for T-Cell Receptor Engineering*," Nature Biotechnology 18:754-759.
Siberil, S. et al. (2006) "*Molecular Aspects of Human FcgammaR Interactions with IgG: Functional and Therapeutic Consequences*," Immunol. Lett. 106:111-118 (2006).
Skolnick et al. (2000) "*From Genes to Protein Structure and Function: Novel Aspects of Computational Approaches in the Genomic Era*," Trends in Biotechnology 18:34-39.
Sleister et al. (2002) "*Subtractive Immunization; A Tool for the Generation of Discriminatory Antibodies to Proteins of Similar Sequence*," J. Immunol. Meth. 261: 213-220.
Smith et al. (1994) "*Recombinant Polymeric IgG: An Approach to Engineering More Potent Antibodies*," Bio/Technology 12:683-688.
Smith-Garvin, J.E. et al. (2009) "*T Cell Activation*," Annu. Rev. Immunol. 27:591-619.
Sondermann et al. (1999) "*Crystal Structure of the Soluble Form of the Human Fcgamma-Receptor IIB: A New Member of the Immunoglobulin Superfamily at 1.7 A Resolution*," EMBO J. 18:1095-1103.
Sondermann et al. (2000) "*The 3.2-A Crystal Structure of the Human Iggl Fc Fragment-Fc GammaRIII Complex*," Nature 406:267-273.
Sondermann et al. (2001) "*Molecular Basis for Immune Complex Recognition: A Comparison of Fc-Receptor Structures*," J. Mol. Biol. 309:737-749.
Sondermann et al. (2002) "*The Structure of Fc Receptor/Ig Complexes: Considerations on Stoichiometry and Potential Inhibitors*," Immunol. Lett. 82:51-56.
St. Clair, E.W. (2009) "*Novel Targeted Therapies for Autoimmunity*," Curr. Opin. Immunol. 21(6):648-657.
Stammers, M. et al. (2000) "*BTL-II : A Polymorphic Locus With Homology to the Butyrophilin Gene Family, Located at the Border of the Major Histocompatibility Complex Class II and Class III Regions in Human and Mouse*," Immunogenetics 51:373-382.
Stancovski et al. (1991) "*Mechanistic Aspects of the Opposing Effects of Monoclonal Antibodies to the ERBB2 Receptor on Tumor Growth*," Proc. Natl. Acad. Sci. (U.S.A.) 88(19):8691-8695.
Stavenhagen, J.B. et al. (2007) "*Fc Optimization of Therapeutic Antibodies Enhances Their Ability to Kill Tumor Cells in vitro and Controls Tumor Expansion in vivo via Low-Affinity ActivatingFc ; Receptors*," Cancer Res 67(18):8882-8890.
Stavenhagen, J.B. et al. (2008) "*Enhancing the Potency of Therapeutic Antibodies via Fc Optimization*," Advan. Enzyme Regul. 48:152-164.
Stefanescu, R. et al. (2004) "*Inhibitory Fc Gamma Receptors: From Gene to Disease*," J. Clin. Immuno. 24(4):315-326.
Steinberger et al. (2004), "*Molecular Characterization of Human 4Ig-B7—H3, a Member of the B7 Family With Four Ig-Like Domains*," J. Immunol. 2004, 172(4):2352-2359.
Stephan, J. et al. (1999) "*Selective Cloning of Cell Surface Proteins Involved in Organ Development: Epithelial Glycoprotein is Involved in Normal Epithelial Differentiation*," Endocrinol. 140:5841-5854.
Stephan et al. (1999) "*Distribution and Function of the Adhesion Molecule BEN During Rat Development*," Dev. Biol. 212:264-277.
Steplewski et al. (1988) "*Biological Activity of Human-Mouse IgG1, IgG2, IgG3, and IgG4 Chimeric Monoclonal Antibodies With Antitumor Specificity*," Proc. Natl. Acad. Sci. (U.S.A.) 85:4852-4856.
Strohmeier et al. (1995) "*Role of the Fc Gamma R Subclasses Fc Gamma RII and Fc Gamma RIII in the Activation of Human Neutrophils by Low and High Valency Immune Complexes*," J Leukocyte Biol 58:415-422.
Su et al. (2007) "*Expression Profile of Fc.Gamma.RIIB on Leukocytes and Its Dysregulation in Systemic Lupus Erythematosus*," J. Immunol. 178:3272-3280.
Subudhi, S.K. et al. (2005) "*The Balance of Immune Responses: Costimulation Versus Coinhibition*," J. Mol. Med. 83:193-202.

(56) References Cited

OTHER PUBLICATIONS

Suh, W.K. et al. (2003) "*The B7 Family Member B7—H3 Preferentially Down-Regulates T Helper Type 1-Mediated Immune Responses*," Nat Immunol. 4(9):899-906.
Sun, M. et al. (2002) "*Characterization of Mouse and Human B7—H3 Genes*," J. Immunol. 168:6294-6297.
Sun, Y. et al. (2006) "*B7—H3 and B7—H4 Expression in Non-small-cell Lung Cancer*," Lung Cancer 53(2):143-151.
Sylvestre et al. (1996) "*A Dominant Role for Mast Cell Fc Receptors in the Arthus Reaction*," Immunity 5:387-390.
Sylvestre et al. (1994) "*Fc Receptors Initiate the Arthus Reaction: Redefining the Inflammatory Cascade*," Science 265:1095-1098.
Takai et al. (1994) "*FcR Gamma Chain Deletion Results in Pleiotrophic Effector Cell Defects*," Cell 76 :519-529.
Takai et al. (1996) "*Augmented Humoral and Anaphylactic Responses in Fc Gamma RII-Deficient Mice*," Nature 379:346-349.
Takai (2002) "*Roles of Fc Receptors in Autoimmunity*," Nature Reviews 2:580-592.
Takai et al. (2003) "*Fc Receptors as Potential Targets for the Treatment of Allergy, Autoimmune Disease and Cancer*," Current Drug Targets—Immune, Endocrine & Metabolic Disorders, 3:187-197.
Takemura, S.I. et al. (2000) "*Construction of a Diabody (Small Recombinant Bispecific Antibody) Using a Refolding System*," Prot. Engin. 13(8):583-588.
Tam et al. (2004) "*A Bispecific Antibody Against Human IgE and Human Fc.gamma.RII That Inhibits Antigen-Induced Histamine Release by Human Mast Cells and Basophils*," Allergy 59:772-780.
Tamm et al. (1996) "*The IgG Binding Site of Human FcγRIIIb Receptor Involves CC' and FG Loops of the Membrane-Proximal Domain*," J. Biol. Chem. 271:3659-3666.
Tang et al. (2001) "*Biosynthesis of a Highly Stable Coiled-Coil Protein Containing Hexafluoroleucine in an Engineered Bacterial Host*," J. Am. Chem. Soc. 123(44): 11089-11090.
Tao et al. (1989) "*Studies of Aglycosylated Chimeric Mouse-Human Igg. Role of Carbohydrate in the Structure and Effector Functions Mediated by the Human Igg Constant Region*," J. Immunol. 143(8):2595-2601.
Tao et al. (1991) "*The Differential Ability of Human IgG1 and IgG4 to Activate Complement is Determined by the COOH-Terminal Sequence of the CH2 Domain*," J Exp Med 173:1025-1028.
Tao et al. (1993) "*Structural Features of Human Immunoglobulin G That Determine Isotype-Specific Differences in Complement Activation*," J. Exper. Med. 178:661-667.
Thomas, S. et al. (2010) "*Molecular Immunology Lessons From Therapeutic T-Cell Receptor Gene Transfer*," Immunology 129(2):170-177.
Tempest, P.R. et al. (1991) "*Reshaping a Human Monoclonal Antibody to Inhibit Human Respiratory Syncytial Virus Infection in vivo*," Bio/Technology 9:266-271.
Tivol, E.A. et al. (1995) "*Loss of CTLA-4 Leads to Massive Lymphoproliferation and Fatal Multiorgan Tissue Destruction, Revealing a Critical Negative Regulatory Role of CTLA-4*," Immunity 3(5):541-547.
Todorovska et al. (2001) "*Design and Application of Diabodies, Triabodies and Tetrabodies for Cancer Targeting*," J. Immunol. Methods. 248(1-2):47-66.
Tran, C.N. et al. (2008) "*Interactions of T Cells With Fibroblast-Like Synoviocytes: Role of the B7 Family Costimulatory Ligand B7—H3*," J Immunol, 180(5):2989-2998.
Tridandapani et al. (2002) "*Regulated Expression and Inhibitory Function of FcgammaRIIB in Human Monocytic Cells*," J. boil. Chem. 277(7):5082-5089.
Umana et al. (1999) "*Engineered Glycoforms of an Antineuroblastoma Igg1 With Optimized Antibody-Dependent Cellular Cytotoxic Activity*," Nat. Biotechnol. 17(2):176-80.
Vaccaro, C. et al. (2006) "*Divergent Activities of an Engineered Antibody in Murine and Human Systems Have Implications for Therapeutic Antibodies*," Proc. Natl. Acad. Sci. (U.S.A.) 103(49):18709-18714.
Vajdos et al. (2002) "*Comprehensive Functional Maps of the Antigen-Binding Site of an Anti-ErbB2 Antibody Obtained with Shotgun Scanning Mutagenesis*," J. Molec. Biol. 320:415-428.
Van Antwerp et al. (2000) "*Fine Affinity Discrimination by Yeast Surface Display and Flow Cytometry*," Biotechnol. Prog. 16:31-37.
Van De Winkel et al. (1995) "*CD32 Cluster Workshop Report*," Leukocyte Typing V: White Cell differentiation antigens 823-825 (Schlossman, Boumsell, Gilks, Harlan, Kishomoto, eds.).
Van den Beuken et al. (2001) "*Building Novel Binding Ligands to B7.1 and B7.2 Based on Human Antibody Single Variable Light Chain Domains*," J. Molec. Biol. 310:591-601.
Van Nguyen et al. (2002) "*Colony Stimulating Factor-1 is Required to Recruit Macrophages Into the Mammary Gland to Facilitate Mammary Ductal Outgrowth*," Devel. Biol. 247(1):11-25.
van Hest et al. (2001) "*Protein-Based Materials, Toward a New Level of Structural Control*," Chem. Comm. 19: 1897-1904.
Van Sorge et al. (2003) "*FcgammaR Polymorphisms: Implications for Function, Disease Susceptibility and Immunotherapy*," Tissue Antigens 61:189-202.
Vandenborre, K. et al. (1999) "*Interaction of CTLA-4 (CD152) With CD80 or CD86 Inhibits Human T-Cell Activation*," Immunology 98(3):413-421.
Vely et al. (1997) "*A New Set of Monoclonal Antibodies Against Human Fc Gamma RII (CD32) and Fc Gamma RIII (CD16): Characterization and Use in Various Assays*," Hybridoma 16(6):519-28.
Verhoeyen, M. et al. (1988) "*Reshaping Human Antibodies: Grafting an Antilysozyme Activity*," Science 239:1534-1536.
Veri, M.C. et al. (2007) "*Monoclonal Antibodies Capable of Discriminating the Human Inhibitory Fcgamma-Receptor IIB (CD32B) From the Activating Fcgamma-Receptor IIA (CD32A): Biochemical, Biological and Functional Characterization*," Immunology 121(3):392-404.
Veri, M.C. et al. (2010) "*Therapeutic Control of B Cell Activation via Recruitment of Fcgamma Receptor IIB (CD32B) Inhibitory Function With a Novel Bispecific Antibody Scaffold*," Arthritis Rheum. 62(7):1933-1943.
Vidarte (2001) "*Serine 132 is the C3 Covalent Attachment Point on the CH1 Domain of Human Igg1*," J. Biol. Chem. 276:38217-38233.
Viglietta, V. et al. (2007) "*Modulating Co-Stimulation*," Neurotherapeutics 4:666-675.
Vingerhoeds et al. (1994) "*Immunoliposomes in vivo*," Immunomethods 4(3):259-272.
Vitetta, E.S. et al. (2006) "*Immunology. Considering Therapeutic Antibodies*," Science 313:308-309.
Von Koskull, H. et al. (1984) "*Identification of Cells from Fetal Bladder Epithelium in Human Amniotic Fluid*," Hum. Genet. 65:262-267.
Vuist et al. (1990) "*Two Distinct Mechanisms of Antitumor Activity Mediated by the Combination of Interleukin 2 and Monoclonal Antibodies*," Canc. Res. 50:5767-5772.
Wallick et al. (1988) "*Glycosylation of a VH Residue of a Monoclonal Antibody Against A(1 →6) Dextran Increases Its Affinity for Antigen*," J. Exper. Med. 168(3):1099-1109.
Wang, S. et al. (2004) "*Co-Signaling Molecules of the B7-CD28 Family in Positive and Negative Regulation of T Lymphocyte Responses*," Microbes Infect. 6:759-766).
Wang et al. (2001) "*Expanding the Genetic Code of Escherichia coli*," Science, 292: 498-500.
Wang et al. (2002) "*Expanding the Genetic Code*," Chem. Comm. 1: 1-11.
Ward et al. (1989) "*Building Activities of a repertoire of single immunoglobulin variable domains secreted from Escherichia coli*," Nature 341:544-546.
Ward et al. (1995) "*The Effector Functions of Immunoglobulins: Implications for Therapy*," Therapeutic Immunology 2:77-94.
Warmerdam et al. (1990) "*Molecular Basis for a Polymorphism of Human Fc Gamma Receptor II (CD32)*," J. Exper. Med. 172(1):19-25.
Warren, H.S. et al.(1999) "*NK Cells and Apoptosis*," Immunol. Cell. Biol. 77(1):64-75.

(56) References Cited

OTHER PUBLICATIONS

Weinrich, V. et al. (1996) "*Epitope Mapping of New Monoclonal Antibodies Recognizing Distinct Human FCRII (CD32) Isoforms*," Hybridoma 15(2):109-116.
Weng et al. (2003) "*Two Immunoglobulin G Fragment C Receptor Polymorphisms Independently Predict Response to Rituximab in Patients With Follicular Lymphoma*," J. Clin. Oncol. 21:3940-3947.
Wheeler (1997) "*Preventive Vaccines for Cervical Cancer*," Salud. Publica d Mexico 39:1-9.
Wiener, E. et al. (1988) "*Differences Between the Activities of Human Monoclonal Iggl and Igg3 Anti-D Antibodies of the Rh Blood Group System in Their Abilities to Mediate Effector Functions of Monocytes*," Immunol. 65:159-163.
Willemsen, R. (2008) "*Selection of Human Antibody Fragments Directed Against Tumor T-Cell Epitopes for Adoptive T-Cell Therapy*," Cytometry A. 73(11):1093-1099.
Wing et al. (1996) "*Mechanism of First-Dose Cytokine-Release Syndrome by CAMPATH 1-H: Involvement of CD16 (FcγRIII) and CD11a/CD18 (LFA-1) on NK Cells*," J. Clin. Invest. 98:2819-2826.
Wingren et al. (1996) "*Comparison of Surface Properties of Human IgA, IgE, IgG and IgM Antibodies With Identical and Different Specificities*," Scand. J. Immunol. 44:430-436.
Winter, G. et al. (1991) "*Man-made Antibodies*," Nature 349:293-299.
Winter, G. et al. (1994) "*Making Antibodies by Phage Display Technology*," Annu. Rev. Immunol. 12.433-455.
Wittrup (2000) "*The Single Cell as a Microplate Well*," Nature Biotechnol. 18:1039-1040.
Wittrup (2001) "*Protein Engineering by Cell-Surface Display*," Curr, Opin. Biotechnol. 12:395-399.
Wolff, E.A. et al. (1993) "*Monoclonal Antibody Homodimers: Enhanced Antitumor Activity in Nude Mice*," Cancer Research 53:2560-2565.
Woof et al. (1986) "*Localisation of the Monocyte-Binding Region on Human Immunoglobulin G*," Molec. Immunol. 23:319-330.
Wright et al. (1997) "*Effect of Glycosylation on Antibody Function: Implications for Genetic Engineering*." Trends Biotechnol. 15(1):26-32.
Wu et al. (2001) "*Multimerization of a Chimeric Anti-DC20 Single-Chain Fv-Fc Fusion Protein is Mediated Through Variable Domain Exchange*," Protein Engineering 14(2):1025-1033.
Wu et al. (1997) "*A Novel Polymorphism of FcγRIIIA (CD16) Alters Receptor Function and Predisposes to Autoimmune Disease*," J. Clin. Invest. 100:1059-1070.
Wu et al. (1999) "*Humanization of a Murine Monoclonal Antibody by Simultaneous Optimization of Framework and CDR Residues*," J. Molec. Biol. 294:151-162.
Xiang J. et al. (2000) "*Study of B72.3 combining sites by molecular odelling and site-directed mutagenesis*," Protein Eng. 13(5):339-344.
Xie et al. (2005) "*A New Format of Bispecific Antibody: Highly Efficient Heterodimerization, Expression and Tumor Cell Lysis*," J. Immunol. Methods 296:95-101.
Xu et al. (1993) "*Antibody-Induced Growth Inhibition is Mediated Through Immunochemically and Functionally Distinct Epitopes on the Extracellular Domain of the c-erbB-2 (HER-2/neu) Gene product p185*," Int. J. Cancer. 53(3):401-408.
Xu et al. (1994) "*Residue at Position 331 in the IgG1 and IgG4 CH2 Domains Contributes to Their Differential Ability to Bind and Activate Complement*," J. Biol. Chem. 269:3469-3474.
Xu, D. et al. (2000) "*In Vitro Characterization of Five Humanized OKT3 Effector Function Variant Antibodies*," Cell. Immunol. 200:16-26.
Xu et al. (2003) "*Fc.gamma.Rs Modulate Cytotoxicity of Anti-Fas Antibodies: Implications for Agonistic Antibody Based Therapeutics*," J Immunol.171:562-68.
Xu, H. et al. (2009) "*MicroRNA miR-29 Modulates Expression of Immunoinhibitory Molecule B7—H3: Potential Implications for Immune Based Therapy of Human Solid Tumors*," Cancer Res. 69(15):5275-6281.
Xu, J. et al. (2006) "*Soluble Mouse B7—H3 Down-Regulates Dendritic Cell Stimulatory Capacity to Allogenic T Cell Proliferation and Production of IL-2 and IFN-Gamma*," Cell Mol Immunol. 3(3):235-240.
Yeung et al. (2002) "*Quantitative Screening of Yeast Surface-Displayed Polypeptide Libraries by Magnetic Bead Capture*," Biotechnol. Prog. 18:212-220.
Yi. K.H. et al. (2009) "*Fine Tuning the Immune Response Through B7—H3 and B7—H4*," Immunol. Rev. 229:145-151.
Zang, X. et al. (2003) "*B7x: A Widely Expressed B7 Family Member That Inhibits T Cell Activation*," Proc. Natl. Acad. Sci. (U.S.A.) 100:10388-10392.
Zang, X. et al. (2007) "*B7—H3 and B7x are Highly Expressed in Human Prostate Cancer and Associated With Disease Spread and Poor Outcome*," Proc. Natl. Acad. Sci. (U.S.A.) 104(49):19458-19463.
Zang, X. et al. (2007) "*The B7 Family and Cancer Therapy: Costimulation and Coinhibition*," Clin. Cancer Res. 13:5271-5279.
Zeidler et al. (2000) "*The Fc-Region of a New Class of Intact Bispecific Antibody Mediates Activation of Accessory Cells and NK Cells and Induces Direct Phagocytosis of Tumour Cells*," Brit. J. Cancer 83:261-266.
Zhang, G. et al. (2008) "*Soluble CD276 (B7—H3) is Released From Monocytes, Dendritic Cells and Activated T Cells and is Detectable in Normal Human Serum*," Immunology 123:538-546.
Zhang, G. et al. (2005) *B7—H3: Another Molecule Marker for Mo-DCs*?
Zhou, P. et al. (2008) "*CD32B is Highly Expressed on Clonal Plasma Cells From Patients With Systemic Light-Chain Amyloidosis and Provides a Target for Monoclonal Antibody-Based Therapy*,"Blood doi:10.1182/blood-2007-11-125526 (5 pages).
Zola et al., 2000, "*CD32 (FcgammaRII)*," J. Biol. Regul. Homeostat. Agents 14(4):311-316.
Zuckier et al. (1998) "*Chimeric Human-Mouse IgG Antibodies With Shuffled Constant Region Exons Demonstrate That Multiple Domains Contribute to In Vivo Half-Life*," Cancer Res 58:3905-3908.
English translation of Chinese Search Report (Chinese Application No. 201180022024.1, Mar. 4, 2010) (3 pages).
Chile Search Report (PCT2012002433, Mar. 9, 2012) (25 pages).
European Search Report (PCT2011026689, Mar. 1, 2011) (10 pages).

* cited by examiner $K_a = 1 \times 10^5$ / $K_d = 5 \times 10^{-3}$ $K_a = 1.2 \times 10^5$ / $K_d = 4.7 \times 10^{-3}$ $K_a = 1.7 \times 10^6$ / $K_d = 1.5 \times 10^{-2}$ $K_a = 1.9 \times 10^5$ / $K_d = 1.6 \times 10^{-2}$

BISPECIFIC MOLECULES THAT ARE IMMUNOREACTIVE WITH IMMUNE EFFECTOR CELLS OF A COMPANION ANIMAL THAT EXPRESS AN ACTIVATING RECEPTOR AND CELLS THAT EXPRESS B7-H3 AND USES THEREOF

CROSS-REFERENCE TO RELATED APPLICATIONS

The present application claims priority to U.S. Patent Application No. 61/772,931 (filed on Mar. 5, 2013, pending), which application is incorporated by reference herein in its entirety.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entireties.

BACKGROUND OF THE INVENTION

1. Field of the Invention

The present invention relates to bispecific molecules that are capable of localizing an immune effector cell that expresses an activating receptor to a B7-H3-expressing cancer cell, so as to thereby facilitate the killing of the cancer cell. In a preferred embodiment, such localization is accomplished using bispecific molecules that are immunoreactive both to an activating receptor of a companion animal immune effector cell and to B7-H3 expressed by a cancer cell. The present invention additionally concerns the use of such bispecific molecules in the treatment of cancer in companion animals. The invention particularly concerns bispecific diabody molecules that bind to (1) an epitope of an activating receptor of a companion animal immune effector cell and (2) an epitope of B7-H3 expressed by a cancer cell of such companion animal. The invention particularly concerns the embodiment wherein such bispecific molecules are capable of mediating, and more preferably enhancing, the activation and targeting of the companion animal's immune effector cells to its B7-H3-expressing cancer cells such that the activated immune effector cells kill the B7-H3-expressing cancer cells.

2. Description of Related Art

The growth and metastasis of tumors depends to a large extent on their capacity to evade host immune surveillance and overcome host defenses. Most tumors express antigens that can be recognized to a variable extent by the host immune system, but in many cases, an inadequate immune response is elicited because of the ineffective activation of effector T cells (Khawli, L. A. et al. (2008) "*Cytokine, Chemokine, and Co-Stimulatory Fusion Proteins for the Immunotherapy of Solid Tumors*," Exper. Pharmacol. 181: 291-328).

CD4+ T-lymphocytes are the essential organizers of most mammalian immune and autoimmune responses (Dong, C. et al. (2003) "*Immune Regulation by Novel Costimulatory Molecules*," Immunolog. Res. 28(1):39-48). The activation of CD4+ helper T-cells has been found to be mediated through co-stimulatory interactions between Antigen Presenting Cells and naive CD4+ T-lymphocytes. Two interactions are required (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol 90:297-339). In the first interaction, an Antigen Presenting Cell must display the relevant target antigen bound to the cell's major histocompatibility complex so that it can bind to the T-cell Receptor ("TCR") of a naive CD4+ T-lymphocyte. In the second interaction, a ligand of the Antigen Presenting Cell must bind to a CD28 receptor of the CD4+ T-lymphocyte (Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321). CD4+ helper T-cells experiencing both stimulatory signals are then capable of responding to cytokines (such as Interleukin-2 and Interleukin-12) to develop into Th1 cells. Such cells produce interferon-gamma (IFN-γ) and tumor necrosis factor-alpha (TNF-α), which mediate inflammatory responses to target cells expressing the target antigen. B-cell activation and proliferation also occurs, resulting in antibody production specific for the target antigen (Bernard, A. et al. (2005) "*T and B Cell Cooperation: A Dance of Life and Death*," Transplantation 79:S8-S11). In the absence of both co-stimulatory signals during TCR engagement, T cells enter a functionally unresponsive state, referred to as clonal anergy (Khawli, L. A. et al. (2008) "*Cytokine, Chemokine, and Co-Stimulatory Fusion Proteins for the Immunotherapy of Solid Tumors*," Exper. Pharmacol. 181:291-328). In pathologic states, Th1 cells are the key players of various organ-specific autoimmune diseases, such as type I diabetes, rheumatoid arthritis, and multiple sclerosis (Dong, C. et al. (2003) "*Immune Regulation by Novel Costimulatory Molecules*," Immunolog. Res. 28(1):39-48).

I. The B7 Superfamily and B7-H3

Investigations into the ligands of the CD28 receptor have led to the characterization of a set of related molecules known as the B7 superfamily (Coyle, A. J. et al. (2001) "*The Expanding B7 Superfamily: Increasing Complexity In Costimulatory Signals Regulating T Cell Function*," Nature Immunol 2(3):203-209; Sharpe, A. H. et al. (2002) "*The B7-CD28 Superfamily*," Nature Rev. Immunol 2:116-126; Greenwald, R. J. et al. (2005) "*The B7 Family Revisited*," Ann. Rev. Immunol. 23:515-548; Collins, M. et al. (2005) "*The B7 Family Of Immune-Regulatory Ligands*," Genome Biol. 6:223.1-223.7; Loke, P. et al. (2004) "*Emerging Mechanisms Of Immune Regulation: The Extended B7 Family And Regulatory T Cells*." Arthritis Res. Ther. 6:208-214; Korman, A. J. et al. (2007) "*Checkpoint Blockade in Cancer Immunotherapy*," Adv. Immunol 90:297-339; Flies, D. B. et al. (2007) "*The New B7s: Playing a Pivotal Role in Tumor Immunity*," J. Immunother. 30(3):251-260; Agarwal, A. et al. (2008) "*The Role Of Positive Costimulatory Molecules In Transplantation And Tolerance*," Curr. Opin. Organ Transplant. 13:366-372; Lenschow, D. J. et al. (1996) "*CD28/B7 System of T Cell Costimulation*," Ann. Rev. Immunol. 14:233-258; Wang, S. et al. (2004) "*Co-Signaling Molecules Of The B7-CD28 Family In Positive And Negative Regulation Of T Lymphocyte Responses*," Microbes Infect. 6:759-766). There are currently seven known members of the B7 superfamily: B7.1 (CD80), B7.2 (CD86), the inducible co-stimulator ligand (ICOS-L), the programmed death-1 ligand (PD-L1), the programmed death-2 ligand (PD-L2), B7-H3 and B7-H4 (Collins, M. et al. (2005) "*The B7 Family Of Immune-Regulatory Ligands*," Genome Biol. 6:223.1-223.7).

B7 superfamily members are in the greater immunoglobulin (Ig) superfamily and thus contain an immunoglobulin-V-like and an immunoglobulin-C-like domain (e.g., IgV- IgC) (Sharpe, A. H. et al. (2002) "*The B7-CD28 Superfamily*," Nature Rev. Immunol. 2:116-126). The IgV and IgC domains of B7-family members are each encoded by single exons, with additional exons encoding leader sequences, transmembrane and cytoplasmic domains. The cytoplasmic domains are short, ranging in length from 19 to 62 amino-acid residues and can be encoded by multiple exons (Collins, M. et al. (2005) "*The B7 Family Of Immune-Regulatory Ligands*," Genome Biol. 6:223.1-223.7). B7-H3 is unique in that the major human form contains two extracellular tandem IgV-IgC domains (i.e., IgV-IgC-IgV-IgC) (Collins, M. et al. (2005) "*The B7 Family Of Immune-Regulatory Ligands*," Genome Biol. 6:223.1-223.7). Canine B7-H3 similarly contains four extracellular tandem immunoglobulin domains. Members of the B7 superfamily are predicted to form back-to-back, non-covalent homodimers at the cell surface, and such homodimers have been found with respect to B7-1 (CD80) and B7-2 (CD86).

B7-1 (CD80) and B7-2 (CD86) have dual specificity for the stimulatory CD28 receptor and the inhibitory CTLA-4 (CD152) receptor (Sharpe, A. H. et al. (2002) "*The B7-CD28 Superfamily*," Nature Rev. Immunol. 2:116-126).

Although B7-H3 was initially thought to comprise only 2 Ig domains (IgV-IgC, 2Ig-B7-H3) (Chapoval, A. et al. (2001) "*B7-H3: A Costimulatory Molecule For T Cell Activation and IFN-γ Production*," Nature Immunol 2:269-274; Sun, M. et al. (2002) "*Characterization of Mouse and Human B7-H3 Genes*," J. Immunol. 168:6294-6297), a four immunoglobulin extracellular domain variant ("4Ig-B7-H3") was identified and has been found to be the more common human form of the protein (Sharpe, A. H. et al. (2002) "*The B7-CD28 Superfamily*," Nature Rev. Immunol. 2:116-126). No functional difference has been observed between the 2Ig-B7-H3 and the 4Ig-B7-H3 forms, since the natural murine form (2Ig) and the human 4Ig form exhibit similar function (Hofineyer, K. et al. (2008) "*The Contrasting Role Of B7-H3*," Proc. Natl. Acad. Sci. (U.S.A.) 105 (30):10277-10278). The 4Ig-B7-H3 molecule inhibits the natural killer cell-mediated lysis of cancer cells (Castriconi, R. et al. "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34): 12640-12645). The human B7-H3 (2Ig form) has been found to promote T-cell activation and IFN-γ production by binding to a putative receptor on activated T cells (Chapoval, A. et al. (2001) "*B7-H3: A Costimulatory Molecule For T Cell Activation and IFN-γ Production*," Nature Immunol. 2:269-274; Xu, H. et al. (2009) "*MicroRNA miR-29 Modulates Expression of Immunoinhibitory Molecule B7-H3: Potential Implications for Immune Based Therapy of Human Solid Tumors*," Cancer Res. 69(15): 5275-6281). Both B7-H4 and B7-H1 are potent inhibitors of immune function when expressed on tumor cells (Flies, D. B. et al. (2007) "*The New B7s: Playing a Pivotal Role in Tumor Immunity*," J. Immunother. 30(3):251-260).

The mode of action of B7-H3 is complex, as the protein mediates both T cell co-stimulation and co-inhibition (Hofineyer, K. et al. (2008) "*The Contrasting Role Of B7-H3*," Proc. Natl. Acad. Sci. (U.S.A.) 105(30):10277-10278; Martin-Orozco, N. et al. (2007) "*Inhibitory Costimulation And Anti-Tumor Immunity*," Semin. Cancer Biol. 17(4):288-298; Subudhi, S. K. et al. (2005) "*The Balance Of Immune Responses: Costimulation Verse Coinhibition*," J. Mol. Med. 83:193-202). B7-H3 binds to (TREM)-like transcript 2 (TLT-2) and co-stimulates T cell activation, but also binds to as yet unidentified receptor(s) to mediate co-inhibition of T cells. In addition, B7-H3, through interactions with unknown receptor(s), is an inhibitor for natural killer cells and osteoblastic cells (Hofineyer, K. et al. (2008) "*The Contrasting Role Of B7-H3*," Proc. Natl. Acad. Sci. (U.S.A.) 105(30):10277-10278). The inhibition may operate through interactions with members of the major signaling pathways through which T cell receptor (TCR) regulates gene transcription (e.g., NFTA, NF-κB, or AP-1 factors).

Molecules that block the ability of a B7 molecule to bind to a T-cell receptor (e.g., CD28) inhibit the immune system and have been proposed as treatments for autoimmune disease (Linsley, P. S. et al. (2009) "*The Clinical Utility Of Inhibiting CD28-Mediated Co-Stimulation*," Immunolog. Rev. 229:307-321). Neuroblastoma cells expressing 4Ig-B7-H3 treated with anti-4Ig-B7-H3 antibodies were more susceptible to NK cells. However, it is unclear whether this activity can be attributed to only antibodies against the 4Ig-B7-H3 form because all reported antibodies raised against the 4Ig-B7-H3 also bound 2Ig-B7H3 (Steinberger, P. et al. (2004) "*Molecular Characterization of Human 4Ig-B7-H3, a Member of the B7 Family with Four Ig-Like Domains*," J. Immunol. 172(4): 2352-2359 and Castriconi et al. (2004) "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34):12640-12645).

B7-H3 is not expressed on resting B or T cells, monocytes, or dendritic cells, but it is induced on dendritic cells by IFN-γ and on monocytes by GM-CSF (Sharpe, A. H. et al. (2002) "*The B7-CD28 Superfamily*," Nature Rev. Immunol 2:116-126). The receptor(s) that bind B7-H3 have not been fully characterized. Early work suggested that such a receptor would need to be rapidly and transiently up-regulated on T cells after activation (Loke, P. et al. (2004) "*Emerging Mechanisms Of Immune Regulation The Extended B7 Family And Regulatory T Cells*." Arthritis Res. Ther. 6:208-214). Recently, the (TREM)-like transcript 2 (TLT-2, or TREML2) receptor (King, R. G. et al. (2006) "*Trem-Like Transcript 2 Is Expressed On Cells Of The Myeloid/Granuloid And B Lymphoid Lineage And Is Up-Regulated In Response To Inflammation*," J. Immunol. 176: 6012-6021; Klesney-Tait, J. et al. (2006) "*The TREM Receptor Family And Signal Integration*," Nat. Immunol 71266-1273; Yi. K. H. et al. (2009) "*Fine Tuning The Immune Response Through B7-H3 And B7-H4*," Immunol Rev. 229: 145-151), which is expressed on myeloid cells has been shown to be capable of binding B7-H3, and of thereby co-stimulating the activation of CD8+ T cells in particular (Zang, X. et al. (2003) "*B7x: A Widely Expressed B7 Family Member That Inhibits T Cell Activation*," Proc. Natl. Acad. Sci. (U.S.A.) 100:10388-10392; Hashiguchi, M. et al. (2008) "*Triggering Receptor Expressed On Myeloid Cell-Like Transcript 2 (TLT-2) Is A Counter-Receptor For B7-H3 And Enhances T Cell Responses*," Proc. Natl. Acad. Sci. (U.S.A.) 105(30):10495-10500; Hofineyer, K. et al. (2008) "*The Contrasting Role Of B7-H3*," Proc. Natl. Acad. Sci. (U.S.A.) 105(30):10277-10278).

In addition to its expression on neuroblastoma cells, human B7-H3 is also known to be expressed on a variety of other cancer cells (e.g., gastric, ovarian and non-small cell lung cancers). B7-H3 protein expression has been immunohistologically detected in tumor cell lines (Chapoval, A. et al. (2001) "*B7-H3: A Costimulatory Molecule For T Cell Activation and IFN-γ Production*," Nature Immunol 2:269-274; Saatian, B. et al. (2004) "*Expression Of Genes For B7-H3 And Other T Cell Ligands By Nasal Epithelial Cells During Differentiation And Activation*," Amer. J. Physiol. Lung Cell. Mol. Physiol. 287:L217-L225; Castriconi et al.

(2004) "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34):12640-12645); Sun, M. et al. (2002) "*Characterization of Mouse and Human B7-H3 Genes*," J. Immunol. 168:6294-6297). mRNA expression has been found in heart, kidney, testes, lung, liver, pancreas, prostate, colon, and osteoblast cells (Collins, M. et al. (2005) "*The B7 Family Of Immune-Regulatory Ligands*," Genome Biol. 6:223.1-223.7). At the protein level, B7-H3 is found in human liver, lung, bladder, testis, prostate, breast, placenta, and lymphoid organs (Hofineyer, K. et al. (2008) "*The Contrasting Role Of B7-H3*," Proc. Natl. Acad. Sci. (U.S.A.) 105(30):10277-10278).

II. Therapeutic Antibodies

In addition to their known uses in diagnostics, antibodies have been shown to be useful as therapeutic agents. For example, immunotherapy, or the use of antibodies for therapeutic purposes has been used in recent years to treat cancer. Passive immunotherapy involves the use of monoclonal antibodies in cancer treatments (see for example, DeVita, Hellman, and Rosenberg's Cancer: Principles & Practice of Oncology, Eighth Edition (2008), DeVita, V. et al. Eds., Lippincott Williams & Wilkins, Philadelphia, Pa., pp. 537-547, 2979-2990). These antibodies can have inherent therapeutic biological activity both by direct inhibition of tumor cell growth or survival and by their ability to recruit the natural cell killing activity of the body's immune system. These agents can be administered alone or in conjunction with radiation or chemotherapeutic agents. Rituximab and trastuzumab, approved for treatment of non-Hodgkin's lymphoma and breast cancer in human patients, respectively, are examples of such therapeutics. Alternatively, antibodies can be used to make antibody conjugates in which the antibody is linked to a toxic agent and directs that agent to the tumor by specifically binding to the tumor. Gemtuzumab ozogamicin is an example of an approved antibody conjugate used for the treatment of leukemia in human patients.

Monoclonal antibodies that bind to cancer cells and have potential uses in cancer diagnosis and therapy have been disclosed (see, for example, the following patent applications which disclose, inter alia, some molecular weights of target proteins: U.S. Pat. No. 6,054,561 (200 kD c-erbB-2 (Her2), and other unknown antigens 40-200 KD in size) and U.S. Pat. No. 5,656,444 (50 kD and 55 kD oncofetal protein)). Examples of antibodies in clinical trials and/or approved for treatment of solid tumors include: trastuzumab (antigen: 180 kD, HER2/neu), edrecolomab (antigen: 40-50 kD, Ep-CAM), anti-human milk fat globules (HMFG1) (200 kD, HMW Mucin), cetuximab (antigens: 150 kD and 170 kD, EGF receptor), alemtuzumab (antigen: 21-28 kD, CD52), and rituximab (antigen: 35 kD, CD20).

An ideal therapeutic and/or diagnostic antibody would be specific for an antigen present on a large number of cancers, but absent or present only at low levels on any normal tissue. The discovery, characterization, and isolation of a novel antibody capable of binding to an antigen that is specifically associated with cancer(s) would be useful in many ways. First, the antibody would have biological activity against such cancer cells and be able to recruit the immune system's response to thereby treat the disease. The antibody could be administered as a therapeutic alone or in combination with current treatments or used to prepare immunoconjugates linked to toxic agents. An antibody with the same specificity but with low or no biological activity when administered alone could also be useful in that an antibody could be used to prepare an immunoconjugate with a radioisotope, a toxin, or a chemotherapeutic agent or liposome containing a chemotherapeutic agent, with the conjugated form being biologically active by virtue of the antibody directing the toxin to the antigen-containing cells.

As discussed above, antibodies and other molecules that specifically bind to human B7-H3 have been described (see, U.S. Pat. Nos. 7,527,969; 7,368,554; 7,358,354; and 7,279,567; United States Patent Application Publications Nos. US 20090087416; US 20090022747; US 20090018315; US20080081346; US 20050202536; US20030103963; US20020168762; PCT Publications Nos. WO 2008/116219; WO 2006/016276; WO 2004/093894; WO 04/001381; WO 2002/32375; WO 2002/10187 and WO 2001/094413; EP 1292619B; Modak, S. et al. (March 1999) "*Disialoganglioside GD2 And Antigen 8H9: Potential Targets For Antibody-Based Immunotherapy Against Desmoplastic Small Round Cell Tumor (DSRCT) And Rhabdomyosarcoma (RMS)*," Proceedings Of The American Association For Cancer Research Annual Meeting, Vol. 40:474 (90$^{th}$ Annual Meeting Of The American Association For Cancer Research; Philadelphia, Pa., US; Apr. 10-14, 1999; Modak, S. et al. (March 2000) "*Radioimmunotargeting To Human Rhabdomyosarcoma Using Monoclonal Antibody 8H9*," Proc. Am. Assoc. Cancer Res. 41:724; Modak, S. et al. (2001) "*Monoclonal Antibody 8H9 Targets A Novel Cell Surface Antigen Expressed By A Wide Spectrum Of Human Solid Tumors*," Cancer Res. 61(10):4048-4054; Steinberger, P. et al. (2004) "*Molecular Characterization of Human 4Ig-B7-H3, a Member of the B7 Family with Four Ig-Like Domains*," J. Immunol. 172(4):2352-2359; Xu, H. et al. (2009) "*MicroRNA miR-29 Modulates Expression of Immunoinhibitory Molecule B7-H3: Potential Implications for Immune Based Therapy of Human Solid Tumors*," Cancer Res. 69(15):5275-6281).

Nevertheless, one aspect desirable for an ideal therapeutic and/or diagnostic antibody would be the discovery and characterization of novel antibodies capable of mediating, and particularly of enhancing the activation of the immune system against cancer cells (especially canine cancer cells) that are associated with any of a variety of canine cancers.

III. Canine and Feline Cancer

Cancer is a major cause of death in domesticated canines. In one study, 45% of dogs that reached 10 years of age or older died of cancer. Withrow, S. J. (2007) ("Why Worry About Cancer In Pets?" in Small Animal Clinical Oncology (Withrow, S. J. et al., eds.) 4th Ed., W.B. Saunders, Philadelphia, Pa., pp. xv-xvii). Squamous cell carcinoma is one of the most common forms of canine cancer. Other common types of canine cancers are mammary (51%, female), prostate (male), connective tissue (17%), melanoma (14%), mouth and throat (10%), lymphoma (10%), and bone (4%) (Kelsey, J. L. et al. (1998) "*Epidemiologic Studies Of Risk Factors For Cancer In Pet Dogs*," Epidemiologic Reviews 20(2):204-217). Greater than 8,000 dogs will die of osteosarcoma each year. Hemangiosarcoma accounts for approximately five percent of all non-skin malignancies. Cancer in cats is not as prevalent as in dogs; however, feline cancer is still a substantial concern. The most common forms of cancer in cats are lymphoma, oral squamous cell carcinoma and fibrosarcoma or soft tissue sarcoma.

Despite all prior advances, a need remains for improved compositions capable of binding to canine and/or feline cancer cells and of facilitating or mediating an immune response against the cancer cells. In addition, a need remains for improved compositions capable of detecting such cancers. It is an object of this invention to identify such compositions. It is another object to provide novel compounds for use in the detection of B7-H3 expression on the surface of canine and/or feline cells.

As described in detail below, the present invention particularly relates to bispecific diabody molecules that bind to (1) an epitope of an activating receptor of a companion animal immune effector cell and (2) an epitope of B7-H3 expressed by a cancer cell of such companion animal The invention particularly concerns the embodiment wherein such bispecific molecules are capable of mediating, and more preferably enhancing, the activation and targeting of the companion animal's immune effector cells to its B7-H3-expressing cancer cells such that the activated immune effector cells kill the B7-H3-expressing cancer cells.

SUMMARY OF THE INVENTION

The present invention relates to bispecific molecules that are capable of localizing an immune effector cell that expresses an activating receptor to a B7-H3-expressing cancer cell, so as to thereby facilitate the killing of the cancer cell. In a preferred embodiment, such localization is accomplished using bispecific molecules that are immunoreactive both to an activating receptor of a companion animal immune effector cell and to B7-H3 expressed by a cancer cell. The present invention additionally concerns the use of such bispecific molecules in the treatment of cancer in companion animals. The invention particularly concerns bispecific diabody molecules that bind to (1) an epitope of an activating receptor of a companion animal immune effector cell and (2) an epitope of B7-H3 expressed by a cancer cell of such companion animal. The invention particularly concerns the embodiment wherein such bispecific molecules are capable of mediating, and more preferably enhancing, the activation and targeting of the companion animal's immune effector cells to B7-H3-expressing cancer cells such that the activated immune effector cells kill the B7-H3-expressing cancer cells.

In detail, the invention concerns a bispecific molecule comprising a first epitope-binding domain and a second epitope binding domain, wherein the first epitope binding domain is capable of binding to an epitope of a molecule present on an immune effector cell of a companion animal that expresses an activating receptor, and the second epitope-binding domain is capable of binding to an epitope of a B7-H3 molecule of a cancer cell of the companion animal The invention particularly concerns the embodiment of such bispecific molecule, wherein the first epitope binding domain binds to an epitope of an activating receptor.

The invention further concerns any of the above-described bispecific molecules, wherein the companion animal is a canine animal.

The invention further concerns any of the above-described bispecific molecules, wherein the companion animal is a feline animal.

The invention further concerns any of the above-described bispecific molecules, wherein the immune effector cell is a T-cell.

The invention further concerns any of the above-described bispecific molecules, wherein the activating receptor is CD3.

The invention further concerns any of the above-described bispecific molecules, wherein the bispecific molecule is a diabody.

The invention further concerns any of the above-described bispecific molecules, wherein the bispecific molecule further comprises a wild-type Fc region or an Fc receptor that comprises one, two, three, four or more amino acid modifications with relative to a wild-type Fc region.

The invention further concerns any of the above-described bispecific molecules, wherein the bispecific molecule further comprises an albumin-binding domain.

The invention further concerns any of the above-described bispecific molecules, wherein the second epitope-binding domain comprises a variable domain that comprises:

(A) $CDR_1$ (SEQ ID NO:25), $CDR_2$ (SEQ ID NO:27) and $CDR_3$ (SEQ ID NO:29) of the light chain of BRCA69D and $CDR_1$ (SEQ ID NO:33), $CDR_2$ (SEQ ID NO:35) and $CDR_3$ (SEQ ID NO:37) of the heavy chain of BRCA69D;

or (B) $CDR_1$ (SEQ ID NO:9), $CDR_2$ (SEQ ID NO:11) and $CDR_3$ (SEQ ID NO:13) of the light chain of BRCA84D and $CDR_1$ (SEQ ID NO:17), $CDR_2$ (SEQ ID NO:19) and $CDR_3$ (SEQ ID NO:21) of the heavy chain of BRCA84D.

The invention further concerns any of the above-described bispecific molecules, wherein the first epitope-binding domain comprises a variable domain that comprises:

(A) $CDR_1$ (SEQ ID NO:93), $CDR_2$ (SEQ ID NO:95) and $CDR_3$ (SEQ ID NO:97) of the light chain of K9CD3-1 and $CDR_1$ (SEQ ID NO:101), $CDR_2$ (SEQ ID NO:103) and $CDR_3$ (SEQ ID NO:105) of the heavy chain of K9CD3-1;

or (B) $CDR_1$ (SEQ ID NO:109), $CDR_2$ (SEQ ID NO:111) and $CDR_3$ (SEQ ID NO:113) of the light chain of K9CD3-2 and $CDR_1$ (SEQ ID NO:117), $CDR_2$ (SEQ ID NO:119) and $CDR_3$ (SEQ ID NO:121) of the heavy chain of K9CD3-2.

The invention further concerns a method of treating cancer in a companion animal which comprises administering to the companion animal an effective amount of a bispecific molecule, wherein the bispecific molecule comprises a first epitope-binding domain, wherein the first epitope binding domain being capable of binding to an epitope of an activating receptor of an immune effector cell of a companion animal, and a second epitope-binding domain, wherein the second epitope-binding domain being capable of binding to an epitope of B7-H3 of the companion animal.

The invention further concerns any of the above-described methods, wherein the companion animal is a canine animal.

The invention further concerns any of the above-described methods, wherein the immune effector cell is a T-cell.

The invention further concerns any of the above-described methods, wherein the activating receptor is CD3.

The invention further concerns any of the above-described methods, wherein the bispecific molecule is a diabody.

The invention further concerns any of the above-described methods, wherein the bispecific molecule further comprises an Fc region.

The invention further concerns any of the above-described methods, wherein the bispecific molecule further comprises an albumin-binding domain.

The invention further concerns any of the above-described methods, wherein the second epitope-binding domain comprises a variable domain that comprises:

(A) $CDR_1$ (SEQ ID NO:25), $CDR_2$ (SEQ ID NO:27) and $CDR_3$ (SEQ ID NO:29) of the light chain of BRCA69D and $CDR_1$ (SEQ ID NO:33), $CDR_2$ (SEQ ID NO:35) and $CDR_3$ (SEQ ID NO:37) of the heavy chain of BRCA69D;

or (B) $CDR_1$ (SEQ ID NO:9), $CDR_2$ (SEQ ID NO:11) and $CDR_3$ (SEQ ID NO:13) of the light chain of BRCA84D and $CDR_1$ (SEQ ID NO:17), $CDR_2$ (SEQ ID NO:19) and $CDR_3$ (SEQ ID NO:21) of the heavy chain of BRCA84D.

The invention further concerns any of the above-described methods, wherein the first epitope-binding domain comprises a variable domain that comprises:

(A) $CDR_1$ (SEQ ID NO:93), $CDR_2$ (SEQ ID NO:95) and $CDR_3$ (SEQ ID NO:97) of the light chain of K9CD3-1 and $CDR_1$ (SEQ ID NO:101), $CDR_2$ (SEQ ID NO:103) and $CDR_3$ (SEQ ID NO:105) of the heavy chain of K9CD3-1;

or (B) $CDR_1$ (SEQ ID NO:109), $CDR_2$ (SEQ ID NO:111) and $CDR_3$ (SEQ ID NO:113) of the light chain of K9CD3-2 and $CDR_1$ (SEQ ID NO:117), $CDR_2$ (SEQ ID NO:119) and $CDR_3$ (SEQ ID NO:121) of the heavy chain of K9CD3-2.

The invention further concerns any of the above methods, wherein the cancer is selected from the group consisting of canine histiocytic sarcoma, canine hemangiosarcoma, canine malignant melanoma, canine mast cell tumor, canine osteosarcoma, canine thyroid carcinoma, canine transitional cell carcinoma, canine squamous cell carcinoma, feline fibrosarcoma, feline mammary sarcoma, and feline squamous cell carcinoma.

BRIEF DESCRIPTION OF THE DRAWINGS

FIGS. 1A-1B show ELISA data. FIGS. 1C-1D (hBRCA84D) and FIG. 1E-1F (BRCA69D) show a B7-H3 SPR analysis (Binding of mAbs (6.25-100 nM) to human and canine B7H3(4Ig)-His captured on anti-His surface (normalized; bivalent binding fit)).

DETAILED DESCRIPTION OF THE INVENTION

Figure 1A:
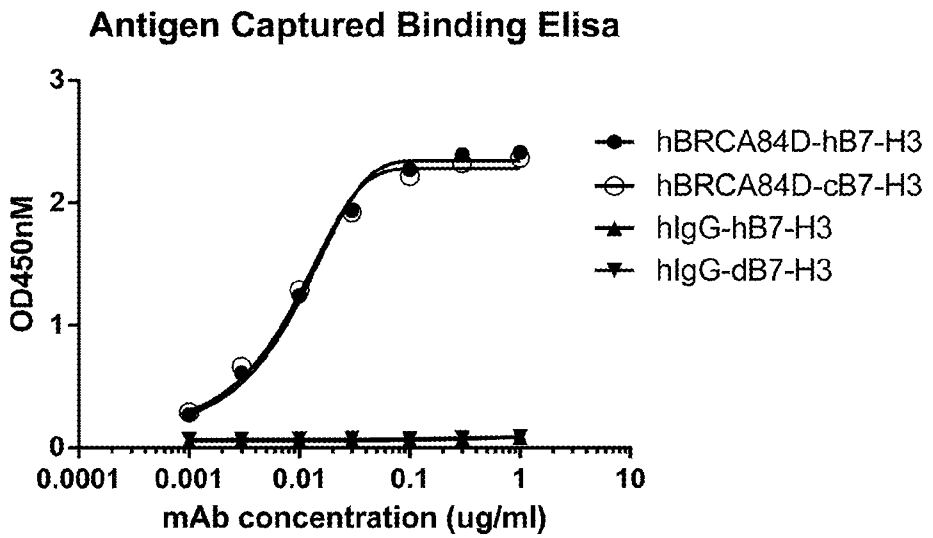
FIGS. 1A-1F show binding data for antibodies binding to human B7-H3 ("hB7-H3") versus canine B7-H3 ("cB7-H3").

The present invention relates to bispecific molecules that are capable of localizing an immune effector cell that expresses an activating receptor to a B7-H3-expressing cancer cell, so as to thereby facilitate the killing of the cancer cell. In a preferred embodiment, such localization is accomplished using bispecific molecules that are immunoreactive both to an activating receptor of a companion animal immune effector cell and to B7-H3 expressed by a cancer cell. The present invention additionally concerns the use of such bispecific molecules in the treatment of cancer in companion animals. The invention particularly concerns bispecific diabody molecules that bind to (1) an epitope of an activating receptor of a companion animal immune effector cell and (2) an epitope of B7-H3 expressed by a cancer cell of such companion animal. The invention particularly concerns the embodiment wherein the bispecific molecules are capable of mediating, and more preferably enhancing, the activation and targeting of the companion animal's immune effector cells to B7-H3-expressing cancer cells such that the activated immune effector cells kill the B7-H3-expressing cancer cells.

The capacity of such bispecific molecules to localize a immune effector cell that expresses an activating receptor to a B7-H3-expressing cancer cell permits such bispecific molecules to be used in the treatment of cancers afflicting companion animals. As indicated above, such localization can be achieved using bispecific molecules that bind B7-H3 and an activating receptor. Alternatively, such localization can be achieved using bispecific molecules that bind B7-H3 and a second molecule that is characteristically present on cells that express an activating receptor.

I. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, MOLECULAR CLONING: A LABORATORY MANUAL, Third Edition (Sambrook et al. Eds., 2001) Cold Spring Harbor Press, Cold Spring Harbor, N.Y.; OLIGONUCLEOTIDE SYNTHESIS: METHODS AND APPLICATIONS (Methods in Molecular Biology), Herdewijn, P., Ed., Humana Press, Totowa, N.J.; OLIGONUCLEOTIDE SYNTHESIS (Gait, M. J., Ed., 1984); METHODS IN MOLECULAR BIOLOGY, Humana Press, Totowa, N.J.; CELL BIOLOGY: A LABORATORY NOTEBOOK (Cellis, J. E., Ed., 1998) Academic Press, New York, N.Y.; ANIMAL CELL CULTURE (Freshney, R. I., Ed., 1987); INTRODUCTION TO CELL AND TISSUE CULTURE (Mather, J. P. and Roberts, P. E., Eds., 1998) Plenum Press, New York, N.Y.; CELL AND TISSUE CULTURE: LABORATORY PROCEDURES (Doyle, A. et al., Eds., 1993-8) John Wiley and Sons, Hoboken, N.J.; METHODS IN ENZYMOLOGY (Academic Press, Inc.) New York, N.Y.; WEIR'S HANDBOOK OF EXPERIMENTAL IMMUNOLOGY (Herzenberg, L. A. et al. Eds. 1997) Wiley-Blackwell Publishers, New York, N.Y.; GENE TRANSFER VECTORS FOR MAMMALIAN CELLS (Miller, J. M. et al. Eds., 1987) Cold Spring Harbor Press, Cold Spring Harbor, N.Y.; CURRENT PROTOCOLS IN MOLECULAR BIOLOGY (Ausubel, F. M. et al., Eds., 1987) Greene Pub. Associates, New York, N.Y.; PCR: THE POLYMERASE CHAIN REACTION, (Mullis, K. et al., Eds., 1994) Birkhä user, Boston Mass.; CURRENT PROTOCOLS IN IMMUNOLOGY (Coligan, J. E. et al., eds., 1991) John Wiley and Sons, Hoboken, N.J.; SHORT PROTOCOLS IN MOLECULAR BIOLOGY (John Wiley and Sons, 1999) Hoboken, N.J.; IMMUNOBIOLOGY 7 (Janeway, C. A. et al. 2007) Garland Science, London, UK; Antibodies (P. Finch, 1997) Stride Publications, Devoran, UK; ANTIBODIES: A PRACTICAL APPROACH (D. Catty, ed., 1989) Oxford University Press, USA, New York N.Y.); MONOCLONAL ANTIBODIES: A PRACTICAL APPROACH (Shepherd, P. et al. Eds., 2000) Oxford University Press, USA, New York N.Y.; USING ANTIBODIES: A LABORATORY MANUAL (Harlow, E. et al. Eds., 1998) Cold Spring Harbor Laboratory Press, Cold Spring Harbor, N.Y.; THE ANTIBODIES (Zanetti, M. et al. Eds. 1995) Harwood Academic Publishers, London, UK); and DEVITA, HELLMAN, AND ROSENBERG'S CANCER: PRINCIPLES & PRACTICE OF ONCOLOGY, EIGHTH EDITION, DeVita, V. et al. Eds. 2008, Lippincott Williams & Wilkins, Philadelphia, Pa.

II. Definitions

As used herein, the term "companion animal" refers to members of the canine family of animals (i.e., "dogs;" Canis lupus familiaris) and to members of the feline family of animals (i.e., "cats;" *Felis catus* or *Felis silvestris catus*). The canine family includes pet dogs, working dogs and sporting dogs. The feline family includes house cats, barn cats and show cats.

As used herein, the term "B7-H3" refers to a member of the B7 family of proteins, a type I membrane protein with Ig-like domains also known as CD276, and particularly to its canine and feline homologs. The term "2Ig-B7-H3" denotes a B7-H3 form that comprises only two Ig-like domains; the term "4Ig-B7-H3" denotes a B7-H3 form that comprises four Ig-like domains (see, Sun, M. et al. (2002) "*Characterization of Mouse and Human B7-H3 Genes*," J. Immunol. 168:6294-6297; Steinberger et al. (2004), "*Molecular Characterization Of Human 4Ig-B7-H3, A Member Of The B7 Family With Four Ig-Like Domains*," J. Immunol. 2004, 172(4):2352-2359 and Castriconi et al. (2004) "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34): 12640-12645).

As used herein, the term "anti-B7-H3 antibody" is intended to denote an antibody that exhibits the abilities to bind to canine B7-H3 and/or feline B7-H3. As used herein, an "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, mutants thereof, naturally occurring variants, fusion proteins comprising an antibody portion with an antigen recognition site of the required specificity, humanized antibodies, chimeric antibodies and caninized antibodies, and any other modified configuration of the immunoglobulin molecule that comprises an antigen recognition site of the required specificity. Throughout this application, the numbering of amino acid residues of the light and heavy chains of antibodies is according to the EU index as in Kabat et al. (1992) SEQUENCES OF PROTEINS OF IMMUNOLOGICAL INTEREST, National Institutes of Health Publication No. 91-3242.

As used herein, an "antigen binding fragment of an antibody" is a portion of an antibody that possesses an at least one antigen recognition site. As used herein, the term encompasses fragments such as Fab, Fab', $F(ab')_2$ Fv), and single chain (scFv).

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody."

The term "humanized antibody" refer to a molecule, generally prepared using recombinant techniques, having an antigen binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions. This eliminates the constant region as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332: 323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five or six) which are altered with respect to the original antibody, which are also termed one or more CDRs "derived from" one or more CDRs from the original antibody.

The term "caninized antibody" refer to a chimeric molecule, generally prepared using recombinant techniques, having an antigen binding site derived from an immunoglobulin from a non-canine species and the remaining immunoglobulin structure of the molecule based upon the structure and/or sequence of a canine immunoglobulin. The techniques are similar to humanizing an antibody; however, canine framework and constant region sequences are used. See U.S. Pat. No. 7,261,890 for examples of such canine framework and constant region sequences The term "BiTEs" (bi-specific T-cell engagers) refers to a single polypeptide chain molecule having two antigen binding domains, one of which binds to a T-cell antigen and the second of which binds to an antigen present on the surface of a target cell (WO 05/061547; Baeuerle, P et al. (2008) "*BiTE: A New Class Of Antibodies That Recruit T Cells*," Drugs of the Future 33: 137-147; Bargou, et al. 2008) "*Tumor Regression in Cancer Patients by Very Low Doses of a T Cell-Engaging Antibody*," Science 321: 974-977).

The term "diabody" refers to a molecule that comprises at least two polypeptide chains that associate through a covalent interaction to form at least two epitope binding sites, which may recognize the same or different epitopes. Each of the polypeptide chains of a diabody comprises an immunoglobulin light chain variable region and an immunoglobulin heavy chain variable region, but these regions do not interact to form an epitope binding site. Rather, the immunoglobulin heavy chain variable region of one (e.g., the first) of the diabody polypeptide chains interacts with the immunoglobulin light chain variable region of a different (e.g., the second) diabody polypeptide chain to form an epitope binding site. Similarly, the immunoglobulin light chain variable region of one (e.g., the first) of the diabody polypeptide chains interacts with the immunoglobulin heavy chain variable region of a different (e.g., the second) diabody polypeptide chain to form an epitope binding site. Diabodies may be monospecific, bispecific, trispecific, etc., thus being able to simultaneously bind one, two, three or more different epitopes (which may be of the same or of different antigens). Diabodies may additionally be monovalent, bivalent, trivalent, tetravalent, pentavalent, hexavelent, etc., thus being able to simultaneously bind one, two, three, four, five, six or more molecules. These two attributes of diabodies (i.e., degree of specificity and valency may be combined, for example to produce bispecific antibodies (i.e., capable of binding two epitopes) that are tetravalent (i.e., capable of binding four sets of epitopes), etc. Diabody molecules are disclosed in PCT Publications WO 2006/113665, WO 2008/157379 and WO 2010/080538.

As used herein, an antibody or a polypeptide is said to "specifically" bind a region of another molecule (i.e., an epitope) if it reacts or associates more frequently, more rapidly, with greater duration and/or with greater affinity with that epitope relative to alternative epitopes. For example, an antibody that specifically binds to a B7-H3 epitope is an antibody that binds this B7-H3 epitope with greater affinity, avidity, more readily, and/or with greater duration than it binds to other B7-H3 epitopes or non-B7-H3 epitopes. It is also understood by reading this definition that, for example, an antibody (or moiety or epitope) that specifically binds to a first target may or may not specifically or preferentially bind to a second target. As such, "specific binding" does not necessarily require (although it can include) exclusive binding. Generally, but not necessarily, reference to binding means "specific" binding.

As used herein, the term "immunologically active" in reference to an epitope being or "remaining immunologically active" refers to the ability of an antibody (e.g., an anti-B7-H3 antibody) to bind to the epitope under different conditions, for example, after the epitope has been subjected to reducing and denaturing conditions.

Different biological functions are associated with anti-B7-H3 antibodies, including, but not limited to one or more of: an ability to specifically bind to B7-H3 (and in particular B7-H3 molecules that are expressed on the surfaces of canine and feline cancer cells (including but not limited to canine histiocytic sarcoma, hemangiosarcoma, malignant melanoma, mast cell tumor, osteosarcoma, thyroid carcinoma, transitional cell carcinoma, and squamous cell carcinoma cancer cells, and feline fibrosarcoma, mammary carcinoma and squamous cell carcinoma cancer cells); an ability to competitively inhibits preferential binding of a known anti-B7-H3-specific antibody to B7-H3, including the ability to preferentially bind to the same B7-H3 epitope to which such antibody preferentially binds; an ability to bind to a portion of B7-H3 that is exposed on the surface of a living cell in vitro or in vivo; an ability to bind to a portion of B7-H3 that is exposed on the surface of a living cancer cell, such as, but not limited to, prostate, lung or kidney cancer cells; an ability to deliver a chemotherapeutic agent to a cancer cell (such as a cancer cell of a canine histiocytic sarcoma, hemangiosarcoma, malignant melanoma, mast cell tumor, osteosarcoma, tyroid carcinoma, transitional cell carcinoma, and squamous cell carcinoma, or a cancer cell of a feline fibrosarcoma, mammary carcinoma and squamous cell carcinoma) expressing B7-H3 on its surface; and/or an ability to deliver a therapeutic agent or detectable marker into a cancer cell expressing B7-H3 on its surface. As discussed herein, polypeptides (including antibodies) of the invention may have any one or more of these characteristics, provided that they exhibit activity with respect to canine B7-H3 and/or feline B7-H3.

An "anti-B7-H3 equivalent antibody" or "anti-B7-H3 equivalent polypeptide" refers to an antibody or a polypeptide having one or more biological functions associated with an anti-B7-H3 antibody, such as, for example binding specificity.

As used herein, the term "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

Agents that are employed in the methods of this invention can be "randomly selected" or "rationally selected or designed." As used herein, an agent is said to be "randomly selected" when the agent is chosen without prior consideration or knowledge of the specific amino acid or other chemical moieties involved in the association of the molecule with its native binding partner(s) or known antibodies. An example of a randomly selected agent is an agent that is identified through the use and screening of a chemical library or a peptide combinatorial library.

As used herein, an agent is said to be "rationally selected or designed" when the agent is chosen on a non-random basis that takes into account the sequence of the target site and/or its conformation in connection with the agent's action. This invention also encompasses agents that act at the sites of interaction between B7-H3 and its native binding partner, although other ligands and their active B7-H3-interactive sites are also encompassed within the scope of this invention, whether currently known or later identified. Agents can be rationally selected or rationally designed by utilizing the peptide sequences that make up the contact sites of the receptor/ligand and/or B7-H3/anti-B7-H3 antibody complex. For example, a rationally selected peptide agent can be a peptide whose amino acid sequence is identical to an epitope appearing on B7-H3 as it is exposed on the surface of a living cell in its native environment. Such an agent will reduce or block the association of the anti-B7-H3 antibody with B7-H3, or the association of B7-H3 with its native ligand, as desired, by binding to the anti-B7-H3 antibody or to the native ligand.

As used herein, the term "labeled," with regard to an antibody, is intended to encompass direct labeling of the antibody by coupling (i.e., physically linking) a detectable substance, such as a radioactive agent or a fluorophore (e.g. phycoerythrin (PE) or fluorescein isothiocyanate (also known as fluoroisothiocyanate or FITC)) to the antibody, as well as indirect labeling of the probe or antibody by reactivity with a detectable substance.

As used herein, the term "association", with regard to an antibody, includes covalent and non-covalent attachment or binding of an agent (e.g., chemotherapeutic agent) to the antibody. The antibody can be associated with an agent (e.g., chemotherapeutic agent) by direct binding or indirect binding via attachment to a common platform, such that the antibody directs the localization of the agent to the cancerous cell to which the antibody binds and wherein the antibody and agent do not substantially dissociate under physiological conditions such that the agent is not targeted to the same cancerous cell to which the antibody binds or such that the agent's potency is not decreased.

The term "biological sample" encompasses a variety of sample types obtained from a companion animal that can be used in a diagnostic or monitoring assay. The definition encompasses saliva, blood and other liquid samples of biological origin, solid tissue samples such as a biopsy specimen or tissue cultures or cells derived therefrom, and the progeny thereof, for example, cells obtained from a tissue sample collected from a companion animal suspected of having cancer. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

The term "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, the term "delaying development of metastasis" means to defer, hinder, slow, retard, stabilize, and/or postpone development of metastasis. This delay can be of varying lengths of time, depending on the history of the cancer and/or individual being treated. As is evident to one skilled in the art, a sufficient or significant delay can, in effect, encompass prevention of metastasis, in that the animal does not develop the metastasis.

As used herein, an "effective amount" of a pharmaceutical composition, in one embodiment, is an amount sufficient to effect beneficial or desired results including, without limitation, clinical results such as shrinking the size of the tumor, retardation of cancerous cell growth, delaying the development of metastasis, decreasing symptoms resulting from the disease, increasing the quality of life of those suffering from the disease, decreasing the dose of other medications required to treat the disease, enhancing the effect of another medication such as via targeting and/or internalization, delaying the progression of the disease, and/or prolonging survival of individuals. An effective amount can be administered in one or more administrations. For purposes of this invention, an effective amount of drug, compound, or pharmaceutical composition is an amount sufficient to reduce the proliferation of (or destroy) cancerous cells and to reduce and/or delay the development, or growth, of metastases of cancerous cells, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art. Typical dosages for antibody administration comprise one or more unit doses between 0.1-to 100 mg/kg/body weight. The preferred dosages comprise 1 to 100 mg/kg/body weight. The most preferred dosages comprise 10 to 100 mg/kg/body weight. Typical doses for bispecific molecule (e.g., antibodies, diabodies (multi-chain or BiTEs) administration comprise one or more unit doses of 0.0001 mg/kg/body weight to 100 mg/kg/body weight. Preferably, the dosage administered is between 0.0001 mg/kg/body weight and 20 mg/kg/body weight, 0.0001 mg/kg/body weight and 10 mg/kg/body weight, 0.0001 mg/kg/body weight and 5 mg/kg/body weight, 0.0001 mg/kg/body weight and 2 mg/kg/body weight, 0.0001 mg/kg/body weight and 1 mg/kg/body weight, or 0.0001 mg/kg/body weight and 0.75 mg/kg/body weight As used herein, a nucleic acid molecule or agent, antibody, composition or cell, etc., is said to be "isolated" when that nucleic acid molecule, agent, antibody, composition, or cell, etc. is substantially separated from contaminant nucleic acid molecules, antibodies, agents, compositions, or cells, etc. naturally present in its original source.

The terms "polypeptide," "oligopeptide," "peptide" and "protein" are used interchangeably herein to refer to polymers of amino acids of any length, but especially lengths greater than 5, 10, 15, 20 or 25 amino acid residues. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or as associated chains.

Also encompassed within the scope of the invention are peptidomimetics of the bispecific molecules described herein. Such peptidomimetics include peptides wherein at least one amino acid residue is substituted with an amino acid residue that is not commonly found in nature, such as the D isomer of the amino acid or an N-alkylated species of the amino acid. In other embodiments, peptidomimetics are constructed by replacing at least one amide bond (—C(═O)—NH—) in a B7-H3 peptide agonist, antagonist or modulators with an amide isostere. Suitable amide isosteres include: $—CH_2—NH—$, $—CH_2—S—$, $—CH_2—S(O)—$, —$CH_2$—$S(O)_2$—, —$CH_2$—$CH_2$—, —CH═CH— (E or Z form), —C(═O)—$CH_2$—, —CH(CN)—NH—, —C(OH)—$CH_2$—, and —O—C(═O)—NH—. The amide bonds in a B7-H3 peptide agonist, antagonist or modulator that are suitable candidates for replacement with amide isosteres include bonds that are hydrolyzable by the endogenous esterases or proteases of the intended subject of B7-H3 peptide agonist, antagonist or modulator treatment.

As used herein, the term "substantially pure" refers to material that is at least 50% pure (i.e., free from contaminants), more preferably at least 90% pure, more preferably at least 95% pure, more preferably at least 98% pure, more preferably at least 99% pure, and most preferably greater than 99% pure.

As used herein, the term "toxin" refers to any substance, which effects an adverse response within a cell. For example, a toxin directed to a cancerous cell would have an adverse, sometimes deleterious effect, on the cancerous cell. Examples of toxins include, but are not limited to, radioisotopes, calicheamicin, and maytansinoids.

As used herein, the terms "treatment" or "treating" denote an approach for obtaining a beneficial or desired result including and preferably a beneficial or desired clinical result. Such beneficial or desired clinical results include, but are not limited to, one or more of the following: reducing the proliferation of (or destroying) cancerous cells or other diseased, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of companion animal recipients.

As used herein, the term "cancer" is intended to encompass a disease characterized by the presence of a cancer cell selected from the group consisting of a cell of an adrenal gland tumor, an AIDS-associated cancer, an alveolar sarcoma, an astrocytic tumor, a squamous cell carcinoma of the bladder, a transitional cell carcinoma of the bladder, a bone cancer, adamantinoma, aneurismal bone cysts, osteochondroma, osteosarcoma, a brain and spinal cord cancer, a metastatic brain tumor, a carotid body tumor, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, an extraskeletal myxoid chondrosarcoma, a fibrogenesis imperfecta ossium, a fibrosarcoma, a fibrous dysplasia of the bone, a gallbladder or bile duct cancer, a gestational trophoblastic disease, a germ cell tumor, a head and neck cancer, a hemangiosarcoma, a histiosarcoma, an islet cell tumor, a kidney cancer (nephroblastoma, papillary renal cell carcinoma), a leukemia, a lipoma/benign lipomatous tumor, a liposarcoma/malignant lipomatous tumor, a liver cancer (hepatoblastoma, hepatocellular carcinoma), a lymphoma, a lung cancer, a mammary carcinoma, a mast cell tumor, a medulloblastoma, a melanoma, a meningioma, a multiple endocrine neoplasia, a multiple myeloma, a myelodysplastic syndrome, a neuroblastoma, a neuroendocrine tumor, an ovarian cancer, an osteosarcoma, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid cancer, a transitional cell carcinoma, and a uterine cancer (carcinoma of the cervix, endometrial carcinoma, and leiomyoma).

III. Methods Of Making Antibodies And Polypeptides

Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing mice, rats or rabbits with an immunogenic amount of cells, cell extracts, or protein preparations that contain canine B7-H3 or feline B7-H3. The immunogen can be, but is not limited to, primary cells, cultured cell lines, cancerous cells, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi. In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant).

In one embodiment, monoclonal antibodies that bind to B7-H3 are obtained by using host cells that over-express B7-H3 as an immunogen. Such cells include, by way of example and not by limitation, canine histiocytic sarcoma, hemangiosarcoma, malignant melanoma, mast cell tumor, osteosarcoma, tyroid carcinoma, transitional cell carcinoma, squamous cell carcinoma cancer cells and feline fibrosarcoma, mammary carcinoma and squamous cell carcinoma cancer cells.

To monitor the antibody response, a small biological sample (e.g., blood) may be obtained from the animal and tested for antibody titer against the immunogen. The spleen and/or several large lymph nodes can be removed and dissociated into single cells. If desired, the spleen cells may be screened (after removal of non-specifically adherent cells) by applying a cell suspension to a plate or to a well coated with the antigen. B-cells, expressing membrane-bound immunoglobulin specific for the antigen, will bind to the plate, and are not rinsed away with the rest of the suspension. Resulting B-cells, or all dissociated spleen cells, can then be fused with myeloma cells (e.g., X63-Ag8.653 and those from the Salk Institute, Cell Distribution Center, San Diego, Calif.). Polyethylene glycol (PEG) may be used to fuse spleen or lymphocytes with myeloma cells to form a hybridoma. The hybridoma is then cultured in a selective medium (e.g., hypoxanthine, aminopterin, thymidine medium, otherwise known as "HAT medium"). The resulting hybridomas are then plated by limiting dilution, and are assayed for the production of antibodies that bind specifically to the immunogen, using, for example, FACS (fluorescence activated cell sorting) or immunohistochemistry (IHC) screening. The selected monoclonal antibody-secreting hybridomas are then cultured either in vitro (e.g., in tissue culture bottles or hollow fiber reactors), or in vivo (e.g., as ascites in mice).

As another alternative to the cell fusion technique, Epstein-Barr Virus (EBV)-immortalized B cells may be used to produce monoclonal antibodies of the subject invention.

The hybridomas are expanded and subcloned, if desired, and supernatants are assayed for anti-immunogen activity by conventional assay procedures (e.g., FACS, IHC, radioimmunoassay, enzyme immunoassay, fluorescence immunoassay, etc.).

In another alternative, anti-B7-H3 monoclonal antibody and any other equivalent antibodies can be sequenced and produced recombinantly by any means known in the art. In one embodiment, anti-B7-H3 monoclonal antibody is sequenced and the polynucleotide sequence is then cloned into a vector for expression or propagation. The sequence encoding the antibody of interest may be maintained in a vector in a host cell and the host cell can then be expanded and frozen for future use.

The polynucleotide sequence of anti-B7-H3 monoclonal antibody and any other equivalent antibodies may be used for genetic manipulation to generate the bispecific molecules of the invention as well as a chimeric antibody, a humanized antibody, or a caninized antibody, to improve the affinity, or other characteristics of the antibody. The general principle in humanizing or caninizing an antibody involves retaining the basic sequence of the antigen-binding portion of the antibody, while swapping the non-human or non-canine remainder of the antibody with human antibody sequences or canine antibody sequences. There are four general steps to humanize or caninize a monoclonal antibody. These are: (1) determining the nucleotide and predicted amino acid sequence of the starting antibody light and heavy variable domains (2) designing the humanized antibody or caninized antibody, i.e., deciding which antibody framework region to use during the humanizing or caninizing process (3) the actual humanizing or caninizing methodologies/techniques and (4) the transfection and expression of the humanized antibody or caninized antibody. See, for example, U.S. Pat. Nos. 4,816,567; 5,807,715; 5,866,692; and 6,331,415.

A number of caninized antibody molecules comprising an antigen-binding site derived from a non-canine immunoglobulin have been described, including chimeric antibodies having rodent or modified rodent V regions and their associated complementarity determining regions (CDRs) fused to canine constant domains (see, for example, U.S. Pat. No. 7,261,890). These caninized molecules are designed to minimize unwanted immunological response toward rodent anti-canine antibody molecules, which limits the duration and effectiveness of therapeutic applications of those moieties in canine recipients.

Single chain variable region fragments ("scFv") may be made by linking light and/or heavy chain variable regions by using a short linking peptide. Bird et al. (1988) ("*Single-Chain Antigen-Binding Proteins*," Science 242:423-426) describes example of linking peptides which bridge approximately 3.5 nm between the carboxy terminus of one variable region and the amino terminus of the other variable region. Linkers of other sequences have been designed and used (Bird et al. (1988) "*Single-Chain Antigen-Binding Proteins*," Science 242:423-426). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention includes modifications to the bispecific molecules of the invention that do not significantly affect their properties and variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention also encompasses fusion proteins comprising one or more fragments or regions from the polypeptides and antibodies of this invention. In one embodiment, a fusion polypeptide is provided that comprises at least 10 contiguous amino acids of variable light chain region and at least 10 amino acids of variable heavy chain region. In another embodiment, the fusion polypeptide contains a heterologous immunoglobulin constant region. In another embodiment, the fusion polypeptide contains a light chain variable region and a heavy chain variable region of an antibody produced from a publicly-deposited hybridoma. For purposes of this invention, an antibody fusion protein contains one or more polypeptide domains that specifically bind to B7-H3 and another amino acid sequence to which it is not attached in the native molecule, for example, a heterologous sequence or a homologous sequence from another region.

An anti-B7-H3 polypeptide, and other B7-H3 agonists, antagonists and modulators can be created by methods known in the art, for example, synthetically or recombinantly. One method of producing B7-H3 peptide agonists, antagonists and modulators involves chemical synthesis of the polypeptide, followed by treatment under oxidizing conditions appropriate to obtain the native conformation, that is, the correct disulfide bond linkages. This can be accomplished using methodologies well known to those skilled in the art (see, e.g., Kelley, R. F. et al. (1990) In: Genetic Engineering Principles and Methods, Setlow, J. K. Ed., Plenum Press, N.Y., vol. 12, pp 1-19; Stewart, J. M et al. (1984) Solid Phase Peptide Synthesis, Pierce Chemical Co., Rockford, Ill.; see also U.S. Pat. Nos. 4,105,603; 3,972,859; 3,842,067; and 3,862,925).

Polypeptides of the invention may be conveniently prepared using solid phase peptide synthesis (Merrifield, B. (1986) "Solid Phase Synthesis," Science 232(4748):341-347; Houghten, R. A. (1985) "*General Method For The Rapid Solid-Phase Synthesis Of Large Numbers Of Peptides: Specificity Of Antigen-Antibody Interaction At The Level Of Individual Amino Acids*," Proc. Natl. Acad. Sci. (U.S.A.) 82(15):5131-5135; Ganesan, A. (2006) "*Solid-Phase Synthesis In The Twenty-First Century*," Mini Rev. Med. Chem. 6(1):3-10).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Suitable methods for expressing antibodies recombinantly in plants or milk have been disclosed (see, for example, Peeters et al. (2001) "*Production Of Antibodies And Antibody Fragments In Plants*," Vaccine 19:2756; Lonberg, N. et al. (1995) "*Human Antibodies From Transgenic Mice*," Int. Rev. Immunol 13:65-93; and Pollock et al. (1999) "*Transgenic Milk As A Method For The Production Of Recombinant Antibodies*," J. Immunol. Methods 231:147-157). Suitable methods for making derivatives of antibodies, e.g., humanized, single chain, etc. are known in the art. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology*," Annu. Rev. Immunol 12.433-455).

The antibodies or protein of interest may be subjected to sequencing by Edman degradation, which is well known to those of skill in the art. The peptide information generated from mass spectrometry or Edman degradation can be used to design probes or primers that are used to clone the protein of interest.

An alternative method of cloning the protein of interest is by "panning" using purified B7-H3 or portions thereof for cells expressing the antibody or protein of interest. The amino acid sequence of human B7-H3 is (SEQ ID NO:1):

```
MLRRRGSPGM GVHVGAALGA LWFCLTGALE VQVPEDPVVA
LVGTDATLCC SFSPEPGFSL AQLNLIWQLT DTKQLVHSFA
EGQDQGSAYA NRTALFPDLL AQGNASLRLQ RVRVADEGSF
TCFVSIRDFG SAAVSLQVAA PYSKPSMTLE PNKDLRPGDT
VTITCSSYRG YPEAEVFWQD GQGVPLTGNV TTSQMANEQG
LFDVHSVLRV VLGANGTYSC LVRNPVLQQD AHGSVTITGQ
PMTFPPEALW VTVGLSVCLI ALLVALAFVC WRKIKQSCEE
ENAGAEDQDG EGEGSKTALQ PLKHSDSKED DGQEIA
```

The cDNA sequence encoding human B7-H3 is (SEQ ID NO:2):

```
atgctgcgtc ggcggggcag ccctggcatg ggtgtgcatg
tgggtgcagc cctgggagca ctgtggttct gcctcacagg
```

-continued

```
agccctggag gtccaggtcc ctgaagaccc agtggtggca
ctggtgggca ccgatgccac cctgtgctgc tccttctccc
ctgagcctgg cttcagcctg gcacagctca acctcatctg
gcagctgaca gataccaaac agctggtgca cagctttgct
gagggccagg accagggcag cgcctatgcc aaccgcacgg
ccctcttccc ggacctgctg gcacagggca acgcatccct
gaggctgcag cgcgtgcgtg tggcggacga gggcagcttc
acctgcttcg tgagcatccg ggatttcggc agcgctgccg
tcagcctgca ggtggccgct ccctactcga agcccagcat
gaccctggag cccaacaagg acctgcggcc aggggacacg
gtgaccatca cgtgctccag ctaccggggc taccctgagg
ctgaggtgtt ctggcaggat gggcagggtg tgcccctgac
tggcaacgtg accacgtcgc agatggccaa cgagcagggc
ttgtttgatg tgcacagcgt cctgcgggtg gtgctgggtg
cgaatggcac ctacagctgc ctggtgcgca accccgtgct
gcagcaggat gcgcacggct ctgtcaccat cacagggcag
cctatgacat tcccccaga ggccctgtgg gtgaccgtgg
ggctgtctgt ctgtctcatt gcactgctgg tggccctggc
tttcgtgtgc tggagaaaga tcaaacagag ctgtgaggag
gagaatgcag gagctgagga ccaggatggg gagggagaag
gctccaagac agccctgcag cctctgaaac actctgacag
caaagaagat gatggacaag aaatagcc
```

The amino acid sequence of canine B7-H3 is (SEQ ID NO:3):

```
MLRRASADVG VRLAAALAAL WFCITGAVEV QVPEDPVVAL
VGTDATLRCS FLPEPGFSLA QLNLIWQLTD TKQLVHSFAE
GRDQGSAYAN RTALFPDLLA QGNASLRLQR VRVADEGSFT
CFVSIRDFGS AAVSLQVAAP YSKPSMTLEP SKDLRPGDTV
TITCSSYRGY PEAEVLWQDG QGAPLTGNVT TSQMANEQGL
FDVRSVLRVV LGANGTYSCL VRNPVLQQDA RGSVTITPHR
SPTGAVEVQV PEDPVVALVG TDATLCCSFS PEPGFSLAQL
NLIWQLTDTK QLVHSFAEGR DQGSAYANRT ALFPDLLAQG
NASLRLQRVR VADEGSFTCF VSIRDFGSAA VSLQVAAPYS
KPSMTLEPSK DLRPGDTVTI TCSSYRGYPE AEVLWQDGQG
APLTGNVTTS QMANEQGLFD VRSVLRVVLG ANGTYSCLVR
NPVLQQDAHG SVTITGQPMT FPPEALWVTV GLSVCLVALL
VALAFVCWRK IKQSCEEENA GAEDQDGDGE GSKTALRPLK
HSESKEDDGQ EIA
```

The cDNA encoding canine B7-H3 is (SEQ ID NO:4):

```
atgctgcgtc gggccagcgc ggatgtgggt gtgcgtttgg
ccgcggccct ggcagcgctg tggttctgca tcacaggcgc
cgtggaggtc caggtgcccg aggaccccgt ggtggccctg
gtgggcaccg atgccaccct gcgctgctcc ttcttgcccg
aacccggctt cagcctggcg cagctcaacc tcatctggca
gctgacggac accaagcagc tggtgcacag cttcgccgag
ggccgggacc agggcagcgc gtacgccaac cgcacggccc
tcttccccga cctgctggcc cagggcaatg cgtccctgcg
gctgcagcgc gtgcgcgtgg ccgatgaggg cagcttcacc
tgcttcgtga gcatccggga cttcggcagc gccgcggtca
gcctgcaggt ggcagctccc tactcgaagc ccagcatgac
cctggagccc agcaaggacc tgcggcccgg ggacacggtg
accatcacgt gctccagcta ccggggctat ccggaggccg
aggtgctctg gcaggatggg cagggcgcac ccctgaccgg
caacgtgacc acatcgcaga tggccaacga gcagggcctg
ttcgacgtgc gcagtgtcct gcgggtggtg ctgggcgcta
acggcaccta cagctgcctg gtgcgcaacc cggtgctgca
gcaggacgcc cgtggctccg tcaccatcac gccccacaga
agtcccacag gcgccgtgga ggtccaggtg cccgaggacc
ccgtggtggc cctggtgggc accgatgcca ccctgtgctg
ctccttctcg cctgaacccg gcttcagcct ggcacagctc
aacctcatct ggcagctgac ggacaccaag cagctggtgc
acagcttcgc cgagggccgg gaccagggca gcgcgtacgc
caaccgcacg gccctcttcc ccgacctgct ggcccagggc
aatgcgtccc tgcggctgca gcgcgtgcgc gtggccgatg
agggcagctt cacctgcttc gtgagcatcc gggacttcgg
cagcgccgcg gtcagcctgc aagtggcagc tccctactcg
aagcccagca tgaccctgga gcccagcaag gacctgcggc
ccggggacac ggtgaccatc acgtgctcca gctaccgggg
ctatccggag gccgaggtgc tctggcagga tgggcagggc
gcacccctga ctggcaacgt gaccacatcg cagatggcca
acgagcaggg cctattcgac gtgcgcagtg tcctgcgggt
ggtgctgggc gctaacggca cctacagctg cctggtgcgc
aacccggtgc tgcagcagga cgctcatggc tctgtcacca
tcacagggca gcccatgaca ttcccccctg aggccctgtg
ggtgaccgtg gggctctctg tatgtcttgt cgcactgctg
gtggccctgg ctttcgtgtg ctggaggaag atcaagcaga
gctgtgagga ggagaatgca ggtgctgagg accaggatgg
```

-continued

```
ggatggagag ggatccaaga ccgccctgcg gcctctgaaa
cactctgaaa gcaaagaaga tgatggacaa gaaatagcc
```

The amino acid sequence of feline B7-H3 is (SEQ ID NO:5):

```
ALEVQVPEDP VVALVGTDAT LRCSFSPEPD FSLAQLNLIW
QLTDTKQLVH SFSEGRDQGS AYANRTALFP DLLAQGNASL
RLQRVRVADE GSFTCFVSIR DFGSAAVSLQ VAAPYSKPSM
TLEPNKDLRP GDMVTITCSS YRGYPEAEVF WQDGQGAPLT
GNVTTSQMAN EQGLFDVRSV LRVVLGANGT YSCLVRNPVL
QQDAHGSVTI TGQPMTFPPE ALWVTVGLSV CLVALLVALA
FVCWRKIKQS CEEENAGAED QDGDGEGSKT
```

The cDNA sequence of feline B7-H3 is (SEQ ID NO:6):

```
GCACTGGAGG TCCAGGTCCC CGAAGACCCC GTGGTGGCCC
TGGTGGGCAC CGATGCCACC CTGCGCTGCT CCTTCTCACC
CGAGCCCGAC TTCAGCCTGG CGCAGCTCAA CCTCATCTGG
CAGCTGACGG ACACCAAACA GCTGGTGCAC AGCTTCTCCG
AGGGCCGGGA CCAGGGCAGC GCCTATGCCA ACCGCACCGC
GCTCTTCCCC GACCTGCTGG CGCAGGGCAA CGCGTCCCTG
CGGCTGCAGC GAGTGCGGGT AGCTGATGAG GGCAGCTTCA
CCTGCTTTGT GAGCATCCGG GACTTCGGCA GCGCTGCAGT
CAGCCTGCAG GTGGCGGCTC CTTACTCGAA GCCCAGCATG
ACCCTGGAGC CCAACAAGGA CCTGCGGCCC GGGGACATGG
TGACCATCAC GTGCTCCAGC TACCGGGGCT ACCCGGAGGC
CGAGGTGTTC TGGCAGGACG GGCAGGGTGC GCCCCTGACC
GGCAACGTGA CCACGTCGCA GATGGCCAAT GAGCAGGGCT
TGTTCGACGT GCGGAGTGTC CTGAGGGTGG TGCTGGGCGC
CAATGGCACC TACAGCTGCC TGGTGCGCAA CCCTGTGCTG
CAGCAGGACG CTCATGGCTC CGTCACCATC ACAGGGCAGC
CCATGACATT CCCTCCCGAG GCCCTGTGGG TGACCGTGGG
GCTCTCTGTC TGCCTTGTCG CCCTGCTGGT GGCCCTGGCC
TTCGTGTGCT GGAGAAAGAT CAAGCAGAGC TGTGAGGAGG
AGAATGCAGG TGCCGAGGAC CAGGACGGGG ATGGAGAAGG
ATCCAAAACA
```

The "panning" procedure may be conducted by obtaining a cDNA library from tissues or cells that express B7-H3, over-expressing the cDNAs in a second cell type, and screening the transfected cells of the second cell type for a specific binding to B7-H3. Detailed descriptions of the methods used in cloning mammalian genes coding for cell surface proteins by "panning" can be found in the art (see, for example, Aruffo, A. et al. (1987) "*Molecular Cloning Of A CD28 cDNA By A High-Efficiency COS Cell Expression System*," Proc. Natl. Acad. Sci. (U.S.A.) 84:8573-8577 and Stephan, J. et al. (1999) "*Selective Cloning Of Cell Surface*

*Proteins Involved In Organ Development: Epithelial Glycoprotein Is Involved In Normal Epithelial Differentiation*," Endocrinol. 140:5841-5854).

cDNAs encoding anti-B7-H3 antibodies, and other B7-H3 peptide agonists, antagonists and modulators can be obtained by reverse transcribing the mRNAs from a particular cell type according to standard methods in the art. Specifically, mRNA can be isolated using various lytic enzymes or chemical solutions according to the procedures set forth in Sambrook et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antibody or protein of interest in cells of a second type. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, even more preferably 20-fold higher than that of the corresponding endogenous antibody or protein of interest, if present, in the host cells. Screening the host cells for a specific binding to B7-H3 is effected by an immunoassay or FACS. A cell over-expressing the antibody or protein of interest can be identified.

Various techniques are also available which may now be employed to produce mutant B7-H3 peptide agonists, antagonists, and modulators which encodes for additions, deletions, or changes in amino acid sequence of the resultant protein relative to the parent B7-H3 peptide agonist, antagonist or modulator molecule.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an anti-B7-H3 polypeptide could be produced by an automated polypeptide synthesizer employing the solid phase method.

IV. Methods For Screening Polypeptides And Monoclonal Antibodies

Several methods may be used to screen polypeptides and monoclonal antibodies that bind to B7-H3. It is understood that "binding" refers to biologically or immunologically relevant specific binding, and does not refer to non-specific binding that may occur, for example, when an immunoglobulin is used at a very high concentration against a non-specific target. In one embodiment, monoclonal antibodies are screened for binding to B7-H3 using standard screening techniques. In this manner, anti-B7-H3 monoclonal antibody was obtained. The preferred hybridomas of the present invention are those that produce antibodies BRCA69D, BRCA84D or PRCA157 (WO 2011/109400).

Additional monoclonal antibodies that bind to B7-H3 may be identified. For this purpose, monoclonal antibodies are screened for their differential ability to bind to cancerous tissues but not to non-cancerous cells. In one embodiment, monoclonal antibodies which bind to B7-H3 and that are also cross-reactive to human cancerous cells or tissues, but not to normal cells or tissues to the same degree, are selected. One method that may be employed for screening is immunohistochemistry (IHC). Standard immunohistochemical techniques are known to those of average skill in the art. See, for example, ANIMAL CELL CULTURE METHODS (J. P. Mather and D. Barnes, eds., Academic Press, NY, Vol. 57, Ch. 18 and 19, pp. 314-350, 1998). Biological samples (e.g., tissues) may be obtained from biopsies, autopsies, or necropsies. To ascertain if B7-H3 is present only on cancerous cells, anti-B7-H3 antibodies may be used to detect the presence of B7-H3 on tissues from individuals with cancer while other non-cancerous tissues from the individual suffering from cancer or tissues from individuals without cancer are used as a control. The tissue can be embedded in a solid or semi-solid substance that prevents damage during freezing (e.g., agarose gel or OCT) and then sectioned for staining Cancers from different organs and at different grades can be used to screen monoclonal antibodies. Examples of tissues that may be used for screening purposes include but are not limited to ovary, breast, lung, prostate, colon, kidney, skin, thyroid, brain, heart, liver, stomach, nerve, blood vessels, bone, upper digestive tract, and pancreas. Examples of different cancer types that may be used for screening purposes include, but are not limited to, carcinomas, adenocarcinomas, sarcomas, adenosarcomas, lymphomas, and leukemias.

In yet another alternative, cancerous cells lines such as canine CF21 and CF32 and human HMEC (BioWhittaker CC-2251), HUVEC (Primary endothelial cells), BT-474 (ATCC#HTB-20), MCF7 (ATCC#HTB22), MDA-MB-175-VII (ATCC#HB-25), MDA-MB-361 (ATCC#HB-27), SKBR3 (ATCC#HTB-30), A549 (ATCC#CCL-185), Calu-3 (ATCC#HTB-55), SKMES-I (ATCC#HTB-58), ES-2 (ATCC#CRL-1978), SKOV3 (ATCC#HTB-77), Panc-1 (ATCC#CRL-1469), AsPC-I (ATCC#CRL-1682), HPAF-II (ATCC#CRL-1997), Hs700T (ATCC#HTB-174), Colo205 (ATCC#CCL-222), HT-29 (ATCC#HTB-38), SW480 (ATCC#CCL-228), SW948 (ATCC#CCL-237), 293 (ATCC #CRL-1573), 786-O (ATCC#CRL-1932), A498 (ATCC#HTB-44), Caki-2 (ATCC#HTB-47), COS-7 (ATCC#CRL-1651), RL-65 (ATCC #CRL-10345), SV-T2 (ATCC#CCL-163.1), 22RV1 (ATCC#CRL-2505), DU145 (ATCC#HTB-81), LNCaP (ATCC#CRL-1740), PC-3 (ATCC#CRL-1435), HT29 (ATCC#HTB-38), Hs746T (ATCC#HTB-135), NCI-N87 (ATCC#CRL-5822) and normal cells from their respective tissues may be used to screen for monoclonal antibodies which are specific for cancerous tissue. Primary, or low passage, cell cultures derived from normal tissues from different organs, including but not limited to, kidney, ovary, breast, lung, prostate, colon, kidney, skin, thyroid, aortic smooth muscle, and endothelial cells can be used as negative controls. The cancerous or non-cancerous cells can be grown on glass slides or coverslips, or on plastic surfaces, or prepared in a CellArray™ device, as described in WO 01/43869, and screened for the binding of antibody using IHC as described above for tissues. Alternatively, cells may be removed from the growth surface using non-proteolytic means and spun into a pellet, which is then embedded and treated as tissues for IHC analysis as described above. Cells may be inoculated into immunodeficient animals, a tumor allowed to grow, and then this tumor may be harvested, embedded, and used as a tissue source for IHC analysis. In another alternative, single cells may be screened by incubating with the primary antibody, a secondary "reporter" antibody linked to a fluorescent molecule and then analyzed using a fluorescent activated cell-sorting (FACS) machine.

Any of several different detection systems may be utilized to detect binding of antibodies to tissue section. Typically, immunohistochemistry involves the binding of a primary antibody to the tissue and then a secondary antibody reactive against the species from the primary antibody was generated and conjugated to a detectable marker (e.g., horseradish peroxidase, HRP, or diaminobenzedine, DAB). One alternative method that may be used is polyclonal mirror image complementary antibodies or polyMICA™ (polyclonal Mirror Image Complementary Antibodies; The Binding Site Limited, Birmingham, UK; Mangham, D. C. et al. (1999) "*A Novel Immunohistochemical Detection System Using Mirror Image Complementary Antibodies* (*MICA*)," Histopathology 35(2):129-33). The PolyMICA™ technique can be used to test binding of primary antibodies (e.g., anti-B7-H3 antibodies) to normal and cancerous tissue. Several kinds of polyMICA™ Detection kits are commercially available: Product No. HK004.D is a polyMICA™ Detection kit which uses DAB chromagen; Product No. HK004.A is a polyMICA™ Detection kit which uses AEC chromagen. Alternatively, the primary antibody may be directly labeled with the detectable marker.

The first step in IHC screening to select for an appropriate antibody is the binding of primary antibodies raised in mice (e.g., anti-B7-H3 antibodies) to one or more immunogens (e.g., cells or tissue samples). In one embodiment, the tissue sample is sections of frozen tissue from different organs. The cells or tissue samples can be either cancerous or non-cancerous.

Frozen tissues can be prepared, sectioned, with or without fixation, and IHC performed by any of a number of methods known to one familiar with the art (see, for example, Stephan et al. (1999) "*Distribution And Function Of The Adhesion Molecule BEN During Rat Development*," Dev. Biol. 212:264-277 and Stephan et al. (1999) "*Selective Cloning Of Cell Surface Proteins Involved In Organ Development Epithelial Glycoprotein Is Involved In Normal Epithelial Differentiation*," Endocrinology 140:5841-5854).

V. Methods Of Characterizing Anti-B7-H3 Antibodies

Any of several methods can be used to characterize anti-B7-H3 antibodies. One method is to identify the epitope to which it binds. Epitope mapping is commercially available from various sources, for example, Pepscan Systems (Lelystad, The Netherlands). Epitope mapping can be used to determine the sequence to which an anti-B7-H3 antibody binds. The epitope can be a linear epitope, i.e., contained in a single stretch of amino acids, or a conformational epitope formed by a three-dimensional interaction of amino acids that may not necessarily be contained in a single stretch.

Peptides of varying lengths (e.g., preferably at least 4-6 amino acids long) can be isolated or synthesized (e.g., chemically or recombinantly) and used for binding assays with anti-B7-H3 antibody. The epitope to which anti-B7-H3 antibody binds can be determined in a systematic screening by using overlapping peptides derived from the extracellular sequence and determining binding by anti-B7-H3 antibody.

Yet another method that can be used to characterize an anti-B7-H3 antibody is to use competition assays with other antibodies known to bind to the same antigen, i.e., B7-H3 to determine if anti-B7-H3 antibodies binds to the same epitope as other antibodies. Examples of commercially available antibodies to B7-H3 may be available and may be identified using the binding assays taught herein. Competition assays are well known to those of skill in the art, and such procedures and illustrative data are detailed further in the Examples. Anti-B7-H3 antibodies can be further characterized by the tissues, type of cancer or type of tumor to which they bind.

As discussed above, a central aspect of the molecules of the present invention relates to their ability to bind canine B7-H3 and/or feline B7-H3. Surprisingly, such antibodies may be readily identified by screening among human B7-H3 reactive antibodies for those that exhibit the ability to additionally bind to the B7-H3 of a desired companion animal. Non-limiting examples of such antibodies include BRCA69D, BRCA84D and PRCA157 (WO 2011/109400)

VI. Methods Of Diagnosing Cancer Using Anti-b7-h3 Antibodies And B7-H3 Modulators Monoclonal antibodies to B7-H3 made by the methods disclosed herein may be used to identify the presence or absence of cancerous cells in a variety of companion animal tissues, including but not limited to, blood, ovary, breast, lung, prostate, colon, kidney, pancreas, skin, thyroid, brain, heart, liver, stomach, nerve, blood vessels, bone, and upper digestive tract, for purposes of diagnosis. Monoclonal antibodies to B7-H3 made by the methods disclosed herein may also be used to identify the presence or absence of cancerous cells, or the level thereof, which are circulating in blood after their release from a solid tumor. Such circulating antigen may be an intact B7-H3 antigen, or a fragment thereof that retains the ability to be detected according to the methods taught herein. Such detection may be effected by FACS analysis using standard methods commonly used in the art. Since such antibodies are capable of binding to the B7-H3 of a canine and/or feline animal, they may be used to diagnose the presence of a B7-H3-associated cancer in such animals.

In a preferred embodiment of the diagnostic methods of this invention, the antibody bears a detectable label. Examples of labels that may be used include a radioactive agent or a fluorophore, such as phycoerythrin or fluorescein isothiocyanate (also known as fluoroisothiocyanate or FITC).

One method of using the antibodies for diagnosis is in vivo tumor imaging by linking the antibody to a radioactive or radio-opaque agent, administering the antibody to the individual and using an x-ray or other imaging machine to visualize the localization of the labeled antibody at the surface of cancer cells expressing the antigen. The antibody is administered at a concentration that promotes binding at physiological conditions.

In vitro techniques for detection of B7-H3 are routine in the art and include enzyme linked immunosorbent assays (ELISAs), immunoprecipitations, immunofluorescence, enzyme immunoassay (EIA), radioimmunoassay (RIA), and Western blot analysis.

In aspects of this invention, methods of radioimaging of tumors or neoplasms, or of measuring the effectiveness of a method of treatment with a radiolabeled antibody, comprising the step of administering a radiolabeled, tumor-specific antibody to an individual following the practice of this invention. The radiolabeled antibody may be a monoclonal or polyclonal antibody comprising a radiolabel, preferably selected from the group consisting of Technetium-99m, Indium-111, Iodine-131, Rhenium-186, Rhenium-188, Samarium-153, Lutetium-177, Copper-64, Scandium-47, Yttrium-90. Monoclonal antibodies labeled with therapeutic radionuclides such as Iodine-131, Rhenium-188, Holmium-166, Samarium-153 and Scandium-47, which do not compromise the immunoreactivity of antibodies and are not broken down in vivo, are especially preferred. The person skilled in the art will appreciate that other radioactive isotopes are known, and may be suitable for specific applications. The radioimaging may be conducted using Single Photon Emission Computer Tomography (SPECT), Position Emission Tomography (PET), Computer Tomography (CT) or Magnetic Resonance Imaging (MRI). Correlative imaging, which permits greater anatomical definition of location of metastases located by radioimmunoimaging, is also contemplated.

In other methods, the cancerous tissues or cells are removed from the companion animal and prepared for immunohistochemistry by methods well known in the art (e.g., embedding in a freezing compound, freezing and sectioning, with or without fixation; fixation and paraffin embedding with or without various methods of antigen retrieval and counterstaining). The monoclonal antibodies may also be used to identify cancerous tissues or cells at different stages of development. The antibodies may also be used to determine which individuals' tumors or cells express the antigen on their surface at a pre-determined level and are thus candidates for immunotherapy using antibodies directed against said antigen. The antibodies may recognize both primary and metastasizing cancers of the blood, ovary, breast, lung, prostate, colon, kidney, pancreas, skin, thyroid, brain, heart, liver, stomach, nerve, blood vessels, bone, and upper digestive tract that express B7-H3. As used herein, detection may include qualitative and/or quantitative detection and may include comparing the level measured to a normal cell for an increased level of expression of B7-H3 in cancerous cells.

The invention also provides methods of aiding diagnosis of cancer (such as but not limited to blood, ovary, breast, lung, prostate, colon, kidney, pancreas, skin, thyroid, brain, heart, liver, stomach, nerve, blood vessels, bone, and upper digestive tract cancers) in a companion animal using the anti-B7-H3 antibodies of the present invention, or any of the derivatives. As used herein, methods for "aiding diagnosis" means that these methods assist in making a clinical determination regarding the classification, or nature, of cancer, and may or may not be conclusive with respect to the definitive diagnosis. Accordingly, a method of aiding diagnosis of a companion animal cancer can comprise the step of detecting the level of B7-H3 in a biological sample from the animal and/or determining the level of B7-H3 expression in the sample. Antibodies recognizing the antigen or a portion thereof may also be used to create diagnostic immunoassays for detecting canine B7-H3 antigen or feline B7-H3 antigen of such animals released or secreted from living or dying cancer cells in bodily fluids, including but not limited to, blood, saliva, urine, pulmonary fluid, or ascites fluid.

Not all cells in a particular tumor of interest will express B7-H3, and cancerous cells or tissues in other tissues may express B7-H3, thus a companion animal should be screened for the presence or absence of B7-H3 on cancerous cells or tissues to determine the usefulness of immunotherapy in the animals. The anti-B7-H3 molecules disclosed herein may be used to determine whether a companion animal diagnosed with cancer may be deemed a candidate for immunotherapy directed against B7-H3. In one embodiment, a cancerous tumor or a biopsy sample may be tested for expression of B7-H3, using the anti-B7-H3 molecules of the present invention. A companion animal whose cancer cells express B7-H3 is a suitable candidate for immunotherapy using the anti-B7-H3 molecules, and particularly the bispecific molecules, of the present invention. Staining with such anti-B7-H3 molecules may also be used to distinguish cancerous tissues from normal tissues in the companion animal.

Methods of using such anti-B7-H3 antibodies for diagnostic purposes are useful both before and after provision of any form of anti-cancer treatment, e.g., chemotherapy or radiation therapy, to determine which tumors are most likely to respond to a given treatment, to assess prognosis of the disease, to assess tumor subtype or origin of metastatic disease, and to assess the progression of the disease or its response to treatment.

Monoclonal antibodies to B7-H3 made by the methods disclosed herein may be used to identify the presence or absence of cancer stem cells in a variety of tissues. Cancer stem cells (CSCs) have been hypothesized to play a role in tumor growth and metastasis (Ghotra, V. P. et al. (2009) "*The Cancer Stem Cell Microenvironment And Anti-Cancer Therapy*," Int. J. Radiat. Biol. 85(11):955-962; Gupta, P. B. et al. (2009) "*Cancer Stem Cells: Mirage Or Reality?*" Nat. Med. 15(9):1010-1012; Lawson, J. C. et al. (2009) "*Cancer Stem Cells In Breast Cancer And Metastasis*," Breast Cancer Res. Treat. 118(2):241-254; Hermann, P. C. et al. (2009) "*Pancreatic Cancer Stem Cells—Insights And Perspectives*," Expert Opin. Biol. Ther. 9(10):1271-1278; Schatton, T. et al. (2009) "*Identification And Targeting Of Cancer Stem Cells*," Bioessays 31(10):1038-1049; Mittal, S. et al. (2009) "*Cancer Stem Cells The Other Face Of Janus*," Amer. J. Med. Sci. 338(2):107-112; Alison, M. R. et al. (2009) "*Stem Cells And Lung Cancer: Future Therapeutic Targets*?" Expert Opin. Biol. Ther. 9(9):1127-1141; Charafe-Jauffret, E. et al. (2009) "*Breast Cancer Stem Cells: Tools And Models To Rely On*," BMC Cancer 9:202; Scopelliti, A. et al. (2009) "*Therapeutic Implications Of Cancer Initiating Cells*," Expert Opin. Biol. Ther. 9(8):1005-1016; PCT Publication WO 2008/091908). Under this hypothesis, the CSCs provide a small, distinct subset of cells within each tumor that are capable of indefinite self-renewal and of developing into the more adult tumor cell(s) that are relatively limited in replication capacity. It has been hypothesized that these cancer stem cells might be more resistant to chemotherapeutic agents, radiation or other toxic conditions, and thus, persist after clinical therapies and later grow into secondary tumors, metastases or be responsible for relapse. It has been suggested that CSCs can arise either from 'normal' tissue stem cells or from more differentiated tissue progenitor cells. While supporting data for this hypothesis is strong for hematopoietic stem and progenitor cells and hematopoietic tumors, less is known about solid tumors and their respective CSCs.

Cancer stem cells have several defining characteristics. Such characteristics are described in PCT Publication WO 2008/091908. Monoclonal antibodies to cell surface targets on cancer stem cells can be used to identify the presence or absence of cancer stem cells in a variety of tissues. Monoclonal antibodies to B7-H3 made by the methods disclosed herein may also be used to identify the presence or absence of cancer stem cells, or the level of cancer stem cells in a sample or tissue or in circulation after their release from a solid tumor. Such circulating antigen may be an intact B7-H3 antigen, or a fragment thereof that retains the ability to be detected according to the methods taught herein. Such detection may be effected by FACS analysis using standard methods commonly used in the art. In another embodiment, such detection may be effected by immunohistochemical analysis of tissue samples using standard methods commonly used in the art.

These uses can involve the formation of a complex between B7-H3 and an antibody that binds specifically to B7-H3 on cancer stem cells. Examples of such antibodies include but are not limited to those anti-B7-H3 monoclonal antibodies produced by the hybridomas BRCA84D, BRCA69D, and PRCA157. The formation of such a complex can be in vitro or in vivo.

Uses for anti-B7-H3 molecules described in this application also encompass the use of other B7-H3 agonists, antagonists and modulators as described herein for the use of identification and treatment of cancer stem cells. In such embodiments, anti-B7-H3 antibodies and other B7-H3 agonists, antagonists and modulators are used for identification, diagnosis or therapeutic treatment of cancer stem cells using similar methods described, and alterations within the scope of the ordinary skilled practitioner are made to tailor the method to the identification/diagnosis or treatment of cancer stem cells.

VII. Preferred Compositions Of The Present Invention

The present invention encompasses compositions, including pharmaceutical compositions, comprising the bispecific molecules of the invention, anti-B7-H3 antibodies, polypeptides derived from anti-B7-H3 antibodies, polynucleotides comprising sequence encoding anti-B7-H3 antibodies, and other agents as described herein.

The invention further provides for conjugates of any B7-H3 peptide agonist, antagonist or modulator, and additional chemical structures that support the intended function or functions of the particular B7-H3 peptide agonist, antagonist or modulator.

These conjugates include B7-H3 peptide agonists, antagonists or modulators covalently bound to a macromolecule such as any insoluble, solid support matrix used in the diagnostic, screening or purification procedures discussed herein. Suitable matrix materials include any substance that is chemically inert, has high porosity and has large numbers of functional groups capable of forming covalent linkages with peptide ligands. Examples of matrix materials and procedures for preparation of matrix-ligand conjugates are described in Dean et al. (Eds) Affinity Chromatography: A Practical Approach, IRL Press (1985); Lowe, "*An Introduction to Affinity Chromatography*", in Work et al. (eds) Laboratory Techniques in Biochemistry and Molecular Biology, Vol. 7, Part II, North-Holland (1979); Porath et al., "*Biospecific Affinity Chromatography*", in Neurath, H. et al. (eds), The Proteins, 3rd ed., Vol. 1, pp. 95-178 (1975); and Schott, H. Affinity Chromatography, Macel Dekker, Inc. NY (1984).

Also provided herein are conjugates of B7-H3 peptide agonist, antagonist or modulator and any reporter moiety used in the diagnostic procedures discussed herein. The B7-H3 peptide agonist, antagonist or modulator agents, polypeptides and proteins of this invention, including anti-B7-H3 antibodies, are further identified and characterized by an ability to specifically bind to B7-H3 molecules that are expressed on the surfaces of human and companion animal cancer cells, and optionally any (one or more) of the following criteria:

(a) an ability to competitively inhibits preferential binding of a known anti-B7-H3 antibody to B7-H3, including the ability to preferentially bind to the same B7-H3 epitope to which the original antibody preferentially binds;

(b) an ability to bind to a portion of B7-H3 that is exposed on the surfaces of living canine or feline animal cells in vitro or in vivo;

(d) an ability to bind to a portion of B7-H3 that is exposed on the surface of living canine or feline animal cancer cells;

(e) an ability to deliver a chemotherapeutic agent to canine or feline animal cancerous cells expressing B7-H3 on their surface; and/or (f) an ability to deliver a therapeutic agent or detectable marker into canine or feline animal cancer cells expressing B7-H3 on their surface.

A preferred antibody of the invention will exhibit differential IHC staining of tumor tissue relative to normal, non-cancerous tissue.

In some embodiments, the bispecific molecules of the invention are made from an antibody that is produced by hybridoma BRCA84D, BRCA69D, or PRCA157, or progeny thereof.

BRCA84D, BRCA69D, and PRCA157 are the preferred B7-H3 antibodies of the present invention due to their cleaner normal tissue IHC profiles, stronger tumor/normal IHC differential, moderate to strong binding (BIACORE™)/IHC), reactivity to canine B7-H3 and feline B7-H3, cross-reactivity to human B7-H3 and cross-reactivity of cynomolgus monkey B7-H3.

The invention also provides polypeptides comprising an amino acid sequence of the antibodies of the invention. In some embodiments, the polypeptide comprises one or more of the light chain and/or heavy chain variable regions of the antibody. In some embodiments, the polypeptide comprises one or more of the light chain and/or heavy chain CDRs of the antibody. In some embodiments, the polypeptide comprises three CDRs of the light chain and/or heavy chain of the antibody. In some embodiments, the polypeptide comprises an amino acid sequence of the antibody that has any of the following: at least 5 contiguous amino acids of a sequence of the original antibody, at least 8 contiguous amino acids, at least about 10 contiguous amino acids, at least about 15 contiguous amino acids, at least about 20 contiguous amino acids, at least about 25 contiguous amino acids, at least about 30 contiguous amino acids, wherein at least 3 of the amino acids are from a variable region of the antibody. In one embodiment, the variable region is from a light chain of the original antibody. In another embodiment, the variable region is from a heavy chain of the antibody. In another embodiment, the 5 (or more) contiguous amino acids are from a complementarity-determining region (CDR) of the antibody.

The amino acid and encoding polynucleotide sequences of the variable light chain and variable heavy chain of BRCA84D, BRCA69D and PRCA157 are shown below along with the respective $CDR_1$, $CDR_2$ and $CDR_3$ domains of each such chain. Those of skill in the art will therefore be able to construct bispecific molecules having such CDRs, as well as antibodies and derivatives thereof, capable of binding to the epitopes recognized by BRCA84D, BRCA69D and PRCA157.

A. Sequences of BRCA84D (1) BRCA84D Light Chain Sequences

Amino Acid Sequence of BRCA84D Variable Light Chain (SEQ ID NO:7):

```
DIAMTQSQKF MSTSVGDRVS VTCKASQNVD TNVAWYQQKP
GQSPKALIYS ASYRYSGVPD RFTGSGSGTD FTLTINNVQS
EDLAEYFCQQ YNNYPFTFGS GTKLEIK
```

Polynucleotide Sequence Encoding BRCA84D Variable Light Chain (SEQ ID NO:8):

```
gacattgcga tgacccagtc tcaaaaattc atgtccacat
cagtaggaga cagggtcagc gtcacctgca aggccagtca
gaatgtggat actaatgtag cctggtatca acagaaacca
gggcaatctc ctaaagcact gatttactcg gcatcctacc
ggtacagtgg agtccctgat cgcttcacag gcagtggatc
tgggacagat ttcactctca ccatcaacaa tgtgcagtct
gaagacttgg cagagtattt ctgtcagcaa tataacaact
atccattcac gttcggctcg gggacaaagt tggaaataaa a
```

BRCA84D Variable Light Chain $CDR_1$ (SEQ ID NO:9): KASQNVDTNVA

Polynucleotide Sequence Encoding BRCA84D Variable Light Chain $CDR_1$ (SEQ ID NO:10): aaggccagtc agaatgtgga tactaatgta gcc BRCA84D Variable Light Chain $CDR_2$ (SEQ ID NO:11): SASYRYS Polynucleotide Sequence Encoding BRCA84D Variable Light Chain $CDR_2$ (SEQ ID NO:12): tcggcatcct accggtacag t BRCA84D Variable Light Chain $CDR_3$ (SEQ ID NO:13): QQYNNYPFT Polynucleotide Sequence Encoding BRCA84D Variable Light Chain $CDR_3$ (SEQ ID NO:14): cagcaatata acaactatcc attcacg (2) BRCA84D Heavy Chain Sequences Amino Acid Sequence of BRCA84D Variable Heavy Chain (SEQ ID NO:15):

```
DVQLVESGGG LVQPGGSRKL SCAASGFTFS SFGMHWVRQA
PEKGLEWVAY ISSDSSAIYY ADTVKGRFTI SRDNPKNTLF
LQMTSLRSED TAMYYCGRGR ENIYYGSRLD YWGQGTTLTV
SS
```

Polynucleotide Sequence Encoding BRCA84D Variable Heavy Chain (SEQ ID NO:16):

```
gatgtgcagc tggtggagtc tgggggaggc ttagtgcagc
ctggagggtc ccggaaactc tcctgtgcag cctctggatt
cactttcagt agctttggaa tgcactgggt tcgtcaggct
ccagagaagg ggctggagtg ggtcgcatac attagtagtg
acagtagtgc catctactat gcagacacag tgaagggccg
```

-continued

```
attcaccatc tccagagaca atcccaagaa caccctgttc
ctgcaaatga ccagtctaag gtctgaggac acggccatgt
attactgtgg aagagggagg gaaaacattt actacggtag
taggcttgac tactggggcc aaggcaccac tctcacagtc
tcctca
```

BRCA84D Variable Heavy Chain $CDR_1$ (SEQ ID NO:17): FGMH

Polynucleotide Sequence Encoding BRCA84D Variable Heavy Chain $CDR_1$ (SEQ ID NO:18): tttggaatgcac BRCA84D Variable Heavy Chain $CDR_2$ (SEQ ID NO:19): YISSDSSAIYYADTVK Polynucleotide Sequence Encoding BRCA84D Variable Heavy Chain $CDR_2$ (SEQ ID NO:20): tacattagta gtgacagtag tgccatctac tatgcagaca cagtgaag BRCA84D Variable Heavy Chain $CDR_3$ (SEQ ID NO:21): GRENIYYGSRLDY Polynucleotide Sequence Encoding BRCA84D Variable Heavy Chain $CDR_3$ (SEQ ID NO:22): gggagggaaa acatttacta cggtagtagg cttgactac B. Sequences of BRCA69D (1) BRCA69D Light Chain Sequences Amino Acid Sequence of BRCA69D Variable Light Chain (SEQ ID NO:23):

```
DIQMTQTTSS LSASLGDRVT ISCRASQDIS NYLNWYQQKP
DGTVKLLIYY TSRLHSGVPS RFSGSGSGTD YSLTIDNLEQ
EDIATYFCQQ GNTLPPTFGG GTKLEIK
```

Polynucleotide Sequence Encoding BRCA69D Variable Light Chain (SEQ ID NO:24):

```
gatatccaga tgacacagac tacatcctcc ctgtctgcct
ctctgggaga cagagtcacc atcagttgca gggcaagtca
ggacattagt aattatttaa actggtatca gcagaaacca
gatggaactg ttaaactcct gatctactac acatcacgat
tacactcagg agtcccatca aggttcagtg gcagtgggtc
tggaacagat tattctctca ccattgacaa cctggagcaa
gaagatattg ccacttactt ttgccaacag ggtaatacgc
ttcctccgac gttcggtgga ggcaccaaac tggaaatcaa a
```

BRCA69D Variable Light Chain $CDR_1$ (SEQ ID NO:25): RASQDISNYLN

Polynucleotide Sequence Encoding BRCA69D Variable Light Chain $CDR_1$ (SEQ ID NO:26): agggcaagtc aggacattag taattattta aac BRCA69D Variable Light Chain $CDR_2$ (SEQ ID NO:27): YTSRLHS Polynucleotide Sequence Encoding BRCA69D Variable Light Chain $CDR_2$ (SEQ ID NO:28): tacacatcac gattacactc a BRCA69D Variable Light Chain $CDR_3$ (SEQ ID NO:29): QQGNTLPPT Polynucleotide Sequence Encoding BRCA69D Variable Light Chain $CDR_3$ (SEQ ID NO:30): caacagggta atacgcttcc tccgacg (2) BRCA69D Heavy Chain Sequences Amino Acid Sequence of BRCA69D Variable Heavy Chain (SEQ ID NO:31):

```
QVQLQQSGAE LARPGASVKL SCKASGYTFT SYWMQWVKQR
PGQGLEWIGT IYPGDGDTRY TQKFKGKATL TADKSSSTAY
MQLSSLASED SAVYYCARRG IPRLWYFDVW GAGTTVTVSS
```

Polynucleotide Sequence Encoding BRCA69D Variable Heavy Chain (SEQ ID NO:32):

```
caggttcagc tccagcagtc tggggctgag ctggcaagac
ctggggcttc agtgaagttg tcctgcaagg cttctggcta
cacctttact agctactgga tgcagtgggt aaaacagagg
cctggacagg gtctggaatg gattgggact atttatcctg
gagatggtga tactaggtac actcagaagt tcaagggcaa
ggccacattg actgcagata aatcctccag cacagcctac
atgcaactca gcagcttggc atctgaggac tctgcggtct
attactgtgc aagaagaggg attccacggc tttggtactt
cgatgtctgg ggcgcaggga ccacggtcac cgtctcctca
```

BRCA69D Variable Heavy Chain $CDR_1$ (SEQ ID NO:33): SYWMQ

Polynucleotide Sequence Encoding BRCA69D Variable Heavy Chain $CDR_1$ (SEQ ID NO:34): agctactgga tgcag BRCA69D Variable Heavy Chain $CDR_2$ (SEQ ID NO:35): TIYPGDGDTR YTQKFKG Polynucleotide Sequence Encoding BRCA69D Variable Heavy Chain $CDR_2$ (SEQ ID NO:36): actatttatc ctggagatgg tgatactagg tacactcag aagttcaagg gc BRCA69D Variable Heavy Chain $CDR_3$ (SEQ ID NO:37): RGIPRLWYFD V Polynucleotide Sequence Encoding BRCA69D Variable Heavy Chain $CDR_3$ (SEQ ID NO:38): agagggattc cacggctttg gtacttcgat gtc C. Sequences of PRCA157

(1) PRCA157 Light Chain Sequences

Amino Acid Sequence of PRCA157 Variable Light Chain (SEQ ID NO:39):

```
DIQMTQSPAS LSVSVGETVT ITCRASESIY SYLAWYQQKQ
GKSPQLLVYN TKTLPEGVPS RFSGSGSGTQ FSLKINSLQP
EDFGRYYCQH HYGTPPWTFG GGTNLEIK
```

Polynucleotide Sequence Encoding PRCA157 Variable Light Chain (SEQ ID NO:40):

```
gacatccaga tgactcagtc tccagcctcc ctatctgtat
ctgtgggaga aactgtcacc attacatgtc gagcaagtga
gagtatttac agttatttag catggtatca gcagaaacag
ggaaaatctc ctcagctcct ggtctataat acaaaaacct
taccagaggg tgtgccatca aggttcagtg gcagtggatc
aggcacacag ttttctctga agatcaacag cctgcagcct
```

-continued

```
gaagattttg ggagatatta ctgtcaacat cattatggta
ctcctccgtg gacgttcggt ggaggcacca acctggaaat
caaa
```

PRCA157 Variable Light Chain $CDR_1$ (SEQ ID NO:41): RASESIYSYLA

Polynucleotide Sequence Encoding PRCA157 Variable Light Chain $CDR_1$ (SEQ ID NO:42): cgagcaagtg agagtattta cagttattta gca PRCA157 Variable Light Chain $CDR_2$ (SEQ ID NO:43): NTKTLPE Polynucleotide Sequence Encoding PRCA157 Variable Light Chain $CDR_2$ (SEQ ID NO:44): aatacaaaaa ccttaccaga g PRCA157 Variable Light Chain $CDR_3$ (SEQ ID NO:45): QHHYGTPPW Polynucleotide Sequence Encoding PRCA157 Variable Light Chain $CDR_3$ (SEQ ID NO:46): caacatcatt atggtactcc tccgtgg (2) PRCA157 Heavy Chain Sequences Amino Acid Sequence of PRCA157 Variable Heavy Chain (SEQ ID NO:47):

```
EVQQVESGGD LVKPGGSLKL SCAASGFTFS SYGMSWVRQT
PDKRLEWVAT INSGGSNTYY PDSLKGRFTI SRDNAKNTLY
LQMRSLKSED TAMYYCARHD GGAMDYWGQG TSVTVSS
```

Polynucleotide Sequence Encoding PRCA157 Variable Heavy Chain (SEQ ID NO:48):

```
gaggtgcagc aggtggagtc gggggggagac ttagtgaagc
ctggagggtc cctgaaactc tcctgtgcag cctctggatt
cactttcagt tcctatggca tgtcttgggt tcgccagact
ccagacaaga ggctggagtg ggtcgcaacc attaatagtg
gtggaagtaa cacctactat ccagacagtt tgaaggggcg
attcaccatc tccagagaca atgccaagaa caccctttac
ctgcaaatgc gcagtctgaa gtctgaggac acagccatgt
attactgtgc aagacatgac gggggagcta tggactactg
gggtcaagga acctcagtca ccgtctcctc a
```

PRCA157 Variable Heavy Chain $CDR_1$ (SEQ ID NO:49): SYGMS

Polynucleotide Sequence Encoding PRCA157 Variable Heavy Chain $CDR_1$ (SEQ ID NO:50): tcctatggca tgtct PRCA157 Variable Heavy Chain $CDR_2$ (SEQ ID NO:51): VATINSGGSN TYYPDSLKG Polynucleotide Sequence Encoding PRCA157 Variable Heavy Chain $CDR_2$ (SEQ ID NO:52): gtcgcaacca ttaatagtgg tggaagtaac acctactatc cagacagttt gaagggg PRCA157 Variable Heavy Chain $CDR_3$ (SEQ ID NO:53): HDGGAMDY Polynucleotide Sequence Encoding PRCA157 Variable Heavy Chain $CDR_3$ (SEQ ID NO:54): catgacgggg gagc-tatgga ctac D. Humanized Antibodies Monoclonal antibody BRCA84D was humanized in order to produce antibodies (generically designated herein as "hBRCA84D") offering improved human therapeutic potential. The sequences of the variable light chain, and the variable heavy chain, and their respective amino acid and polynucleotide sequences of a resulting humanized antibody (designated herein as "hBRCA84D-1") are provided below:

Humanized BRCA84D-1 Variable Light Chain (SEQ ID NO:55):

```
DIQLTQSPSF LSASVGDRVT ITCKASQNVD TNVAWYQQKP
GKAPKLLIYS ASYRYSGVPS RFSGSGSGTD FTLTISSLQP
EDFATYYCQQ YNNYPFTFGQ GTKLEIK
```

Polynucleotide Sequence Encoding Humanized BRCA84D-1 Variable Light Chain (SEQ ID NO:56):

```
gacatccagc tgacccagtc cccctccttc ctgtctgcct
ccgtgggcga cagagtgacc atcacatgca aggcctccca
gaacgtggac accaacgtgg cctggtatca gcagaagcct
ggcaaggccc ctaagctgct gatctactcc gcctcctacc
ggtactccgg cgtgccttcc aggttctccg gctccggctc
tggcaccgac ttcaccctga ccatctccag cctgcagcct
gaggacttcg ccacctacta ctgccagcag tacaacaact
accctttcac cttcggccag ggcaccaagc tggaaatcaa
g
```

Humanized BRCA84D-1 Variable Light Chain $CDR_1$ (SEQ ID NO:57): KASQNVDTNVA

Polynucleotide Sequence Encoding Humanized BRCA84D-1 Variable Light Chain $CDR_1$ (SEQ ID NO:58): aaggccagtc agaatgtgga tactaatgta gcc Humanized BRCA84D-1 Variable Light Chain $CDR_2$ (SEQ ID NO:59): SASYRYS Polynucleotide Sequence Encoding Humanized BRCA84D-1 Variable Light Chain $CDR_2$ (SEQ ID NO:60): tcggcatcct accggtacag t Humanized BRCA84D-1 Variable Light Chain $CDR_3$ (SEQ ID NO:61): QQYNNYPFT Polynucleotide Sequence Encoding Humanized BRCA84D-1 Variable Light Chain $CDR_3$ (SEQ ID NO:62): cagcaatata acaactatcc attcacg Amino Acid Sequence of Humanized BRCA84D-1 Variable Heavy Chain (SEQ ID NO:63):

```
EVQLVESGGG LVQPGGSLRL SCAASGFTFS SFGMHWVRQA
PGKGLEWVAY ISSDSSAIYY ADTVKGRFTI SRDNAKNSLY
LQMNSLRDED TAVYYCARGR ENIYYGSRLD YWGQGTTVTV
SS
```

Polynucleotide Sequence Encoding Humanized BRCA84D-1 Variable Heavy Chain (SEQ ID NO:64):

```
gaggtgcagc tggtcgagtc tggcggagga ctggtgcagc
ctggcggctc cctgagactg tcttgcgccg cctccggctt
caccttctcc agcttcggca tgcactgggt ccgccaggct
ccaggcaagg gactggaatg ggtggcctac atctcctccg
```

-continued

```
actcctccgc catctactac gccgacaccg tgaagggcag
gttcaccatc tcccgggaca acgccaagaa ctccctgtac
ctgcagatga actccctgcg ggacgaggac accgccgtgt
actactgcgc cagaggccgg gagaatatct actacggctc
ccggctggat tattggggcc agggcaccac cgtgaccgtg
tcctct
```

Humanized BRCA84D-1 Variable Heavy Chain $CDR_1$ (SEQ ID NO:65): FGMH

Polynucleotide Sequence Encoding Humanized BRCA84D-1 Variable Heavy Chain $CDR_1$ (SEQ ID NO:66): tttggaatgcac Humanized BRCA84D Variable Heavy Chain $CDR_2$ (SEQ ID NO:67): YISSDSSAIYYADTVK Polynucleotide Sequence Encoding Humanized BRCA84D-1 Variable Heavy Chain $CDR_2$ (SEQ ID NO:68): tacattagta gtgacagtag tgccatctac tatgcagaca cagtgaag Humanized BRCA84D-1 Variable Heavy Chain $CDR_3$ (SEQ ID NO:69): GRENIYYGSRLDY Polynucleotide Sequence Encoding Humanized BRCA84D-1 Variable Heavy Chain $CDR_3$ (SEQ ID NO:70): gggagggaaa acatttacta cggtagtagg cttgactac In order to obtain hBRCA84D species that exhibit improved affinity for human B7-H3, polynucleotides encoding the light or heavy chains of hBRCA84D-1 (i.e., hBRCA84D-1VL or hBRCA84D-1VH, respectively) were subjected to mutagenesis, and mutated hBRCA84D-1 light chain derivatives hBRCA84D-2VL, hBRCA84D-3VL, hBRCA84D-4VL, hBRCA84D-5VL, and hBRCA84D-6VL and mutated hBRCA84D-1 heavy chain derivatives hBRCA84D-2VH, hBRCA84D-3VH, and hBRCA84D-4VH were isolated and characterized. The amino acid and polynucleotide sequences of the variable light and heavy chains of these antibodies are presented below:

hBRCA84D-2VL (SEQ ID NO:71):

```
DIQLTQSPSF LSASVGDRVT ITCKASQNVD TNVAWYQQKP
GKAPKALIYS ASYRYSGVPS RFSGSGSGTD FTLTISSLQP
EDFATYYCQQ YNNYPFTFGQ GTKLEIK
```

Polynucleotide Encoding hBRCA84D-2VL (SEQ ID NO:72):

```
gacatccagc tgacccagtc cccctccttc ctgtctgcct
ccgtgggcga cagagtgacc atcacatgca aggcctccca
gaacgtggac accaacgtgg cctggtatca gcagaagcct
ggcaaggccc ctaaggcgct gatctactcc gcctcctacc
ggtactccgg cgtgccttcc aggttctccg gctccggctc
tggcaccgac ttcaccctga ccatctccag cctgcagcct
gaggacttcg ccacctacta ctgccagcag tacaacaact
accctttcac cttcggccag ggcaccaagc tggaaatcaa
g
```

hBRCA84D-3VL (SEQ ID NO:73):

```
DIQLTQSPSF LSASVGDRVS VTCKASQNVD TNVAWYQQKP
GKAPKLLIYS ASYRYSGVPS RFSGSGSGTD FTLTISSLQP
EDFATYYCQQ YNNYPFTFGQ GTKLEIK
```

Polynucleotide Encoding hBRCA84D-3VL (SEQ ID NO:74):

```
gacatccagc tgacccagtc cccctccttc ctgtctgcct
ccgtgggcga cagagtgtcc gtcacatgca aggcctccca
gaacgtggac accaacgtgg cctggtatca gcagaagcct
ggcaaggccc ctaagctgct gatctactcc gcctcctacc
ggtactccgg cgtgccttcc aggttctccg gctccggctc
tggcaccgac ttcaccctga ccatctccag cctgcagcct
gaggacttcg ccacctacta ctgccagcag tacaacaact
accctttcac cttcggccag ggcaccaagc tggaaatcaa
g
```

hBRCA84D-4VL (SEQ ID NO:75):

```
DIQLTQSPSF LSASVGDRVT ITCKASQNVD TNVAWYQQKP
GQAPKLLIYS ASYRYSGVPS RFSGSGSGTD FTLTISSLQP
EDFATYYCQQ YNNYPFTFGQ GTKLEIK
```

Polynucleotide Encoding hBRCA84D-4VL (SEQ ID NO:76):

```
gacatccagc tgacccagtc cccctccttc ctgtctgcct
ccgtgggcga cagagtgacc atcacatgca aggcctccca
gaacgtggac accaacgtgg cctggtatca gcagaagcct
ggccaggccc ctaagctgct gatctactcc gcctcctacc
ggtactccgg cgtgccttcc aggttctccg gctccggctc
tggcaccgac ttcaccctga ccatctccag cctgcagcct
gaggacttcg ccacctacta ctgccagcag tacaacaact
accctttcac cttcggccag ggcaccaagc tggaaatcaa g
```

hBRCA84D-5VL (SEQ ID NO:77):

```
DIQLTQSPSF LSASVGDRVT ITCKASQNVD TNVAWYQQKP
GQAPKALIYS ASYRYSGVPS RFSGSGSGTD FTLTISSLQP
EDFATYYCQQ YNNYPFTFGQ GTKLEIK
```

Polynucleotide Encoding hBRCA84D-5VL (SEQ ID NO:78):

```
gacatccagc tgacccagtc cccctccttc ctgtctgcct
ccgtgggcga cagagtgacc atcacatgca aggcctccca
gaacgtggac accaacgtgg cctggtatca gcagaagcct
ggccaggccc ctaaggcgct gatctactcc gcctcctacc
ggtactccgg cgtgccttcc aggttctccg gctccggctc
tggcaccgac ttcaccctga ccatctccag cctgcagcct
gaggacttcg ccacctacta ctgccagcag tacaacaact
accctttcac cttcggccag ggcaccaagc tggaaatcaa g
```

hBRCA84D-6VL (SEQ ID NO:79):

```
DIQLTQSPSF LSASVGDRVT ITCKASQNVD TNVAWYQQKP
GKAPKLLIYS ASYRYSGVPS RFSGSGSGTD FTLTISSLQP
EDFAEYYCQQ YNNYPFTFGQ GTKLEIK
```

Polynucleotide Encoding hBRCA84D-6VL (SEQ ID NO:80):

```
gacatccagc tgacccagtc cccctccttc ctgtctgcct
ccgtgggcga cagagtgacc atcacatgca aggcctccca
gaacgtggac accaacgtgg cctggtatca gcagaagcct
ggcaaggccc ctaagctgct gatctactcc gcctcctacc
ggtactccgg cgtgccttcc aggttctccg gctccggctc
tggcaccgac ttcaccctga ccatctccag cctgcagcct
gaggacttcg ccgagtacta ctgccagcag tacaacaact
accctttcac cttcggccag ggcaccaagc tggaaatcaa g
```

hBRCA84D-2VH (SEQ ID NO:81):

```
EVQLVESGGG LVQPGGSLRL SCAASGFTFS SFGMHWVRQA
PGKGLEWVAY ISSDSSAIYY ADTVKGRFTI SRDNAKNSLY
LQMNSLRDED TAVYYCGRGR ENIYYGSRLD YWGQGTTVTV SS
```

Polynucleotide Encoding hBRCA84D-2VH (SEQ ID NO:82):

```
gaggtgcagc tggtcgagtc tggcggagga ctggtgcagc
ctggcggctc cctgagactg tcttgcgccg cctccggctt
```

-continued caccttctcc agcttcggca tgcactgggt ccgccaggct ccaggcaagg gactggaatg ggtggcctac atctcctccg actcctccgc catctactac gccgacaccg tgaagggcag gttcaccatc tcccgggaca acgccaagaa ctccctgtac ctgcagatga actccctgcg ggacgaggac accgccgtgt actactgcgg cagaggccgg gagaatatct actacggctc ccggctggat tattggggcc agggcaccac cgtgaccgtg tcctct hBRCA84D-3VH (SEQ ID NO:83):

EVQLVESGGG LVQPGGSLRL SCAASGFTFS SFGMHWVRQA

PGKGLEWVAY ISSDSSAIYY ADTVKGRFTI SRDNAKNSLY

LQMNSLRDED TAMYYCGRGR ENIYYGSRLD YWGQGTTVTV SS

Polynucleotide Encoding hBRCA84D-3VH (SEQ ID NO:84):

gaggtgcagc tggtcgagtc tggcggagga ctggtgcagc ctggcggctc cctgagactg tcttgcgccg cctccggctt caccttctcc agcttcggca tgcactgggt ccgccaggct ccaggcaagg gactggaatg ggtggcctac atctcctccg actcctccgc catctactac gccgacaccg tgaagggcag gttcaccatc tcccgggaca acgccaagaa ctccctgtac ctgcagatga actccctgcg ggacgaggac accgccatgt -continued actactgcgg cagaggccgg gagaatatct actacggctc ccggctggat tattggggcc agggcaccac cgtgaccgtg tcctct hBRCA84D-4VH (SEQ ID NO:85):

EVQLVESGGG LVQPGGSLRL SCAASGFTFS SFGMHWVRQA

PGKGLEWVAY ISSDSSAIYY ADTVKGRFTI SRDNAKNSLY

LQMNSLRSED TAVYYCARGR ENIYYGSRLD YWGQGTTVTV SS

Polynucleotide Encoding hBRCA84D-4VH (SEQ ID NO:86):

gaggtgcagc tggtcgagtc tggcggagga ctggtgcagc ctggcggctc cctgagactg tcttgcgccg cctccggctt caccttctcc agcttcggca tgcactgggt ccgccaggct ccaggcaagg gactggaatg ggtggcctac atctcctccg actcctccgc catctactac gccgacaccg tgaagggcag gttcaccatc tcccgggaca acgccaagaa ctccctgtac ctgcagatga actccctgcg gagcgaggac accgccgtgt actactgcgc cagaggccgg gagaatatct actacggctc ccggctggat tattggggcc agggcaccac cgtgaccgtg tcctct Table 1 list the hBRCA84D variable light chain and variable heavy chain mutations studied; number refers to the kabat numbering system.

TABLE 1

| Variable Light Chain | | | | | | Variable Heavy Chain | | | |
|---|---|---|---|---|---|---|---|---|---|
| Kabat Position | 20 | 21 | 42 | 46 | 85 | Kabat Position | 84 | 89 | 93 |
| BRCA84D (SEQ ID NO: 7) | S | V | Q | A | E | BRCA84D (SEQ ID NO: 15) | S | M | G |
| hBRCA84D-1VL (SEQ ID NO: 55) | T | I | K | L | T | hBRCA84D-1VH (SEQ ID NO: 63) | D | V | A |
| hBRCA84D-2VL (SEQ ID NO: 71) | T | I | K | A | T | hBRCA84D-2VH (SEQ ID NO: 81) | D | V | G |
| hBRCA84D-3VL (SEQ ID NO: 73) | S | V | K | L | T | hBRCA84D-3VH (SEQ ID NO: 83) | D | M | G |
| hBRCA84D-4VL (SEQ ID NO: 75) | T | I | Q | L | T | hBRCA84D-4VH (SEQ ID NO: 85) | S | V | A |
| hBRCA84D-5VL (SEQ ID NO: 77) | T | I | Q | A | T | | | | |
| hBRCA84D-6VL (SEQ ID NO: 79) | T | I | K | L | E | | | | |

The amino acid and encoding polynucleotide sequences of the chimeric BRCA84D-1 are as follows:

chBRCA84D Light Chain (SEQ ID NO:87):

```
DIAMTQSQKF MSTSVGDRVS VTCKASQNVD TNVAWYQQKP
GQSPKALIYS ASYRYSGVPD RFTGSGSGTD FTLTINNVQS
EDLAEYFCQQ YNNYPFTFGS GTKLEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGEC
```

Polynucleotide Encoding chBRCA84D Light Chain (SEQ ID NO:88):

```
gacattgcga tgacccagtc tcaaaaattc atgtccacat
cagtaggaga cagggtcagc gtcacctgca aggccagtca
gaatgtggat actaatgtag cctggtatca acagaaacca
gggcaatctc ctaaagcact gatttactcg gcatcctacc
ggtacagtgg agtccctgat cgcttcacag gcagtggatc
tgggacagat ttcactctca ccatcaacaa tgtgcagtct
gaagacttgg cagagtattt ctgtcagcaa tataacaact
atccattcac gttcggctcg gggacaaagt tggaaataaa
acgtacggtg gctgcaccat ctgtcttcat cttcccgcca
tctgatgagc agttgaaatc tggaactgcc tctgttgtgt
gcctgctgaa taacttctat cccagagagg ccaaagtaca
gtggaaggtg gataacgccc tccaatcggg taactcccag
gagagtgtca cagagcagga cagcaaggac agcacctaca
gcctcagcag caccctgacg ctgagcaaag cagactacga
gaaacacaaa gtctacgcct gcgaagtcac ccatcagggc
ctgagctcgc ccgtcacaaa gagcttcaac aggggagagt gt
```

chBRCA84D Heavy Chain (SEQ ID NO:89):

```
DVQLVESGGG LVQPGGSRKL SCAASGFTFS SFGMHWVRQA
PEKGLEWVAY ISSDSSAIYY ADTVKGRFTI SRDNPKNTLF
LQMTSLRSED TAMYYCGRGR ENIYYGSRLD YWGQGTTLTV
SSASTKGPSV FPLAPSSKST SGGTAALGCL VKDYFPEPVT
VSWNSGALTS GVHTFPAVLQ SSGLYSLSSV VTVPSSSLGT
QTYICNVNHK PSNTKVDKRV EPKSCDKTHT CPPCPAPELL
GGPSVFLFPP KPKDTLMISR TPEVTCVVVD VSHEDPEVKF
NWYVDGVEVH NAKTKPREEQ YNSTYRVVSV LTVLHQDWLN
GKEYKCKVSN KALPAPIEKT ISKAKGQPRE PQVYTLPPSR
DELTKNQVSL TCLVKGFYPS DIAVEWESNG QPENNYKTTP
PVLDSDGSFF LYSKLTVDKS RWQQGNVFSC SVMHEALHNH
YTQKSLSLSP GK
```

Polynucleotide Encoding chBRCA84D Heavy Chain (SEQ ID NO:90):

```
gatgtgcagc tggtggagtc tgggggaggc ttagtgcagc
ctggagggtc ccggaaactc tcctgtgcag cctctggatt
cactttcagt agctttggaa tgcactgggt tcgtcaggct
ccagagaagg ggctggagtg ggtcgcatac attagtagtg
acagtagtgc catctactat gcagacacag tgaagggccg
attcaccatc tccagagaca atcccaagaa caccctgttc
ctgcaaatga ccagtctaag gtctgaggac acggccatgt
attactgtgg aagagggagg gaaaacattt actacggtag
taggcttgac tactggggcc aaggcaccac tctcacagtc
tcctcagcct ccaccaaggg cccatcggtc ttccccctgg
caccctcctc caagagcacc tctgggggca cagcggccct
gggctgcctg gtcaaggact acttccccga accggtgacg
gtgtcgtgga actcaggcgc cctgaccagc ggcgtgcaca
ccttcccggc tgtcctacag tcctcaggac tctactccct
cagcagcgtg gtgaccgtgc cctccagcag cttgggcacc
cagacctaca tctgcaacgt gaatcacaag cccagcaaca
ccaaggtgga caagagagtt gagcccaaat cttgtgacaa
aactcacaca tgcccaccgt gcccagcacc tgaactcctg
gggggaccgt cagtcttcct cttcccccca aaacccaagg
acaccctcat gatctcccgg acccctgagg tcacatgcgt
ggtggtggac gtgagccacg aagaccctga ggtcaagttc
aactggtacg tggacggcgt ggaggtgcat aatgccaaga
caaagccgcg ggaggagcag tacaacagca cgtaccgtgt
ggtcagcgtc ctcaccgtcc tgcaccagga ctggctgaat
ggcaaggagt acaagtgcaa ggtctccaac aaagccctcc
cagcccccat cgagaaaacc atctccaaag ccaaagggca
gccccgagaa ccacaggtgt acaccctgcc cccatcccgg
gatgagctga ccaagaacca ggtcagcctg acctgcctgg
tcaaaggctt ctatcccagc gacatcgccg tggagtggga
gagcaatggg cagccggaga acaactacaa gaccacgcct
cccgtgctgg actccgacgg ctccttcttc ctctacagca
agctcaccgt ggacaagagc aggtggcagc aggggaacgt
cttctcatgc tccgtgatgc atgaggctct gcacaaccac
tacacgcaga agagcctctc cctgtctccg ggtaaa
```

E. Canine Anti-CD3 Antibodies

Antibodies immunoreactive to an activating receptor (e.g., CD3, CD16, CD32, CD64, T-cell receptor, NKG2D, etc.) of a companion animal immune effector cell can be obtained using the methods described above. Particularly preferred anti-CD3 antibodies are K9CD3-1 and K9CD3-2 which are immunoreactive to canine CD3. The amino acid and encoding polynucleotide sequences of the variable light chain and variable heavy chain of K9CD3-1 and K9CD3-2 are shown below along with the respective $CDR_1$, $CDR_2$, and $CDR_3$ domains of each such chain. Those of skill in the art will therefore be able to construct bispecific molecules having such CDRs, as well as antibodies and derivatives thereof, capable of binding to the epitopes recognized by K9CD3-1 and K9CD3-2.

1. Sequences of K9CD3-1 a. K9CD3-1 Light Chain Sequences

Amino Acid Sequence of K9CD3-1 Variable Light Chain (SEQ ID NO:91):

```
DILLTQSPAT LSVTPGETVS LSCRASQSIF KNLHWYQQKS
HRSPRLLIKY ASDSISGIPS RFTGSGSGTD YTLSINSVKP
EDEGVYYCLQ AYSTPWTFGG GTKLEIK
```

Polynucleotide Sequence Encoding K9CD3-1 Variable Light Chain (SEQ ID NO:92):

```
gacatcctgc tgacccagtc tccagccacc ctgtctgtga
ctccaggaga aacagtcagt ctttcctgta gggccagcca
gagtattttc aagaacctac actggtatca acagaaatca
catcggtctc caaggcttct catcaagtat gcttctgatt
ccatctctgg gatcccctcc aggttcactg gcagtggatc
ggggacagat tacactctca gtatcaacag tgtgaagccc
gaagatgaag gagtatatta ctgtcttcaa gcttacagca
caccgtggac gttcggtgga ggcaccaaac tggaaatcaa a
```

K9CD3-1 Variable Light Chain $CDR_1$ (SEQ ID NO:93): RASQSIFKNLH

Polynucleotide Sequence Encoding K9CD3-1 Variable Light Chain $CDR_1$ (SEQ ID NO:94): agggccagccagagtattttcaagaacctacac K9CD3-1 Variable Light Chain $CDR_2$ (SEQ ID NO:95): YASDSISGIPS Polynucleotide Sequence Encoding K9CD3-1 Variable Light Chain $CDR_2$ (SEQ ID NO:96): tatgcttctgattccatctct K9CD3-1 Variable Light Chain $CDR_3$ (SEQ ID NO:97): LQAYSTPWT Polynucleotide Sequence Encoding K9CD3-1 Variable Light Chain $CDR_3$ (SEQ ID NO:98): cttcaagcttacagcacaccgtggacg b. K9CD3-1 Heavy Chain Sequences Amino Acid Sequence of K9CD3-1 Variable Heavy Chain (SEQ ID NO:99):

```
EVQLQQSGPE LVKPGASVKI SCKASGYTFS DYNMHWVKQS
HGESLEWIGY IYPYNGGTYY NQKFKSKATL TVDNSSSTAY
MEFRSLTSED SAVYYCARLV YFDYWGQGTA LTVSS
```

Polynucleotide Sequence Encoding K9CD3-1 Variable Heavy Chain (SEQ ID NO:100):

```
gaggtccagc ttcagcagtc aggacctgag ctggtgaaac
ctggggcctc agtgaagata tcctgcaagg cttctggata
cacattctct gactacaaca tgcactgggt gaaacagagc
```

-continued

```
catggagaga gccttgagtg gattggatat atttatcctt
acaatggtgg tacttactac aaccagaaat tcaagagcaa
ggccacattg actgtagaca attcctccag cacagcctac
atggagttcc gcagcctgac atctgaggac tctgcagtct
attactgtgc aaggctggtt tactttgact actggggcca
aggcaccgct ctcacagtct cctcc
```

K9CD3-1 Variable Heavy Chain $CDR_1$ (SEQ ID NO:101): DYNMH

Polynucleotide Sequence Encoding K9CD3-1 Variable Heavy Chain $CDR_1$ (SEQ ID NO:102): gactacaacatgcac K9CD3-1 Variable Heavy Chain $CDR_2$ (SEQ ID NO:103): YIYPYNGGTYYNQKFKS Polynucleotide Sequence Encoding K9CD3-1 Variable Heavy Chain $CDR_2$ (SEQ ID NO:104): tatatttatccttacaatggtggtacttactacaaccagaaattcaagagc K9CD3-1 Variable Heavy Chain $CDR_3$ (SEQ ID NO:105): LVYFDY Polynucleotide Sequence Encoding K9CD3-1 Variable Heavy Chain $CDR_3$ (SEQ ID NO:106): ctggtttactttgactac 2. Sequences of K9CD3-2 a. K9CD3-2 Light Chain Sequences

Amino Acid Sequence of K9CD3-2 Variable Light Chain (SEQ ID NO:107):

```
NIVMTQSPKS MSMSVGERVT LNCKASENVD SYVSWYQQKP
KQSPTLLIYG ASNRSTGVPD RFTGSGSVTD FTLTITSVQA
EDLAYYHCGQ TYSYPFTFGS GTKLEIK
```

Polynucleotide Sequence Encoding K9CD3-2 Variable Light Chain (SEQ ID NO:108):

```
aacattgtga tgacccaatc tcccaaatcc atgtccatgt
cagttggaga gagggtcacc ttgaactgca aggccagtga
gaatgtggat tcttatgtgt cctggtatca gcagaaacca
aaacagtctc ctacattact gatttacggg gcatccaacc
ggtccactgg ggtccccgat cgcttcacag gcagcggatc
tgtaacagat ttcactctga ccatcaccag tgtgcaggct
gaagaccttg catattatca ctgtggacag acttacagtt
atccattcac gttcggctcg gggacaaagt tggaaataaa a
```

K9CD3-2 Variable Light Chain $CDR_1$ (SEQ ID NO:109): KASENVDSYVS

Polynucleotide Sequence Encoding K9CD3-2 Variable Light Chain $CDR_1$ (SEQ ID NO:110): aaggccagtgagaatgtggattcttatgtgtcc K9CD3-2 Variable Light Chain $CDR_2$ (SEQ ID NO:111): GASNRST Polynucleotide Sequence Encoding K9CD3-2 Variable Light Chain $CDR_2$ (SEQ ID NO:112): ggggcatccaaccggtccact K9CD3-2 Variable Light Chain $CDR_3$ (SEQ ID NO:113): GQTYSYPFT Polynucleotide Sequence Encoding K9CD3-2 Variable Light Chain $CDR_3$ (SEQ ID NO:114): ggacagacttacagttatccattcacg b. K9CD3-2 Heavy Chain Sequences Amino Acid Sequence of K9CD3-2 Variable Heavy Chain (SEQ ID NO:115):

```
EVQLVESGGG LVQPKGSLTL SCAASGFTFN IFAMNWVRQA
PGKGLEWVAR IRSKNNYFAT YYAASVRDRF TISRDDSQSM
VYLQMNNLKT EDTGMYYCVR RGYFDVWGAG TTVTVSS
```

Polynucleotide Sequence Encoding K9CD3-2 Variable Heavy Chain (SEQ ID NO:116):

```
gaggtgcagc ttgttgagtc tggtggagga ttggtgcagc
ctaaagggtc attgacactc tcatgtgcag cctctggatt
caccttcaat atcttcgcca tgaactgggt ccgccaggct
ccaggaaagg gtttggaatg ggttgctcgt ataagaagta
aaaataatta ttttgcaaca tattatgctg cttcagtgag
agacaggttc accatctcca gagatgattc acaaagcatg
gtctatcttc aaatgaacaa cttgaaaact gaggacacag
gcatgtatta ctgtgtgaga cggggatact tcgatgtctg
gggcgcaggg accacggtca ccgtctcctc c
```

K9CD3-2 Variable Heavy Chain $CDR_1$ (SEQ ID NO:117): IFAMN

Polynucleotide Sequence Encoding K9CD3-2 Variable Heavy Chain $CDR_1$ (SEQ ID NO:118): atcttcgccatgaac K9CD3-2 Variable Heavy Chain $CDR_2$ (SEQ ID NO:119): RIRSKNNYFATYYAASVRD Polynucleotide Sequence Encoding K9CD3-2 Variable Heavy Chain $CDR_2$ (SEQ ID NO:120): cgtataagaagtaaaaataattattttgcaacatattatgctgcttcagtgagagac K9CD3-2 Variable Heavy Chain $CDR_3$ (SEQ ID NO:121): RGYFDV Polynucleotide Sequence Encoding K9CD3-2 Variable Heavy Chain $CDR_3$ (SEQ ID NO:122): cggggatacttcgatgtc F. B7-H3 DART (Dual Affinity Retargeting Reagent) Diabodies As discussed above, the present invention additionally encompasses "DART" (dual affinity retargeting reagent) diabody molecules that comprise at least two polypeptide chains which form at least two epitope binding sites, at least one of which specifically binds to B7-H3.

In preferred embodiments, the first polypeptide chain of the DART diabody comprises:

(i) a domain (A) comprising a binding region of a light chain variable domain of a first immunoglobulin (VL1) specific for an epitope (1);

(ii) a domain (B) comprising a binding region of a heavy chain variable domain of a second immunoglobulin (VH2) specific for an epitope (2); and (iii) a domain (C).

The second polypeptide chain of such a DART diabody comprises:

(i) a domain (D) comprising a binding region of a light chain variable domain of the second immunoglobulin (VL2) specific for epitope (2);

(ii) a domain (E) comprising a binding region of a heavy chain variable domain of the first immunoglobulin (VH1) specific for epitope (1); and (iii) a domain (F).

The DART diabody domains (A) and (B) do not associate with one another to form an epitope binding site. Similarly, the DART diabody domains (D) and (E) do not associate with one another to form an epitope binding site. Rather, DART diabody domains (A) and (E) associate to form a binding site that binds epitope (1); said DART diabody domains (B) and (D) associate to form a binding site that binds said epitope (2). Domains (C) and (F) are covalently associated together. Methods for forming DART diabody molecules and specific orientations of the DART diabody domains are disclosed in US Patent Publications Nos. 2010/0174053, US 2009/0060910 and US 2007/0004909.

Each polypeptide chain of the DART diabody molecule comprises a VL domain and a VH domain, which are covalently linked such that the domains are constrained from self-assembly. Interaction of two of the polypeptide chains will produce two VL-VH pairings, forming two eptipope binding sites, i.e., a bivalent molecule. Neither the VH or VL domain is constrained to any position within the polypeptide chain, i.e., restricted to the amino (N) or carboxy (C) terminus. In one embodiment, the VL domain is N-terminal to the VH domain. In a second embodiment, the VH domain is N-terminal to the VL domain. The only restriction to either embodiment is that a complimentary polypeptide chain be available in order to form functional diabody. Where the VL and VH domains are derived from the same antibody, the two complimentary polypeptide chains may be identical. For example, where the binding domains are derived from an antibody specific for epitope A (i.e., the binding domain is formed from a $VL_A$-$VH_A$ interaction), each polypeptide will comprise a $VH_A$ and a $VL_A$. Homodimerization of two polypeptide chains of the antibody will result in the formation two $VL_A$-$VH_A$ binding sites, resulting in a bivalent monospecific antibody. Where the VL and VH domains are derived from antibodies specific for different antigens, formation of a functional bispecific diabody requires the interaction of two different polypeptide chains, i.e., formation of a heterodimer For example, for a bispecific diabody, one polypeptide chain will comprise a $VL_A$ and a $VL_B$; homodimerization of said chain will result in the formation of two $VL_A$-$VH_B$ binding sites, either of no binding or of unpredictable binding. In contrast, where two differing polypeptide chains are free to interact, e.g., in a recombinant expression system, one comprising a $VL_A$ and a $VH_B$ and the other comprising a $VL_B$ and a $VH_A$, two differing binding sites will form: $VL_A$-$VH_A$ and $VL_B$-$VH_B$. For all diabody polypeptide chain pairs, the possibly of misalignment or mis-binding of the two chains is a possibility, i.e., interaction of VL-VL or VH-VH domains; however, purification of functional diabodies is easily managed based on the immunospecificity of the properly dimerized binding site using any affinity based method known in the art or exemplified herein, e.g., affinity chromatography.

One or more of the polypeptide chains of the diabody may optionally comprise an Fc domain or portion thereof (e.g. a CH2 domain, or CH3 domain). The Fc domain or portion thereof may be derived from any immunoglobulin isotype or allotype including, but not limited to, IgA, IgD, IgG, IgE and IgM. In preferred embodiments, the Fc domain (or portion thereof) is derived from IgG. In specific embodiments, the IgG isotype is IgG1, IgG2, IgG3 or IgG4 or an allotype thereof. In one embodiment, the diabody molecule comprises an Fc domain, which Fc domain comprises a CH2 domain and CH3 domain independently selected from any immunoglobulin isotype (i.e. an Fc domain comprising the CH2 domain derived from IgG and the CH3 domain derived from IgE, or the CH2 domain derived from IgG1 and the CH3 domain derived from IgG2, etc.). The Fc domain may be engineered into a polypeptide chain comprising the diabody molecule of the invention in any position relative to other domains or portions of said polypeptide chain (e.g., the Fc domain, or portion thereof, may be c-terminal to both the VL and VH domains of the polypeptide of the chain; may be n-terminal to both the VL and VH domains; or may be N-terminal to one domain and c-terminal to another (i.e., between two domains of the polypeptide chain)).

The Fc domains in the polypeptide chains of the diabody molecules preferentially dimerize, resulting in the formation of a diabody molecule that exhibits immunoglobulin-like properties, e.g., Fc-FcγR, interactions. Fc comprising diabodies may be dimers, e.g., comprised of two polypeptide chains, each comprising a VH domain, a VL domain and an Fc domain. Dimerization of said polypeptide chains results in a bivalent diabody comprising an Fc domain, albeit with a structure distinct from that of an unmodified bivalent antibody. Such diabody molecules will exhibit altered phenotypes relative to a wild-type immunoglobulin, e.g., altered serum half-life, binding properties, etc. In other embodiments, diabody molecules comprising Fc domains may be tetramers. Such tetramers comprise two 'heavier' polypeptide chains, i.e., a polypeptide chain comprising a VL, a VH and an Fc domain, and two 'lighter' polypeptide chains, i.e., polypeptide chain comprising a VL and a VH. The lighter and heavier chains interact to form a monomer, and said monomers interact via their unpaired Fc domains to form an Ig-like molecule. Such an Ig-like diabody is tetravalent and may be monospecific, bispecific or tetraspecific.

Formation of a tetraspecific diabody molecule as described supra requires the interaction of four differing polypeptide chains. Such interactions are difficult to achieve with efficiency within a single cell recombinant production system, due to the many variants of potential chain mispairings. One solution to increase the probability of mispairings, is to engineer "knobs-into-holes" type mutations into the desired polypeptide chain pairs. Such mutations favor heterodimerization over homodimerization. For example, with respect to Fc-Fc-interactions, an amino acid substitution (preferably a substitution with an amino acid comprising a bulky side group forming a 'knob', e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) "*'Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety.

The invention also encompasses diabody molecules comprising variant Fc or variant hinge-Fc domains (or portion thereof), which variant Fc domain comprises at least one amino acid modification (e.g. substitution, insertion deletion) relative to a comparable wild-type Fc domain or hinge-Fc domain (or portion thereof). Molecules comprising variant Fc domains or hinge-Fc domains (or portion thereof) (e.g., antibodies) normally have altered phenotypes relative to molecules comprising wild-type Fc domains or hinge-Fc domains or portions thereof. The variant phenotype may be expressed as altered serum half-life, altered stability, altered susceptibility to cellular enzymes or altered effector function as assayed in an NK dependent or macrophage dependent assay. Fc domain modifications identified as altering effector function are disclosed above. A large number of substitutions in the Fc domain of human IgG1 that increase binding to activating receptors (e.g., FcγRIIA (CD16A) and reduce binding to inhibitory receptors (e.g., FcγRIIB (CD32B) are known in the art and are described in Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890. Exemplary variants of human IgG1 Fc domains with reduced binding to CD32B and/or increased binding to CD16A contain F243L, R929P, Y300L, V3051 or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V3051 and P296L substitution. In another embodiment, the human IgG1 Fc domain variant contains an N297Q substitution, as this mutation abolishes FcR binding.

The present invention also encompasses molecules comprising a hinge domain. The hinge domain may be derived from any immunoglobulin isotype or allotype including IgA, IgD, IgG, IgE and IgM. In preferred embodiments, the hinge domain is derived from IgG, wherein the IgG isotype is IgG1, IgG2, IgG3 or IgG4, or an allotpye thereof. Said hinge domain may be engineered into a polypeptide chain comprising the diabody molecule together with an Fc domain such that the diabody molecule comprises a hinge-Fc domain. In certain embodiments, the hinge and Fc domain are independently selected from any immunoglobulin isotype known in the art or exemplified herein. In other embodiments the hinge and Fc domain are separated by at least one other domain of the polypeptide chain, e.g., the VL domain. The hinge domain, or optionally the hinge-Fc domain, may be engineered in to a polypeptide of the invention in any position relative to other domains or portions of said polypeptide chain. In certain embodiments, a polypeptide chain of the invention comprises a hinge domain, which hinge domain is at the C-terminus of the polypeptide chain, wherein said polypeptide chain does not comprise an Fc domain. In yet other embodiments, a polypeptide chain of the invention comprises a hinge-Fc domain, which hinge-Fc domain is at the C-terminus of the polypeptide chain. In further embodiments, a polypeptide chain of the invention comprises a hinge-Fc domain, which hinge-Fc domain is at the N-terminus of the polypeptide chain.

Each domain of the polypeptide chain of the diabody, i.e., the VL, VH and Fc domain may be separated by a peptide linker. The peptide linker may be 0, 1, 2, 3, 4, 5, 6, 7, 8, or 9. amino acids. In certain embodiments the amino acid linker sequence is GGGSGGGG (SEQ ID NO:123) encoded by the nucleic acid sequence ggaggcggat ccggaggcgg aggc (SEQ ID NO:124). The polypeptide chains of the diabody molecule may be engineered to comprise at least one cysteine residue that will interact with a counterpart cysteine residue on a second polypeptide chain of the diabody to form an inter-chain disulfide bond. Such interchain disulfide bonds serve to stabilize the diabody molecule, thereby improving expression and recovery in recombinant systems, resulting in a stable and consistent formulation and improving the stability of the isolated and/or purified product in vivo. The cysteine residue may be introduced as a single amino acid or as part of larger amino-acid sequence, e.g. a hinge domain, in any portion of the polypeptide chain. In a specific embodiment, the cysteine residue may be engineered to occur at the C-terminus of the polypeptide chain. In some embodiments, the cysteine residue is introduced into the polypeptide chain within the amino acid sequence LGGC. In a specific embodiment, the C-terminus of the polypeptide chains comprising the diabody molecule of the invention comprises the amino acid sequence LGGC (SEQ ID NO:125). In another embodiment, the cysteine residue is introduced into the polypeptide within an amino acid sequence comprising a hinge domain, e.g. EPKSCDKTHTCPP (SEQ ID NO:126) or ESKYGPPCPS (SEQ ID NO:127). In a specific embodiment, the C-terminus of a polypeptide chain of the diabody molecule of the invention comprises the amino acid sequence of an IgG hinge domain, e.g. SEQ ID NO:126 or SEQ ID NO:127. In another embodiment, the C-terminus of a polypeptide chain of a diabody molecule of the invention comprises the amino acid sequence VEPKSC (SEQ ID NO:128), which can be encoded by nucleotide sequence gttgagccca aatcttgt (SEQ ID NO:129). In other embodiments, the cysteine residue in introduced into the polypeptide chain within the amino acid sequence LGGCFNRGEC (SEQ ID NO:130), which can be encoded by the nucleotide sequence ctgggaggct gcttcaacag gggagagtgt (SEQ ID NO:131). In a specific embodiment, the C-terminus of a polypeptide chain comprising the diabody of the invention comprises the amino acid sequence LGGCFNRGEC (SEQ ID NO:130). In yet other embodiments, the cysteine residue in introduced into the polypeptide chain within the amino acid sequence FNRGEC (SEQ ID NO:132), which can be encoded by the nucleotide sequence ttcaacaggg gagagtgt (SEQ ID NO:133). In a specific embodiment, the C-terminus of a polypeptide chain comprising the diabody of the invention comprises the amino acid sequence FNRGEC (SEQ ID NO:132).

In certain embodiments, the diabody molecule comprises at least two polypeptide chains, each of which comprise the amino acid sequence LGGC (SEQ ID NO:125) and are covalently linked by a disulfide bond between the cysteine residues in the LGGC (SEQ ID NO:125) sequences. In certain embodiments, the diabody molecule comprises at least two polypeptide chains, each of which comprise the amino acid sequence GGCGGG (SEQ ID NO:134) and are covalently linked by a disulfide bond between the cysteine residues in the GGCGGG (SEQ ID NO:134) sequences. In another specific embodiment, the diabody molecule comprises at least two polypeptide chains, one of which comprises the sequence FNRGEC (SEQ ID NO:132) while the other comprises a hinge domain (containing at least one cysteine residue), wherein said at least two polypeptide chains are covalently linked by a disulfide bond between the cysteine residue in FNRGEC (SEQ ID NO:132) and a cysteine residue in the hinge domain. In particular aspects, the cysteine residue responsible for the disulfide bond located in the hinge domain is Cys-128 (as numbered according to Kabat EU; located in the hinge domain of an unmodified, intact IgG heavy chain) and the counterpart cysteine residue is Cys-214 (as numbered according to Kabat EU; located at the C-terminus of an unmodified, intact IgG light chain) (Elkabetz et al. (2005) "*Cysteines In CH1 Underlie Retention Of Unassembled Ig Heavy Chains*," J. Biol. Chem. 280:14402-14412). In yet other embodiments, the at least one cysteine residue is engineered to occur at the N-terminus of the amino acid chain. In still other embodiments, the at least one cysteine residue is engineered to occur in the linker portion of the polypeptide chain of the diabody molecule. In further embodiments, the VH or VL domain is engineered to comprise at least one amino acid modification relative to the parental VH or VL domain such that said amino acid modification comprises a substitution of a parental amino acid with cysteine.

In still another aspect of this embodiment, the Domain (C) of the first polypeptide chain comprises the amino acid sequence VEPKSC (SEQ ID NO:128), derived from the hinge domain of a human IgG, and which can be encoded by the nucleotide sequence gttgagccca aatcttgt (SEQ ID NO:129). In another aspect of this embodiment, the Domain (F) of the second polypeptide chain comprises the amino acid sequence VEPKSC (SEQ ID NO:128). In certain aspects of this embodiment, Domain (C) of the first polypeptide chain comprises the C-terminal 6 amino acids of the human kappa light chain, FNRGEC (SEQ ID NO:132); and Domain (F) of the second polypeptide chain comprises the amino acid sequence VEPKSC (SEQ ID NO:128) or a hinge domain. In other aspects of this embodiment, Domain (F) of the second polypeptide chain comprises the C-terminal 6 amino acids of the human kappa light chain, FNRGEC (SEQ ID NO:132); and Domain (C) of the first polypeptide chain comprises the amino acid sequence VEPKSC (SEQ ID NO:128) or a hinge domain.

As will be appreciated in view of the foregoing, the individual polypeptides of a bispecific diabody can form two species of homodimers and one species of heterodimer In one embodiment of the present invention, a charged polypeptide can be added to the C-terminus of one, or more preferably, both diabody polypeptides. By selecting charged polypeptides of opposite charge for the individual polypeptides of the bispecific diabody, the inclusion of such charged polypeptides favors formation of heterodimers and lessens formation of homodimers. Preferably, a positively charged polypeptide will contain a substantial content of arginine, glutamine, histidine and/or lysine (or mixtures of such amino acids) and a negatively charged polypeptide will contain a substantial content of aspartate or glutamate (or a mixture of such amino acids). Positively charged polypeptides containing a substantial content of lysine and negatively charged polypeptides containing a substantial content of glutamate are particularly preferred. In order to maximize the electrostatic attraction between such opposingly charged polypeptides, it is preferred to employ polypeptides capable of spontaneously assuming a helical conformation.

Thus, in a preferred embodiment, a positively charged, "E-coil" will be appended to one of the polypeptides being used to form a bispecific diabody and a negatively charged "K-coil" will be appended to the second of the diabody's polypeptides. A particularly preferred E-coil will have the sequence: $(EVAALEK)_4$ [i.e. (SEQ ID NO:135) EVAALEKEVAALEKEVAALE KEVAALEK]. A particularly preferred K-coil will have the sequence: $(KVAALKE)_4$ [i.e. (SEQ ID NO:136) KVAALKEKVAALKEKVAALKEKVAALKE].

A preferred diabody polypeptide possessing such an E-coil will have the general sequence: [VL Domain]-[GGGSGGGG]-[VH Domain]-[$(EVAALEK)_4$]-GGGNS, where VL is the diabody's variable light Ig domain, GGGSGGGG is SEQ ID NO:123, VH is the diabody's variable heavy Ig domain, $(EVAALEK)_4$ is SEQ ID NO:135, and GGGNS is SEQ ID NO:137. A preferred diabody polypeptide possessing such a K-coil will have the general sequence: [VL Domain]-[GGGSGGGG]-[VH Domain]-[$(KVAALKE)_4$]-GGGNS, where VL is the diabody's variable light Ig domain, GGGSGGGG is SEQ ID NO:123, VH is the diabody's variable heavy Ig domain, $(KVAALKE)_4$ is SEQ ID NO:136, and GGGNS is SEQ ID NO:137.

In a further embodiment, Fc-regions can be linked to the E and/or K coils of E-coil or K-coli diabody. Furthering the separation between the Fc regions and the diabody VH domain of an Fc-containing diabody is desirable in cases in which a less separated arrangement of such domains results in diminished interaction between such domains and their binding ligands or otherwise interferes with diabody assembly. Although separators of any amino acid sequence may be employed, it is preferable to employ separators that form an α helix coils, so as to maximally extend and project the Fc domain away from the variable domains. Because the above-described coiled polypeptides of opposing charge additionally function to promote heterodimer formation, such molecules are particularly preferred separators. Such coil-containing Fc-DART diabody molecules provide benefits similar to those of Fc-DART diabodies, including improved serum half-life and effector function recruitment. The above-described E-coil and K-coil polypeptides are particularly preferred for this purpose. Thus, in a preferred embodiment, the E-coil Fc-containing diabody will have the general sequence: [VL Domain]-[GGGSGGGG]-[VH Domain]-[$(EVAALEK)_4$]-GGG-Fc domain starting with D234 (Kabat numbering), where VL is the diabody's variable light Ig domain, GGGSGGGG is SEQ ID NO:123, VH is the diabody's variable heavy Ig domain and $(EVAALEK)_4$ is SEQ ID NO:135. Similarly, in a preferred embodiment, the K-coil Fc-containing DART diabody will have the general sequence: [VL Domain]-[GGGSGGGG]-[VH Domain]-[$(KVAALKE)_4$]-GGG-Fc domain starting with D234 (Kabat numbering), where VL is the diabody's variable light Ig domain, GGGSGGGG is SEQ ID NO:126, VH is the diabody's variable heavy Ig domain and $(KVAALKE)_4$ is SEQ ID NO:136.

As indicated above, a coil-containing diabody molecule or a coil-containing Fc-containing diabody molecule may contain only a single such coil separator, or it may contain more than one such separators (e.g., two separators, preferably of opposite charge, of which one is linked to each of the VH domain of the diabody's polypeptides). By linking the Fc region to such separator molecule(s), the ability to make bivalent, tetravalent, etc. versions of the Fc-diabody molecules by chain swapping is enhanced. Fc-diabody molecules can thus be produced that form monomers or dimers depending upon whether the Fc domain is linked to one or both of the diabody VH domains G. Versatility of B7-H3 Bispecific Molecules The bispecific molecules of the invention can simultaneously bind two separate and distinct epitopes. In preferred embodiments, at least one epitope binding site is specific for a determinant expressed on an immune effector cell (e.g. CD3, CD16, CD32, CD64, T-cell receptor, NKG2D, etc.) which are expressed on T lymphocytes, natural killer (NK) cells or other mononuclear cells. In one embodiment, the diabody molecule binds to the effector cell determinant and also activates said effector cell. In this regard, the bispecific molecules of the invention may exhibit Ig-like functionality independent of whether they further comprise an Fc domain (e.g., as assayed in any effector function assay known in the art or exemplified herein (e.g., ADCC assay). In certain embodiments the bispecific diabody of the invention binds both a cancer antigen on a tumor cell and an effector cell determinant while activating said cell.

The invention further encompasses incorporation of unnatural amino acids to generate the diabodies of the invention. Such methods are known to those skilled in the art such as those using the natural biosynthetic machinery to allow incorporation of unnatural amino acids into proteins, see, e.g., Wang et al. (2002) "*Expanding The Genetic Code*," Chem. Comm. 1:1-11; Wang et al. (2001) "*Expanding The Genetic Code Of Escherichia coli*," Science, 292: 498-500; van Hest et al. (2001) "*Protein-Based Materials, Toward A New Level Of Structural Control*," Chem. Comm. 19: 1897-1904, each of which is incorporated herein by reference in its entirety. Alternative strategies focus on the enzymes responsible for the biosynthesis of amino acyl-tRNA, see, e.g., Tang et al. (2001) "*Biosynthesis Of A Highly Stable Coiled-Coil Protein Containing Hexafluoroleucine In An Engineered Bacterial Host*," J. Am. Chem. Soc. 123(44): 11089-11090; Kiick et al. (2001) "*Identification Of An Expanded Set Of Translationally Active Methionine Analogues In Escherichia coli*," FEBS Lett. 502(1-2):25-30; each of which is incorporated herein by reference in its entirety. In some embodiments, the invention encompasses methods of modifying a VL, VH or Fc domain of a molecule of the invention by adding or deleting a glycosylation site. Methods for modifying the carbohydrate of proteins are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety.

VIII. Methods Of Using B7-H3 Modulators And Anti-B7-H3 Antibodies For Therapeutic Purposes The bispecific molecules of the present invention may be used for therapeutic purposes in companion animals with cancer or other proliferative diseases. Therapy with such bispecific molecules can involve formation of complexes both in vitro and in vivo as described above. In one embodiment, such bispecific molecules can bind to and reduce the proliferation of cancerous cells. It is understood that the bispecific molecule is administered at a concentration that promotes binding to both of its recognized epitopes at physiological (e.g., in vivo) conditions. In another embodiment, such bispecific molecules can be used for immunotherapy directed at cancerous cells of different tissues such as colon, lung, breast, prostate, ovary, pancreas, kidney and other types of cancer such as sarcoma. In another embodiment, such bispecific molecules alone can bind to and reduce cell division in the cancer cell. In another embodiment, such bispecific molecules can bind to cancerous cells and delay the development of metastasis. In yet another embodiment, an individual with cancer is given palliative treatment with such bispecific molecules. Palliative treatment of a cancer individual involves treating or lessening the adverse symptoms of the disease, or iatrogenic symptoms resulting from other treatments given for the disease without directly affecting the cancer progression. This includes treatments for easing of pain, nutritional support, sexual problems, psychological distress, depression, fatigue, psychiatric disorders, nausea, vomiting, etc.

Various formulations of the bispecific molecules of the invention may be used for administration. In some embodiments, bispecific molecules or fragments thereof may be administered neat. In addition to the pharmacologically active agent, the compositions of the present invention may contain suitable pharmaceutically acceptable carriers comprising excipients and auxiliaries that are well known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient. Excipients as well as formulations for parenteral and non-parenteral drug delivery are set forth in Remington: The Science And Practice Of Pharmacy, 21st Edition, Lippincott Williams & Wilkins Publishing (2005). Suitable formulations for oral administration include hard or soft gelatin capsules, pills, tablets, including coated tablets, elixirs, suspensions, syrups or inhalations and controlled release forms thereof. Generally, these agents are formulated for administration by injection (e.g., intraperitoneally, intravenously, subcutaneously, intramuscularly, etc.), although other forms of administration (e.g., oral, mucosal, etc.) can be also used. Accordingly, the bispecific molecules are preferably combined with pharmaceutically acceptable vehicles such as saline, Ringer's solution, dextrose solution, and the like.

Empirical considerations, such as the biological half-life, generally will contribute to the determination of the dosage. Frequency of administration may be determined and adjusted over the course of therapy, and is based on reducing the number of cancerous cells, maintaining the reduction of cancerous cells, reducing the proliferation of cancerous cells, or delaying the development of metastasis. Alternatively, sustained continuous release formulations of the bispecific molecules may be appropriate. Various formulations and devices for achieving sustained release are known in the art.

In one embodiment, dosages for the bispecific molecules of the present invention may be determined empirically in individuals who have been given one or more administration(s). Individuals are given incremental dosages of the bispecific molecule. To assess efficacy of the bispecific molecules, a marker of the specific cancer disease state can be followed. These include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer), a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of cancer, the stage of cancer, whether the cancer has begun to metastasize to other location in the individual, and the past and concurrent treatments being used.

Other formulations include suitable delivery forms known in the art including, but not limited to, carriers such as liposomes. See, for example, Mahato et al. (1997) "*Cationic Lipid-Based Gene Delivery Systems: Pharmaceutical Perspectives*," Pharm. Res. 14:853-859. Liposomal preparations include, but are not limited to, cytofectins, multilamellar vesicles and unilamellar vesicles.

The ability of the bispecific molecules of the present invention to specifically bind to canine B7-H3 and/or to feline B7-H3 permits evaluations of their pharmacology and pharmkokinetics relevant to human therapeutics to be conducted in non-primate animals.

Having now generally described the invention, the same will be more readily understood through reference to the following examples, which are provided by way of illustration and are not intended to be limiting of the present invention unless specified.

EXAMPLE 1

Ability of Human B7-H3 Antibody to Bind Canine B7-H3

Figure 1B:
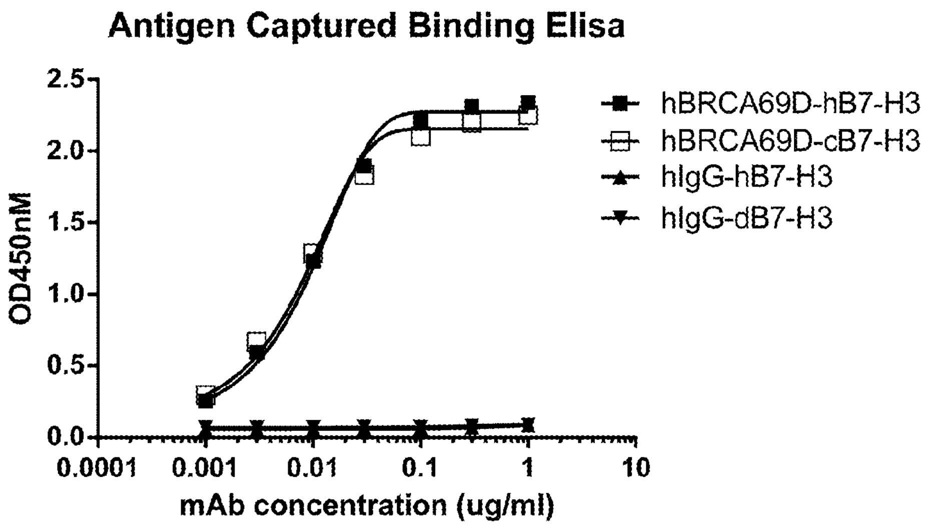
Figure 1C:
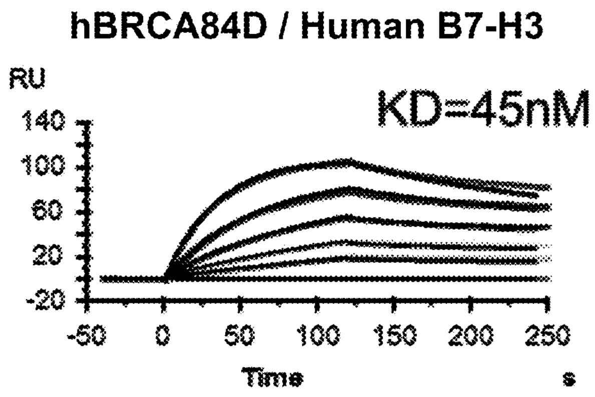
Figure 1D:
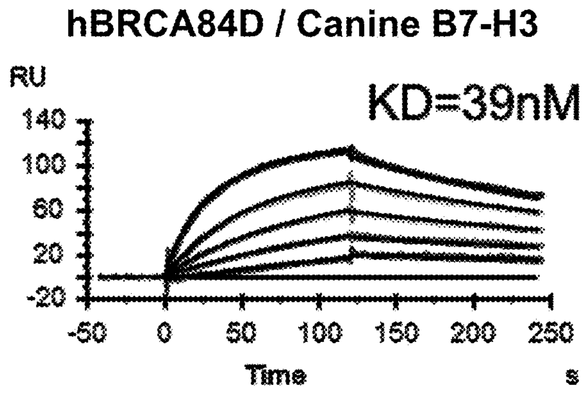
Figure 1E:
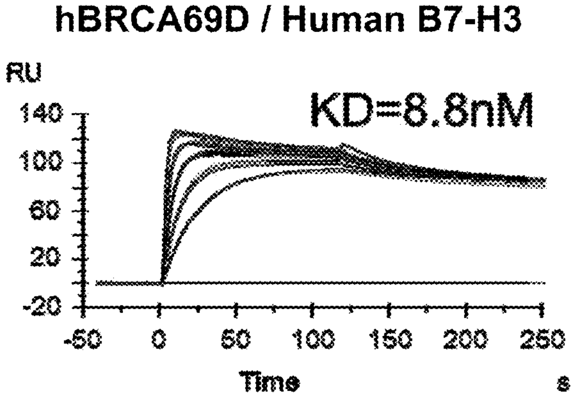
Figure 1F:
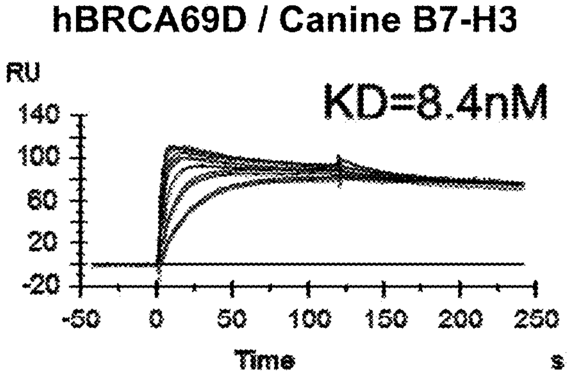

Antibodies hBRCA84D and hBRCA69D were tested in an ELISA for binding to canine B7-H3. Briefly, soluble human B7-H3 and canine B7-H3 were expressed in CHO cells. Each soluble molecule was engineered to express a 6× His tag at the carboxy terminus to aid in purification of the expressed protein. The molecules were purified by nickel column chromatography using standard techniques. ELISA plates were coated with the soluble B7-H3 and allowed to dry. The plates were washed and blocked using standard ELISA techniques. The wells were probed with either hBRCA84D, hBRCA69D or a control hIgG. Secondary detection reagent was added and binding was determined As shown in FIG. 1A (hBRCA84D) and FIG. 1B (hBRCA69D), the antibodies were able to bind to soluble canine B7-H3 (cB7-H3). To determine binding affinity of the hBRCA84D and hBRCA69D antibodies to soluble canine B7-H3, SPR analysis was conducted. As shown in FIGS. 1C and 1D (hBRCA84D) and FIGS. 1E and 1F (BRCA69D) the binding affinities are similar to the binding of the antibodies to soluble human B7-H3 (shown in FIG. 1A and FIG. 1B, respectively).

EXAMPLE 2

Ability of Anti-Human B7-H3 Antibody to Bind Canine and Feline B7-H3 in Tumor Tissues Antibody BRCA69D was evaluated for its ability to bind to B7-H3 receptor of canine and feline in tumor tissues. The results of IHC analyses for feline cancer tissue are shown in Table 2 and Table 3.

TABLE 2

| Feline IHC Summary | | |
|---|---|---|
| Diagnosis | Positive Rate | ≥2 + Positive Rate |
| Fibrosarcoma | 20% (1/5) | 0% (0/5) |
| Mammary Carcinoma | 60% (3/5) | 40% (2/5) |
| Squamous Cell Carcinoma | 80% (4/5) | 80% (4/5) |

Figure 2:
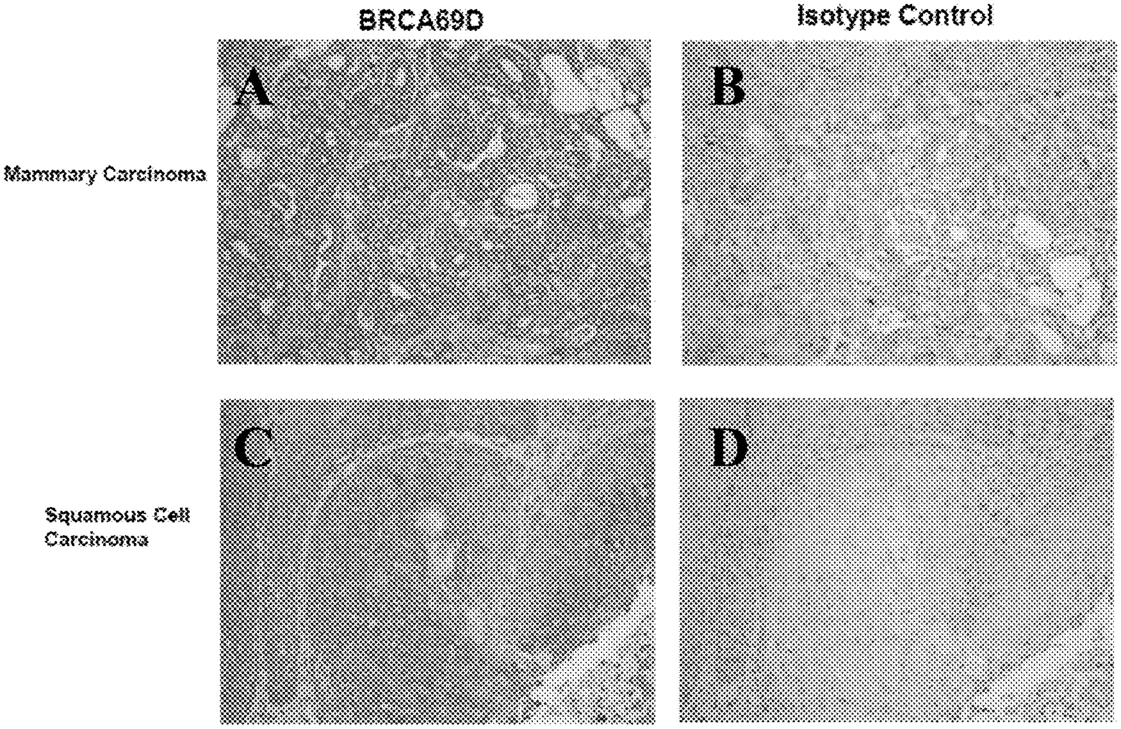
FIG. 2, Panels A-D, show representative IHC biopsies of feline cancers.

As disclosed in Table 2, BRCA69D was found to be able to bind to the feline B7-H3 receptor in tumor tissue samples and to accurately detect feline cancer tissue. Thus, BRCA69D may be used to diagnose and detect feline cancers associated with B7-H3 expression, in the same manner as it may be used be used to diagnose and detect human cancers associated with B7-H3 expression. Representative biopsy sections are shown in FIG. 2.

Table 3 presents the results of IHC studies of the ability of BRCA69D to bind to the canine B7-H3 receptor in canine tumor tissue samples and to accurately detect canine cancer tissue.

TABLE 3

| Canine IHC Summary | | |
|---|---|---|
| Diagnosis | Positive Rate | ≥2 + Positive Rate |
| Histiocytic Sarcoma | 60% (3/5) | 40% (2/5) |
| Hemangiosarcoma | 100% (5/5) | 20% (1/5) |
| Malignant Melanoma | 33% (1/3) | 0% (0/3) |
| Mast Cell Tumor High Grade | 100% (5/5) | 80% (4/5) |
| Osteosarcoma | 100% (5/5) | 40% (2/5) |
| Thyroid Carcinoma | 100% (5/5) | 100% (5/5) |
| Transitional Cell Carcinoma | 80% (4/5) | 80% (4/5) |
| Squamous Cell Carcinoma | 100% (5/5) | 100% (5/5) |

Figure 3:
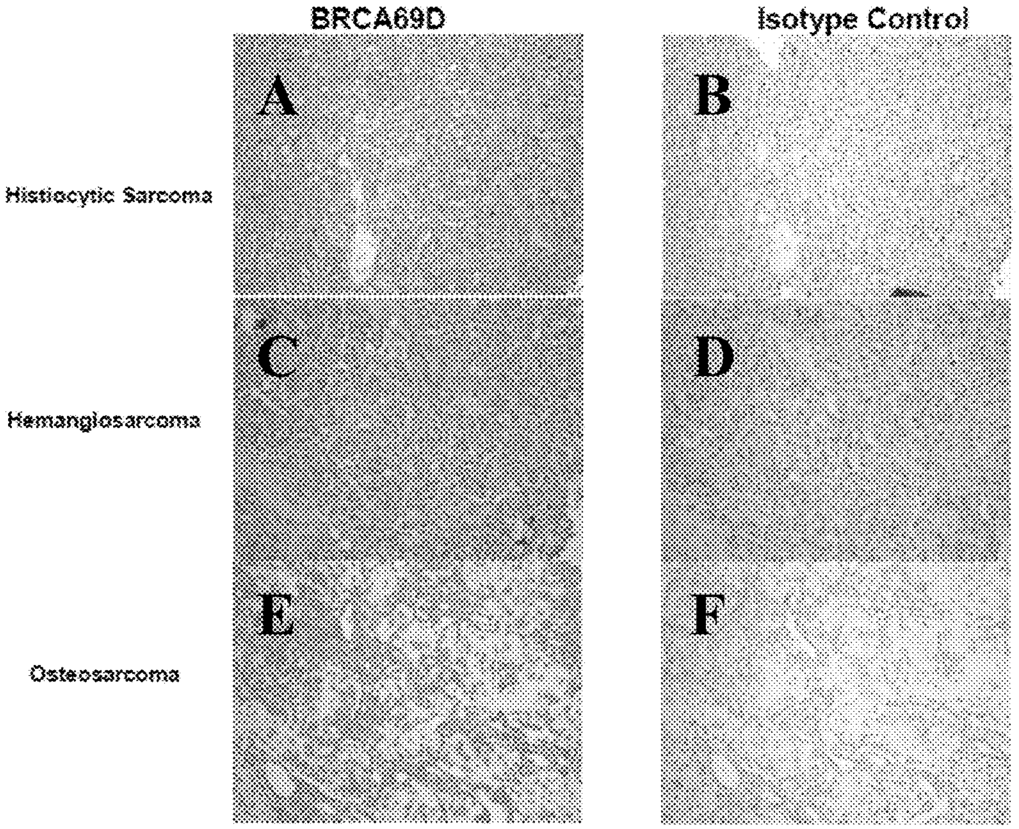
FIG. 3, Panels A-F show representative IHC biopsies of canine cancers.
Figure 4:
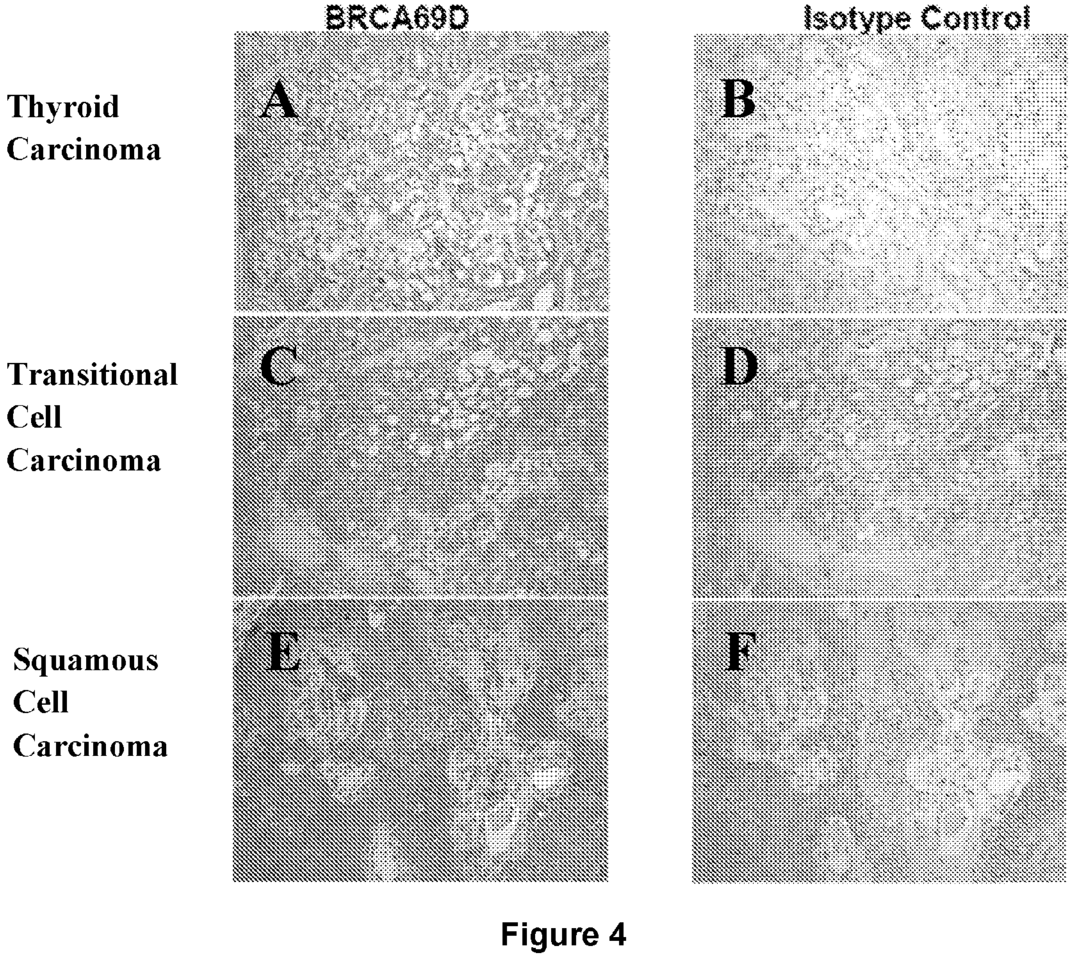
FIG. 4, Panels A-F show representative IHC biopsies of canine cancers.

As disclosed in Table 3, BRCA69D was found to be able to bind to the canine B7-H3 receptor in tumor tissue samples and to accurately detect canine cancer tissue. Thus, BRCA69D may be used to diagnose and detect canine cancers associated with B7-H3 expression, in the same manner as it may be used be used to diagnose and detect human cancers associated with B7-H3 expression. Representative biopsy sections are shown in FIG. 3 and FIG. 4.

EXAMPLE 3

Bispecific Molecules Specific for B7-H3 and CD3 Mediate Potent Redirected T-Cell Killing Bispecific molecules specific for canine CD3 and B7-H3 (K9CD3×B7-H3) were prepared as a dual affinity retargeting (DART) diabody reagents. Such bispecific molecules have the ability to localize a T-cell (by binding such T-cell to the CD3 portion of a CD3-binding bispecific molecule) to the location of a cancer cell (by binding such cancer cell to the B7-H3 binding portion of the bispecific molecule). The localized T-cell can then mediate the killing of the cancer cell in a process termed "redirected" killing.

The K9CD3×B7-H3 bispecific molecule was constructed having the anti-CD3 variable domains of K9CD3-1 and the anti-B7-H3 variable domains of hBRCA84D-2:

Chain 1 sequence (SEQ ID NO:138):

```
DIQLTQSPSF LSASVGDRVT ITCKASQNVD TNVAWYQQKP
GKAPKALIYS ASYRYSGVPS RFSGSGSGTD FTLTISSLQP
```

-continued

```
EDFATYYCQQ YNNYPFTFGQ GTKLEIKGGG SGGGGEVQLQ
QSGPELVKPG ASVKISCKAS GYTFSDYNMH WVKQSHGESL
EWIGYIYPYN GGTYYNQKFK SKATLTVDNS SSTAYMEFRS
LTSEDSAVYY CARLVYFDYW GQGTALTVSS GGCGGGEVAA
LEKEVAALEK EVAALEKEVA ALEK
```

Polynucleotide Encoding Chain 1 (SEQ ID NO:139):

```
gacatccagc tgacccagtc cccctccttc ctgtctgcct
ccgtgggcga cagagtgacc atcacatgca aggcctccca
gaacgtggac accaacgtgg cctggtatca gcagaagcct
ggcaaggccc ctaaggcgct gatctactcc gcctcctacc
ggtactccgg cgtgccttcc aggttctccg gctccggctc
tggcaccgac ttcaccctga ccatctccag cctgcagcct
gaggacttcg ccacctacta ctgccagcag tacaacaact
accctttcac cttcggccag ggcaccaagc tggaaatcaa
gggaggcgga tccggcggcg gaggcgaggt ccagcttcag
cagtcaggac ctgagctggt gaaacctggg gcctcagtga
agatatcctg caaggcttct ggatacacat tctctgacta
caacatgcac tgggtgaaac agagccatgg agagagcctt
gagtggattg gatatattta tccttacaat ggtggtactt
actacaacca gaaattcaag agcaaggcca cattgactgt
agacaattcc tccagcacag cctacatgga gttccgcagc
ctgacatctg aggactctgc agtctattac tgtgcaaggc
tggtttactt tgactactgg ggccaaggca ccgctctcac
agtctcctcc ggaggatgtg gcggtggaga agtggccgca
ctggagaaag aggttgctgc tttggagaag gaggtcgctg
cacttgaaaa ggaggtcgca gccctggaga aa
```

Chain 2 sequence (SEQ ID NO:140):

```
DILLTQSPAT LSVTPGETVS LSCRASQSIF KNLHWYQQKS
HRSPRLLIKY ASDSISGIPS RFTGSGSGTD YTLSINSVKP
EDEGVYYCLQ AYSTPWTFGG GTKLEIKGGG SGGGGEVQLV
ESGGGLVQPG GSLRLSCAAS GFTFSSFGMH WVRQAPGKGL
EWVAYISSDS SAIYYADTVK GRFTISRDNA KNSLYLQMNS
LRDEDTAVYY CGRGRENIYY GSRLDYWGQG TTVTVSSGGC
GGGKVAALKE KVAALKEKVA ALKEKVAALK E
```

Polynucleotide Encoding Chain 2 (SEQ ID NO:141):

```
gacatcctgc tgacccagtc tccagccacc ctgtctgtga
ctccaggaga aacagtcagt ctttcctgta gggccagcca
gagtattttc aagaacctac actggtatca acagaaatca
```

-continued

```
catcggtctc caaggcttct catcaagtat gcttctgatt
ccatctctgg gatcccctcc aggttcactg gcagtggatc
ggggacagat tacactctca gtatcaacag tgtgaagccc
gaagatgaag gagtatatta ctgtcttcaa gcttacagca
caccgtggac gttcggtgga ggcaccaaac tggaaatcaa
aggaggcgga tccggcggcg gaggcgaggt gcagctggtc
gagtctggcg gaggactggt gcagcctggc ggctccctga
gactgtcttg cgccgcctcc ggcttcacct tctccagctt
cggcatgcac tgggtccgcc aggctccagg caagggactg
gaatgggtgg cctacatctc ctccgactcc tccgccatct
actacgccga caccgtgaag ggcaggttca ccatctcccg
ggacaacgcc aagaactccc tgtacctgca gatgaactcc
ctgcgggacg aggacaccgc cgtgtactac tgcggcagag
gccgggagaa tatctactac ggctcccggc tggattattg
gggccagggc accaccgtga ccgtgtcctc cggaggatgt
ggcggtggaa aagtggccgc actgaaggag aaagttgctg
ctttgaaaga gaaggtcgcc gcacttaagg aaaaggtcgc
agccctgaaa gag
```

The K9CD3×B7-H3 bispecific molecule was constructed having the anti-CD3 variable domains of K9CD3-1 and the anti-B7-H3 variable domains of hBRCA69D:

Chain 1 sequence (SEQ ID NO:142):

```
DILLTQSPAT LSVTPGETVS LSCRASQSIF KNLHWYQQKS
HRSPRLLIKY ASDSISGIPS RFTGSGSGTD YTLSINSVKP
EDEGVYYCLQ AYSTPWTFGG GTKLEIKGGG SGGGGQVQLV
QSGAEVKKPG ASVKVSCKAS GYTFTSYWMQ WVRQAPGQGL
EWMGTIYPGD GDTRYTQKFK GRVTITADKS TSTAYMELSS
LRSEDTAVYY CARRGIPRLW YFDVWGQGTT VTVSSGGCGG
GKVAALKEKV AALKEKVAAL KEKVAALKE
```

Polynucleotide Encoding Chain 1 (SEQ ID NO:143):

```
gacatcctgc tgacccagtc tccagccacc ctgtctgtga
ctccaggaga aacagtcagt ctttcctgta gggccagcca
gagtattttc aagaacctac actggtatca acagaaatca
catcggtctc caaggcttct catcaagtat gcttctgatt
ccatctctgg gatcccctcc aggttcactg gcagtggatc
ggggacagat tacactctca gtatcaacag tgtgaagccc
gaagatgaag gagtatatta ctgtcttcaa gcttacagca
caccgtggac gttcggtgga ggcaccaaac tggaaatcaa
aggaggcgga tccggcggag gggtcaggt gcagctggtg
cagagcgggg cagaggtgaa gaaaccaggt gccagcgtga
aggtgtcttg caaagccagt ggctacactt tcacctccta
ttggatgcag tgggtcagac aggctccagg acagggactg
gaatggatgg gcaccatcta ccctggggac ggtgatacta
gatataccca gaagtttaaa ggacgcgtga caattactgc
tgacaagtca acctccacag catacatgga gctgtccagc
ctgcgatctg aagatacagc cgtgtactat tgtgctaggc
ggggcatccc caggctgtgg tatttcgacg tgtggggcca
gggaaccaca gtgactgtgt cttccggagg atgtggcggt
ggaaaagtgg ccgcactgaa ggagaaagtt gctgctttga
aagagaaggt cgccgcactt aaggaaaagg tcgcagccct
gaaagag
```

Chain 2 sequence (SEQ ID NO:144):

```
DIQMTQSPSS LSASVGDRVT ITCRASQDIS NYLNWYQQKP
GKAPKLLIYY TSRLHSGVPS RFSGSGSGTD FTLTISSLQP
EDIATYYCQQ GNTLPPTFGG GTKLEIKGGG GSGGGGEVQL
QQSGPELVKP GASVKISCKA SGYTFSDYNM HWVKQSHGES
LEWIGYIYPY NGGTYYNQKF KSKATLTVDN SSSTAYMEFR
SLTSEDSAVY YCARLVYFDY WGQGTALTVS SGGCGGGEVA
ALEKEVAALE KEVAALEKEV AALEK
```

Polynucleotide Encoding Chain 2 (SEQ ID NO:145):

```
gacatccaga tgacacagtc tccatccagc ctgtcagcct
ccgtgggaga cagggtgacc atcacatgcc gggctagtca
ggatatcagt aactacctga actggtacca gcagaagcca
ggaaaagcac ccaagctgct gatttactat acctcaaggc
tgcactccgg tgtgcctagc agattcagcg gttctggcag
tggaaccgac tttactctga ccatctctag tctgcagcca
gaggatattg ccacatacta ttgtcagcag ggcaacacac
tgcccccctac tttcggcgga gggaccaagc tggaaataaa
aggagggggt ggatccggcg gcggaggcga ggtccagctt
cagcagtcag gacctgagct ggtgaaacct ggggcctcag
tgaagatatc ctgcaaggct tctggataca cattctctga
ctacaacatg cactgggtga aacagagcca tggagagagc
cttgagtgga ttggatatat ttatccttac aatggtggta
cttactacaa ccagaaattc aagagcaagg ccacattgac
tgtagacaat tcctccagca cagcctacat ggagttccgc
agcctgacat ctgaggactc tgcagtctat tactgtgcaa
ggctggttta ctttgactac tggggccaag gcaccgctct
cacagtctcc tccggaggat gtggcggtgg agaagtggcc
```

-continued

```
gcactggaga aagaggttgc tgctttggag aaggaggtcg

ctgcacttga aaaggaggtc gcagccctgg agaaa
```

The K9CD3×B7-H3 bispecific molecule was constructed having the anti-CD3 variable domains of K9CD3-2 and the anti-B7-H3 variable domains of hBRCA84D-2:

Chain 1 sequence (SEQ ID NO:146):

```
NIVMTQSPKS MSMSVGERVT LNCKASENVD SYVSWYQQKP

KQSPTLLIYG ASNRSTGVPD RFTGSGSVTD FTLTITSVQA

EDLAYYHCGQ TYSYPFTFGS GTKLEIKGGG SGGGGEVQLV

ESGGGLVQPG GSLRLSCAAS GFTFSSFGMH WVRQAPGKGL

EWVAYISSDS SAIYYADTVK GRFTISRDNA KNSLYLQMNS

LRDEDTAVYY CGRGRENIYY GSRLDYWGQG TTVTVSSGGC

GGGEVAALEK EVAALEKEVA ALEKEVAALE K
```

Polynucleotide Encoding Chain 1 (SEQ ID NO:147):

```
aacattgtga tgacccaatc tcccaaatcc atgtccatgt

cagttggaga gagggtcacc ttgaactgca aggccagtga

gaatgtggat tcttatgtgt cctggtatca gcagaaacca

aaacagtctc ctacattact gatttacggg gcatccaacc

ggtccactgg ggtccccgat cgcttcacag gcagcggatc

tgtaacagat ttcactctga ccatcaccag tgtgcaggct

gaagaccttg catattatca ctgtggacag acttacagtt

atccattcac gttcggctcg gggacaaagt tggaaataaa

aggaggcgga tccggcggcg gaggcgaggt gcagctggtc

gagtctggcg gaggactggt gcagcctggc ggctccctga

gactgtcttg cgccgcctcc ggcttcacct tctccagctt

cggcatgcac tgggtccgcc aggctccagg caagggactg

gaatgggtgg cctacatctc ctccgactcc tccgccatct

actacgccga caccgtgaag ggcaggttca ccatctcccg

ggacaacgcc aagaactccc tgtacctgca gatgaactcc

ctgcgggacg aggacaccgc cgtgtactac tgcggcagag

gccgggagaa tatctactac ggctcccggc tggattattg

gggccagggc accaccgtga ccgtgtcctc cggaggatgt

ggcggtggag aagtggccgc actggagaaa gaggttgctg

ctttggagaa ggaggtcgct gcacttgaaa aggaggtcgc

agccctggag aaa
```

Chain 2 sequence (SEQ ID NO:148):

```
DIQLTQSPSF LSASVGDRVT ITCKASQNVD TNVAWYQQKP

GKAPKALIYS ASYRYSGVPS RFSGSGSGTD FTLTISSLQP

EDFATYYCQQ YNNYPFTFGQ GTKLEIKGGG SGGGGEVQLV
```

-continued

```
ESGGGLVQPK GSLTLSCAAS GFTFNIFAMN WVRQAPGKGL

EWVARIRSKN NYFATYYAAS VRDRFTISRD DSQSMVYLQM

NNLKTEDTGM YYCVRRGYFD VWGAGTTVTV SSGGCGGGKV

AALKEKVAAL KEKVAALKEK VAALKE
```

Polynucleotide Encoding Chain 2 (SEQ ID NO:149):

```
gacatccagc tgacccagtc cccctccttc ctgtctgcct

ccgtgggcga cagagtgacc atcacatgca aggcctccca

gaacgtggac accaacgtgg cctggtatca gcagaagcct

ggcaaggccc ctaaggcgct gatctactcc gcctcctacc

ggtactccgg cgtgccttcc aggttctccg gctccggctc

tggcaccgac ttcaccctga ccatctccag cctgcagcct

gaggacttcg ccacctacta ctgccagcag tacaacaact

accctttcac cttcggccag ggcaccaagc tggaaatcaa

gggaggcgga tccggcggcg gaggcgaggt gcagcttgtt

gagtctggtg gaggattggt gcagcctaaa gggtcattga

cactctcatg tgcagcctct ggattcacct tcaatatctt

cgccatgaac tgggtccgcc aggctccagg aaagggtttg

gaatgggttg ctcgtataag aagtaaaaat aattattttg

caacatatta tgctgcttca gtgagagaca ggttcaccat

ctccagagat gattcacaaa gcatggtcta tcttcaaatg

aacaacttga aaactgagga cacaggcatg tattactgtg

tgagacgggg atacttcgat gtctggggcg cagggaccac

ggtcaccgtc tcctccggag gatgtggcgg tggaaaagtg

gccgcactga aggagaaagt tgctgctttg aaagagaagg

tcgccgcact taaggaaaag gtcgcagccc tgaaagag
```

The K9CD3×B7-H3 bispecific molecule was constructed having the anti-CD3 variable domains of K9CD3-2 and the anti-B7-H3 variable domains of hBRCA69D:

Chain 1 sequence (SEQ ID NO:150):

```
NIVMTQSPKS MSMSVGERVT LNCKASENVD SYVSWYQQKP

KQSPTLLIYG ASNRSTGVPD RFTGSGSVTD FTLTITSVQA

EDLAYYHCGQ TYSYPFTFGS GTKLEIKGGG SGGGGQVQLV

QSGAEVKKPG ASVKVSCKAS GYTFTSYWMQ WVRQAPGQGL

EWMGTIYPGD GDTRYTQKFK GRVTITADKS TSTAYMELSS

LRSEDTAVYY CARRGIPRLW YFDVWGQGTT VTVSSGGCGG

GEVAALEKEV AALEKEVAAL EKEVAALEK
```

Polynucleotide Encoding Chain 1 (SEQ ID NO:151):

```
aacattgtga tgacccaatc tcccaaatcc atgtccatgt

cagttggaga gagggtcacc ttgaactgca aggccagtga

gaatgtggat tcttatgtgt cctggtatca gcagaaacca
```

-continued

```
aaacagtctc ctacattact gatttacggg gcatccaacc
ggtccactgg ggtccccgat cgcttcacag gcagcggatc
tgtaacagat ttcactctga ccatcaccag tgtgcaggct
gaagaccttg catattatca ctgtggacag acttacagtt
atccattcac gttcggctcg gggacaaagt tggaaataaa
aggaggcgga tccggcggag ggggtcaggt gcagctggtg
cagagcgggg cagaggtgaa gaaaccaggt gccagcgtga
aggtgtcttg caaagccagt ggctacactt tcacctccta
ttggatgcag tgggtcagac aggctccagg acagggactg
gaatggatgg gcaccatcta ccctggggac ggtgatacta
gatataccca gaagtttaaa ggacgcgtga caattactgc
tgacaagtca acctccacag catacatgga gctgtccagc
ctgcgatctg aagatacagc cgtgtactat tgtgctaggc
ggggcatccc caggctgtgg tatttcgacg tgtggggcca
gggaaccaca gtgactgtgt cttccggagg atgtggcggt
ggagaagtgg ccgcactgga gaaagaggtt gctgctttgg
agaargaggt cgctgcactt gaaaaggagg tcgcagccct
ggagaaa
```

Chain 2 sequence (SEQ ID NO:152):

```
DIQMTQSPSS LSASVGDRVT ITCRASQDIS NYLNWYQQKP
GKAPKLLIYY TSRLHSGVPS RFSGSGSGTD FTLTISSLQP
EDIATYYCQQ GNTLPPTFGG GTKLEIKGGG GSGGGGEVQL
VESGGGLVQP KGSLTLSCAA SGFTFNIFAM NWVRQAPGKG
LEWVARIRSK NNYFATYYAA SVRDRFTISR DDSQSMVYLQ
MNNLKTEDTG MYYCVRRGYF DVWGAGTTVT VSSGGCGGGK
VAALKEKVAA LKEKVAALKE KVAALKE
```

Polynucleotide Encoding Chain 2 (SEQ ID NO: 153):

```
gacatccaga tgacacagtc tccatccagc ctgtcagcct
ccgtgggaga cagggtgacc atcacatgcc gggctagtca
ggatatcagt aactacctga actggtacca gcagaagcca
ggaaaagcac ccaagctgct gatttactat acctcaaggc
tgcactccgg tgtgcctagc agattcagcg gttctggcag
tggaaccgac tttactctga ccatctctag tctgcagcca
gaggatattg ccacatacta ttgtcagcag ggcaacacac
tgccccctac tttcggcgga gggaccaagc tggaaataaa
aggagggggt ggatccggcg gcggaggcga ggtgcagctt
gttgagtctg gtggaggatt ggtgcagcct aaagggtcat
tgacactctc atgtgcagcc tctggattca ccttcaatat
cttcgccatg aactgggtcc gccaggctcc aggaaagggt
```

-continued

```
ttggaatggg ttgctcgtat aagaagtaaa aataattatt
ttgcaacata ttatgctgct tcagtgagag acaggttcac
catctccaga gatgattcac aaagcatggt ctatcttcaa
atgaacaact tgaaaactga ggacacaggc atgtattact
gtgtgagacg gggatacttc gatgtctggg gcgcagggac
cacggtcacc gtctcctccg gaggatgtgg cggtggaaaa
gtggccgcac tgaaggagaa agttgctgct ttgaaagaga
aggtcgccgc acttaaggaa aaggtcgcag ccctgaaaga
g
```

Figure 5A:
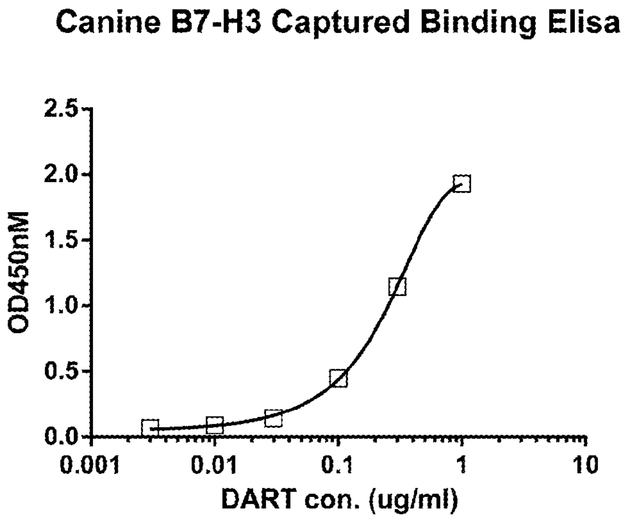
FIGS. 5A-5D shows PBMCs from canine being redirected to kill canine B7-H3-positive tumor lines or a human B7-H3-positive tumor line.
Figure 5B:
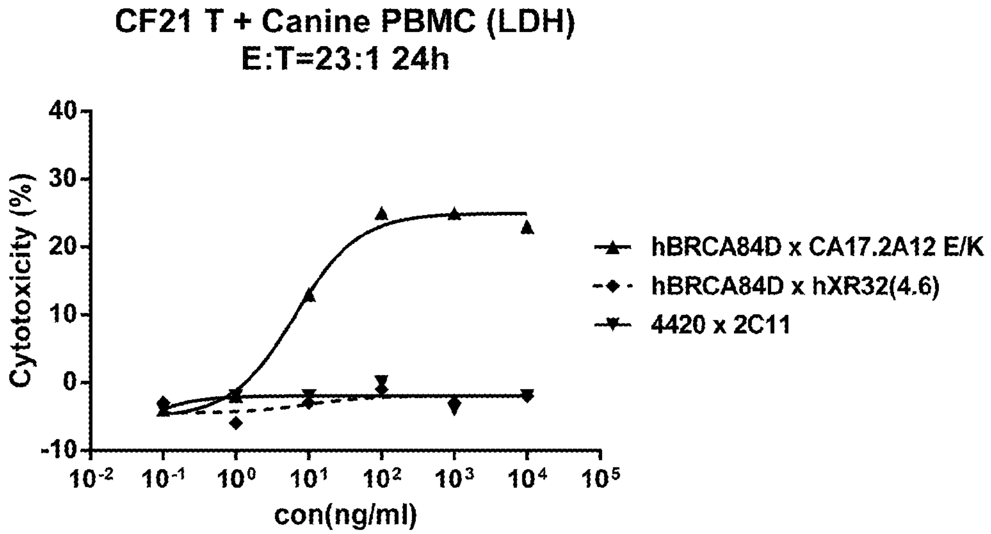
Figure 5C:
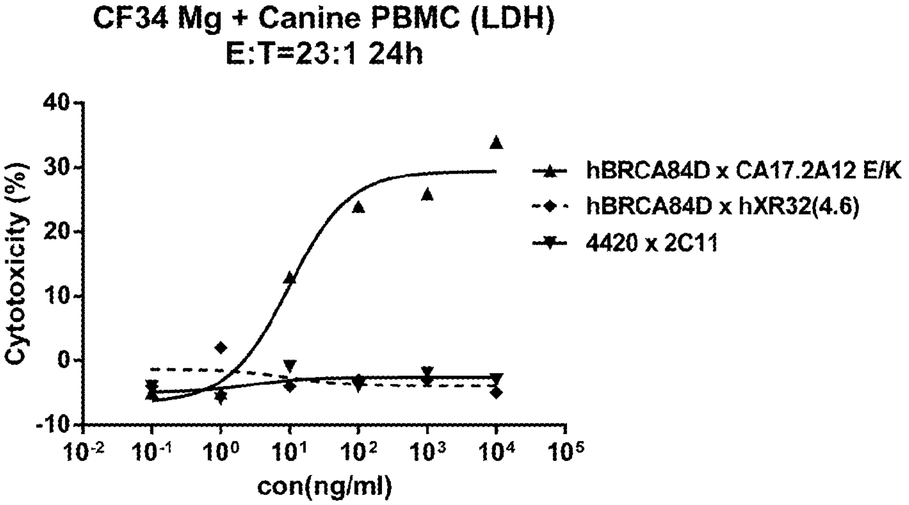
Figure 5D:
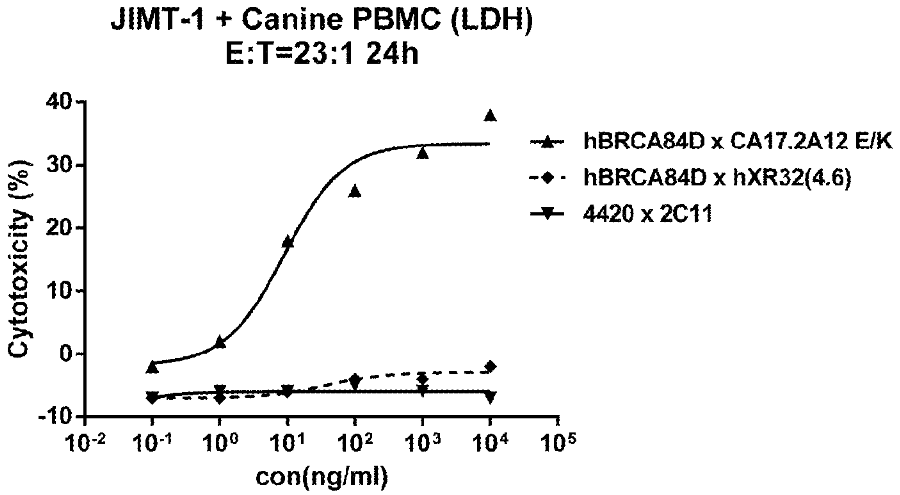

Binding of the bispecific molecule (SEQ ID NO:138 and SEQ ID NO:140) to canine B7-H3 was measured by ELISA (FIG. 5A). In order to demonstrate the ability of the bispecific molecule to mediate redirected killing of cancer cells, the above described K9CD3×B7-H3 bispecific molecule (SEQ ID NO:138 and SEQ ID NO:140) was incubated at various concentrations with target cells (canine mammary gland cancer cell lines CF21 and CF32 and human breast tumor cell line JIMT-1) and effector cells (canine PBMCs) at an effector to target ratio of 23:1. Cytotoxicity was determined (LDH assay). The results are shown in FIGS. 5B and 5C (canine cells) and FIG. 5D (human cells) and demonstrate the ability of the K9CD3×B7-H3 bispecific molecule to mediate redirected killing of B7-H3-expressing cancer cells with canine PBMCs.

EXAMPLE 4

Bispecific Molecules Comprising an Fc Region Specific for B7-H3 and CD3 Mediate Potent Redirected T-Cell Killing A K9CD3×B7-H3 bispecific molecule can be constructed having the anti-CD3 variable domains of K9CD3-1 and the anti-B7-H3 variable domains of hBRCA69D and further comprising an Fc region. Such molecule can be constructed by expressing three polypeptide chains in the same cell. The first polypeptide chain will comprise the light chain variable domain for K9CD3-1, a short linker, the variable heavy chain domain for hBRCA69D, an *E coli* domain and last a CH2 and CH3 domain of a canine IgG1 Fc. To ensure that chain 1 heterodimerizes with chain 2, an *E coli* domain is added. To ensure that chain 1 does not homodimerize at the CH2 and CH3 domains, the sequence has been modified to include a knob at position 366 (T366W modification) (see U.S. Pat. Nos. 5,731,168; 5,807,706; 5,821,333; 7,429,652; 7,642,228; 7,695,936; and 8,216,80). To disable the Fc region alanine residues were incorporated at positions 234 and 235 (see U.S. Pat. No. 5,624,821). Such sequence is shown in SEQ ID NO:154 and the polynucleotide sequence is shown in SEQ ID NO:155 (residues 234-235 and 366 are shown underlined).

Chain 1 sequence (SEQ ID NO:154):

```
DILLTQSPAT LSVTPGETVS LSCRASQSIF KNLHWYQQKS
HRSPRLLIKY ASDSISGIPS RFTGSGSGTD YTLSINSVKP
EDEGVYYCLQ AYSTPWTFGG GTKLEIKGGG SGGGGQVQLV
```

-continued

QSGAEVKKPG ASVKVSCKAS GYTFTSYWMQ WVRQAPGQGL

EWMGTIYPGD GDTRYTQKFK GRVTITADKS TSTAYMELSS

LRSEDTAVYY CARRGIPRLW YFDVWGQGTT VTVSSGGCGG

GEVAALEKEV AALEKEVAAL EKEVAALEKG GGRVPRPPDC

PKCPAPEAAG GPSVFIFPPK PKDTLLIART PEVTCVVVDL

DPEDPEVQIS WFVDGKQMQT AKTQPREEQF QGTYRVVSVL

PIGHQDWLKG KQFTCKVNNK ALPSPIERTI SKARGQAHQP

SVYVLPPSRE ELSKNTVSLW CLIKDFFPPD IDVEWQSNGQ

QEPESKYRTT PPQLDEDGSY FLYSKLSVDK SRWQRGDTFI

CAVMHEALHN HYTQESLSHS PGK

Polynucleotide Encoding Chain 1 (SEQ ID NO:155):

gacatcctgc tgacccagtc tccagccacc ctgtctgtga ctccaggaga aacagtcagt ctttcctgta gggccagcca gagtattttc aagaacctac actggtatca acagaaatca catcggtctc caaggcttct catcaagtat gcttctgatt ccatctctgg gatcccctcc aggttcactg gcagtggatc ggggacagat tacactctca gtatcaacag tgtgaagccc gaagatgaag gagtatatta ctgtcttcaa gcttacagca caccgtggac gttcggtgga ggcaccaaac tggaaatcaa aggaggcgga tccggcggag gggtcaggt gcagctggtg cagagcgggg cagaggtgaa gaaaccaggt gccagcgtga aggtgtcttg caaagccagt ggctacactt tcacctccta ttggatgcag tgggtcagac aggctccagg acagggactg gaatggatgg gcaccatcta ccctggggac ggtgatacta gatataccca gaagtttaaa ggacgcgtga caattactgc tgacaagtca acctccacag catacatgga gctgtccagc ctgcgatctg aagatacagc cgtgtactat tgtgctaggc ggggcatccc caggctgtgg tatttcgacg tgtggggcca gggaaccaca gtgactgtgt cttccggagg atgtggcggt ggagaagtgg ccgcactgga gaaagaggtt gctgctttgg agaaggaggt cgctgcactt gaaaaggagg tcgcagccct ggagaaaggc ggcgggaggg tgcctcgacc acctgattgc ccaaagtgtc cagctcccga agccgctggc ggaccctccg tgttcatctt tccacccaag cctaaagaca cactgctgat tgcaaggacc ccagaggtga catgcgtggt cgtggacctg gaccccgagg accctgaagt ccagatcagc tggttcgtgg atgggaagca gatgcagaca gccaaaactc agccaaggga ggaacagttt caaggtactt accgggtcgt gtctgtgctg cccattggcc accaggactg gctgaaggga aaacagttta cctgcaaggt gaacaacaag gccctgcctt ccccaatcga -continued gcgaacaatt agcaaggcac gtggacaggc acatcagcca agcgtctacg tgctgcctcc atcccgagag gaactgagca agaacactgt ctctctgtgg tgtctgatca aagatttctt tccccctgac attgatgtgg agtggcagtc taatggacag caggagcctg agagtaagta tcggaccaca ccaccccagc tggacgaaga tggcagttac ttcctgtata gtaagctgtc agtggacaaa tccagatggc agcgcggaga taccttcatc tgcgcagtga tgcacgaagc actgcacaat cactacaccc aggagtcact gagccatagc ccagggaag The second polypeptide chain will comprise the light chain variable domain for hBRCA69D, a short linker, the variable heavy chain domain for K9CD3-1 and followed by a K coil domain. The addition of the K coil domain is used to ensure heterodimerization with chain 1 at its *E coli* domain. Such sequence is shown in SEQ ID NO:156 and the polynucleotide sequence is shown in SEQ ID NO:157.

Chain 2 sequence (SEQ ID NO:156):

DIQMTQSPSS LSASVGDRVT ITCRASQDIS NYLNWYQQKP

GKAPKLLIYY TSRLHSGVPS RFSGSGSGTD FTLTISSLQP

EDIATYYCQQ GNTLPPTFGG GTKLEIKGGG GSGGGGEVQL

QQSGPELVKP GASVKISCKA SGYTFSDYNM HWVKQSHGES

LEWIGYIYPY NGGTYYNQKF KSKATLTVDN SSSTAYMEFR

SLTSEDSAVY YCARLVYFDY WGQGTALTVS SGGCGGGKVA

ALKEKVAALK EKVAALKEKV AALKE

Polynucleotide Encoding Chain 2 (SEQ ID NO:157):

gacatccaga tgacacagtc tccatccagc ctgtcagcct ccgtgggaga cagggtgacc atcacatgcc gggctagtca ggatatcagt aactacctga actggtacca gcagaagcca ggaaaagcac ccaagctgct gatttactat acctcaaggc tgcactccgg tgtgcctagc agattcagcg gttctggcag tggaaccgac tttactctga ccatctctag tctgcagcca gaggatattg ccacatacta ttgtcagcag ggcaacacac tgccccctac tttcggcgga gggaccaagc tggaaataaa aggagggggt ggatccggcg gcggaggcga ggtccagctt cagcagtcag gacctgagct ggtgaaacct ggggcctcag tgaagatatc ctgcaaggct tctggataca cattctctga ctacaacatg cactgggtga aacagagcca tggagagagc cttgagtgga ttggatatat ttatccttac aatggtggta cttactacaa ccagaaattc aagagcaagg ccacattgac tgtagacaat tcctccagca cagcctacat ggacttccgc agcctgacat ctgaggactc tgcactctat tactgtgcaa -continued

```
ggctggttta ctttgactac tggggccaag gcaccgctct

cacagtctcc tccgaagaat gtggcggtgg aaaagtggcc

gcactgaagg agaaagttgc tgctttgaaa gagaaggtcg

ccgcacttaa ggaaaaggtc gcagccctga aagag
```

The third polypeptide chain will comprise the CH2 and CH3 domain of a canine IgG1 Fc region. To accept the knob created in the Fc region of Chain 1, three substitutions were made in Chain 3 to create a hole (T366S, L368A and Y407V). A modification at position 435 (H435R) was used to prevent homodimers of Chain 3 from binding to Protein A, thus aiding in purification of the bispecific molecule. Such sequence is shown in SEQ ID NO:158 (with the relevant residues underlined) and the polynucleotide sequence is shown in SEQ ID NO:159.

K9 IgFc ala ala (residues 234-235; shown underlined) Hole Chain 3 (SEQ ID NO:158):

```
RVPRPPDCPK CPAPEAAGGP SVFIFPPKPK DTLLIARTPE

VTCVVVDLDP EDPEVQISWF VDGKQMQTAK TQPREEQFQG

TYRVVSVLPI GHQDWLKGKQ FTCKVNNKAL PSPIERTISK

ARGQAHQPSV YVLPPSREEL SKNTVSLSCA IKDFFPPDID

VEWQSNGQQE PESKYRTTPP QLDEDGSYFL VSKLSVDKSR

WQRGDTFICA VMHEALHNRY TQESLSHSPG K
```

K9 IgFc ala ala Hole Chain 3 (SEQ ID NO:159):

```
agggtgcctc gaccacctga ttgcccaaag tgtccagctc

ccgaagccgc tggcggaccc tccgtgttca tctttccacc

caagcctaaa gacacactgc tgattgcaag gaccccagag

gtgacatgcg tggtcgtgga cctggacccc gaggaccctg
```

-continued

```
aagtccagat cagctggttc gtggatggga agcagatgca

gacagccaaa actcagccaa gggaggaaca gtttcaaggt

acttaccggg tcgtgtctgt gctgcccatt ggccaccagg

actggctgaa gggaaaacag tttacctgca aggtgaacaa

caaggccctg ccttccccaa tcgagcgaac aattagcaag

gcacgtggac aggcacatca gccaagcgtc tacgtgctgc

ctccatcccg agaggaactg agcaagaaca ctgtctctct

gtcctgtgcc atcaaagatt tctttccccc tgacattgat

gtggagtggc agtctaatgg acagcaggag cctgagagta

agtatcggac cacaccaccc cagctggacg aagatggcag

ttacttcctg gtgagtaagc tgtcagtgga caaatccaga

tggcagcgcg gagatacctt catctgcgca gtgatgcacg

aagcactgca caatagatac acccaggagt cactgagcca

tagcccaggg aag
```

Vectors encoding the three chains are transfected into CHO cells. Following appropriate selection, the cells are cultured in medium for 7 days. Culture medium and cells are harvested. The bispecific molecule is purified using chromatography methods well known in the art.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

SEQUENCE LISTING

```
<160> NUMBER OF SEQ ID NOS: 159

<210> SEQ ID NO 1
<211> LENGTH: 316
<212> TYPE: PRT
<213> ORGANISM: Homo sapiens

<400> SEQUENCE: 1

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
```

-continued

```
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315


<210> SEQ ID NO 2
<211> LENGTH: 948
<212> TYPE: DNA
<213> ORGANISM: Homo sapiens

<400> SEQUENCE: 2

atgctgcgtc ggcggggcag ccctggcatg ggtgtgcatg tgggtgcagc cctgggagca      60

ctgtggttct gcctcacagg agccctggag gtccaggtcc ctgaagaccc agtggtggca     120

ctggtgggca ccgatgccac cctgtgctgc tccttctccc ctgagcctgg cttcagcctg     180

gcacagctca acctcatctg gcagctgaca gataccaaac agctggtgca cagctttgct     240

gagggccagg accagggcag cgcctatgcc aaccgcacgg ccctcttccc ggacctgctg     300

gcacagggca acgcatccct gaggctgcag cgcgtgcgtg tggcggacga gggcagcttc     360

acctgcttcg tgagcatccg ggatttcggc agcgctgccg tcagcctgca ggtggccgct     420

ccctactcga agcccagcat gaccctggag cccaacaagg acctgcggcc aggggacacg     480

gtgaccatca cgtgctccag ctaccggggc taccctgagg ctgaggtgtt ctggcaggat     540

gggcagggtg tgcccctgac tggcaacgtg accacgtcgc agatggccaa cgagcagggc     600

ttgtttgatg tgcacagcgt cctgcgggtg gtgctgggtg cgaatggcac ctacagctgc     660

ctggtgcgca accccgtgct gcagcaggat gcgcacggct ctgtcaccat cacagggcag     720

cctatgacat tcccccaga ggccctgtgg gtgaccgtgg ggctgtctgt ctgtctcatt      780

gcactgctgg tggccctggc tttcgtgtgc tggagaaaga tcaaacagag ctgtgaggag     840
```

```
gagaatgcag gagctgagga ccaggatggg gagggagaag gctccaagac agccctgcag    900

cctctgaaac actctgacag caaagaagat gatggacaag aaatagcc                948


<210> SEQ ID NO 3
<211> LENGTH: 533
<212> TYPE: PRT
<213> ORGANISM: Canis familiaris

<400> SEQUENCE: 3

Met Leu Arg Arg Ala Ser Ala Asp Val Gly Val Arg Leu Ala Ala Ala
1               5                   10                  15

Leu Ala Ala Leu Trp Phe Cys Ile Thr Gly Ala Val Glu Val Gln Val
            20                  25                  30

Pro Glu Asp Pro Val Val Ala Leu Val Gly Thr Asp Ala Thr Leu Arg
        35                  40                  45

Cys Ser Phe Leu Pro Glu Pro Gly Phe Ser Leu Ala Gln Leu Asn Leu
    50                  55                  60

Ile Trp Gln Leu Thr Asp Thr Lys Gln Leu Val His Ser Phe Ala Glu
65                  70                  75                  80

Gly Arg Asp Gln Gly Ser Ala Tyr Ala Asn Arg Thr Ala Leu Phe Pro
                85                  90                  95

Asp Leu Leu Ala Gln Gly Asn Ala Ser Leu Arg Leu Gln Arg Val Arg
            100                 105                 110

Val Ala Asp Glu Gly Ser Phe Thr Cys Phe Val Ser Ile Arg Asp Phe
        115                 120                 125

Gly Ser Ala Ala Val Ser Leu Gln Val Ala Ala Pro Tyr Ser Lys Pro
    130                 135                 140

Ser Met Thr Leu Glu Pro Ser Lys Asp Leu Arg Pro Gly Asp Thr Val
145                 150                 155                 160

Thr Ile Thr Cys Ser Ser Tyr Arg Gly Tyr Pro Glu Ala Glu Val Leu
                165                 170                 175

Trp Gln Asp Gly Gln Gly Ala Pro Leu Thr Gly Asn Val Thr Thr Ser
            180                 185                 190

Gln Met Ala Asn Glu Gln Gly Leu Phe Asp Val Arg Ser Val Leu Arg
        195                 200                 205

Val Val Leu Gly Ala Asn Gly Thr Tyr Ser Cys Leu Val Arg Asn Pro
    210                 215                 220

Val Leu Gln Gln Asp Ala Arg Gly Ser Val Thr Ile Thr Pro His Arg
225                 230                 235                 240

Ser Pro Thr Gly Ala Val Glu Val Gln Val Pro Glu Asp Pro Val Val
                245                 250                 255

Ala Leu Val Gly Thr Asp Ala Thr Leu Cys Cys Ser Phe Ser Pro Glu
            260                 265                 270

Pro Gly Phe Ser Leu Ala Gln Leu Asn Leu Ile Trp Gln Leu Thr Asp
        275                 280                 285

Thr Lys Gln Leu Val His Ser Phe Ala Glu Gly Arg Asp Gln Gly Ser
    290                 295                 300

Ala Tyr Ala Asn Arg Thr Ala Leu Phe Pro Asp Leu Leu Ala Gln Gly
305                 310                 315                 320

Asn Ala Ser Leu Arg Leu Gln Arg Val Arg Val Ala Asp Glu Gly Ser
                325                 330                 335

Phe Thr Cys Phe Val Ser Ile Arg Asp Phe Gly Ser Ala Ala Val Ser
            340                 345                 350
```

-continued

```
Leu Gln Val Ala Ala Pro Tyr Ser Lys Pro Ser Met Thr Leu Glu Pro
        355                 360                 365

Ser Lys Asp Leu Arg Pro Gly Asp Thr Val Thr Ile Thr Cys Ser Ser
    370                 375                 380

Tyr Arg Gly Tyr Pro Glu Ala Glu Val Leu Trp Gln Asp Gly Gln Gly
385                 390                 395                 400

Ala Pro Leu Thr Gly Asn Val Thr Thr Ser Gln Met Ala Asn Glu Gln
                405                 410                 415

Gly Leu Phe Asp Val Arg Ser Val Leu Arg Val Val Leu Gly Ala Asn
            420                 425                 430

Gly Thr Tyr Ser Cys Leu Val Arg Asn Pro Val Leu Gln Gln Asp Ala
        435                 440                 445

His Gly Ser Val Thr Ile Thr Gly Gln Pro Met Thr Phe Pro Pro Glu
    450                 455                 460

Ala Leu Trp Val Thr Val Gly Leu Ser Val Cys Leu Val Ala Leu Leu
465                 470                 475                 480

Val Ala Leu Ala Phe Val Cys Trp Arg Lys Ile Lys Gln Ser Cys Glu
                485                 490                 495

Glu Glu Asn Ala Gly Ala Glu Asp Gln Asp Gly Asp Gly Glu Gly Ser
            500                 505                 510

Lys Thr Ala Leu Arg Pro Leu Lys His Ser Glu Ser Lys Glu Asp Asp
        515                 520                 525

Gly Gln Glu Ile Ala
    530
```

<210> SEQ ID NO 4
<211> LENGTH: 1599
<212> TYPE: DNA
<213> ORGANISM: Canis familiaris

<400> SEQUENCE: 4

```
atgctgcgtc gggccagcgc ggatgtgggt gtgcgtttgg ccgcggccct ggcagcgctg     60

tggttctgca tcacaggcgc cgtggaggtc caggtgcccg aggaccccgt ggtggccctg    120

gtgggcaccg atgccaccct gcgctgctcc ttcttgcccg aacccggctt cagcctggcg    180

cagctcaacc tcatctggca gctgacggac accaagcagc tggtgcacag cttcgccgag    240

ggccgggacc agggcagcgc gtacgccaac cgcacggccc tcttccccga cctgctggcc    300

cagggcaatg cgtccctgcg gctgcagcgc gtgcgcgtgg ccgatgaggg cagcttcacc    360

tgcttcgtga gcatccggga cttcggcagc gccgcggtca gcctgcaggt ggcagctccc    420

tactcgaagc ccagcatgac cctggagccc agcaaggacc tgcggcccgg ggacacggtg    480

accatcacgt gctccagcta ccggggctat ccggaggccg aggtgctctg gcaggatggg    540

cagggcgcac ccctgaccgg caacgtgacc acatcgcaga tggccaacga gcagggcctg    600

ttcgacgtgc gcagtgtcct gcgggtggtg ctgggcgcta acggcaccta cagctgcctg    660

gtgcgcaacc cggtgctgca gcaggacgcc cgtggctccg tcaccatcac gccccacaga    720

agtcccacag gcgccgtgga ggtccaggtg cccgaggacc ccgtggtggc cctggtgggc    780

accgatgcca ccctgtgctg ctccttctcg cctgaacccg gcttcagcct ggcacagctc    840

aacctcatct ggcagctgac ggacaccaag cagctggtgc acagcttcgc cgagggccgg    900

gaccagggca gcgcgtacgc caaccgcacg gccctcttcc ccgacctgct ggcccagggc    960

aatgcgtccc tgcggctgca gcgcgtgcgc gtggccgatg agggcagctt cacctgcttc   1020

gtgagcatcc gggacttcgg cagcgccgcg gtcagcctgc aagtggcagc tccctactcg   1080
```

-continued

```
aagcccagca tgaccctgga gcccagcaag gacctgcggc ccggggacac ggtgaccatc   1140

acgtgctcca gctaccgggg ctatccggag gccgaggtgc tctggcagga tgggcagggc   1200

gcacccctga ctggcaacgt gaccacatcg cagatggcca acgagcaggg cctattcgac   1260

gtgcgcagtg tcctgcgggt ggtgctgggc gctaacggca cctacagctg cctggtgcgc   1320

aacccggtgc tgcagcagga cgctcatggc tctgtcacca tcacagggca gcccatgaca   1380

ttccccccctg aggccctgtg ggtgaccgtg gggctctctg tatgtcttgt cgcactgctg   1440

gtggccctgg ctttcgtgtg ctggaggaag atcaagcaga gctgtgagga ggagaatgca   1500

ggtgctgagg accaggatgg ggatggagag ggatccaaga ccgccctgcg gcctctgaaa   1560

cactctgaaa gcaaagaaga tgatggacaa gaaatagcc                          1599
```

<210> SEQ ID NO 5
<211> LENGTH: 270
<212> TYPE: PRT
<213> ORGANISM: Felis catus

<400> SEQUENCE: 5

```
Ala Leu Glu Val Gln Val Pro Glu Asp Pro Val Val Ala Leu Val Gly
1               5                   10                  15

Thr Asp Ala Thr Leu Arg Cys Ser Phe Ser Pro Glu Pro Asp Phe Ser
            20                  25                  30

Leu Ala Gln Leu Asn Leu Ile Trp Gln Leu Thr Asp Thr Lys Gln Leu
        35                  40                  45

Val His Ser Phe Ser Glu Gly Arg Asp Gln Gly Ser Ala Tyr Ala Asn
    50                  55                  60

Arg Thr Ala Leu Phe Pro Asp Leu Leu Ala Gln Gly Asn Ala Ser Leu
65                  70                  75                  80

Arg Leu Gln Arg Val Arg Val Ala Asp Glu Gly Ser Phe Thr Cys Phe
                85                  90                  95

Val Ser Ile Arg Asp Phe Gly Ser Ala Ala Val Ser Leu Gln Val Ala
            100                 105                 110

Ala Pro Tyr Ser Lys Pro Ser Met Thr Leu Glu Pro Asn Lys Asp Leu
        115                 120                 125

Arg Pro Gly Asp Met Val Thr Ile Thr Cys Ser Ser Tyr Arg Gly Tyr
    130                 135                 140

Pro Glu Ala Glu Val Phe Trp Gln Asp Gly Gln Gly Ala Pro Leu Thr
145                 150                 155                 160

Gly Asn Val Thr Thr Ser Gln Met Ala Asn Glu Gln Gly Leu Phe Asp
                165                 170                 175

Val Arg Ser Val Leu Arg Val Val Leu Gly Ala Asn Gly Thr Tyr Ser
            180                 185                 190

Cys Leu Val Arg Asn Pro Val Leu Gln Gln Asp Ala His Gly Ser Val
        195                 200                 205

Thr Ile Thr Gly Gln Pro Met Thr Phe Pro Pro Glu Ala Leu Trp Val
    210                 215                 220

Thr Val Gly Leu Ser Val Cys Leu Val Ala Leu Leu Val Ala Leu Ala
225                 230                 235                 240

Phe Val Cys Trp Arg Lys Ile Lys Gln Ser Cys Glu Glu Glu Asn Ala
                245                 250                 255

Gly Ala Glu Asp Gln Asp Gly Asp Gly Glu Gly Ser Lys Thr
            260                 265                 270
```

<210> SEQ ID NO 6
<211> LENGTH: 810
<212> TYPE: DNA
<213> ORGANISM: Felis catus

<400> SEQUENCE: 6

```
gcactggagg tccaggtccc cgaagacccc gtggtggccc tggtgggcac cgatgccacc     60

ctgcgctgct ccttctcacc cgagcccgac ttcagcctgg cgcagctcaa cctcatctgg    120

cagctgacgg acaccaaaca gctggtgcac agcttctccg agggccggga ccagggcagc    180

gcctatgcca accgcaccgc gctcttcccc gacctgctgg cgcagggcaa cgcgtccctg    240

cggctgcagc gagtgcgggt agctgatgag ggcagcttca cctgctttgt gagcatccgg    300

gacttcggca gcgctgcagt cagcctgcag gtggcggctc cttactcgaa gcccagcatg    360

accctggagc ccaacaagga cctgcggccc ggggacatgg tgaccatcac gtgctccagc    420

taccggggct acccggaggc cgaggtgttc tggcaggacg ggcagggtgc gcccctgacc    480

ggcaacgtga ccacgtcgca gatggccaat gagcagggct tgttcgacgt gcggagtgtc    540

ctgagggtgg tgctgggcgc caatggcacc tacagctgcc tggtgcgcaa ccctgtgctg    600

cagcaggacg ctcatggctc cgtcaccatc acagggcagc ccatgacatt ccctcccgag    660

gccctgtggg tgaccgtggg gctctctgtc tgccttgtcg ccctgctggt ggccctggcc    720

ttcgtgtgct ggagaaagat caagcagagc tgtgaggagg agaatgcagg tgccgaggac    780

caggacgggg atggagaagg atccaaaaca                                     810
```

<210> SEQ ID NO 7
<211> LENGTH: 107
<212> TYPE: PRT
<213> ORGANISM: Artificial Sequence
<220> FEATURE:
<223> OTHER INFORMATION: Amino Acid Sequence of BRCA84D Variable Light Chain

<400> SEQUENCE: 7

```
Asp Ile Ala Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Ser Gly Thr Lys Leu Glu Ile Lys
            100                 105
```

<210> SEQ ID NO 8
<211> LENGTH: 321
<212> TYPE: DNA
<213> ORGANISM: Artificial Sequence
<220> FEATURE:
<223> OTHER INFORMATION: Polynucleotide Sequence Encoding BRCA84D Variable Light Chain

<400> SEQUENCE: 8

```
gacattgcga tgacccagtc tcaaaaattc atgtccacat cagtaggaga cagggtcagc     60
```

```
gtcacctgca aggccagtca gaatgtggat actaatgtag cctggtatca acagaaacca    120

gggcaatctc ctaaagcact gatttactcg gcatcctacc ggtacagtgg agtccctgat    180

cgcttcacag gcagtggatc tgggacagat ttcactctca ccatcaacaa tgtgcagtct    240

gaagacttgg cagagtattt ctgtcagcaa tataacaact atccattcac gttcggctcg    300

gggacaaagt tggaaataaa a                                              321


<210> SEQ ID NO 9
<211> LENGTH: 11
<212> TYPE: PRT
<213> ORGANISM: Artificial Sequence
<220> FEATURE:
<223> OTHER INFORMATION: BRCA84D Variable Light Chain CDR1

<400> SEQUENCE: 9

Lys Ala Ser Gln Asn Val Asp Thr Asn Val Ala
1               5                   10


<210> SEQ ID NO 10
<211> LENGTH: 33
<212> TYPE: DNA
<213> ORGANISM: Artificial Sequence
<220> FEATURE:
<223> OTHER INFORMATION: Polynucleotide Sequence Encoding BRCA84D
      Variable Light Chain CDR1

<400> SEQUENCE: 10

aaggccagtc agaatgtgga tactaatgta gcc                                  33


<210> SEQ ID NO 11
<211> LENGTH: 7
<212> TYPE: PRT
<213> ORGANISM: Artificial Sequence
<220> FEATURE:
<223> OTHER INFORMATION: BRCA84D Variable Light Chain CDR2

<400> SEQUENCE: 11

Ser Ala Ser Tyr Arg Tyr Ser
1               5


<210> SEQ ID NO 12
<211> LENGTH: 21
<212> TYPE: DNA
<213> ORGANISM: Artificial Sequence
<220> FEATURE:
<223> OTHER INFORMATION: Polynucleotide Sequence Encoding BRCA84D
      Variable Light Chain CDR2

<400> SEQUENCE: 12

tcggcatcct accggtacag t                                               21


<210> SEQ ID NO 13
<211> LENGTH: 9
<212> TYPE: PRT
<213> ORGANISM: Artificial Sequence
<220> FEATURE:
<223> OTHER INFORMATION: BRCA84D Variable Light Chain CDR3

<400> SEQUENCE: 13

Gln Gln Tyr Asn Asn Tyr Pro Phe Thr
1               5


<210> SEQ ID NO 14
<211> LENGTH: 27
```

<212> TYPE: DNA
<213> ORGANISM: Artificial Sequence
<220> FEATURE:
<223> OTHER INFORMATION: Polynucleotide Sequence Encoding BRCA84D Variable Light Chain CDR3

<400> SEQUENCE: 14
cagcaatata acaactatcc attcacg 27

<210> SEQ ID NO 15
<211> LENGTH: 122
<212> TYPE: PRT
<213> ORGANISM: Artificial Sequence
<220> FEATURE:
<223> OTHER INFORMATION: Amino Acid Sequence of BRCA84D Variable Heavy Chain

<400> SEQUENCE: 15

```
Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Leu Thr Val Ser Ser
        115                 120
```

<210> SEQ ID NO 16
<211> LENGTH: 366
<212> TYPE: DNA
<213> ORGANISM: Artificial Sequence
<220> FEATURE:
<223> OTHER INFORMATION: Polynucleotide Sequence Encoding BRCA84D Variable Heavy Chain

<400> SEQUENCE: 16

```
gatgtgcagc tggtggagtc tgggggaggc ttagtgcagc ctggagggtc ccggaaactc     60

tcctgtgcag cctctggatt cactttcagt agctttggaa tgcactgggt tcgtcaggct    120

ccagagaagg ggctggagtg ggtcgcatac attagtagtg acagtagtgc catctactat    180

gcagacacag tgaagggccg attcaccatc tccagagaca atcccaagaa caccctgttc    240

ctgcaaatga ccagtctaag gtctgaggac acggccatgt attactgtgg aagagggagg    300

gaaaacattt actacggtag taggcttgac tactggggcc aaggcaccac tctcacagtc    360

tcctca                                                               366
```

<210> SEQ ID NO 17
<211> LENGTH: 4
<212> TYPE: PRT
<213> ORGANISM: Artificial Sequence
<220> FEATURE:
<223> OTHER INFORMATION: BRCA84D Variable Heavy Chain CDR1

<400> SEQUENCE: 17

Phe Gly Met His
1

<210> SEQ ID NO 18
<211> LENGTH: 12
<212> TYPE: DNA
<213> ORGANISM: Artificial Sequence
<220> FEATURE:
<223> OTHER INFORMATION: Polynucleotide Sequence Encoding BRCA84D Variable Heavy Chain CDR1

<400> SEQUENCE: 18
tttggaatgc ac 12

<210> SEQ ID NO 19
<211> LENGTH: 16
<212> TYPE: PRT
<213> ORGANISM: Artificial Sequence
<220> FEATURE:
<223> OTHER INFORMATION: BRCA84D Variable Heavy Chain CDR2

<400> SEQUENCE: 19

Tyr Ile Ser Ser Asp Ser Ser Ala Ile Tyr Tyr Ala Asp Thr Val Lys
1 5 10 15

<210> SEQ ID NO 20
<211> LENGTH: 48
<212> TYPE: DNA
<213> ORGANISM: Artificial Sequence
<220> FEATURE:
<223> OTHER INFORMATION: Polynucleotide Sequence Encoding BRCA84D Variable Heavy Chain CDR2

<400> SEQUENCE: 20
tacattagta gtgacagtag tgccatctac tatgcagaca cagtgaag 48

<210> SEQ ID NO 21
<211> LENGTH: 13
<212> TYPE: PRT
<213> ORGANISM: Artificial Sequence
<220> FEATURE:
<223> OTHER INFORMATION: BRCA84D Variable Heavy Chain CDR3

<400> SEQUENCE: 21

Gly Arg Glu Asn Ile Tyr Tyr Gly Ser Arg Leu Asp Tyr
1 5 10

<210> SEQ ID NO 22
<211> LENGTH: 39
<212> TYPE: DNA
<213> ORGANISM: Artificial Sequence
<220> FEATURE:
<223> OTHER INFORMATION: Polynucleotide Sequence Encoding BRCA84D Variable Heavy Chain CDR3

<400> SEQUENCE: 22
gggagggaaa acatttacta cggtagtagg cttgactac 39

<210> SEQ ID NO 23
<211> LENGTH: 107
<212> TYPE: PRT
<213> ORGANISM: Artificial Sequence
<220> FEATURE:
<223> OTHER INFORMATION: Amino Acid Sequence of BRCA69D Variable Light Chain

<400> SEQUENCE: 23

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asp Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105


<210> SEQ ID NO 24
<211> LENGTH: 321
<212> TYPE: DNA
<213> ORGANISM: Artificial Sequence
<220> FEATURE:
<223> OTHER INFORMATION: Polynucleotide Sequence Encoding BRCA69D
      Variable Light Chain

<400> SEQUENCE: 24

gatatccaga tgacacagac tacatcctcc ctgtctgcct ctctgggaga cagagtcacc      60

atcagttgca gggcaagtca ggacattagt aattatttaa actggtatca gcagaaacca     120

gatggaactg ttaaactcct gatctactac acatcacgat tacactcagg agtcccatca     180

aggttcagtg gcagtgggtc tggaacagat tattctctca ccattgacaa cctggagcaa     240

gaagatattg ccacttactt ttgccaacag ggtaatacgc ttcctccgac gttcggtgga     300

ggcaccaaac tggaaatcaa a                                               321


<210> SEQ ID NO 25
<211> LENGTH: 11
<212> TYPE: PRT
<213> ORGANISM: Artificial Sequence
<220> FEATURE:
<223> OTHER INFORMATION: BRCA69D Variable Light Chain CDR1

<400> SEQUENCE: 25

Arg Ala Ser Gln Asp Ile Ser Asn Tyr Leu Asn
1               5                   10


<210> SEQ ID NO 26
<211> LENGTH: 33
<212> TYPE: DNA
<213> ORGANISM: Artificial Sequence
<220> FEATURE:
<223> OTHER INFORMATION: Polynucleotide Sequence Encoding BRCA69D
      Variable Light Chain CDR1

<400> SEQUENCE: 26

agggcaagtc aggacattag taattattta aac                                   33


<210> SEQ ID NO 27
<211> LENGTH: 7
<212> TYPE: PRT
<213> ORGANISM: Artificial Sequence
<220> FEATURE:
<223> OTHER INFORMATION: BRCA69D Variable Light Chain CDR2
```

<400> SEQUENCE: 27

Tyr Thr Ser Arg Leu His Ser
1               5

<210> SEQ ID NO 28
<211> LENGTH: 21
<212> TYPE: DNA
<213> ORGANISM: Artificial Sequence
<220> FEATURE:
<223> OTHER INFORMATION: Polynucleotide Sequence Encoding BRCA69D Variable Light Chain CDR2

<400> SEQUENCE: 28
tacacatcac gattacactc a 21

<210> SEQ ID NO 29
<211> LENGTH: 9
<212> TYPE: PRT
<213> ORGANISM: Artificial Sequence
<220> FEATURE:
<223> OTHER INFORMATION: BRCA69D Variable Light Chain CDR3

<400> SEQUENCE: 29

Gln Gln Gly Asn Thr Leu Pro Pro Thr
1               5

<210> SEQ ID NO 30
<211> LENGTH: 27
<212> TYPE: DNA
<213> ORGANISM: Artificial Sequence
<220> FEATURE:
<223> OTHER INFORMATION: Polynucleotide Sequence Encoding BRCA69D Variable Light Chain CDR3

<400> SEQUENCE: 30
caacagggta atacgcttcc tccgacg 27

<210> SEQ ID NO 31
<211> LENGTH: 120
<212> TYPE: PRT
<213> ORGANISM: Artificial Sequence
<220> FEATURE:
<223> OTHER INFORMATION: Amino Acid Sequence of BRCA69D Variable Heavy Chain

<400> SEQUENCE: 31

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Arg Gly Ile Pro Arg Leu Trp Tyr Phe Asp Val Trp Gly Ala
            100                 105                 110

Gly Thr Thr Val Thr Val Ser Ser
        115                 120

<210> SEQ ID NO 32
<211> LENGTH: 360
<212> TYPE: DNA
<213> ORGANISM: Artificial Sequence
<220> FEATURE:
<223> OTHER INFORMATION: Polynucleotide Sequence Encoding BRCA69D Variable Heavy Chain

<400> SEQUENCE: 32
caggttcagc tccagcagtc tggggctgag ctggcaagac ctggggcttc agtgaagttg 60
tcctgcaagg cttctggcta cacctttact agctactgga tgcagtgggt aaaacagagg 120
cctggacagg gtctggaatg gattgggact atttatcctg gagatggtga tactaggtac 180
actcagaagt tcaagggcaa ggccacattg actgcagata aatcctccag cacagcctac 240
atgcaactca gcagcttggc atctgaggac tctgcggtct attactgtgc aagaagaggg 300
attccacggc tttggtactt cgatgtctgg ggcgcaggga ccacggtcac cgtctcctca 360

<210> SEQ ID NO 33
<211> LENGTH: 5
<212> TYPE: PRT
<213> ORGANISM: Artificial Sequence
<220> FEATURE:
<223> OTHER INFORMATION: BRCA69D Variable Heavy Chain CDR1

<400> SEQUENCE: 33

Ser Tyr Trp Met Gln
1 5

<210> SEQ ID NO 34
<211> LENGTH: 15
<212> TYPE: DNA
<213> ORGANISM: Artificial Sequence
<220> FEATURE:
<223> OTHER INFORMATION: Polynucleotide Sequence Encoding BRCA69D Variable Heavy Chain CDR1

<400> SEQUENCE: 34
agctactgga tgcag 15

<210> SEQ ID NO 35
<211> LENGTH: 17
<212> TYPE: PRT
<213> ORGANISM: Artificial Sequence
<220> FEATURE:
<223> OTHER INFORMATION: BRCA69D Variable Heavy Chain CDR2

<400> SEQUENCE: 35

Thr Ile Tyr Pro Gly Asp Gly Asp Thr Arg Tyr Thr Gln Lys Phe Lys
1 5 10 15

Gly

<210> SEQ ID NO 36
<211> LENGTH: 51
<212> TYPE: DNA
<213> ORGANISM: Artificial Sequence
<220> FEATURE:
<223> OTHER INFORMATION: Polynucleotide Sequence Encoding BRCA69D Variable Heavy Chain CDR2

<400> SEQUENCE: 36
actatttatc ctggagatgg tgatactagg tacactcaga agttcaaggg c 51

<210> SEQ ID NO 37

<211> LENGTH: 11
<212> TYPE: PRT
<213> ORGANISM: Artificial Sequence
<220> FEATURE:
<223> OTHER INFORMATION: BRCA69D Variable Heavy Chain CDR3

<400> SEQUENCE: 37

Arg Gly Ile Pro Arg Leu Trp Tyr Phe Asp Val
1 5 10

<210> SEQ ID NO 38
<211> LENGTH: 33
<212> TYPE: DNA
<213> ORGANISM: Artificial Sequence
<220> FEATURE:
<223> OTHER INFORMATION: Polynucleotide Sequence Encoding BRCA69D Variable Heavy Chain CDR3

<400> SEQUENCE: 38
agagggattc cacggctttg gtacttcgat gtc 33

<210> SEQ ID NO 39
<211> LENGTH: 108
<212> TYPE: PRT
<213> ORGANISM: Artificial Sequence
<220> FEATURE:
<223> OTHER INFORMATION: Amino Acid Sequence of PRCA157 Variable Light Chain

<400> SEQUENCE: 39

Asp Ile Gln Met Thr Gln Ser Pro Ala Ser Leu Ser Val Ser Val Gly
1 5 10 15

Glu Thr Val Thr Ile Thr Cys Arg Ala Ser Glu Ser Ile Tyr Ser Tyr
20 25 30

Leu Ala Trp Tyr Gln Gln Lys Gln Gly Lys Ser Pro Gln Leu Leu Val
35 40 45

Tyr Asn Thr Lys Thr Leu Pro Glu Gly Val Pro Ser Arg Phe Ser Gly
50 55 60

Ser Gly Ser Gly Thr Gln Phe Ser Leu Lys Ile Asn Ser Leu Gln Pro
65 70 75 80

Glu Asp Phe Gly Arg Tyr Tyr Cys Gln His His Tyr Gly Thr Pro Pro
85 90 95

Trp Thr Phe Gly Gly Gly Thr Asn Leu Glu Ile Lys
100 105

<210> SEQ ID NO 40
<211> LENGTH: 324
<212> TYPE: DNA
<213> ORGANISM: Artificial Sequence
<220> FEATURE:
<223> OTHER INFORMATION: Polynucleotide Sequence Encoding PRCA157 Variable Light Chain

<400> SEQUENCE: 40
gacatccaga tgactcagtc tccagcctcc ctatctgtat ctgtgggaga aactgtcacc 60
attacatgtc gagcaagtga gagtatttac agttatttag catggtatca gcagaaacag 120
ggaaaatctc ctcagctcct ggtctataat acaaaaacct taccagaggg tgtgccatca 180
aggttcagtg gcagtggatc aggcacacag ttttctctga agatcaacag cctgcagcct 240
gaagattttg ggagatatta ctgtcaacat cattatggta ctcctccgtg gacgttcggt 300
ggaggcacca acctggaaat caaa 324

<210> SEQ ID NO 41
<211> LENGTH: 11
<212> TYPE: PRT
<213> ORGANISM: Artificial Sequence
<220> FEATURE:
<223> OTHER INFORMATION: PRCA157 Variable Light Chain CDR1

<400> SEQUENCE: 41

Arg Ala Ser Glu Ser Ile Tyr Ser Tyr Leu Ala
1 5 10

<210> SEQ ID NO 42
<211> LENGTH: 33
<212> TYPE: DNA
<213> ORGANISM: Artificial Sequence
<220> FEATURE:
<223> OTHER INFORMATION: Polynucleotide Sequence Encoding PRCA157 Variable Light Chain CDR1

<400> SEQUENCE: 42
cgagcaagtg agagtattta cagttattta gca 33

<210> SEQ ID NO 43
<211> LENGTH: 7
<212> TYPE: PRT
<213> ORGANISM: Artificial Sequence
<220> FEATURE:
<223> OTHER INFORMATION: PRCA157 Variable Light Chain CDR2

<400> SEQUENCE: 43

Asn Thr Lys Thr Leu Pro Glu
1 5

<210> SEQ ID NO 44
<211> LENGTH: 21
<212> TYPE: DNA
<213> ORGANISM: Artificial Sequence
<220> FEATURE:
<223> OTHER INFORMATION: Polynucleotide Sequence Encoding PRCA157 Variable Light Chain CDR2

<400> SEQUENCE: 44
aatacaaaaa ccttaccaga g 21

<210> SEQ ID NO 45
<211> LENGTH: 9
<212> TYPE: PRT
<213> ORGANISM: Artificial Sequence
<220> FEATURE:
<223> OTHER INFORMATION: PRCA157 Variable Light Chain CDR3

<400> SEQUENCE: 45

Gln His His Tyr Gly Thr Pro Pro Trp
1 5

<210> SEQ ID NO 46
<211> LENGTH: 27
<212> TYPE: DNA
<213> ORGANISM: Artificial Sequence
<220> FEATURE:
<223> OTHER INFORMATION: Polynucleotide Sequence Encoding PRCA157 Variable Light Chain CDR3

<400> SEQUENCE: 46
caacatcatt atggtactcc tccgtgg 27

```
<210> SEQ ID NO 47
<211> LENGTH: 117
<212> TYPE: PRT
<213> ORGANISM: Artificial Sequence
<220> FEATURE:
<223> OTHER INFORMATION: Amino Acid Sequence of PRCA157 Variable Heavy
      Chain

<400> SEQUENCE: 47

Glu Val Gln Gln Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Asn Ser Gly Gly Ser Asn Thr Tyr Tyr Pro Asp Ser Leu
    50                  55                  60

Lys Gly Arg Phe Thr Ile Ser Arg Asp Asn Ala Lys Asn Thr Leu Tyr
65                  70                  75                  80

Leu Gln Met Arg Ser Leu Lys Ser Glu Asp Thr Ala Met Tyr Tyr Cys
                85                  90                  95

Ala Arg His Asp Gly Gly Ala Met Asp Tyr Trp Gly Gln Gly Thr Ser
            100                 105                 110

Val Thr Val Ser Ser
        115


<210> SEQ ID NO 48
<211> LENGTH: 351
<212> TYPE: DNA
<213> ORGANISM: Artificial Sequence
<220> FEATURE:
<223> OTHER INFORMATION: Polynucleotide Sequence Encoding PRCA157
      Variable Heavy Chain

<400> SEQUENCE: 48

gaggtgcagc aggtggagtc gggggagac ttagtgaagc ctggagggtc cctgaaactc     60

tcctgtgcag cctctggatt cactttcagt tcctatggca tgtcttgggt tcgccagact    120

ccagacaaga ggctggagtg ggtcgcaacc attaatagtg gtggaagtaa cacctactat    180

ccagacagtt tgaaggggcg attcaccatc tccagagaca atgccaagaa caccctttac    240

ctgcaaatgc gcagtctgaa gtctgaggac acagccatgt attactgtgc aagacatgac    300

gggggagcta tggactactg gggtcaagga acctcagtca ccgtctcctc a             351


<210> SEQ ID NO 49
<211> LENGTH: 5
<212> TYPE: PRT
<213> ORGANISM: Artificial Sequence
<220> FEATURE:
<223> OTHER INFORMATION: PRCA157 Variable Heavy Chain CDR1

<400> SEQUENCE: 49

Ser Tyr Gly Met Ser
1               5


<210> SEQ ID NO 50
<211> LENGTH: 15
<212> TYPE: DNA
<213> ORGANISM: Artificial Sequence
<220> FEATURE:
<223> OTHER INFORMATION: Polynucleotide Sequence Encoding PRCA157
      Variable Heavy Chain CDR1
```

<400> SEQUENCE: 50
tcctatggca tgtct 15

<210> SEQ ID NO 51
<211> LENGTH: 19
<212> TYPE: PRT
<213> ORGANISM: Artificial Sequence
<220> FEATURE:
<223> OTHER INFORMATION: PRCA157 Variable Heavy Chain CDR2

<400> SEQUENCE: 51

Val Ala Thr Ile Asn Ser Gly Gly Ser Asn Thr Tyr Tyr Pro Asp Ser
1 5 10 15

Leu Lys Gly

<210> SEQ ID NO 52
<211> LENGTH: 57
<212> TYPE: DNA
<213> ORGANISM: Artificial Sequence
<220> FEATURE:
<223> OTHER INFORMATION: Polynucleotide Sequence Encoding PRCA157
Variable Heavy Chain CDR2

<400> SEQUENCE: 52
gtcgcaacca ttaatagtgg tggaagtaac acctactatc cagacagttt gaagggg 57

<210> SEQ ID NO 53
<211> LENGTH: 8
<212> TYPE: PRT
<213> ORGANISM: Artificial Sequence
<220> FEATURE:
<223> OTHER INFORMATION: PRCA157 Variable Heavy Chain CDR3

<400> SEQUENCE: 53

His Asp Gly Gly Ala Met Asp Tyr
1 5

<210> SEQ ID NO 54
<211> LENGTH: 24
<212> TYPE: DNA
<213> ORGANISM: Artificial Sequence
<220> FEATURE:
<223> OTHER INFORMATION: Polynucleotide Sequence Encoding PRCA157
Variable Heavy Chain CDR3

<400> SEQUENCE: 54
catgacgggg gagctatgga ctac 24

<210> SEQ ID NO 55
<211> LENGTH: 107
<212> TYPE: PRT
<213> ORGANISM: Artificial Sequence
<220> FEATURE:
<223> OTHER INFORMATION: Humanized BRCA84D-1 Variable Light Chain

<400> SEQUENCE: 55

Asp Ile Gln Leu Thr Gln Ser Pro Ser Phe Leu Ser Ala Ser Val Gly
1 5 10 15

Asp Arg Val Thr Ile Thr Cys Lys Ala Ser Gln Asn Val Asp Thr Asn
20 25 30

Val Ala Trp Tyr Gln Gln Lys Pro Gly Lys Ala Pro Lys Leu Leu Ile
35 40 45

Tyr Ser Ala Ser Tyr Arg Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Asn Tyr Pro Phe
85 90 95

Thr Phe Gly Gln Gly Thr Lys Leu Glu Ile Lys
100 105

<210> SEQ ID NO 56
<211> LENGTH: 321
<212> TYPE: DNA
<213> ORGANISM: Artificial Sequence
<220> FEATURE:
<223> OTHER INFORMATION: Polynucleotide Sequence Encoding Humanized BRCA84D-1 Variable Light Chain

<400> SEQUENCE: 56
gacatccagc tgacccagtc cccctccttc ctgtctgcct ccgtgggcga cagagtgacc 60
atcacatgca aggcctccca gaacgtggac accaacgtgg cctggtatca gcagaagcct 120
ggcaaggccc ctaagctgct gatctactcc gcctcctacc ggtactccgg cgtgccttcc 180
aggttctccg gctccggctc tggcaccgac ttcaccctga ccatctccag cctgcagcct 240
gaggacttcg ccacctacta ctgccagcag tacaacaact accctttcac cttcggccag 300
ggcaccaagc tggaaatcaa g 321

<210> SEQ ID NO 57
<211> LENGTH: 11
<212> TYPE: PRT
<213> ORGANISM: Artificial Sequence
<220> FEATURE:
<223> OTHER INFORMATION: Humanized BRCA84D-1 Variable Light Chain CDR1

<400> SEQUENCE: 57

Lys Ala Ser Gln Asn Val Asp Thr Asn Val Ala
1 5 10

<210> SEQ ID NO 58
<211> LENGTH: 33
<212> TYPE: DNA
<213> ORGANISM: Artificial Sequence
<220> FEATURE:
<223> OTHER INFORMATION: Polynucleotide Sequence Encoding Humanized BRCA84D-1 Variable Light Chain CDR1

<400> SEQUENCE: 58
aaggccagtc agaatgtgga tactaatgta gcc 33

<210> SEQ ID NO 59
<211> LENGTH: 7
<212> TYPE: PRT
<213> ORGANISM: Artificial Sequence
<220> FEATURE:
<223> OTHER INFORMATION: Humanized BRCA84D-1 Variable Light Chain CDR2

<400> SEQUENCE: 59

Ser Ala Ser Tyr Arg Tyr Ser
1 5

<210> SEQ ID NO 60
<211> LENGTH: 21
<212> TYPE: DNA
<213> ORGANISM: Artificial Sequence
<220> FEATURE:
<223> OTHER INFORMATION: Polynucleotide Sequence Encoding Humanized BRCA84D-1 Variable Light Chain CDR2

<400> SEQUENCE: 60
tcggcatcct accggtacag t 21

<210> SEQ ID NO 61
<211> LENGTH: 9
<212> TYPE: PRT
<213> ORGANISM: Artificial Sequence
<220> FEATURE:
<223> OTHER INFORMATION: Humanized BRCA84D-1 Variable Light Chain CDR3

<400> SEQUENCE: 61

Gln Gln Tyr Asn Asn Tyr Pro Phe Thr
1 5

<210> SEQ ID NO 62
<211> LENGTH: 27
<212> TYPE: DNA
<213> ORGANISM: Artificial Sequence
<220> FEATURE:
<223> OTHER INFORMATION: Polynucleotide Sequence Encoding Humanized BRCA84D-1 Variable Light Chain CDR3

<400> SEQUENCE: 62
cagcaatata acaactatcc attcacg 27

<210> SEQ ID NO 63
<211> LENGTH: 122
<212> TYPE: PRT
<213> ORGANISM: Artificial Sequence
<220> FEATURE:
<223> OTHER INFORMATION: Amino Acid Sequence of Humanized BRCA84D-1 Variable Heavy Chain

<400> SEQUENCE: 63

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Phe
20 25 30

Gly Met His Trp Val Arg Gln Ala Pro Gly Lys Gly Leu Glu Trp Val
35 40 45

Ala Tyr Ile Ser Ser Asp Ser Ser Ala Ile Tyr Tyr Ala Asp Thr Val
50 55 60

Lys Gly Arg Phe Thr Ile Ser Arg Asp Asn Ala Lys Asn Ser Leu Tyr
65 70 75 80

Leu Gln Met Asn Ser Leu Arg Asp Glu Asp Thr Ala Val Tyr Tyr Cys
85 90 95

Ala Arg Gly Arg Glu Asn Ile Tyr Tyr Gly Ser Arg Leu Asp Tyr Trp
100 105 110

Gly Gln Gly Thr Thr Val Thr Val Ser Ser
115 120

<210> SEQ ID NO 64
<211> LENGTH: 366
<212> TYPE: DNA
<213> ORGANISM: Artificial Sequence
<220> FEATURE:
<223> OTHER INFORMATION: Polynucleotide Sequence Encoding Humanized BRCA84D-1 Variable Heavy Chain

<400> SEQUENCE: 64
gaggtgcagc tggtcgagtc tggcggagga ctggtgcagc ctggcggctc cctgagactg 60
tcttgcgccg cctccggctt caccttctcc agcttcggca tgcactgggt ccgccaggct 120
ccaggcaagg gactggaatg ggtggcctac atctcctccg actcctccgc catctactac 180
gccgacaccg tgaagggcag gttcaccatc tcccgggaca acgccaagaa ctccctgtac 240
ctgcagatga actccctgcg ggacgaggac accgccgtgt actactgcgc cagaggccgg 300
gagaatatct actacggctc ccggctggat tattggggcc agggcaccac cgtgaccgtg 360
tcctct 366

<210> SEQ ID NO 65
<211> LENGTH: 4
<212> TYPE: PRT
<213> ORGANISM: Artificial Sequence
<220> FEATURE:
<223> OTHER INFORMATION: Humanized BRCA84D-1 Variable Heavy Chain CDR1

<400> SEQUENCE: 65

Phe Gly Met His
1

<210> SEQ ID NO 66
<211> LENGTH: 12
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Heavy Chain CDR1

<400> SEQUENCE: 66
tttggaatgc ac 12

<210> SEQ ID NO 67
<211> LENGTH: 16
<212> TYPE: PRT
<213> ORGANISM: Artificial Sequence
<220> FEATURE:
<223> OTHER INFORMATION: Humanized BRCA84D Variable Heavy Chain CDR2

<400> SEQUENCE: 67

Tyr Ile Ser Ser Asp Ser Ser Ala Ile Tyr Tyr Ala Asp Thr Val Lys
1               5                   10                  15

<210> SEQ ID NO 68
<211> LENGTH: 48
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Heavy Chain CDR2

<400> SEQUENCE: 68
tacattagta gtgacagtag tgccatctac tatgcagaca cagtgaag 48

<210> SEQ ID NO 69
<211> LENGTH: 13
<212> TYPE: PRT
<213> ORGANISM: Artificial Sequence
<220> FEATURE:
<223> OTHER INFORMATION: Humanized BRCA84D-1 Variable Heavy Chain CDR3

<400> SEQUENCE: 69

Gly Arg Glu Asn Ile Tyr Tyr Gly Ser Arg Leu Asp Tyr
1               5                   10

<210> SEQ ID NO 70
<211> LENGTH: 39
<212> TYPE: DNA
<213> ORGANISM: Artificial Sequence
<220> FEATURE:
<223> OTHER INFORMATION: Polynucleotide Sequence Encoding Humanized
BRCA84D-1 Variable Heavy Chain CDR3

<400> SEQUENCE: 70
gggagggaaa acatttacta cggtagtagg cttgactac 39

<210> SEQ ID NO 71
<211> LENGTH: 107
<212> TYPE: PRT
<213> ORGANISM: Artificial Sequence
<220> FEATURE:
<223> OTHER INFORMATION: hBRCA84D-2VL

<400> SEQUENCE: 71

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105
```

<210> SEQ ID NO 72
<211> LENGTH: 321
<212> TYPE: PRT
<213> ORGANISM: Artificial Sequence
<220> FEATURE:
<223> OTHER INFORMATION: Polynucleotide Encoding hBRCA84D-2VL

<400> SEQUENCE: 72

```
Gly Ala Cys Ala Thr Cys Cys Ala Gly Cys Thr Gly Ala Cys Cys Cys
1               5                   10                  15

Ala Gly Thr Cys Cys Cys Cys Cys Thr Cys Cys Thr Thr Cys Cys Thr
            20                  25                  30

Gly Thr Cys Thr Gly Cys Cys Thr Cys Cys Gly Thr Gly Gly Gly Cys
        35                  40                  45

Gly Ala Cys Ala Gly Ala Gly Thr Gly Ala Cys Cys Ala Thr Cys Ala
    50                  55                  60

Cys Ala Thr Gly Cys Ala Ala Gly Gly Cys Cys Thr Cys Cys Cys Ala
65                  70                  75                  80

Gly Ala Ala Cys Gly Thr Gly Gly Ala Cys Ala Cys Cys Ala Ala Cys
                85                  90                  95

Gly Thr Gly Gly Cys Cys Thr Gly Gly Thr Ala Thr Cys Ala Gly Cys
            100                 105                 110

Ala Gly Ala Ala Gly Cys Cys Thr Gly Gly Cys Ala Ala Gly Gly Cys
        115                 120                 125

Cys Cys Cys Thr Ala Ala Gly Gly Cys Gly Cys Thr Gly Ala Thr Cys
    130                 135                 140
```

```
Thr Ala Cys Thr Cys Cys Gly Cys Cys Thr Cys Cys Thr Ala Cys Cys
145                 150                 155                 160

Gly Gly Thr Ala Cys Thr Cys Cys Gly Gly Cys Gly Thr Gly Cys Cys
                165                 170                 175

Thr Thr Cys Cys Ala Gly Gly Thr Thr Cys Thr Cys Cys Gly Gly Cys
            180                 185                 190

Thr Cys Cys Gly Gly Cys Thr Cys Thr Gly Gly Cys Ala Cys Cys Gly
        195                 200                 205

Ala Cys Thr Thr Cys Ala Cys Cys Cys Thr Gly Ala Cys Cys Ala Thr
    210                 215                 220

Cys Thr Cys Cys Ala Gly Cys Cys Thr Gly Cys Ala Gly Cys Cys Thr
225                 230                 235                 240

Gly Ala Gly Gly Ala Cys Thr Thr Cys Gly Cys Cys Ala Cys Cys Thr
                245                 250                 255

Ala Cys Thr Ala Cys Thr Gly Cys Cys Ala Gly Cys Ala Gly Thr Ala
            260                 265                 270

Cys Ala Ala Cys Ala Ala Cys Thr Ala Cys Cys Cys Thr Thr Thr Cys
        275                 280                 285

Ala Cys Cys Thr Thr Cys Gly Gly Cys Cys Ala Gly Gly Gly Cys Ala
    290                 295                 300

Cys Cys Ala Ala Gly Cys Thr Gly Gly Ala Ala Ala Thr Cys Ala Ala
305                 310                 315                 320

Gly
```

<210> SEQ ID NO 73
<211> LENGTH: 107
<212> TYPE: PRT
<213> ORGANISM: Artificial Sequence
<220> FEATURE:
<223> OTHER INFORMATION: hBRCA84D-3VL

<400> SEQUENCE: 73

```
Asp Ile Gln Leu Thr Gln Ser Pro Ser Phe Leu Ser Ala Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105
```

<210> SEQ ID NO 74
<211> LENGTH: 321
<212> TYPE: DNA
<213> ORGANISM: Artificial Sequence
<220> FEATURE:
<223> OTHER INFORMATION: Polynucleotide Encoding hBRCA84D-3VL

<400> SEQUENCE: 74

```
gacatccagc tgacccagtc cccctccttc ctgtctgcct ccgtgggcga cagagtgtcc     60
```

gtcacatgca aggcctccca gaacgtggac accaacgtgg cctggtatca gcagaagcct 120
ggcaaggccc ctaagctgct gatctactcc gcctcctacc ggtactccgg cgtgccttcc 180
aggttctccg gctccggctc tggcaccgac ttcaccctga ccatctccag cctgcagcct 240
gaggacttcg ccacctacta ctgccagcag tacaacaact accctttcac cttcggccag 300
ggcaccaagc tggaaatcaa g 321

<210> SEQ ID NO 75
<211> LENGTH: 107
<212> TYPE: PRT
<213> ORGANISM: Artificial Sequence
<220> FEATURE:
<223> OTHER INFORMATION: hBRCA84D-4VL

<400> SEQUENCE: 75

Asp Ile Gln Leu Thr Gln Ser Pro Ser Phe Leu Ser Ala Ser Val Gly
1 5 10 15

Asp Arg Val Thr Ile Thr Cys Lys Ala Ser Gln Asn Val Asp Thr Asn
20 25 30

Val Ala Trp Tyr Gln Gln Lys Pro Gly Gln Ala Pro Lys Leu Leu Ile
35 40 45

Tyr Ser Ala Ser Tyr Arg Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Asn Tyr Pro Phe
85 90 95

Thr Phe Gly Gln Gly Thr Lys Leu Glu Ile Lys
100 105

<210> SEQ ID NO 76
<211> LENGTH: 321
<212> TYPE: DNA
<213> ORGANISM: Artificial Sequence
<220> FEATURE:
<223> OTHER INFORMATION: Polynucleotide Encoding hBRCA84D-4VL

<400> SEQUENCE: 76
gacatccagc tgacccagtc cccctccttc ctgtctgcct ccgtgggcga cagagtgacc 60
atcacatgca aggcctccca gaacgtggac accaacgtgg cctggtatca gcagaagcct 120
ggccaggccc ctaagctgct gatctactcc gcctcctacc ggtactccgg cgtgccttcc 180
aggttctccg gctccggctc tggcaccgac ttcaccctga ccatctccag cctgcagcct 240
gaggacttcg ccacctacta ctgccagcag tacaacaact accctttcac cttcggccag 300
ggcaccaagc tggaaatcaa g 321

<210> SEQ ID NO 77
<211> LENGTH: 107
<212> TYPE: PRT
<213> ORGANISM: Artificial Sequence
<220> FEATURE:
<223> OTHER INFORMATION: hBRCA84D-5VL

<400> SEQUENCE: 77

Asp Ile Gln Leu Thr Gln Ser Pro Ser Phe Leu Ser Ala Ser Val Gly
1 5 10 15

Asp Arg Val Thr Ile Thr Cys Lys Ala Ser Gln Asn Val Asp Thr Asn
20 25 30

```
Val Ala Trp Tyr Gln Gln Lys Pro Gly Gln Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105


<210> SEQ ID NO 78
<211> LENGTH: 321
<212> TYPE: DNA
<213> ORGANISM: Artificial Sequence
<220> FEATURE:
<223> OTHER INFORMATION: Polynucleotide Encoding hBRCA84D-5VL

<400> SEQUENCE: 78

gacatccagc tgacccagtc cccctccttc ctgtctgcct ccgtgggcga cagagtgacc      60

atcacatgca aggcctccca gaacgtggac accaacgtgg cctggtatca gcagaagcct     120

ggccaggccc ctaaggcgct gatctactcc gcctcctacc ggtactccgg cgtgccttcc     180

aggttctccg gctccggctc tggcaccgac ttcaccctga ccatctccag cctgcagcct     240

gaggacttcg ccacctacta ctgccagcag tacaacaact accctttcac cttcggccag     300

ggcaccaagc tggaaatcaa g                                               321


<210> SEQ ID NO 79
<211> LENGTH: 107
<212> TYPE: PRT
<213> ORGANISM: Artificial Sequence
<220> FEATURE:
<223> OTHER INFORMATION: hBRCA84D-6VL

<400> SEQUENCE: 79

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Tyr Cys Gln Gln Tyr Asn Asn Tyr Pro Phe
                85                  90                  95

Thr Phe Gly Gln Gly Thr Lys Leu Glu Ile Lys
            100                 105


<210> SEQ ID NO 80
<211> LENGTH: 321
<212> TYPE: DNA
<213> ORGANISM: Artificial Sequence
<220> FEATURE:
<223> OTHER INFORMATION: Polynucleotide Encoding hBRCA84D-6VL

<400> SEQUENCE: 80

gacatccagc tgacccagtc cccctccttc ctgtctgcct ccgtgggcga cagagtgacc      60
```

atcacatgca aggcctccca gaacgtggac accaacgtgg cctggtatca gcagaagcct 120
ggcaaggccc ctaagctgct gatctactcc gcctcctacc ggtactccgg cgtgccttcc 180
aggttctccg gctccggctc tggcaccgac ttcaccctga ccatctccag cctgcagcct 240
gaggacttcg ccgagtacta ctgccagcag tacaacaact accctttcac cttcggccag 300
ggcaccaagc tggaaatcaa g 321

<210> SEQ ID NO 81
<211> LENGTH: 122
<212> TYPE: PRT
<213> ORGANISM: Artificial Sequence
<220> FEATURE:
<223> OTHER INFORMATION: hBRCA84D-2VH

<400> SEQUENCE: 81

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Phe
20 25 30

Gly Met His Trp Val Arg Gln Ala Pro Gly Lys Gly Leu Glu Trp Val
35 40 45

Ala Tyr Ile Ser Ser Asp Ser Ser Ala Ile Tyr Tyr Ala Asp Thr Val
50 55 60

Lys Gly Arg Phe Thr Ile Ser Arg Asp Asn Ala Lys Asn Ser Leu Tyr
65 70 75 80

Leu Gln Met Asn Ser Leu Arg Asp Glu Asp Thr Ala Val Tyr Tyr Cys
85 90 95

Gly Arg Gly Arg Glu Asn Ile Tyr Tyr Gly Ser Arg Leu Asp Tyr Trp
100 105 110

Gly Gln Gly Thr Thr Val Thr Val Ser Ser
115 120

<210> SEQ ID NO 82
<211> LENGTH: 366
<212> TYPE: DNA
<213> ORGANISM: Artificial Sequence
<220> FEATURE:
<223> OTHER INFORMATION: Polynucleotide Encoding hBRCA84D-2VH

<400> SEQUENCE: 82
gaggtgcagc tggtcgagtc tggcggagga ctggtgcagc ctggcggctc cctgagactg 60
tcttgcgccg cctccggctt caccttctcc agcttcggca tgcactgggt ccgccaggct 120
ccaggcaagg gactggaatg ggtggcctac atctcctccg actcctccgc catctactac 180
gccgacaccg tgaagggcag gttcaccatc tcccgggaca acgccaagaa ctccctgtac 240
ctgcagatga actccctgcg ggacgaggac accgccgtgt actactgcgg cagaggccgg 300
gagaatatct actacggctc ccggctggat tattggggcc agggcaccac cgtgaccgtg 360
tcctct 366

<210> SEQ ID NO 83
<211> LENGTH: 122
<212> TYPE: PRT
<213> ORGANISM: Artificial Sequence
<220> FEATURE:
<223> OTHER INFORMATION: hBRCA84D-3VH

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Met Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser
        115                 120


<210> SEQ ID NO 84
<211> LENGTH: 366
<212> TYPE: DNA
<213> ORGANISM: Artificial Sequence
<220> FEATURE:
<223> OTHER INFORMATION: Polynucleotide Encoding hBRCA84D-3VH

<400> SEQUENCE: 84

gaggtgcagc tggtcgagtc tggcggagga ctggtgcagc ctggcggctc cctgagactg      60

tcttgcgccg cctccggctt caccttctcc agcttcggca tgcactgggt ccgccaggct     120

ccaggcaagg gactggaatg ggtggcctac atctcctccg actcctccgc catctactac     180

gccgacaccg tgaagggcag gttcaccatc tcccgggaca acgccaagaa ctccctgtac     240

ctgcagatga actccctgcg ggacgaggac accgccatgt actactgcgg cagaggccgg     300

gagaatatct actacggctc ccggctggat tattggggcc agggcaccac cgtgaccgtg     360

tcctct                                                                366


<210> SEQ ID NO 85
<211> LENGTH: 122
<212> TYPE: PRT
<213> ORGANISM: Artificial Sequence
<220> FEATURE:
<223> OTHER INFORMATION: hBRCA84D-4VH

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ser Glu Asp Thr Ala Val Tyr Tyr Cys
                85                  90                  95

Ala Arg Gly Arg Glu Asn Ile Tyr Tyr Gly Ser Arg Leu Asp Tyr Trp
            100                 105                 110
```

Gly Gln Gly Thr Thr Val Thr Val Ser Ser
        115                 120

<210> SEQ ID NO 86
<211> LENGTH: 366
<212> TYPE: DNA
<213> ORGANISM: Artificial Sequence
<220> FEATURE:
<223> OTHER INFORMATION: Polynucleotide Encoding hBRCA84D-4VH

<400> SEQUENCE: 86
gaggtgcagc tggtcgagtc tggcggagga ctggtgcagc ctggcggctc cctgagactg 60
tcttgcgccg cctccggctt caccttctcc agcttcggca tgcactgggt ccgccaggct 120
ccaggcaagg gactggaatg ggtggcctac atctcctccg actcctccgc catctactac 180
gccgacaccg tgaagggcag gttcaccatc tcccgggaca acgccaagaa ctccctgtac 240
ctgcagatga actccctgcg gagcgaggac accgccgtgt actactgcgc cagaggccgg 300
gagaatatct actacggctc ccggctggat tattggggcc agggcaccac cgtgaccgtg 360
tcctct 366

<210> SEQ ID NO 87
<211> LENGTH: 214
<212> TYPE: PRT
<213> ORGANISM: Artificial Sequence
<220> FEATURE:
<223> OTHER INFORMATION: chBRCA84D Light Chain

<400> SEQUENCE: 87

Asp Ile Ala Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 88
<211> LENGTH: 642
<212> TYPE: DNA
<213> ORGANISM: Artificial Sequence
<220> FEATURE:
<223> OTHER INFORMATION: Polynucleotide Encoding chBRCA84D Light Chain

<400> SEQUENCE: 88
gacattgcga tgacccagtc tcaaaaattc atgtccacat cagtaggaga cagggtcagc 60
gtcacctgca aggccagtca gaatgtggat actaatgtag cctggtatca acagaaacca 120
gggcaatctc ctaaagcact gatttactcg gcatcctacc ggtacagtgg agtccctgat 180
cgcttcacag gcagtggatc tgggacagat ttcactctca ccatcaacaa tgtgcagtct 240
gaagacttgg cagagtattt ctgtcagcaa tataacaact atccattcac gttcggctcg 300
gggacaaagt tggaaataaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 89
<211> LENGTH: 452
<212> TYPE: PRT
<213> ORGANISM: Artificial Sequence
<220> FEATURE:
<223> OTHER INFORMATION: chBRCA84D Heavy Chain

<400> SEQUENCE: 89

Asp Val Gln Leu Val Glu Ser Gly Gly Gly Leu Val Gln Pro Gly Gly
1 5 10 15

Ser Arg Lys Leu Ser Cys Ala Ala Ser Gly Phe Thr Phe Ser Ser Phe
20 25 30

Gly Met His Trp Val Arg Gln Ala Pro Glu Lys Gly Leu Glu Trp Val
35 40 45

Ala Tyr Ile Ser Ser Asp Ser Ser Ala Ile Tyr Tyr Ala Asp Thr Val
50 55 60

Lys Gly Arg Phe Thr Ile Ser Arg Asp Asn Pro Lys Asn Thr Leu Phe
65 70 75 80

Leu Gln Met Thr Ser Leu Arg Ser Glu Asp Thr Ala Met Tyr Tyr Cys
85 90 95

Gly Arg Gly Arg Glu Asn Ile Tyr Tyr Gly Ser Arg Leu Asp Tyr Trp
100 105 110

Gly Gln Gly Thr Thr Leu Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn

```
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 90
<211> LENGTH: 1356
<212> TYPE: DNA
<213> ORGANISM: Artificial Sequence
<220> FEATURE:
<223> OTHER INFORMATION: Polynucleotide Encoding chBRCA84D Heavy Chain

<400> SEQUENCE: 90

gatgtgcagc tggtggagtc tgggggaggc ttagtgcagc ctggagggtc ccggaaactc      60

tcctgtgcag cctctggatt cactttcagt agctttggaa tgcactgggt tcgtcaggct     120

ccagagaagg ggctggagtg ggtcgcatac attagtagtg acagtagtgc catctactat     180

gcagacacag tgaagggccg attcaccatc tccagagaca atcccaagaa caccctgttc     240

ctgcaaatga ccagtctaag gtctgaggac acggccatgt attactgtgg aagagggagg     300

gaaaacattt actacggtag taggcttgac tactggggcc aaggcaccac tctcacagtc     360

tcctcagcct ccaccaaggg cccatcggtc ttccccctgg caccctcctc caagagcacc     420

tctgggggca cagcggccct gggctgcctg gtcaaggact acttccccga accggtgacg     480

gtgtcgtgga actcaggcgc cctgaccagc ggcgtgcaca ccttcccggc tgtcctacag     540

tcctcaggac tctactccct cagcagcgtg gtgaccgtgc cctccagcag cttgggcacc     600
```

```
cagacctaca tctgcaacgt gaatcacaag cccagcaaca ccaaggtgga caagagagtt    660

gagcccaaat cttgtgacaa aactcacaca tgcccaccgt gcccagcacc tgaactcctg    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacaacagca cgtaccgtgt ggtcagcgtc ctcaccgtcc tgcaccagga ctggctgaat    960

ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gatgagctga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260

aggtggcagc aggggaacgt cttctcatgc tccgtgatgc atgaggctct gcacaaccac   1320

tacacgcaga agagcctctc cctgtctccg ggtaaa                             1356
```

<210> SEQ ID NO 91
<211> LENGTH: 107
<212> TYPE: PRT
<213> ORGANISM: Artificial Sequence
<220> FEATURE:
<223> OTHER INFORMATION: Amino Acid Sequence of K9CD3-1 Variable Light Chain

<400> SEQUENCE: 91

```
Asp Ile Leu Leu Thr Gln Ser Pro Ala Thr Leu Ser Val Thr Pro Gly
1               5                   10                  15

Glu Thr Val Ser Leu Ser Cys Arg Ala Ser Gln Ser Ile Phe Lys Asn
            20                  25                  30

Leu His Trp Tyr Gln Gln Lys Ser His Arg Ser Pro Arg Leu Leu Ile
        35                  40                  45

Lys Tyr Ala Ser Asp Ser Ile Ser Gly Ile Pro Ser Arg Phe Thr Gly
    50                  55                  60

Ser Gly Ser Gly Thr Asp Tyr Thr Leu Ser Ile Asn Ser Val Lys Pro
65                  70                  75                  80

Glu Asp Glu Gly Val Tyr Tyr Cys Leu Gln Ala Tyr Ser Thr Pro Trp
                85                  90                  95

Thr Phe Gly Gly Gly Thr Lys Leu Glu Ile Lys
            100                 105
```

<210> SEQ ID NO 92
<211> LENGTH: 321
<212> TYPE: DNA
<213> ORGANISM: Artificial Sequence
<220> FEATURE:
<223> OTHER INFORMATION: Polynucleotide Sequence Encoding K9CD3-1 Variable Light Chain

<400> SEQUENCE: 92

```
gacatcctgc tgacccagtc tccagccacc ctgtctgtga ctccaggaga aacagtcagt     60

ctttcctgta gggccagcca gagtattttc aagaacctac actggtatca acagaaatca    120

catcggtctc caaggcttct catcaagtat gcttctgatt ccatctctgg gatcccctcc    180

aggttcactg gcagtggatc ggggacagat tacactctca gtatcaacag tgtgaagccc    240

gaagatgaag gagtatatta ctgtcttcaa gcttacagca caccgtggac gttcggtgga    300
```

ggcaccaaac tggaaatcaa a 321

<210> SEQ ID NO 93
<211> LENGTH: 11
<212> TYPE: PRT
<213> ORGANISM: Artificial Sequence
<220> FEATURE:
<223> OTHER INFORMATION: K9CD3-1 Variable Light Chain CDR1

<400> SEQUENCE: 93

Arg Ala Ser Gln Ser Ile Phe Lys Asn Leu His
1 5 10

<210> SEQ ID NO 94
<211> LENGTH: 33
<212> TYPE: DNA
<213> ORGANISM: Artificial Sequence
<220> FEATURE:
<223> OTHER INFORMATION: Polynucleotide Sequence Encoding K9CD3-1 Variable Light Chain CDR1

<400> SEQUENCE: 94
agggccagcc agagtatttt caagaaccta cac 33

<210> SEQ ID NO 95
<211> LENGTH: 11
<212> TYPE: PRT
<213> ORGANISM: Artificial Sequence
<220> FEATURE:
<223> OTHER INFORMATION: K9CD3-1 Variable Light Chain CDR2

<400> SEQUENCE: 95

Tyr Ala Ser Asp Ser Ile Ser Gly Ile Pro Ser
1 5 10

<210> SEQ ID NO 96
<211> LENGTH: 21
<212> TYPE: DNA
<213> ORGANISM: Artificial Sequence
<220> FEATURE:
<223> OTHER INFORMATION: Polynucleotide Sequence Encoding K9CD3-1 Variable Light Chain CDR2

<400> SEQUENCE: 96
tatgcttctg attccatctc t 21

<210> SEQ ID NO 97
<211> LENGTH: 9
<212> TYPE: PRT
<213> ORGANISM: Artificial Sequence
<220> FEATURE:
<223> OTHER INFORMATION: K9CD3-1 Variable Light Chain CDR3

<400> SEQUENCE: 97

Leu Gln Ala Tyr Ser Thr Pro Trp Thr
1 5

<210> SEQ ID NO 98
<211> LENGTH: 27
<212> TYPE: DNA
<213> ORGANISM: Artificial Sequence
<220> FEATURE:
<223> OTHER INFORMATION: Polynucleotide Sequence Encoding K9CD3-1 Variable Light Chain CDR3

<400> SEQUENCE: 98

-continued cttcaagctt acagcacacc gtggacg 27

<210> SEQ ID NO 99
<211> LENGTH: 115
<212> TYPE: PRT
<213> ORGANISM: Artificial Sequence
<220> FEATURE:
<223> OTHER INFORMATION: Amino Acid Sequence of K9CD3-1 Variable Heavy Chain

<400> SEQUENCE: 99

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Thr Phe Ser Asp Tyr
20 25 30

Asn Met His Trp Val Lys Gln Ser His Gly Glu Ser Leu Glu Trp Ile
35 40 45

Gly Tyr Ile Tyr Pro Tyr Asn Gly Gly Thr Tyr Tyr Asn Gln Lys Phe
50 55 60

Lys Ser Lys Ala Thr Leu Thr Val Asp Asn Ser Ser Ser Thr Ala Tyr
65 70 75 80

Met Glu Phe Arg Ser Leu Thr Ser Glu Asp Ser Ala Val Tyr Tyr Cys
85 90 95

Ala Arg Leu Val Tyr Phe Asp Tyr Trp Gly Gln Gly Thr Ala Leu Thr
100 105 110

Val Ser Ser
115

<210> SEQ ID NO 100
<211> LENGTH: 345
<212> TYPE: DNA
<213> ORGANISM: Artificial Sequence
<220> FEATURE:
<223> OTHER INFORMATION: Polynucleotide Sequence Encoding K9CD3-1 Variable Heavy Chain

<400> SEQUENCE: 100
gaggtccagc ttcagcagtc aggacctgag ctggtgaaac ctggggcctc agtgaagata 60
tcctgcaagg cttctggata cacattctct gactacaaca tgcactgggt gaaacagagc 120
catggagaga gccttgagtg gattggatat atttatcctt acaatggtgg tacttactac 180
aaccagaaat tcaagagcaa ggccacattg actgtagaca attcctccag cacagcctac 240
atggagttcc gcagcctgac atctgaggac tctgcagtct attactgtgc aaggctggtt 300
tactttgact actggggcca aggcaccgct ctcacagtct cctcc 345

<210> SEQ ID NO 101
<211> LENGTH: 5
<212> TYPE: PRT
<213> ORGANISM: Artificial Sequence
<220> FEATURE:
<223> OTHER INFORMATION: K9CD3-1 Variable Heavy Chain CDR1

<400> SEQUENCE: 101

Asp Tyr Asn Met His
1 5

<210> SEQ ID NO 102
<211> LENGTH: 15
<212> TYPE: DNA
<213> ORGANISM: Artificial Sequence
<220> FEATURE:

<223> OTHER INFORMATION: Polynucleotide Sequence Encoding K9CD3-1 Variable Heavy Chain CDR1

<400> SEQUENCE: 102
gactacaaca tgcac 15

<210> SEQ ID NO 103
<211> LENGTH: 17
<212> TYPE: PRT
<213> ORGANISM: Artificial Sequence
<220> FEATURE:
<223> OTHER INFORMATION: K9CD3-1 Variable Heavy Chain CDR2

<400> SEQUENCE: 103

Tyr Ile Tyr Pro Tyr Asn Gly Gly Thr Tyr Tyr Asn Gln Lys Phe Lys
1 5 10 15

Ser

<210> SEQ ID NO 104
<211> LENGTH: 51
<212> TYPE: DNA
<213> ORGANISM: Artificial Sequence
<220> FEATURE:
<223> OTHER INFORMATION: Polynucleotide Sequence Encoding K9CD3-1 Variable Heavy Chain CDR2

<400> SEQUENCE: 104
tatatttatc cttacaatgg tggtacttac tacaaccaga aattcaagag c 51

<210> SEQ ID NO 105
<211> LENGTH: 6
<212> TYPE: PRT
<213> ORGANISM: Artificial Sequence
<220> FEATURE:
<223> OTHER INFORMATION: K9CD3-1 Variable Heavy Chain CDR3

<400> SEQUENCE: 105

Leu Val Tyr Phe Asp Tyr
1 5

<210> SEQ ID NO 106
<211> LENGTH: 18
<212> TYPE: DNA
<213> ORGANISM: Artificial Sequence
<220> FEATURE:
<223> OTHER INFORMATION: Polynucleotide Sequence Encoding K9CD3-1 Variable Heavy Chain CDR3

<400> SEQUENCE: 106
ctggtttact ttgactac 18

<210> SEQ ID NO 107
<211> LENGTH: 107
<212> TYPE: PRT
<213> ORGANISM: Artificial Sequence
<220> FEATURE:
<223> OTHER INFORMATION: Amino Acid Sequence of K9CD3-2 Variable Light Chain

<400> SEQUENCE: 107

Asn Ile Val Met Thr Gln Ser Pro Lys Ser Met Ser Met Ser Val Gly
1 5 10 15

Glu Arg Val Thr Leu Asn Cys Lys Ala Ser Glu Asn Val Asp Ser Tyr
20 25 30

Val Ser Trp Tyr Gln Gln Lys Pro Lys Gln Ser Pro Thr Leu Leu Ile

```
        35                  40                  45

Tyr Gly Ala Ser Asn Arg Ser Thr Gly Val Pro Asp Arg Phe Thr Gly
    50                  55                  60

Ser Gly Ser Val Thr Asp Phe Thr Leu Thr Ile Thr Ser Val Gln Ala
65                  70                  75                  80

Glu Asp Leu Ala Tyr Tyr His Cys Gly Gln Thr Tyr Ser Tyr Pro Phe
                85                  90                  95

Thr Phe Gly Ser Gly Thr Lys Leu Glu Ile Lys
            100                 105


<210> SEQ ID NO 108
<211> LENGTH: 321
<212> TYPE: DNA
<213> ORGANISM: Artificial Sequence
<220> FEATURE:
<223> OTHER INFORMATION: Polynucleotide Sequence Encoding K9CD3-2
      Variable Light Chain

<400> SEQUENCE: 108

aacattgtga tgacccaatc tcccaaatcc atgtccatgt cagttggaga gagggtcacc      60

ttgaactgca aggccagtga gaatgtggat tcttatgtgt cctggtatca gcagaaacca     120

aaacagtctc ctacattact gatttacggg gcatccaacc ggtccactgg ggtccccgat     180

cgcttcacag gcagcggatc tgtaacagat ttcactctga ccatcaccag tgtgcaggct     240

gaagaccttg catattatca ctgtggacag acttacagtt atccattcac gttcggctcg     300

gggacaaagt tggaaataaa a                                               321


<210> SEQ ID NO 109
<211> LENGTH: 11
<212> TYPE: PRT
<213> ORGANISM: Artificial Sequence
<220> FEATURE:
<223> OTHER INFORMATION: K9CD3-2 Variable Light Chain CDR1

<400> SEQUENCE: 109

Lys Ala Ser Glu Asn Val Asp Ser Tyr Val Ser
1               5                   10


<210> SEQ ID NO 110
<211> LENGTH: 33
<212> TYPE: DNA
<213> ORGANISM: Artificial Sequence
<220> FEATURE:
<223> OTHER INFORMATION: Polynucleotide Sequence Encoding K9CD3-2
      Variable Light Chain CDR1

<400> SEQUENCE: 110

aaggccagtg agaatgtgga ttcttatgtg tcc                                   33


<210> SEQ ID NO 111
<211> LENGTH: 7
<212> TYPE: PRT
<213> ORGANISM: Artificial Sequence
<220> FEATURE:
<223> OTHER INFORMATION: K9CD3-2 Variable Light Chain CDR2

<400> SEQUENCE: 111

Gly Ala Ser Asn Arg Ser Thr
1               5


<210> SEQ ID NO 112
<211> LENGTH: 21
```

-continued

<212> TYPE: DNA
<213> ORGANISM: Artificial Sequence
<220> FEATURE:
<223> OTHER INFORMATION: Polynucleotide Sequence Encoding K9CD3-2
Variable Light Chain CDR2

<400> SEQUENCE: 112
ggggcatcca accggtccac t 21

<210> SEQ ID NO 113
<211> LENGTH: 9
<212> TYPE: PRT
<213> ORGANISM: Artificial Sequence
<220> FEATURE:
<223> OTHER INFORMATION: K9CD3-2 Variable Light Chain CDR3

<400> SEQUENCE: 113

Gly Gln Thr Tyr Ser Tyr Pro Phe Thr
1 5

<210> SEQ ID NO 114
<211> LENGTH: 27
<212> TYPE: DNA
<213> ORGANISM: Artificial Sequence
<220> FEATURE:
<223> OTHER INFORMATION: Polynucleotide Sequence Encoding K9CD3-2
Variable Light Chain CDR3

<400> SEQUENCE: 114
ggacagactt acagttatcc attcacg 27

<210> SEQ ID NO 115
<211> LENGTH: 117
<212> TYPE: PRT
<213> ORGANISM: Artificial Sequence
<220> FEATURE:
<223> OTHER INFORMATION: Amino Acid Sequence of K9CD3-2 Variable Heavy
Chain

<400> SEQUENCE: 115

Glu Val Gln Leu Val Glu Ser Gly Gly Gly Leu Val Gln Pro Lys Gly
1 5 10 15

Ser Leu Thr Leu Ser Cys Ala Ala Ser Gly Phe Thr Phe Asn Ile Phe
20 25 30

Ala Met Asn Trp Val Arg Gln Ala Pro Gly Lys Gly Leu Glu Trp Val
35 40 45

Ala Arg Ile Arg Ser Lys Asn Asn Tyr Phe Ala Thr Tyr Tyr Ala Ala
50 55 60

Ser Val Arg Asp Arg Phe Thr Ile Ser Arg Asp Asp Ser Gln Ser Met
65 70 75 80

Val Tyr Leu Gln Met Asn Asn Leu Lys Thr Glu Asp Thr Gly Met Tyr
85 90 95

Tyr Cys Val Arg Arg Gly Tyr Phe Asp Val Trp Gly Ala Gly Thr Thr
100 105 110

Val Thr Val Ser Ser
115

<210> SEQ ID NO 116
<211> LENGTH: 351
<212> TYPE: DNA
<213> ORGANISM: Artificial Sequence
<220> FEATURE:
<223> OTHER INFORMATION: Polynucleotide Sequence Encoding K9CD3-2
Variable Heavy Chain

<400> SEQUENCE: 116
gaggtgcagc ttgttgagtc tggtggagga ttggtgcagc ctaaagggtc attgacactc 60
tcatgtgcag cctctggatt caccttcaat atcttcgcca tgaactgggt ccgccaggct 120
ccaggaaagg gtttggaatg ggttgctcgt ataagaagta aaaataatta ttttgcaaca 180
tattatgctg cttcagtgag agacaggttc accatctcca gagatgattc acaaagcatg 240
gtctatcttc aaatgaacaa cttgaaaact gaggacacag gcatgtatta ctgtgtgaga 300
cggggatact tcgatgtctg gggcgcaggg accacggtca ccgtctcctc c 351

<210> SEQ ID NO 117
<211> LENGTH: 5
<212> TYPE: PRT
<213> ORGANISM: Artificial Sequence
<220> FEATURE:
<223> OTHER INFORMATION: K9CD3-2 Variable Heavy Chain CDR1

<400> SEQUENCE: 117

Ile Phe Ala Met Asn
1 5

<210> SEQ ID NO 118
<211> LENGTH: 15
<212> TYPE: DNA
<213> ORGANISM: Artificial Sequence
<220> FEATURE:
<223> OTHER INFORMATION: Polynucleotide Sequence Encoding K9CD3-2 Variable Heavy Chain CDR1

<400> SEQUENCE: 118
atcttcgcca tgaac 15

<210> SEQ ID NO 119
<211> LENGTH: 19
<212> TYPE: PRT
<213> ORGANISM: Artificial Sequence
<220> FEATURE:
<223> OTHER INFORMATION: K9CD3-2 Variable Heavy Chain CDR2

<400> SEQUENCE: 119

Arg Ile Arg Ser Lys Asn Asn Tyr Phe Ala Thr Tyr Tyr Ala Ala Ser
1 5 10 15

Val Arg Asp

<210> SEQ ID NO 120
<211> LENGTH: 57
<212> TYPE: DNA
<213> ORGANISM: Artificial Sequence
<220> FEATURE:
<223> OTHER INFORMATION: Polynucleotide Sequence Encoding K9CD3-2 Variable Heavy Chain CDR2

<400> SEQUENCE: 120
cgtataagaa gtaaaaataa ttattttgca acatattatg ctgcttcagt gagagac 57

<210> SEQ ID NO 121
<211> LENGTH: 6
<212> TYPE: PRT
<213> ORGANISM: Artificial Sequence
<220> FEATURE:
<223> OTHER INFORMATION: K9CD3-2 Variable Heavy Chain CDR3

<400> SEQUENCE: 121

Arg Gly Tyr Phe Asp Val
1 5

<210> SEQ ID NO 122
<211> LENGTH: 18
<212> TYPE: DNA
<213> ORGANISM: Artificial Sequence
<220> FEATURE:
<223> OTHER INFORMATION: Polynucleotide Sequence Encoding K9CD3-2 Variable Heavy Chain CDR3

<400> SEQUENCE: 122
cggggatact tcgatgtc 18

<210> SEQ ID NO 123
<211> LENGTH: 8
<212> TYPE: PRT
<213> ORGANISM: Artificial Sequence
<220> FEATURE:
<223> OTHER INFORMATION: Linker

<400> SEQUENCE: 123

Gly Gly Gly Ser Gly Gly Gly Gly
1 5

<210> SEQ ID NO 124
<211> LENGTH: 24
<212> TYPE: DNA
<213> ORGANISM: Artificial Sequence
<220> FEATURE:
<223> OTHER INFORMATION: Polynucleotide Encoding GGGSGGGG Linker

<400> SEQUENCE: 124
ggaggcggat ccggaggcgg aggc 24

<210> SEQ ID NO 125
<211> LENGTH: 4
<212> TYPE: PRT
<213> ORGANISM: Artificial Sequence
<220> FEATURE:
<223> OTHER INFORMATION: Linker at C-Terminus

<400> SEQUENCE: 125

Leu Gly Gly Cys
1

<210> SEQ ID NO 126
<211> LENGTH: 13
<212> TYPE: PRT
<213> ORGANISM: Artificial Sequence
<220> FEATURE:
<223> OTHER INFORMATION: Hinge Domain Containing Cysteine Residue

<400> SEQUENCE: 126

Glu Pro Lys Ser Cys Asp Lys Thr His Thr Cys Pro Pro
1 5 10

<210> SEQ ID NO 127
<211> LENGTH: 10
<212> TYPE: PRT
<213> ORGANISM: Artificial Sequence
<220> FEATURE:
<223> OTHER INFORMATION: Hinge Domain Containing Cysteine Residue

<400> SEQUENCE: 127

Glu Ser Lys Tyr Gly Pro Pro Cys Pro Ser
1 5 10

<210> SEQ ID NO 128
<211> LENGTH: 6
<212> TYPE: PRT
<213> ORGANISM: Artificial Sequence
<220> FEATURE:
<223> OTHER INFORMATION: C-Terminal Amino Acid Sequence

<400> SEQUENCE: 128

Val Glu Pro Lys Ser Cys
1               5

<210> SEQ ID NO 129
<211> LENGTH: 18
<212> TYPE: DNA
<213> ORGANISM: Artificial Sequence
<220> FEATURE:
<223> OTHER INFORMATION: Polynucleotide Encoding VEPKSC

<400> SEQUENCE: 129
gttgagccca aatcttgt 18

<210> SEQ ID NO 130
<211> LENGTH: 10
<212> TYPE: PRT
<213> ORGANISM: Artificial Sequence
<220> FEATURE:
<223> OTHER INFORMATION: Cysteine Containing Amino Acid Sequence

<400> SEQUENCE: 130

Leu Gly Gly Cys Phe Asn Arg Gly Glu Cys
1               5                   10

<210> SEQ ID NO 131
<211> LENGTH: 30
<212> TYPE: DNA
<213> ORGANISM: Artificial Sequence
<220> FEATURE:
<223> OTHER INFORMATION: Polynucleotide Encoding LGGCFNRGEC

<400> SEQUENCE: 131
ctgggaggct gcttcaacag gggagagtgt 30

<210> SEQ ID NO 132
<211> LENGTH: 6
<212> TYPE: PRT
<213> ORGANISM: Artificial Sequence
<220> FEATURE:
<223> OTHER INFORMATION: Cysteine Containing Diabody Sequence

<400> SEQUENCE: 132

Phe Asn Arg Gly Glu Cys
1               5

<210> SEQ ID NO 133
<211> LENGTH: 18
<212> TYPE: DNA
<213> ORGANISM: Artificial Sequence
<220> FEATURE:
<223> OTHER INFORMATION: Polynucleotide Encoding FNRGEC Peptide

<400> SEQUENCE: 133
ttcaacaggg gagagtgt 18

<210> SEQ ID NO 134
<211> LENGTH: 6

<212> TYPE: PRT
<213> ORGANISM: Artificial Sequence
<220> FEATURE:
<223> OTHER INFORMATION: Diabody Polypeptide Chain Linker

<400> SEQUENCE: 134

Gly Gly Cys Gly Gly Gly
1 5

<210> SEQ ID NO 135
<211> LENGTH: 28
<212> TYPE: PRT
<213> ORGANISM: Artificial Sequence
<220> FEATURE:
<223> OTHER INFORMATION: Amino Acid Sequence of E-coil

<400> SEQUENCE: 135

Glu Val Ala Ala Leu Glu Lys Glu Val Ala Ala Leu Glu Lys Glu Val
1 5 10 15

Ala Ala Leu Glu Lys Glu Val Ala Ala Leu Glu Lys
20 25

<210> SEQ ID NO 136
<211> LENGTH: 28
<212> TYPE: PRT
<213> ORGANISM: Artificial Sequence
<220> FEATURE:
<223> OTHER INFORMATION: Amino Acid Sequence of K-coil

<400> SEQUENCE: 136

Lys Val Ala Ala Leu Lys Glu Lys Val Ala Ala Leu Lys Glu Lys Val
1 5 10 15

Ala Ala Leu Lys Glu Lys Val Ala Ala Leu Lys Glu
20 25

<210> SEQ ID NO 137
<211> LENGTH: 5
<212> TYPE: PRT
<213> ORGANISM: Artificial Sequence
<220> FEATURE:
<223> OTHER INFORMATION: Linker

<400> SEQUENCE: 137

Gly Gly Gly Asn Ser
1 5

<210> SEQ ID NO 138
<211> LENGTH: 264
<212> TYPE: PRT
<213> ORGANISM: Artificial Sequence
<220> FEATURE:
<223> OTHER INFORMATION: Amino Acid Sequence of Chain 1 of K9CD3 x B7-H3
Bispecific Molecule Having the Anti-CD3 Variable Domains of
K9CD3-1 and the Anti-B7-H3 Variable Domains of hBRCA84D-2

<400> SEQUENCE: 138

Asp Ile Gln Leu Thr Gln Ser Pro Ser Phe Leu Ser Ala Ser Val Gly
1 5 10 15

Asp Arg Val Thr Ile Thr Cys Lys Ala Ser Gln Asn Val Asp Thr Asn
20 25 30

Val Ala Trp Tyr Gln Gln Lys Pro Gly Lys Ala Pro Lys Ala Leu Ile
35 40 45

Tyr Ser Ala Ser Tyr Arg Tyr Ser Gly Val Pro Ser Arg Phe Ser Gly
50 55 60

-continued

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Asn Tyr Pro Phe
85 90 95

Thr Phe Gly Gln Gly Thr Lys Leu Glu Ile Lys Gly Gly Gly Ser Gly
100 105 110

Gly Gly Gly Glu Val Gln Leu Gln Gln Ser Gly Pro Glu Leu Val Lys
115 120 125

Pro Gly Ala Ser Val Lys Ile Ser Cys Lys Ala Ser Gly Tyr Thr Phe
130 135 140

Ser Asp Tyr Asn Met His Trp Val Lys Gln Ser His Gly Glu Ser Leu
145 150 155 160

Glu Trp Ile Gly Tyr Ile Tyr Pro Tyr Asn Gly Gly Thr Tyr Tyr Asn
165 170 175

Gln Lys Phe Lys Ser Lys Ala Thr Leu Thr Val Asp Asn Ser Ser Ser
180 185 190

Thr Ala Tyr Met Glu Phe Arg Ser Leu Thr Ser Glu Asp Ser Ala Val
195 200 205

Tyr Tyr Cys Ala Arg Leu Val Tyr Phe Asp Tyr Trp Gly Gln Gly Thr
210 215 220

Ala Leu Thr Val Ser Ser Gly Gly Cys Gly Gly Gly Glu Val Ala Ala
225 230 235 240

Leu Glu Lys Glu Val Ala Ala Leu Glu Lys Glu Val Ala Ala Leu Glu
245 250 255

Lys Glu Val Ala Ala Leu Glu Lys
260

<210> SEQ ID NO 139
<211> LENGTH: 792
<212> TYPE: DNA
<213> ORGANISM: Artificial Sequence
<220> FEATURE:
<223> OTHER INFORMATION: Polynucelotide Encoding Amino Acid Sequence of Chain 1 of K9CD3 x B7-H3 Bispecific Molecule Having the Anti-CD3 Variable Domains of K9CD3-1 and the Anti-B7-H3 Variable Domains of hBRCA84D-2

<400> SEQUENCE: 139
gacatccagc tgacccagtc cccctccttc ctgtctgcct ccgtgggcga cagagtgacc 60
atcacatgca aggcctccca gaacgtggac accaacgtgg cctggtatca gcagaagcct 120
ggcaaggccc ctaaggcgct gatctactcc gcctcctacc ggtactccgg cgtgccttcc 180
aggttctccg gctccggctc tggcaccgac ttcaccctga ccatctccag cctgcagcct 240
gaggacttcg ccacctacta ctgccagcag tacaacaact accctttcac cttcggccag 300
ggcaccaagc tggaaatcaa gggaggcgga tccggcggcg gaggcgaggt ccagcttcag 360
cagtcaggac ctgagctggt gaaacctggg gcctcagtga agatatcctg caaggcttct 420
ggatacacat tctctgacta caacatgcac tgggtgaaac agagccatgg agagagcctt 480
gagtggattg gatatattta tccttacaat ggtggtactt actacaacca gaaattcaag 540
agcaaggcca cattgactgt agacaattcc tccagcacag cctacatgga gttccgcagc 600
ctgacatctg aggactctgc agtctattac tgtgcaaggc tggtttactt tgactactgg 660
ggccaaggca ccgctctcac agtctcctcc ggaggatgtg gcggtggaga agtggccgca 720
ctggagaaag aggttgctgc tttggagaag gaggtcgctg cacttgaaaa ggaggtcgca 780
gccctggaga aa 792

<210> SEQ ID NO 140
<211> LENGTH: 271
<212> TYPE: PRT
<213> ORGANISM: Artificial Sequence
<220> FEATURE:
<223> OTHER INFORMATION: Amino Acid Sequence of Chain 2 of K9CD3 x B7-H3 Bispecific Molecule Having the Anti-CD3 Variable Domains of K9CD3-1 and the Anti-B7-H3 Variable Domains of hBRCA84D-2

<400> SEQUENCE: 140

```
Asp Ile Leu Leu Thr Gln Ser Pro Ala Thr Leu Ser Val Thr Pro Gly
1               5                   10                  15

Glu Thr Val Ser Leu Ser Cys Arg Ala Ser Gln Ser Ile Phe Lys Asn
            20                  25                  30

Leu His Trp Tyr Gln Gln Lys Ser His Arg Ser Pro Arg Leu Leu Ile
        35                  40                  45

Lys Tyr Ala Ser Asp Ser Ile Ser Gly Ile Pro Ser Arg Phe Thr Gly
    50                  55                  60

Ser Gly Ser Gly Thr Asp Tyr Thr Leu Ser Ile Asn Ser Val Lys Pro
65                  70                  75                  80

Glu Asp Glu Gly Val Tyr Tyr Cys Leu Gln Ala Tyr Ser Thr Pro Trp
                85                  90                  95

Thr Phe Gly Gly Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Ser Ser Phe Gly Met His Trp Val Arg Gln Ala Pro Gly Lys Gly Leu
145                 150                 155                 160

Glu Trp Val Ala Tyr Ile Ser Ser Asp Ser Ser Ala Ile Tyr Tyr Ala
                165                 170                 175

Asp Thr Val Lys Gly Arg Phe Thr Ile Ser Arg Asp Asn Ala Lys Asn
            180                 185                 190

Ser Leu Tyr Leu Gln Met Asn Ser Leu Arg Asp Glu Asp Thr Ala Val
        195                 200                 205

Tyr Tyr Cys Gly Arg Gly Arg Glu Asn Ile Tyr Tyr Gly Ser Arg Leu
    210                 215                 220

Asp Tyr Trp Gly Gln Gly Thr Thr Val Thr Val Ser Ser Gly Gly Cys
225                 230                 235                 240

Gly Gly Gly Lys Val Ala Ala Leu Lys Glu Lys Val Ala Ala Leu Lys
                245                 250                 255

Glu Lys Val Ala Ala Leu Lys Glu Lys Val Ala Ala Leu Lys Glu
            260                 265                 270
```

<210> SEQ ID NO 141
<211> LENGTH: 813
<212> TYPE: DNA
<213> ORGANISM: Artificial Sequence
<220> FEATURE:
<223> OTHER INFORMATION: Polynucelotide Encoding Amino Acid Sequence of Chain 2 of K9CD3 x B7-H3 Bispecific Molecule Having the Anti-CD3 Variable Domains of K9CD3-1 and the Anti-B7-H3 Variable Domains of hBRCA84D-2

<400> SEQUENCE: 141

```
gacatcctgc tgacccagtc tccagccacc ctgtctgtga ctccaggaga aacagtcagt     60
```

-continued

```
ctttcctgta gggccagcca gagtattttc aagaacctac actggtatca acagaaatca    120

catcggtctc caaggcttct catcaagtat gcttctgatt ccatctctgg gatcccctcc    180

aggttcactg gcagtggatc ggggacagat tacactctca gtatcaacag tgtgaagccc    240

gaagatgaag gagtatatta ctgtcttcaa gcttacagca caccgtggac gttcggtgga    300

ggcaccaaac tggaaatcaa aggaggcgga tccggcggcg gaggcgaggt gcagctggtc    360

gagtctggcg gaggactggt gcagcctggc ggctccctga gactgtcttg cgccgcctcc    420

ggcttcacct tctccagctt cggcatgcac tgggtccgcc aggctccagg caagggactg    480

gaatgggtgg cctacatctc ctccgactcc tccgccatct actacgccga caccgtgaag    540

ggcaggttca ccatctcccg ggacaacgcc aagaactccc tgtacctgca gatgaactcc    600

ctgcgggacg aggacaccgc cgtgtactac tgcggcagag gccgggagaa tatctactac    660

ggctcccggc tggattattg ggccagggc accaccgtga ccgtgtcctc cggaggatgt    720

ggcggtggaa aagtggccgc actgaaggag aaagttgctg ctttgaaaga gaaggtcgcc    780

gcacttaagg aaaaggtcgc agccctgaaa gag                                 813
```

```
<210> SEQ ID NO 142
<211> LENGTH: 269
<212> TYPE: PRT
<213> ORGANISM: Artificial Sequence
<220> FEATURE:
<223> OTHER INFORMATION: Amino Acid Sequence of Chain 1 of K9CD3 x B7-H3
      Bispecific Molecule Having the Anti-CD3 Variable Domains of
      K9CD3-1 and the Anti-B7-H3 Variable Domains of hBRCA69D

<400> SEQUENCE: 142

Asp Ile Leu Leu Thr Gln Ser Pro Ala Thr Leu Ser Val Thr Pro Gly
1               5                   10                  15

Glu Thr Val Ser Leu Ser Cys Arg Ala Ser Gln Ser Ile Phe Lys Asn
            20                  25                  30

Leu His Trp Tyr Gln Gln Lys Ser His Arg Ser Pro Arg Leu Leu Ile
        35                  40                  45

Lys Tyr Ala Ser Asp Ser Ile Ser Gly Ile Pro Ser Arg Phe Thr Gly
    50                  55                  60

Ser Gly Ser Gly Thr Asp Tyr Thr Leu Ser Ile Asn Ser Val Lys Pro
65                  70                  75                  80

Glu Asp Glu Gly Val Tyr Tyr Cys Leu Gln Ala Tyr Ser Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Met Gln Trp Val Arg Gln Ala Pro Gly Gln Gly Leu
145                 150                 155                 160

Glu Trp Met Gly Thr Ile Tyr Pro Gly Asp Gly Asp Thr Arg Tyr Thr
                165                 170                 175

Gln Lys Phe Lys Gly Arg Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Arg Arg Gly Ile Pro Arg Leu Trp Tyr Phe Asp Val
    210                 215                 220
```

Trp Gly Gln Gly Thr Thr Val Thr Val Ser Ser Gly Gly Cys Gly Gly
225 230 235 240

Gly Lys Val Ala Ala Leu Lys Glu Lys Val Ala Ala Leu Lys Glu Lys
245 250 255

Val Ala Ala Leu Lys Glu Lys Val Ala Ala Leu Lys Glu
260 265

<210> SEQ ID NO 143
<211> LENGTH: 807
<212> TYPE: DNA
<213> ORGANISM: Artificial Sequence
<220> FEATURE:
<223> OTHER INFORMATION: Polynucleotide Encoding Amino Acid Sequence of Chain 1 of K9CD3 x B7-H3 Bispecific Molecule Having the Anti-CD3 Variable Domains of K9CD3-1 and the Anti-B7-H3 Variable Domains of hBRCA69D

<400> SEQUENCE: 143
gacatcctgc tgacccagtc tccagccacc ctgtctgtga ctccaggaga aacagtcagt 60
ctttcctgta gggccagcca gagtattttc aagaacctac actggtatca acagaaatca 120
catcggtctc caaggcttct catcaagtat gcttctgatt ccatctctgg gatcccctcc 180
aggttcactg gcagtggatc ggggacagat tacactctca gtatcaacag tgtgaagccc 240
gaagatgaag gagtatatta ctgtcttcaa gcttacagca caccgtggac gttcggtgga 300
ggcaccaaac tggaaatcaa aggaggcgga tccggcggag gggtcaggt gcagctggtg 360 cagagcgggg cagaggtgaa gaaaccaggt gccagcgtga aggtgtcttg caaagccagt 420
ggctacactt tcacctccta ttggatgcag tgggtcagac aggctccagg acagggactg 480
gaatggatgg gcaccatcta ccctggggac ggtgatacta gatataccca gaagtttaaa 540
ggacgcgtga caattactgc tgacaagtca acctccacag catacatgga gctgtccagc 600
ctgcgatctg aagatacagc cgtgtactat tgtgctaggc ggggcatccc caggctgtgg 660
tatttcgacg tgtggggcca gggaaccaca gtgactgtgt cttccggagg atgtggcggt 720
ggaaaagtgg ccgcactgaa ggagaaagtt gctgctttga aagagaaggt cgccgcactt 780
aaggaaaagg tcgcagccct gaaagag 807

<210> SEQ ID NO 144
<211> LENGTH: 265
<212> TYPE: PRT
<213> ORGANISM: Artificial Sequence
<220> FEATURE:
<223> OTHER INFORMATION: Amino Acid Sequence of Chain 2 of K9CD3 x B7-H3 Bispecific Molecule Having the Anti-CD3 Variable Domains of K9CD3-1 and the Anti-B7-H3 Variable Domains of hBRCA69D

<400> SEQUENCE: 144

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Thr Tyr Tyr Cys Gln Gln Gly Asn Thr Leu Pro Pro

-continued

```
                85                  90                  95

Thr Phe Gly Gly Gly Thr Lys Leu Glu Ile Lys Gly Gly Gly Gly Ser
            100                 105                 110

Gly Gly Gly Gly Glu Val Gln Leu Gln Gln Ser Gly Pro Glu Leu Val
        115                 120                 125

Lys Pro Gly Ala Ser Val Lys Ile Ser Cys Lys Ala Ser Gly Tyr Thr
    130                 135                 140

Phe Ser Asp Tyr Asn Met His Trp Val Lys Gln Ser His Gly Glu Ser
145                 150                 155                 160

Leu Glu Trp Ile Gly Tyr Ile Tyr Pro Tyr Asn Gly Gly Thr Tyr Tyr
                165                 170                 175

Asn Gln Lys Phe Lys Ser Lys Ala Thr Leu Thr Val Asp Asn Ser Ser
            180                 185                 190

Ser Thr Ala Tyr Met Glu Phe Arg Ser Leu Thr Ser Glu Asp Ser Ala
        195                 200                 205

Val Tyr Tyr Cys Ala Arg Leu Val Tyr Phe Asp Tyr Trp Gly Gln Gly
    210                 215                 220

Thr Ala Leu Thr Val Ser Ser Gly Gly Cys Gly Gly Gly Glu Val Ala
225                 230                 235                 240

Ala Leu Glu Lys Glu Val Ala Ala Leu Glu Lys Glu Val Ala Ala Leu
                245                 250                 255

Glu Lys Glu Val Ala Ala Leu Glu Lys
            260                 265
```

<210> SEQ ID NO 145
<211> LENGTH: 795
<212> TYPE: DNA
<213> ORGANISM: Artificial Sequence
<220> FEATURE:
<223> OTHER INFORMATION: Polynucleotide Encoding Amino Acid Sequence of Chain 2 of K9CD3 x B7-H3 Bispecific Molecule Having the Anti-CD3 Variable Domains of K9CD3-1 and the Anti-B7-H3 Variable Domains of hBRCA69D

<400> SEQUENCE: 145

```
gacatccaga tgacacagtc tccatccagc ctgtcagcct ccgtgggaga cagggtgacc     60

atcacatgcc gggctagtca ggatatcagt aactacctga actggtacca gcagaagcca    120

ggaaaagcac ccaagctgct gatttactat acctcaaggc tgcactccgg tgtgcctagc    180

agattcagcg gttctggcag tggaaccgac tttactctga ccatctctag tctgcagcca    240

gaggatattg ccacatacta ttgtcagcag ggcaacacac tgccccctac tttcggcgga    300

gggaccaagc tggaaataaa aggagggggt ggatccggcg gcggaggcga ggtccagctt    360

cagcagtcag gacctgagct ggtgaaacct ggggcctcag tgaagatatc ctgcaaggct    420

tctggataca cattctctga ctacaacatg cactgggtga aacagagcca tggagagagc    480

cttgagtgga ttggatatat ttatccttac aatggtggta cttactacaa ccagaaattc    540

aagagcaagg ccacattgac tgtagacaat tcctccagca cagcctacat ggagttccgc    600

agcctgacat ctgaggactc tgcagtctat tactgtgcaa ggctggttta ctttgactac    660

tggggccaag gcaccgctct cacagtctcc tccggaggat gtggcggtgg agaagtggcc    720

gcactggaga aagaggttgc tgctttggag aaggaggtcg ctgcacttga aaaggaggtc    780

gcagccctgg agaaa                                                     795
```

<210> SEQ ID NO 146
<211> LENGTH: 271

<212> TYPE: PRT
<213> ORGANISM: Artificial Sequence
<220> FEATURE:
<223> OTHER INFORMATION: Amino Acid Sequence of Chain 1 of K9CD3 x B7-H3 Bispecific Molecule Having the Anti-CD3 Variable Domains of K9CD3-2 and the Anti-B7-H3 Variable Domains of hBRCA84D-2

<400> SEQUENCE: 146

```
Asn Ile Val Met Thr Gln Ser Pro Lys Ser Met Ser Met Ser Val Gly
1               5                   10                  15

Glu Arg Val Thr Leu Asn Cys Lys Ala Ser Glu Asn Val Asp Ser Tyr
            20                  25                  30

Val Ser Trp Tyr Gln Gln Lys Pro Lys Gln Ser Pro Thr Leu Leu Ile
        35                  40                  45

Tyr Gly Ala Ser Asn Arg Ser Thr Gly Val Pro Asp Arg Phe Thr Gly
    50                  55                  60

Ser Gly Ser Val Thr Asp Phe Thr Leu Thr Ile Thr Ser Val Gln Ala
65                  70                  75                  80

Glu Asp Leu Ala Tyr Tyr His Cys Gly Gln Thr Tyr Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Ser Ser Phe Gly Met His Trp Val Arg Gln Ala Pro Gly Lys Gly Leu
145                 150                 155                 160

Glu Trp Val Ala Tyr Ile Ser Ser Asp Ser Ser Ala Ile Tyr Tyr Ala
                165                 170                 175

Asp Thr Val Lys Gly Arg Phe Thr Ile Ser Arg Asp Asn Ala Lys Asn
            180                 185                 190

Ser Leu Tyr Leu Gln Met Asn Ser Leu Arg Asp Glu Asp Thr Ala Val
        195                 200                 205

Tyr Tyr Cys Gly Arg Gly Arg Glu Asn Ile Tyr Tyr Gly Ser Arg Leu
    210                 215                 220

Asp Tyr Trp Gly Gln Gly Thr Thr Val Thr Val Ser Ser Gly Gly Cys
225                 230                 235                 240

Gly Gly Gly Glu Val Ala Ala Leu Glu Lys Glu Val Ala Ala Leu Glu
                245                 250                 255

Lys Glu Val Ala Ala Leu Glu Lys Glu Val Ala Ala Leu Glu Lys
            260                 265                 270
```

<210> SEQ ID NO 147
<211> LENGTH: 813
<212> TYPE: DNA
<213> ORGANISM: Artificial Sequence
<220> FEATURE:
<223> OTHER INFORMATION: Polynucleotide Encoding Amino Acid Sequence of Chain 1 of K9CD3 x B7-H3 Bispecific Molecule Having the Anti-CD3 Variable Domains of K9CD3-2 and the Anti-B7-H3 Variable Domains of hBRCA84D-2

<400> SEQUENCE: 147

```
aacattgtga tgacccaatc tcccaaatcc atgtccatgt cagttggaga gagggtcacc      60

ttgaactgca aggccagtga gaatgtggat tcttatgtgt cctggtatca gcagaaacca     120

aaacagtctc ctacattact gatttacggg gcatccaacc ggtccactgg ggtccccgat     180
```

```
cgcttcacag gcagcggatc tgtaacagat ttcactctga ccatcaccag tgtgcaggct    240

gaagaccttg catattatca ctgtggacag acttacagtt atccattcac gttcggctcg    300

gggacaaagt tggaaataaa aggaggcgga tccggcggcg gaggcgaggt gcagctggtc    360

gagtctggcg gaggactggt gcagcctggc ggctccctga gactgtcttg cgccgcctcc    420

ggcttcacct tctccagctt cggcatgcac tgggtccgcc aggctccagg caagggactg    480

gaatgggtgg cctacatctc ctccgactcc tccgccatct actacgccga caccgtgaag    540

ggcaggttca ccatctcccg ggacaacgcc aagaactccc tgtacctgca gatgaactcc    600

ctgcgggacg aggacaccgc cgtgtactac tgcggcagag gccgggagaa tatctactac    660

ggctcccggc tggattattg gggccagggc accaccgtga ccgtgtcctc cggaggatgt    720

ggcggtggag aagtggccgc actggagaaa gaggttgctg ctttggagaa ggaggtcgct    780

gcacttgaaa aggaggtcgc agccctggag aaa                                 813
```

```
<210> SEQ ID NO 148
<211> LENGTH: 266
<212> TYPE: PRT
<213> ORGANISM: Artificial Sequence
<220> FEATURE:
<223> OTHER INFORMATION: Amino Acid Sequence of Chain 2 of K9CD3 x B7-H3
      Bispecific Molecule Having the Anti-CD3 Variable Domains of
      K9CD3-2 and the Anti-B7-H3 Variable Domains of hBRCA84D-2

<400> SEQUENCE: 148

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Lys Gly Ser Leu Thr Leu Ser Cys Ala Ala Ser Gly Phe Thr Phe
    130                 135                 140

Asn Ile Phe Ala Met Asn Trp Val Arg Gln Ala Pro Gly Lys Gly Leu
145                 150                 155                 160

Glu Trp Val Ala Arg Ile Arg Ser Lys Asn Asn Tyr Phe Ala Thr Tyr
                165                 170                 175

Tyr Ala Ala Ser Val Arg Asp Arg Phe Thr Ile Ser Arg Asp Asp Ser
            180                 185                 190

Gln Ser Met Val Tyr Leu Gln Met Asn Asn Leu Lys Thr Glu Asp Thr
        195                 200                 205

Gly Met Tyr Tyr Cys Val Arg Arg Gly Tyr Phe Asp Val Trp Gly Ala
    210                 215                 220

Gly Thr Thr Val Thr Val Ser Ser Gly Gly Cys Gly Gly Gly Lys Val
225                 230                 235                 240
```

-continued

```
Ala Ala Leu Lys Glu Lys Val Ala Ala Leu Lys Glu Lys Val Ala Ala
                245                 250                 255

Leu Lys Glu Lys Val Ala Ala Leu Lys Glu
            260                 265


<210> SEQ ID NO 149
<211> LENGTH: 798
<212> TYPE: DNA
<213> ORGANISM: Artificial Sequence
<220> FEATURE:
<223> OTHER INFORMATION: Polynucleotide Encoding Amino Acid Sequence of
      Chain 2 of K9CD3 x B7-H3 Bispecific Molecule Having the Anti-CD3
      Variable Domains of K9CD3-2 and the Anti-B7-H3 Variable Domains of
      hBRCA84D-2

<400> SEQUENCE: 149

gacatccagc tgacccagtc cccctccttc ctgtctgcct ccgtgggcga cagagtgacc      60

atcacatgca aggcctccca gaacgtggac accaacgtgg cctggtatca gcagaagcct     120

ggcaaggccc ctaaggcgct gatctactcc gcctcctacc ggtactccgg cgtgccttcc     180

aggttctccg gctccggctc tggcaccgac ttcaccctga ccatctccag cctgcagcct     240

gaggacttcg ccacctacta ctgccagcag tacaacaact accctttcac cttcggccag     300

ggcaccaagc tggaaatcaa gggaggcgga tccggcggcg gaggcgaggt gcagcttgtt     360

gagtctggtg gaggattggt gcagcctaaa gggtcattga cactctcatg tgcagcctct     420

ggattcacct tcaatatctt cgccatgaac tgggtccgcc aggctccagg aaagggtttg     480

gaatgggttg ctcgtataag aagtaaaaat aattattttg caacatatta tgctgcttca     540

gtgagagaca ggttcaccat ctccagagat gattcacaaa gcatggtcta tcttcaaatg     600

aacaacttga aaactgagga cacaggcatg tattactgtg tgagacgggg atacttcgat     660

gtctggggcg cagggaccac ggtcaccgtc tcctccggag gatgtggcgg tggaaaagtg     720

gccgcactga aggagaaagt tgctgctttg aaagagaagg tcgccgcact taaggaaaag     780

gtcgcagccc tgaaagag                                                   798


<210> SEQ ID NO 150
<211> LENGTH: 269
<212> TYPE: PRT
<213> ORGANISM: Artificial Sequence
<220> FEATURE:
<223> OTHER INFORMATION: Amino Acid Sequence of Chain 1 of K9CD3 x B7-H3
      Bispecific Molecule Having the Anti-CD3 Variable Domains of
      K9CD3-2 and the Anti-B7-H3 Variable Domains of hBRCA69D

<400> SEQUENCE: 150

Asn Ile Val Met Thr Gln Ser Pro Lys Ser Met Ser Met Ser Val Gly
1               5                   10                  15

Glu Arg Val Thr Leu Asn Cys Lys Ala Ser Glu Asn Val Asp Ser Tyr
            20                  25                  30

Val Ser Trp Tyr Gln Gln Lys Pro Lys Gln Ser Pro Thr Leu Leu Ile
        35                  40                  45

Tyr Gly Ala Ser Asn Arg Ser Thr Gly Val Pro Asp Arg Phe Thr Gly
    50                  55                  60

Ser Gly Ser Val Thr Asp Phe Thr Leu Thr Ile Thr Ser Val Gln Ala
65                  70                  75                  80

Glu Asp Leu Ala Tyr Tyr His Cys Gly Gln Thr Tyr Ser Tyr Pro Phe
                85                  90                  95

Thr Phe Gly Ser Gly Thr Lys Leu Glu Ile Lys Gly Gly Gly Ser Gly
            100                 105                 110
```

```
Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Met Gln Trp Val Arg Gln Ala Pro Gly Gln Gly Leu
145                 150                 155                 160

Glu Trp Met Gly Thr Ile Tyr Pro Gly Asp Gly Asp Thr Arg Tyr Thr
                165                 170                 175

Gln Lys Phe Lys Gly Arg Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Arg Arg Gly Ile Pro Arg Leu Trp Tyr Phe Asp Val
    210                 215                 220

Trp Gly Gln Gly Thr Thr Val Thr Val Ser Ser Gly Gly Cys Gly Gly
225                 230                 235                 240

Gly Glu Val Ala Ala Leu Glu Lys Glu Val Ala Ala Leu Glu Lys Glu
                245                 250                 255

Val Ala Ala Leu Glu Lys Glu Val Ala Ala Leu Glu Lys
            260                 265


<210> SEQ ID NO 151
<211> LENGTH: 807
<212> TYPE: DNA
<213> ORGANISM: Artificial Sequence
<220> FEATURE:
<223> OTHER INFORMATION: Polynucleotide Encoding Amino Acid Sequence of
      Chain 1 of K9CD3 x B7-H3 Bispecific Molecule Having the Anti-CD3
      Variable Domains of K9CD3-2 and the Anti-B7-H3 Variable Domains of
      hBRCA69D

<400> SEQUENCE: 151

aacattgtga tgacccaatc tcccaaatcc atgtccatgt cagttggaga gagggtcacc     60

ttgaactgca aggccagtga gaatgtggat tcttatgtgt cctggtatca gcagaaacca    120

aaacagtctc ctacattact gatttacggg gcatccaacc ggtccactgg ggtccccgat    180

cgcttcacag gcagcggatc tgtaacagat ttcactctga ccatcaccag tgtgcaggct    240

gaagaccttg catattatca ctgtggacag acttacagtt atccattcac gttcggctcg    300

gggacaaagt tggaaataaa aggaggcgga tccggcggag gggtcaggt gcagctggtg    360

cagagcgggg cagaggtgaa gaaaccaggt gccagcgtga aggtgtcttg caaagccagt    420

ggctacactt tcacctccta ttggatgcag tgggtcagac aggctccagg acagggactg    480

gaatggatgg gcaccatcta ccctggggac ggtgatacta gatataccca gaagtttaaa    540

ggacgcgtga caattactgc tgacaagtca acctccacag catacatgga gctgtccagc    600

ctgcgatctg aagatacagc cgtgtactat tgtgctaggc ggggcatccc caggctgtgg    660

tatttcgacg tgtggggcca gggaaccaca gtgactgtgt cttccggagg atgtggcggt    720

ggagaagtgg ccgcactgga gaaagaggtt gctgctttgg agaargaggt cgctgcactt    780

gaaaaggagg tcgcagccct ggagaaa                                         807


<210> SEQ ID NO 152
<211> LENGTH: 267
<212> TYPE: PRT
<213> ORGANISM: Artificial Sequence
<220> FEATURE:
<223> OTHER INFORMATION: Amino Acid Sequence of Chain 2 of K9CD3 x B7-H3
```

Bispecific Molecule Having the Anti-CD3 Variable Domains of K9CD3-2 and the Anti-B7-H3 Variable Domains of hBRCA69D

<400> SEQUENCE: 152

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Thr Tyr Tyr Cys Gln Gln Gly Asn Thr Leu Pro Pro
85 90 95

Thr Phe Gly Gly Gly Thr Lys Leu Glu Ile Lys Gly Gly Gly Gly Ser
100 105 110

Gly Gly Gly Gly Glu Val Gln Leu Val Glu Ser Gly Gly Gly Leu Val
115 120 125

Gln Pro Lys Gly Ser Leu Thr Leu Ser Cys Ala Ala Ser Gly Phe Thr
130 135 140

Phe Asn Ile Phe Ala Met Asn Trp Val Arg Gln Ala Pro Gly Lys Gly
145 150 155 160

Leu Glu Trp Val Ala Arg Ile Arg Ser Lys Asn Asn Tyr Phe Ala Thr
165 170 175

Tyr Tyr Ala Ala Ser Val Arg Asp Arg Phe Thr Ile Ser Arg Asp Asp
180 185 190

Ser Gln Ser Met Val Tyr Leu Gln Met Asn Asn Leu Lys Thr Glu Asp
195 200 205

Thr Gly Met Tyr Tyr Cys Val Arg Arg Gly Tyr Phe Asp Val Trp Gly
210 215 220

Ala Gly Thr Thr Val Thr Val Ser Ser Gly Gly Cys Gly Gly Gly Lys
225 230 235 240

Val Ala Ala Leu Lys Glu Lys Val Ala Ala Leu Lys Glu Lys Val Ala
245 250 255

Ala Leu Lys Glu Lys Val Ala Ala Leu Lys Glu
260 265

<210> SEQ ID NO 153
<211> LENGTH: 801
<212> TYPE: DNA
<213> ORGANISM: Artificial Sequence
<220> FEATURE:
<223> OTHER INFORMATION: Polynucleotide Encoding Amino Acid Sequence of Chain 2 of K9CD3 x B7-H3 Bispecific Molecule Having the Anti-CD3 Variable Domains of K9CD3-2 and the Anti-B7-H3 Variable Domains of hBRCA69D

<400> SEQUENCE: 153
gacatccaga tgacacagtc tccatccagc ctgtcagcct ccgtgggaga cagggtgacc 60
atcacatgcc gggctagtca ggatatcagt aactacctga actggtacca gcagaagcca 120
ggaaaagcac ccaagctgct gatttactat acctcaaggc tgcactccgg tgtgcctagc 180
agattcagcg gttctggcag tggaaccgac tttactctga ccatctctag tctgcagcca 240
gaggatattg ccacatacta ttgtcagcag ggcaacacac tgccccctac tttcggcgga 300

-continued

```
gggaccaagc tggaaataaa aggagggggt ggatccggcg gcggaggcga ggtgcagctt    360

gttgagtctg gtggaggatt ggtgcagcct aaagggtcat tgacactctc atgtgcagcc    420

tctggattca ccttcaatat cttcgccatg aactgggtcc gccaggctcc aggaaagggt    480

ttggaatggg ttgctcgtat aagaagtaaa aataattatt ttgcaacata ttatgctgct    540

tcagtgagag acaggttcac catctccaga gatgattcac aaagcatggt ctatcttcaa    600

atgaacaact tgaaaactga ggacacaggc atgtattact gtgtgagacg gggatacttc    660

gatgtctggg gcgcagggac cacggtcacc gtctcctccg gaggatgtgg cggtggaaaa    720

gtggccgcac tgaaggagaa agttgctgct ttgaaagaga aggtcgccgc acttaaggaa    780

aaggtcgcag ccctgaaaga g                                              801
```

<210> SEQ ID NO 154
<211> LENGTH: 503
<212> TYPE: PRT
<213> ORGANISM: Artificial Sequence
<220> FEATURE:
<223> OTHER INFORMATION: Amino Acid Sequence of Chain 1 of K9CD3 x B7-H3 Bispecific Molecule Having the Anti-CD3 Variable Domains of K9CD3-1 and the Anti-B7-H3 Variable Domains of hBRCA69D and Modified CH2-CH3 Region

<400> SEQUENCE: 154

```
Asp Ile Leu Leu Thr Gln Ser Pro Ala Thr Leu Ser Val Thr Pro Gly
1               5                   10                  15

Glu Thr Val Ser Leu Ser Cys Arg Ala Ser Gln Ser Ile Phe Lys Asn
            20                  25                  30

Leu His Trp Tyr Gln Gln Lys Ser His Arg Ser Pro Arg Leu Leu Ile
        35                  40                  45

Lys Tyr Ala Ser Asp Ser Ile Ser Gly Ile Pro Ser Arg Phe Thr Gly
    50                  55                  60

Ser Gly Ser Gly Thr Asp Tyr Thr Leu Ser Ile Asn Ser Val Lys Pro
65                  70                  75                  80

Glu Asp Glu Gly Val Tyr Tyr Cys Leu Gln Ala Tyr Ser Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Met Gln Trp Val Arg Gln Ala Pro Gly Gln Gly Leu
145                 150                 155                 160

Glu Trp Met Gly Thr Ile Tyr Pro Gly Asp Gly Asp Thr Arg Tyr Thr
                165                 170                 175

Gln Lys Phe Lys Gly Arg Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Arg Arg Gly Ile Pro Arg Leu Trp Tyr Phe Asp Val
    210                 215                 220

Trp Gly Gln Gly Thr Thr Val Thr Val Ser Ser Gly Gly Cys Gly Gly
225                 230                 235                 240

Gly Glu Val Ala Ala Leu Glu Lys Glu Val Ala Ala Leu Glu Lys Glu
                245                 250                 255
```

-continued

```
Val Ala Ala Leu Glu Lys Glu Val Ala Ala Leu Glu Lys Gly Gly Gly
            260                 265                 270

Arg Val Pro Arg Pro Pro Asp Cys Pro Lys Cys Pro Ala Pro Glu Ala
        275                 280                 285

Ala Gly Gly Pro Ser Val Phe Ile Phe Pro Pro Lys Pro Lys Asp Thr
    290                 295                 300

Leu Leu Ile Ala Arg Thr Pro Glu Val Thr Cys Val Val Val Asp Leu
305                 310                 315                 320

Asp Pro Glu Asp Pro Glu Val Gln Ile Ser Trp Phe Val Asp Gly Lys
                325                 330                 335

Gln Met Gln Thr Ala Lys Thr Gln Pro Arg Glu Glu Gln Phe Gln Gly
            340                 345                 350

Thr Tyr Arg Val Val Ser Val Leu Pro Ile Gly His Gln Asp Trp Leu
        355                 360                 365

Lys Gly Lys Gln Phe Thr Cys Lys Val Asn Asn Lys Ala Leu Pro Ser
    370                 375                 380

Pro Ile Glu Arg Thr Ile Ser Lys Ala Arg Gly Gln Ala His Gln Pro
385                 390                 395                 400

Ser Val Tyr Val Leu Pro Pro Ser Arg Glu Glu Leu Ser Lys Asn Thr
                405                 410                 415

Val Ser Leu Trp Cys Leu Ile Lys Asp Phe Phe Pro Pro Asp Ile Asp
            420                 425                 430

Val Glu Trp Gln Ser Asn Gly Gln Gln Glu Pro Glu Ser Lys Tyr Arg
        435                 440                 445

Thr Thr Pro Pro Gln Leu Asp Glu Asp Gly Ser Tyr Phe Leu Tyr Ser
    450                 455                 460

Lys Leu Ser Val Asp Lys Ser Arg Trp Gln Arg Gly Asp Thr Phe Ile
465                 470                 475                 480

Cys Ala Val Met His Glu Ala Leu His Asn His Tyr Thr Gln Glu Ser
                485                 490                 495

Leu Ser His Ser Pro Gly Lys
            500
```

```
<210> SEQ ID NO 155
<211> LENGTH: 1509
<212> TYPE: DNA
<213> ORGANISM: Artificial Sequence
<220> FEATURE:
<223> OTHER INFORMATION: Polynucleoitide Encoding Amino Acid Sequence of
      Chain 1 of K9CD3 x B7-H3 Bispecific Molecule Having the Anti-CD3
      Variable Domains of K9CD3-1 and the Anti-B7-H3 Variable Domains of
      hBRCA69D and Modified CH2-CH3 Region

<400> SEQUENCE: 155

gacatcctgc tgacccagtc tccagccacc ctgtctgtga ctccaggaga aacagtcagt      60

ctttcctgta gggccagcca gagtattttc aagaacctac actggtatca acagaaatca     120

catcggtctc caaggcttct catcaagtat gcttctgatt ccatctctgg gatcccctcc     180

aggttcactg gcagtggatc ggggacagat tacactctca gtatcaacag tgtgaagccc     240

gaagatgaag gagtatatta ctgtcttcaa gcttacagca caccgtggac gttcggtgga     300

ggcaccaaac tggaaatcaa aggaggcgga tccggcggag ggggtcaggt gcagctggtg     360

cagagcgggg cagaggtgaa gaaaccaggt gccagcgtga aggtgtcttg caaagccagt     420

ggctacactt tcacctccta ttggatgcag tgggtcagac aggctccagg acagggactg     480

gaatggatgg gcaccatcta ccctggggac ggtgatacta gatataccca gaagtttaaa     540
```

-continued

```
ggacgcgtga caattactgc tgacaagtca acctccacag catacatgga gctgtccagc    600

ctgcgatctg aagatacagc cgtgtactat tgtgctaggc ggggcatccc caggctgtgg    660

tatttcgacg tgtggggcca gggaaccaca gtgactgtgt cttccggagg atgtggcggt    720

ggagaagtgg ccgcactgga gaaagaggtt gctgctttgg agaaggaggt cgctgcactt    780

gaaaaggagg tcgcagccct ggagaaaggc ggcgggaggg tgcctcgacc acctgattgc    840

ccaaagtgtc cagctcccga agccgctggc ggaccctccg tgttcatctt tccacccaag    900

cctaaagaca cactgctgat tgcaaggacc ccagaggtga catgcgtggt cgtggacctg    960

gaccccgagg accctgaagt ccagatcagc tggttcgtgg atgggaagca gatgcagaca   1020

gccaaaactc agccaaggga ggaacagttt caaggtactt accgggtcgt gtctgtgctg   1080

cccattggcc accaggactg gctgaaggga aaacagttta cctgcaaggt gaacaacaag   1140

gccctgcctt ccccaatcga gcgaacaatt agcaaggcac gtggacaggc acatcagcca   1200

agcgtctacg tgctgcctcc atcccgagag gaactgagca agaacactgt ctctctgtgg   1260

tgtctgatca aagatttctt tccccctgac attgatgtgg agtggcagtc taatggacag   1320

caggagcctg agagtaagta tcggaccaca ccaccccagc tggacgaaga tggcagttac   1380

ttcctgtata gtaagctgtc agtggacaaa tccagatggc agcgcggaga taccttcatc   1440

tgcgcagtga tgcacgaagc actgcacaat cactacaccc aggagtcact gagccatagc   1500

ccagggaag                                                           1509


<210> SEQ ID NO 156
<211> LENGTH: 265
<212> TYPE: PRT
<213> ORGANISM: Artificial Sequence
<220> FEATURE:
<223> OTHER INFORMATION: Amino Acid Sequence of Chain 2 of K9CD3 x B7-H3
      Bispecific Molecule Having the Anti-CD3 Variable Domains of
      K9CD3-1 and the Anti-B7-H3 Variable Domains of hBRCA69D and
      Modified CH2-CH3 Region

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys Gly Gly Gly Gly Ser
            100                 105                 110

Gly Gly Gly Gly Glu Val Gln Leu Gln Gln Ser Gly Pro Glu Leu Val
        115                 120                 125

Lys Pro Gly Ala Ser Val Lys Ile Ser Cys Lys Ala Ser Gly Tyr Thr
    130                 135                 140

Phe Ser Asp Tyr Asn Met His Trp Val Lys Gln Ser His Gly Glu Ser
145                 150                 155                 160

Leu Glu Trp Ile Gly Tyr Ile Tyr Pro Tyr Asn Gly Gly Thr Tyr Tyr
                165                 170                 175
```

```
Asn Gln Lys Phe Lys Ser Lys Ala Thr Leu Thr Val Asp Asn Ser Ser
            180                 185                 190

Ser Thr Ala Tyr Met Glu Phe Arg Ser Leu Thr Ser Glu Asp Ser Ala
        195                 200                 205

Val Tyr Tyr Cys Ala Arg Leu Val Tyr Phe Asp Tyr Trp Gly Gln Gly
    210                 215                 220

Thr Ala Leu Thr Val Ser Ser Gly Gly Cys Gly Gly Gly Lys Val Ala
225                 230                 235                 240

Ala Leu Lys Glu Lys Val Ala Ala Leu Lys Glu Lys Val Ala Ala Leu
                245                 250                 255

Lys Glu Lys Val Ala Ala Leu Lys Glu
            260                 265
```

<210> SEQ ID NO 157
<211> LENGTH: 795
<212> TYPE: DNA
<213> ORGANISM: Artificial Sequence
<220> FEATURE:
<223> OTHER INFORMATION: Polynucleotide Encoding Amino Acid Sequence of Chain 2 of K9CD3 x B7-H3 Bispecific Molecule Having the Anti-CD3 Variable Domains of K9CD3-1 and the Anti-B7-H3 Variable Domains of hBRCA69D and Modified CH2-CH3 Region

<400> SEQUENCE: 157

```
gacatccaga tgacacagtc tccatccagc ctgtcagcct ccgtgggaga cagggtgacc      60

atcacatgcc gggctagtca ggatatcagt aactacctga actggtacca gcagaagcca     120

ggaaaagcac ccaagctgct gatttactat acctcaaggc tgcactccgg tgtgcctagc     180

agattcagcg gttctggcag tggaaccgac tttactctga ccatctctag tctgcagcca     240

gaggatattg ccacatacta ttgtcagcag ggcaacacac tgccccctac tttcggcgga     300

gggaccaagc tggaaataaa aggagggggt ggatccggcg gcggaggcga ggtccagctt     360

cagcagtcag gacctgagct ggtgaaacct ggggcctcag tgaagatatc ctgcaaggct     420

tctggataca cattctctga ctacaacatg cactgggtga aacagagcca tggagagagc     480

cttgagtgga ttggatatat ttatccttac aatggtggta cttactacaa ccagaaattc     540

aagagcaagg ccacattgac tgtagacaat tcctccagca cagcctacat ggagttccgc     600

agcctgacat ctgaggactc tgcagtctat tactgtgcaa ggctggttta ctttgactac     660

tggggccaag gcaccgctct cacagtctcc tccggaggat gtggcggtgg aaaagtggcc     720

gcactgaagg agaaagttgc tgctttgaaa gagaaggtcg ccgcacttaa ggaaaaggtc     780

gcagccctga aagag                                                      795
```

<210> SEQ ID NO 158
<211> LENGTH: 231
<212> TYPE: PRT
<213> ORGANISM: Artificial Sequence
<220> FEATURE:
<223> OTHER INFORMATION: K9 IgFc ala ala Hole Chain 3

<400> SEQUENCE: 158

```
Arg Val Pro Arg Pro Pro Asp Cys Pro Lys Cys Pro Ala Pro Glu Ala
1               5                   10                  15

Ala Gly Gly Pro Ser Val Phe Ile Phe Pro Pro Lys Pro Lys Asp Thr
            20                  25                  30

Leu Leu Ile Ala Arg Thr Pro Glu Val Thr Cys Val Val Val Asp Leu
        35                  40                  45
```

-continued

```
Asp Pro Glu Asp Pro Glu Val Gln Ile Ser Trp Phe Val Asp Gly Lys
    50                  55                  60

Gln Met Gln Thr Ala Lys Thr Gln Pro Arg Glu Glu Gln Phe Gln Gly
65                  70                  75                  80

Thr Tyr Arg Val Val Ser Val Leu Pro Ile Gly His Gln Asp Trp Leu
                85                  90                  95

Lys Gly Lys Gln Phe Thr Cys Lys Val Asn Asn Lys Ala Leu Pro Ser
            100                 105                 110

Pro Ile Glu Arg Thr Ile Ser Lys Ala Arg Gly Gln Ala His Gln Pro
        115                 120                 125

Ser Val Tyr Val Leu Pro Pro Ser Arg Glu Glu Leu Ser Lys Asn Thr
    130                 135                 140

Val Ser Leu Ser Cys Ala Ile Lys Asp Phe Phe Pro Pro Asp Ile Asp
145                 150                 155                 160

Val Glu Trp Gln Ser Asn Gly Gln Gln Glu Pro Glu Ser Lys Tyr Arg
                165                 170                 175

Thr Thr Pro Pro Gln Leu Asp Glu Asp Gly Ser Tyr Phe Leu Val Ser
            180                 185                 190

Lys Leu Ser Val Asp Lys Ser Arg Trp Gln Arg Gly Asp Thr Phe Ile
        195                 200                 205

Cys Ala Val Met His Glu Ala Leu His Asn Arg Tyr Thr Gln Glu Ser
    210                 215                 220

Leu Ser His Ser Pro Gly Lys
225                 230


<210> SEQ ID NO 159
<211> LENGTH: 693
<212> TYPE: DNA
<213> ORGANISM: Artificial Sequence
<220> FEATURE:
<223> OTHER INFORMATION: Polynucelotide Encoding K9 IgFc ala ala Hole
      Chain 3

<400> SEQUENCE: 159

agggtgcctc gaccacctga ttgcccaaag tgtccagctc ccgaagccgc tggcggaccc      60

tccgtgttca tctttccacc caagcctaaa gacacactgc tgattgcaag gaccccagag     120

gtgacatgcg tggtcgtgga cctggacccc gaggaccctg aagtccagat cagctggttc     180

gtggatggga agcagatgca gacagccaaa actcagccaa gggaggaaca gtttcaaggt     240

acttaccggg tcgtgtctgt gctgcccatt ggccaccagg actggctgaa gggaaaacag     300

tttacctgca aggtgaacaa caaggccctg ccttccccaa tcgagcgaac aattagcaag     360

gcacgtggac aggcacatca gccaagcgtc tacgtgctgc ctccatcccg agaggaactg     420

agcaagaaca ctgtctctct gtcctgtgcc atcaaagatt tctttccccc tgacattgat     480

gtggagtggc agtctaatgg acagcaggag cctgagagta agtatcggac cacaccaccc     540

cagctggacg aagatggcag ttacttcctg gtgagtaagc tgtcagtgga caaatccaga     600

tggcagcgcg gagatacctt catctgcgca gtgatgcacg aagcactgca caatagatac     660

acccaggagt cactgagcca tagcccaggg aag                                  693
```

What is claimed is:

1. A bispecific molecule comprising:

(A) a first epitope-binding domain, said first epitope-binding domain being capable of binding to an epitope of CD3 expressed on the surface of an immune effector cell of a companion animal, wherein said companion animal is a canine animal or a feline animal, and wherein said first epitope-binding domain comprises the amino acid sequences of:

(1) $CDR_1$ (SEQ ID NO:93), $CDR_2$ (SEQ ID NO:95) and $CDR_3$ (SEQ ID NO:97) of the light chain of K9CD3-1 and $CDR_1$ (SEQ ID NO:101), $CDR_2$ (SEQ ID NO:103) and $CDR_3$ (SEQ ID NO:105) of the heavy chain of K9CD3-1;

or (2) $CDR_1$ (SEQ ID NO:109), $CDR_2$ (SEQ ID NO:111) and $CDR_3$ (SEQ ID NO:113) of the light chain of K9CD3-2 and $CDR_1$ (SEQ ID NO:117), $CDR_2$ (SEQ ID NO:119) and $CDR_3$ (SEQ ID NO:121) of the heavy chain of K9CD3-2; and (B) a second epitope-binding domain, said second epitope-binding domain being capable of binding to an epitope of a cancer cell of said companion animal that expresses B7-H3.

2. The bispecific molecule of claim 1, wherein the companion animal is a canine animal.

3. The bispecific molecule of claim 1, wherein said immune effector cell is a T-cell.

4. The bispecific molecule of claim 1, wherein said bispecific molecule is a diabody molecule.

5. The bispecific molecule of claim 1, wherein said bispecific molecule further comprises an Fc region, and/or an albumin-binding domain.

6. The bispecific molecule of claim 1, wherein said second epitope-binding domain comprises a variable domain that comprises:

(A) $CDR_1$ (SEQ ID NO:25), $CDR_2$ (SEQ ID NO:27) and $CDR_3$ (SEQ ID NO:29) of the light chain of BRCA69D and $CDR_1$ (SEQ ID NO:33), $CDR_2$ (SEQ ID NO:35) and $CDR_3$ (SEQ ID NO:37) of the heavy chain of BRCA69D;

or (B) $CDR_1$ (SEQ ID NO:9), $CDR_2$ (SEQ ID NO:11) and $CDR_3$ (SEQ ID NO:13) of the light chain of BRCA84D and $CDR_1$ (SEQ ID NO:17), $CDR_2$ (SEQ ID NO:19) and $CDR_3$ (SEQ ID NO:21) of the heavy chain of BRCA84D.

7. A method of treating cancer in a companion animal which comprises administering to said companion animal a bispecific molecule, wherein said bispecific molecule comprises:

(A) a first epitope-binding domain, said first epitope-binding domain being capable of binding to an epitope of CD3 expressed on the surface of an immune effector cell of a companion animal, wherein said companion animal is a canine animal or a feline animal, and wherein said first epitope-binding domain comprises the amino acid sequences of:

(1) $CDR_1$ (SEQ ID NO:93), $CDR_2$ (SEQ ID NO:95) and $CDR_3$ (SEQ ID NO:97) of the light chain of K9CD3-1 and $CDR_1$ (SEQ ID NO:101), $CDR_2$ (SEQ ID NO:103) and $CDR_3$ (SEQ ID NO:105) of the heavy chain of K9CD3-1;

or (2) $CDR_1$ (SEQ ID NO:109), $CDR_2$ (SEQ ID NO:111) and $CDR_3$ (SEQ ID NO:113) of the light chain of K9CD3-2 and $CDR_1$ (SEQ ID NO:117), $CDR_2$ (SEQ ID NO:119) and $CDR_3$ (SEQ ID NO:121) of the heavy chain of K9CD3-2; and (B) a second epitope-binding domain, said second epitope-binding domain being capable of binding to an epitope of a cancer cell of said companion animal that expresses B7-H3;

wherein said bispecific molecule is administered to said companion animal in an amount effective to cause said molecule to bind to both said immune effector cell and said cancer cell, to thereby co-localize said cells and facilitate the killing of said cancer cell by said immune effector cell.

8. The method of claim 7, wherein said companion animal is a canine animal.

9. The method of claim 7, wherein said immune effector cell is a T-cell.

10. The method of claim 7, wherein said bispecific molecule is a diabody molecule.

11. The method of claim 7, wherein said bispecific molecule further comprises an Fc region and/or an albumin-binding domain.

12. The method of claim 7, wherein said second epitope-binding domain comprises a variable domain that comprises:

(A) $CDR_1$ (SEQ ID NO:25), $CDR_2$ (SEQ ID NO:27) and $CDR_3$ (SEQ ID NO:29) of the light chain of BRCA69D and $CDR_1$ (SEQ ID NO:33), $CDR_2$ (SEQ ID NO:35) and $CDR_3$ (SEQ ID NO:37) of the heavy chain of BRCA69D;

or (B) $CDR_1$ (SEQ ID NO:9), $CDR_2$ (SEQ ID NO:11) and $CDR_3$ (SEQ ID NO:13) of the light chain of BRCA84D and $CDR_1$ (SEQ ID NO:17), $CDR_2$ (SEQ ID NO:19) and $CDR_3$ (SEQ ID NO:21) of the heavy chain of BRCA84D.

13. The method of claim 7, wherein the cancer is selected from the group consisting of canine histiocytic sarcoma, canine hemangiosarcoma, canine malignant melanoma, canine mast cell tumor, canine osteosarcoma, canine thyroid carcinoma, canine transitional cell carcinoma, canine squamous cell carcinoma, feline fibrosarcoma, feline mammary sarcoma, and feline squamous cell carcinoma.

14. A K9CD3xB7-H3 bispecific molecule comprising SEQ ID NO:154, SEQ ID NO:156 and SEQ ID NO:158.

* * * * *